United States Patent
Hwang et al.

(10) Patent No.: US 10,693,076 B2
(45) Date of Patent: *Jun. 23, 2020

(54) CONDENSED-CYCLIC COMPOUND AND ORGANIC LIGHT-EMITTING DEVICE COMPRISING THE SAME

(71) Applicant: Samsung Display Co., Ltd., Yongin-si, Gyeonggi-do (KR)

(72) Inventors: Jinsoo Hwang, Yongin-si (KR); Myeongsuk Kim, Yongin-si (KR); Sungwook Kim, Yongin-si (KR)

(73) Assignee: Samsung Display Co., Ltd. (KR)

( * ) Notice: Subject to any disclaimer, the term of this patent is extended or adjusted under 35 U.S.C. 154(b) by 202 days.

This patent is subject to a terminal disclaimer.

(21) Appl. No.: 15/703,770

(22) Filed: Sep. 13, 2017

(65) Prior Publication Data

US 2018/0076392 A1 Mar. 15, 2018

(30) Foreign Application Priority Data

Sep. 13, 2016 (KR) .......... 10-2016-0118212

(51) Int. Cl.
*H01L 51/00* (2006.01)
*C07F 3/00* (2006.01)
(Continued)

(52) U.S. Cl.
CPC ........ *H01L 51/0058* (2013.01); *C07D 307/77* (2013.01); *C07D 307/91* (2013.01);
(Continued)

(58) Field of Classification Search
None
See application file for complete search history.

(56) References Cited

U.S. PATENT DOCUMENTS 8,901,298 B2  12/2014  Parham et al.
9,126,970 B2 *  9/2015  Pflumm ............... C07D 209/82
(Continued)

FOREIGN PATENT DOCUMENTS

KR  10-2011-0088378 A  8/2011
KR  10-2013-0051807 A  5/2013
(Continued)

*Primary Examiner* — Robert S Loewe
(74) *Attorney, Agent, or Firm* — Innovation Counsel LLP

(57) ABSTRACT

A condensed-cyclic compound and an organic light-emitting device including the same are provided. The condensed-cyclic compound is represented by Formula 1:

(Continued)

10

190

150

110

-continued

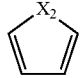

Formula 2B wherein, in Formulae 1, 2A, and 2B, ring $A_1$ is selected from a benzene group, a naphthalene group, a pyridine group, a pyrimidine group, a pyrazine group, a quinoline group, an isoquinoline group, a quinoxaline group, a quinazoline group, and a cinnoline group; ring $A_2$ is selected from a pyridine group, a pyrimidine group, a pyrazine group, a quinoline group, an isoquinoline group, a quinoxaline group, a quinazoline group, and a cinnoline group; and ring $A_3$ is selected from groups represented by Formula 2A and groups represented by Formula 2B. Further details about the compounds are presented.

20 Claims, 4 Drawing Sheets

(51) Int. Cl.

| | | |
|---|---|---|
| *C07D 307/77* | (2006.01) | |
| *C07D 307/91* | (2006.01) | |
| *C07D 403/04* | (2006.01) | |
| *C07D 405/10* | (2006.01) | |
| *C07D 405/12* | (2006.01) | |
| *C07D 405/14* | (2006.01) | |
| *C07D 409/04* | (2006.01) | |
| *C07D 409/14* | (2006.01) | |
| *C07D 471/10* | (2006.01) | |
| *C07F 9/655* | (2006.01) | |
| *C07F 9/6558* | (2006.01) | |
| *H01L 51/50* | (2006.01) | |

(52) U.S. Cl.
CPC ......... *C07D 403/04* (2013.01); *C07D 405/10* (2013.01); *C07D 405/12* (2013.01); *C07D 405/14* (2013.01); *C07D 409/04* (2013.01); *C07D 409/14* (2013.01); *C07D 471/10* (2013.01); *C07F 3/006* (2013.01); *C07F 9/65517* (2013.01); *C07F 9/65586* (2013.01); *H01L 51/0052* (2013.01); *H01L 51/0072* (2013.01); *H01L 51/0073* (2013.01); *H01L 51/5012* (2013.01); *H01L 51/5056* (2013.01); *H01L 51/5072* (2013.01); *H01L 51/5092* (2013.01); *H01L 51/5096* (2013.01); *H01L 51/0067* (2013.01); *H01L 2251/558* (2013.01)

(56) References Cited

U.S. PATENT DOCUMENTS

| | | | |
|---|---|---|---|
| 9,288,869 B2 | 3/2016 | Han et al. | |
| 10,186,666 B2 * | 1/2019 | Kim | H01L 51/0067 |
| 2013/0240796 A1 * | 9/2013 | Parham | C07D 403/10 |
| | | | 252/500 |
| 2014/0225040 A1 | 8/2014 | Parham et al. | |
| 2014/0225046 A1 | 8/2014 | Jatsch et al. | |
| 2015/0060808 A1 * | 3/2015 | Kim | H01L 51/0052 |
| | | | 257/40 |
| 2015/0318478 A1 | 11/2015 | Pflumm et al. | |
| 2016/0043330 A1 * | 2/2016 | Kim | H01L 51/0085 |
| | | | 257/40 |
| 2016/0126475 A1 * | 5/2016 | Lee | H01L 51/0072 |
| | | | 257/40 |
| 2016/0126479 A1 | 5/2016 | Hwang et al. | |
| 2016/0190466 A1 * | 6/2016 | Pfister | H01L 51/0056 |
| | | | 252/500 |
| 2016/0214942 A1 * | 7/2016 | Parham | C07D 401/14 |
| 2016/0218300 A1 * | 7/2016 | Xia | H01L 51/0072 |
| 2016/0293848 A1 | 10/2016 | Kim et al. | |
| 2016/0308147 A1 * | 10/2016 | Parham | C07F 15/0033 |

FOREIGN PATENT DOCUMENTS

| | | | | |
|---|---|---|---|---|
| KR | 10-2013-0122602 A | | 11/2013 | |
| KR | 10-1381505 B1 | | 3/2014 | |
| KR | 10-2014-0054132 A | | 5/2014 | |
| KR | 10-2014-0069199 A | | 6/2014 | |
| KR | 20150006802 A | * | 1/2015 | ........... C07D 487/10 |
| KR | 10-2015-0132660 A | | 11/2015 | |
| KR | 10-2016-0053423 A | | 5/2016 | |
| KR | 10-2016-0119904 A | | 10/2016 | |
| WO | WO-2011025282 | * | 3/2011 | ............ C09K 11/06 |
| WO | WO-2014104600 A1 | * | 7/2014 | ............ H05B 33/14 |
| WO | WO-2016017919 A2 | * | 2/2016 | ........... C07D 307/91 |

* cited by examiner

| 190 |
|---|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

CONDENSED-CYCLIC COMPOUND AND ORGANIC LIGHT-EMITTING DEVICE COMPRISING THE SAME

CROSS-REFERENCE TO RELATED APPLICATION

This application claims the benefit of Korean Patent Application No. 10-2016-0118212, filed on Sep. 13, 2016 in the Korean Intellectual Property Office, the disclosure of which is incorporated herein in its entirety by reference.

BACKGROUND

1. Field

One or more embodiments relate to a condensed-cyclic compound and an organic light-emitting device including the same.

2. Description of the Related Art

Organic light-emitting devices (OLEDs) are self-emission devices that have wide viewing angles, high contrast ratios, and short response times. In addition, the OLEDs exhibit high luminance, driving voltage, and response speed characteristics, and produce full-color images.

Organic light-emitting devices may include a first electrode disposed on a substrate. Organic light-emitting devices may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. The excitons may transition from an excited state to a ground state, thus generating light.

SUMMARY

One or more embodiments include a condensed-cyclic compound and an organic light-emitting device including the same.

Additional aspects will be set forth in part in the description which follows and, in part, will be apparent from the description, or are learned by practice of the presented embodiments.

According to one or more embodiments, a condensed-cyclic compound is represented by Formula 1:

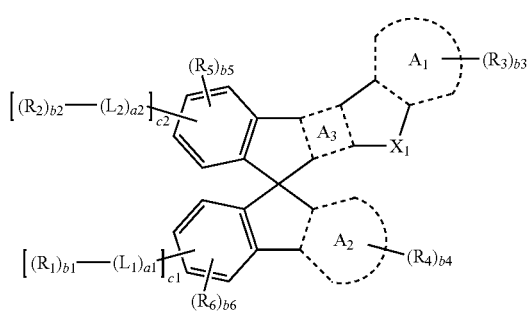

Formula 1

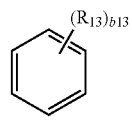

Formula 2A

Formula 2B wherein, in Formulae 1, 2A, and 2B, ring $A_1$ is selected from a benzene group, a naphthalene group, a pyridine group, a pyrimidine group, a pyrazine group, a quinoline group, an isoquinoline group, a quinoxaline group, a quinazoline group, and a cinnoline group, ring $A_2$ is selected from a pyridine group, a pyrimidine group, a pyrazine group, a quinoline group, an isoquinoline group, a quinoxaline group, a quinazoline group, and a cinnoline group, ring $A_3$ is selected from groups represented by Formula 2A and groups represented by Formula 2B, $X_1$ is selected from N-[$(L_{11})_{a11}$-$(R_{11})_{b11}$], O, and S, $X_2$ is selected from N-[$(L_{12})_{a12}$-$(R_{12})_{b12}$], O, and S, $L_1$ and $L_2$ are each independently selected from substituted or unsubstituted condensed polycyclic groups, in which 3 or more carbocyclic groups are condensed with each other, a1 and a2 are each independently an integer from 1 to 5; when a1 is 2 or greater, at least two $L_1$ (s) are identical to or different from each other; when a2 is 2 or greater, at least two $L_2$ (s) are identical to or different from each other, $L_{11}$ is selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group, a11 is an integer from 0 to 5, $L_{12}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a12 is an integer from 0 to 5, $R_{11}$ is selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group, b11 is an integer from 1 to 4, $R_1$ to $R_6$, $R_{12}$, and $R_{13}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, b1, b2, b5, b6, and b12 are each independently an integer from 0 to 4, b3 and b4 are each independently an integer from 0 to 6, b13 is selected from 0, 1, and 2, c1 and c2 are each independently an integer from 0 to 4, a sum of c1 and c2 is 1 or greater, at least one substituent of the substituted condensed polycyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group.

According to one or more embodiments, an organic light-emitting device includes: a first electrode; a second electrode facing the first electrode; and an organic layer disposed between the first electrode and the second electrode, wherein the organic layer includes an emission layer and at least one condensed-cyclic compound described above.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view illustrating an organic light-emitting device according to an embodiment;

FIG. 2 is a schematic cross-sectional view illustrating an organic light-emitting device according to an embodiment;

FIG. 3 is a schematic cross-sectional view illustrating an organic light-emitting device according to an embodiment; and FIG. 4 is a schematic cross-sectional view illustrating an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A condensed-cyclic compound may be represented by Formula 1:

Formula 1

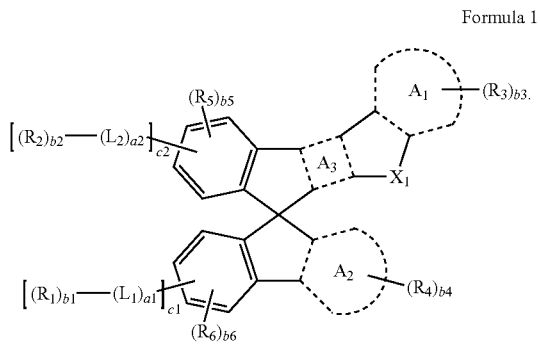

Rings $A_1$ and $A_2$ in Formula 1 may each independently be fused to an adjacent 5-membered ring by sharing a carbon atom. In Formula 1, ring $A_1$ may be selected from a benzene group, a naphthalene group, a pyridine group, a pyrimidine group, a pyrazine group, a quinoline group, an isoquinoline group, a quinoxaline group, a quinazoline group, and a cinnoline group, and ring $A_2$ may be selected from a pyridine group, a pyrimidine group, a pyrazine group, a quinoline group, an isoquinoline group, a quinoxaline group, a quinazoline group, and a cinnoline group.

In some embodiments, in Formula 1, ring $A_1$ may be selected from a benzene group and a naphthalene group, and ring $A_2$ may be selected from a pyridine group, a quinoline group, and an isoquinoline group.

In Formula 1, ring $A_3$ may be fused to two adjacent 5-membered rings by sharing carbon atoms. In Formula 1, ring $A_3$ may be selected from groups represented by Formula 2A and groups represented by Formula 2B.

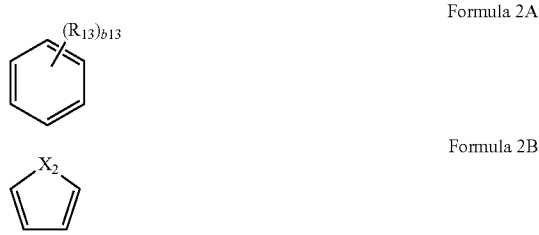

Formula 2A

Formula 2B $R_{13}$ and $b_{13}$ in Formula 2A and $X_2$ in Formula 2B may be the same as those described herein.

In one embodiment, in Formula 1, ring $A_3$ may be a group represented by Formula 2A, but embodiments are not limited thereto.

$X_1$ in Formula 1 may be N-$[(L_{11})_{a11}$-$(R_{11})_{b11}]$, O, or S, and $X_2$ in Formula 2B may be N-$[(L_{12})_{a12}$-$(R_{12})_{b12}]$, O, or S.

In some embodiments, in Formula 1, $X_1$ may be N-$[(L_{11})_{a1}$-$(R_{11})_{b11}]$.

In Formula 1, $L_1$ and $L_2$ may each independently be selected from substituted or unsubstituted condensed polycyclic groups, in which 3 or more carbocyclic groups may be condensed with each other. $L_1$ and $L_2$ may include carbon atoms as ring-forming atoms, but may not include heteroatoms (e.g., N, O, S, or P) as ring forming-atoms. Therefore, for example, a naphthylene group may not be $L_1$ or $L_2$ because a naphthylene group is a condensed polycyclic group in which two carbocyclic groups are condensed; and a pyridinylene group may not be $L_1$ or $L_2$ because a pyridinylene group contains N as a ring-forming atom.

In one embodiment, in Formula 1, $L_1$ and $L_2$ may each independently be selected from an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si$(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, in Formula 1, $L_1$ and $L_2$ may each independently be selected from a phenalenylene group, a phenanthrenylene group, an anthracenylene group, a fluoranthenylene group, a triphenylenylene group, a pyrenylene group, a chrysenylene group, and a perylenylene group; and a phenalenylene group, a phenanthrenylene group, an anthracenylene group, a fluoranthenylene group, a triphenylenylene group, a pyrenylene group, a chrysenylene group, and a perylenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 1, a1 and a2 may each independently be an integer from 1 to 5; when a1 is 2 or greater, at least two $L_1$ (s) may be identical to or different from each other; and when a2 is 2 or greater, at least two $L_2$ (s) may be identical to or different from each other. That is, in Formula 1, $L_1$ may be essentially present in a group represented by *-[($L_1$)$_{a1}$-($R_1$)$_{b1}$], and $L_2$ may be essentially present in a group represented by *-[($L_2$)$_{a2}$-($R_2$)$_{b2}$].

In one embodiment, in Formula 1, a1 and a2 may each independently be 1 or 2. In some embodiments, in Formula 1, a1 and a2 may each independently be 1, but embodiments are not limited thereto.

In Formulae 1, 2A, and 2B, $L_{11}$ may be selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group, and $L_{12}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, $L_{11}$ may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, and $L_{12}$ may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, $L_1$ and $L_2$ may each independently be selected from groups represented by Formulae 3-8, 3-9, 3-25, and 3-35 to 3-41, $L_{11}$ may be selected from groups represented by Formulae 3-1 to 3-9, 3-25, and 3-33 to 3-41, wherein $Y_1$ in Formulae 3-3 and 3-4 may be C($Z_3$)($Z_4$), and $L_{12}$ may be selected from groups represented by Formulae 3-1 to 3-41:

Formula 3-1
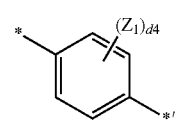

Formula 3-2
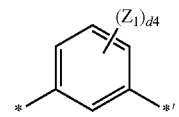

Formula 3-3
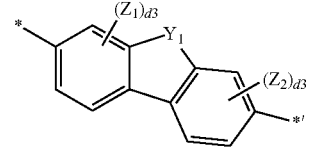

Formula 3-4
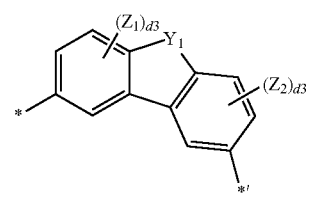

Formula 3-5
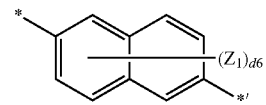

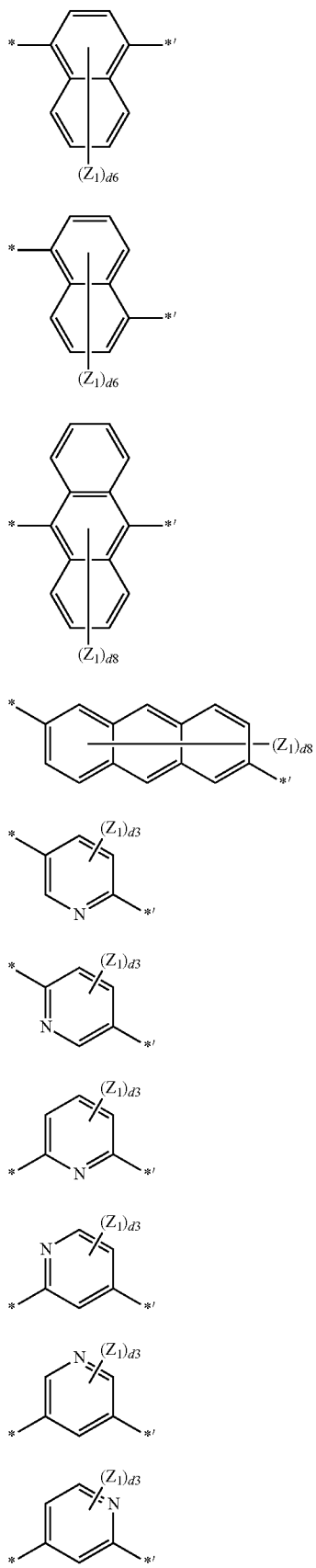
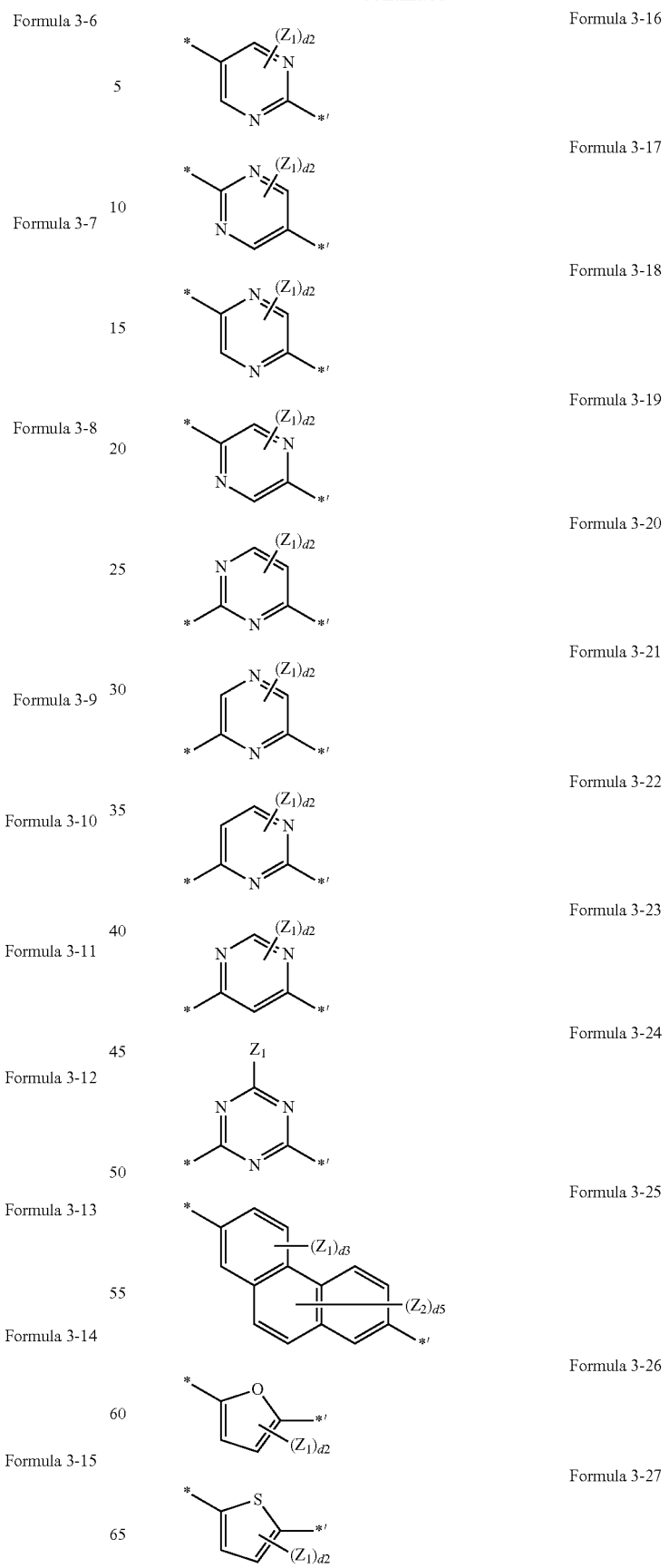

-continued
Formula 3-28
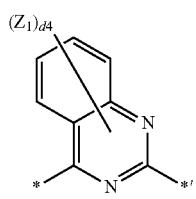
Formula 3-29
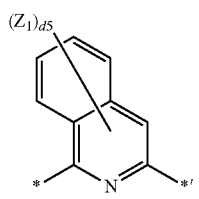
Formula 3-30
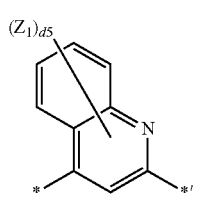
Formula 3-31
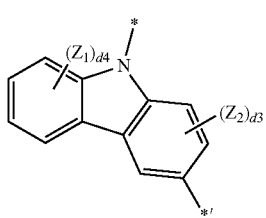
Formula 3-32
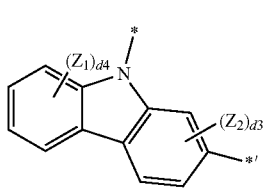
Formula 3-33
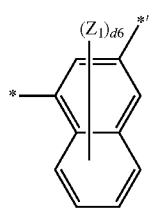
Formula 3-34
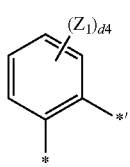
Formula 3-35
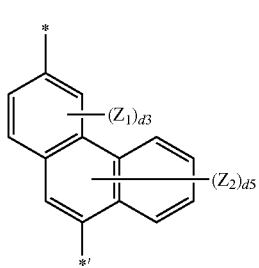
-continued
Formula 3-36
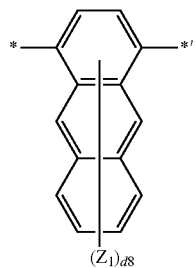
Formula 3-37
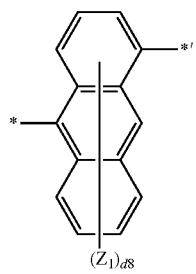
Formula 3-38
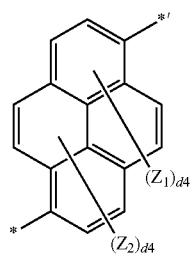
Formula 3-39
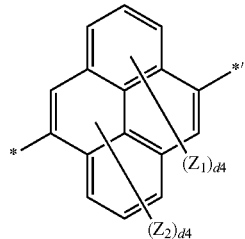
Formula 3-40
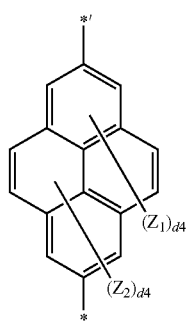

-continued

Formula 3-41

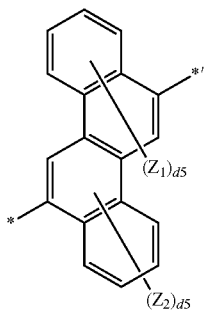

wherein, in Formulae 3-1 to 3-41, $Y_1$ may be O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, a phenanthrolinyl group, and —Si$(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be an integer selected from 1 and 2,
d3 may be an integer from 1 to 3,
d4 may be an integer from 1 to 4,
d5 may be an integer from 1 to 5,
d6 may be an integer from 1 to 6,
d8 may be an integer from 1 to 8, and
* and *' each indicate a binding site to an adjacent atom.

In some embodiments, $L_1$ and $L_2$ may each independently be selected from groups represented by Formulae 4-11, 4-13, 4-27, and 4-29 to 4-35, $L_{11}$ may be selected from groups represented by Formulae 4-1, 4-3, 4-5, 4-7 to 4-13, 4-17, and 4-24 to 4-35, and $L_{12}$ may be selected from groups represented by Formulae 4-1 to 4-35, but embodiments are not limited thereto:

Formula 4-1

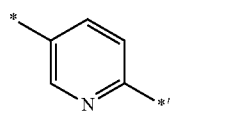

Formula 4-2

Formula 4-3

Formula 4-4

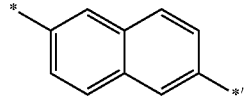

Formula 4-5

Formula 4-6

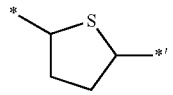

Formula 4-7

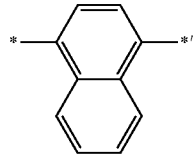

Formula 4-8

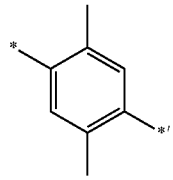

Formula 4-9

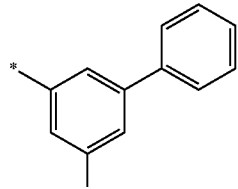

Formula 4-10

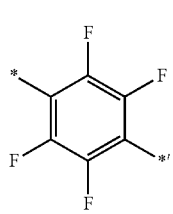

Formula 4-11

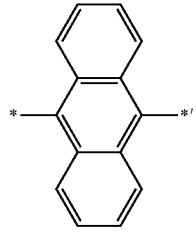

Formula 4-12

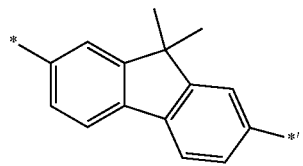

-continued
Formula 4-13
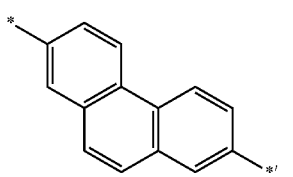
Formula 4-14
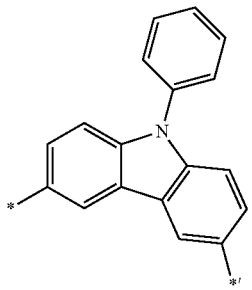
Formula 4-15
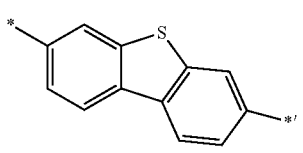
Formula 4-16
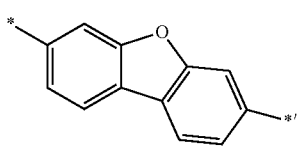
Formula 4-17
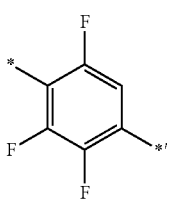
Formula 4-18
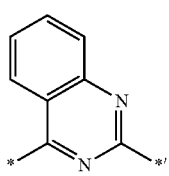
Formula 4-19
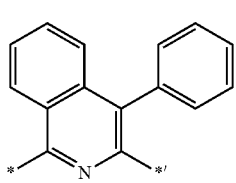
Formula 4-20
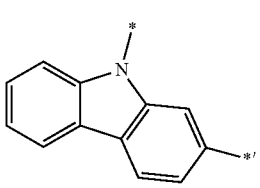
Formula 4-21
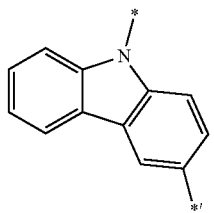
Formula 4-22
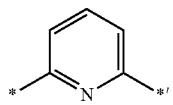
Formula 4-23
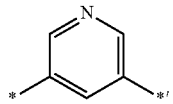
Formula 4-24
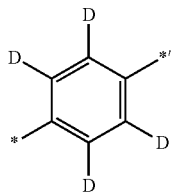
Formula 4-25
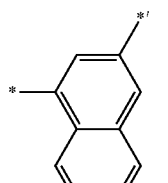
Formula 4-26
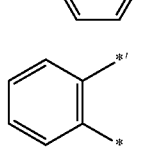
Formula 4-27
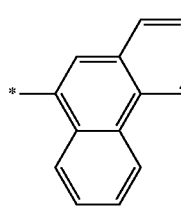
Formula 4-28
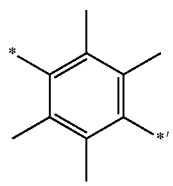
Formula 4-29
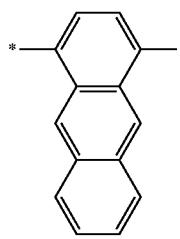

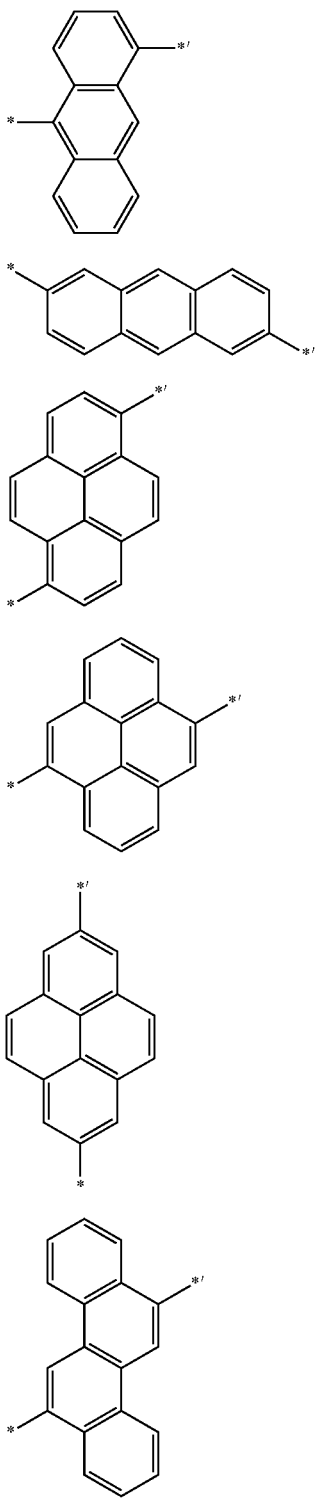

Formula 4-30

Formula 4-31

Formula 4-32

Formula 4-33

Formula 4-34

Formula 4-35 wherein, in Formulae 4-1 to 4-35, * and *' each indicate a binding site to an adjacent atom.

In the above formulae, a11 and a12 may each independently be an integer from 0 to 5; when a11 is 2 or greater, at least two $L_{11}$ (s) may be identical to or different from each other; and when a12 is 2 or greater, at least two $L_2$ (s) may be identical to or different from each other.

In one embodiment, in the above formulae, a11 and a12 may each independently be 0, 1, or 2. In some embodiments, in the above formulae, a11 and a12 may each independently be or 0 or 1, but embodiments are not limited thereto.

In the above formulae, $R_{11}$ may be selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group.

In some embodiments, $R_{11}$ may be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In some embodiments, $R_{11}$ may be selected from groups represented by Formulae 5-1 to 5-19:

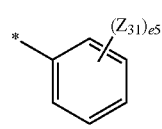

Formula 5-1

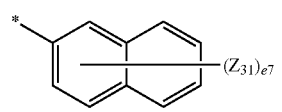

Formula 5-2

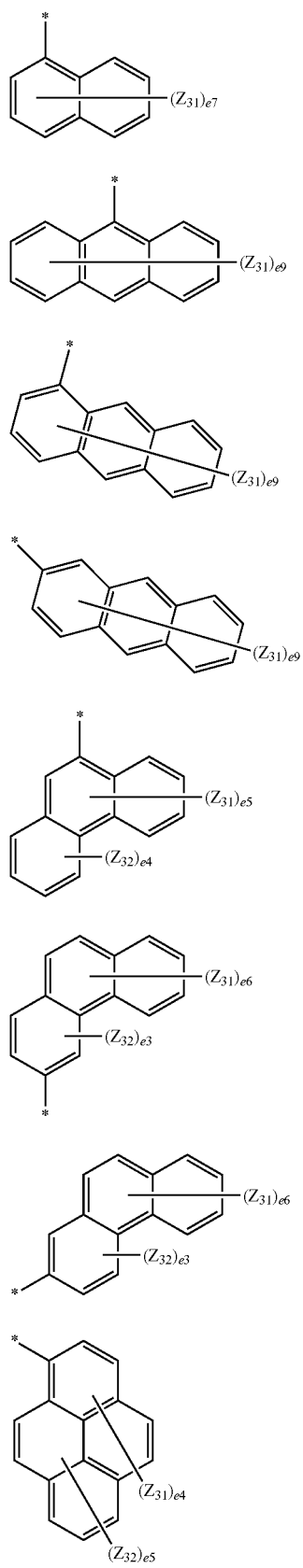
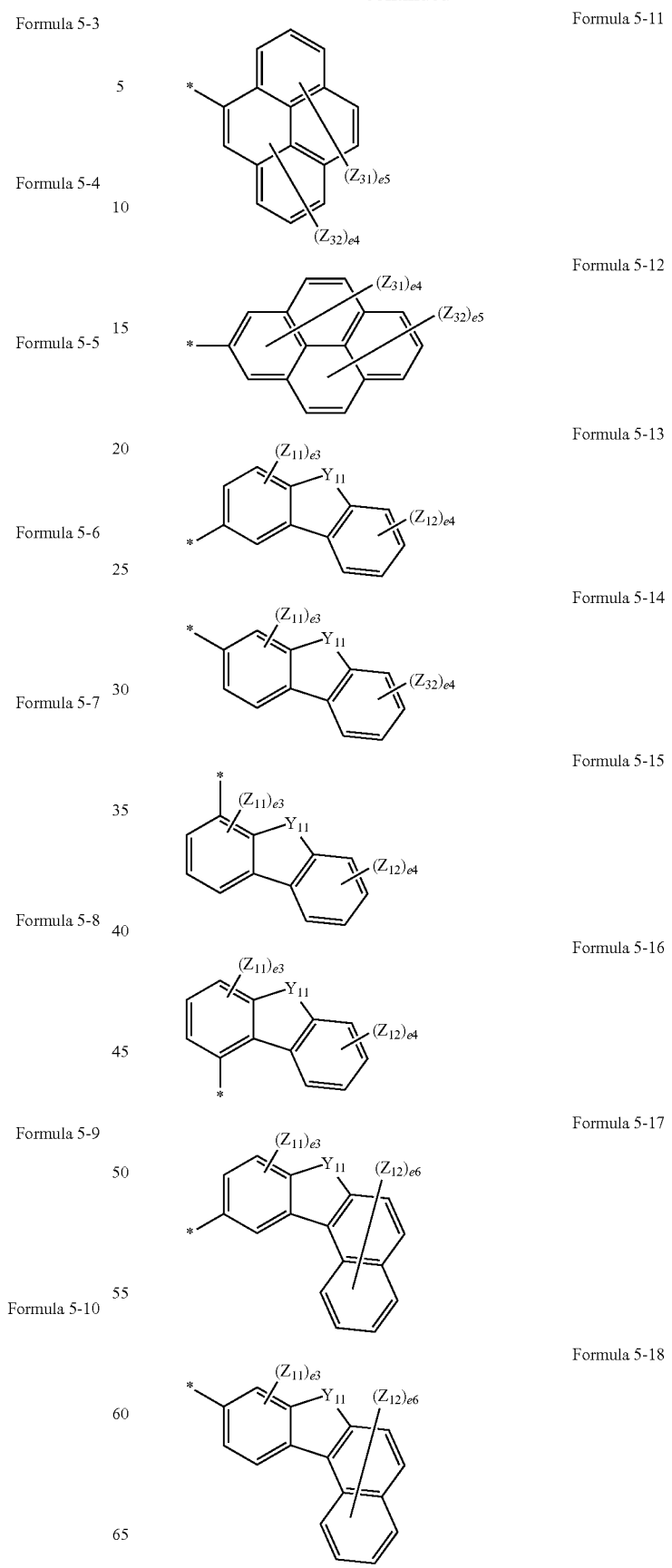

Formula 5-19

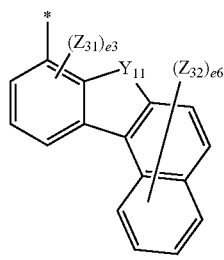

wherein, in Formulae 5-1 to 5-19, $Y_{11}$ may be $C(Z_{13})(Z_{14})$, $Z_{11}$ to $Z_{14}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a biphenyl group, a terphenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, e3 may be an integer from 1 to 3, e4 may be an integer from 1 to 4, e5 may be an integer from 1 to 5, e6 may be an integer from 1 to 6, e7 may be an integer from 1 to 7, e9 may be an integer from 1 to 9, and

* indicates a binding site to an adjacent atom.

In some embodiments, $R_{11}$ may be selected from groups represented by Formulae 6-1 to 6-27:

Formula 6-1

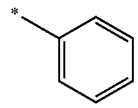

Formula 6-2

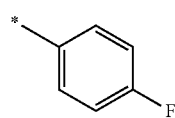

Formula 6-3

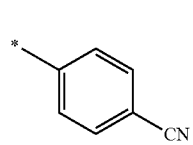

Formula 6-4

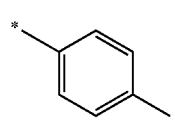

Formula 6-5

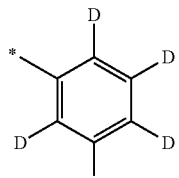

Formula 6-6

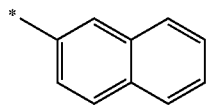

Formula 6-7

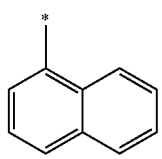

Formula 6-8

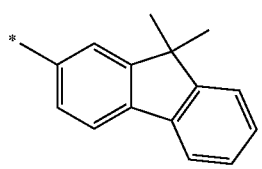

Formula 6-9

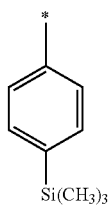

Formula 6-10

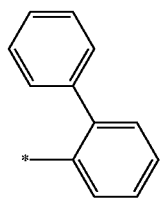

Formula 6-11

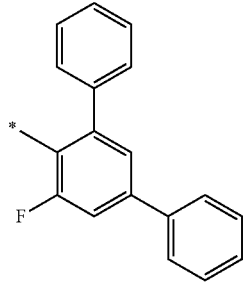

Formula 6-12

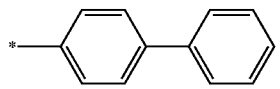

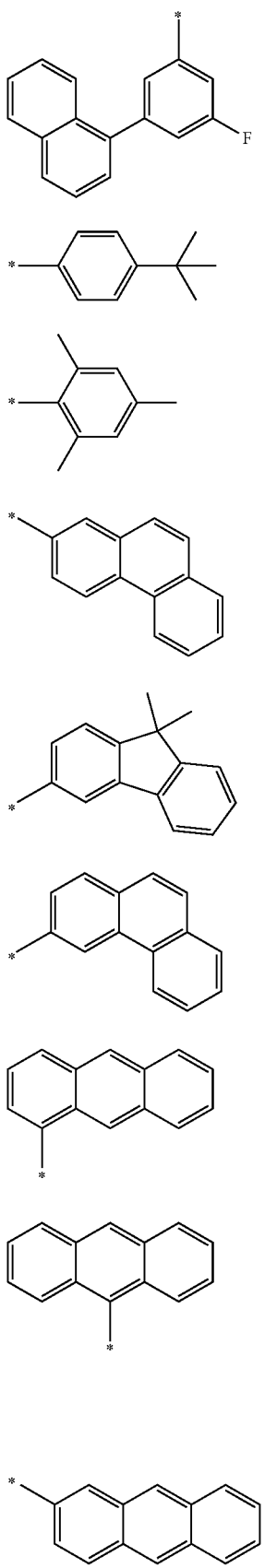

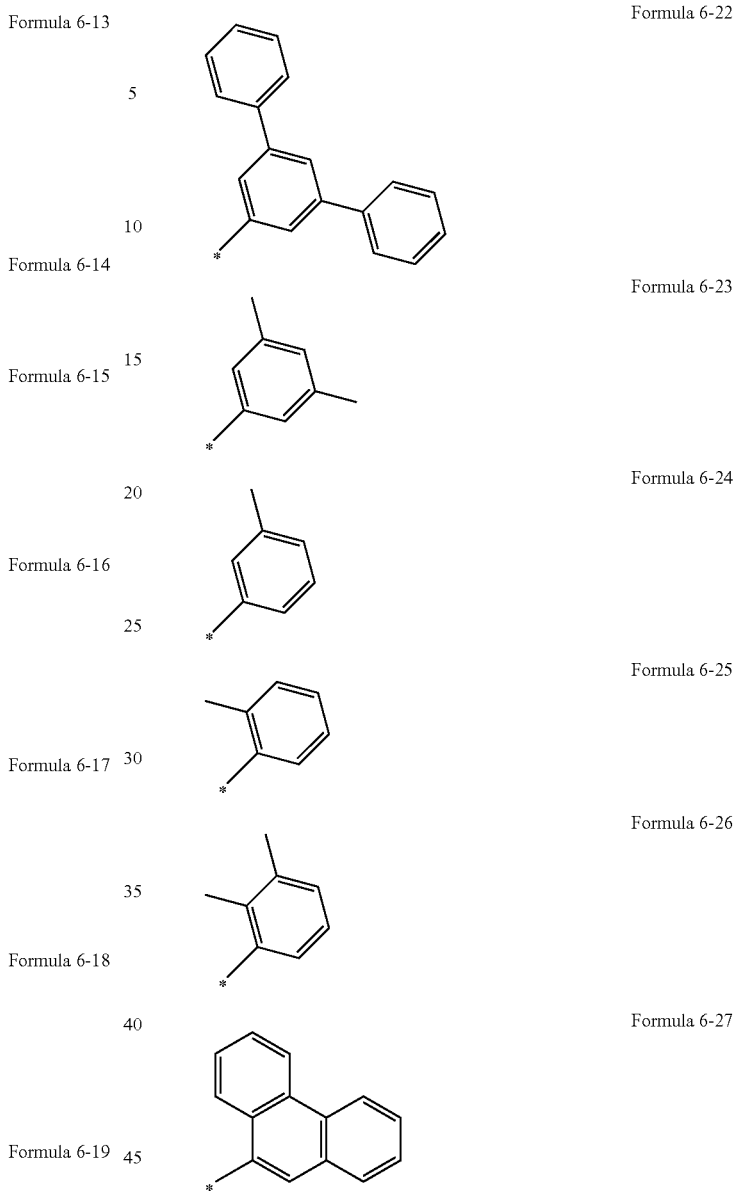

wherein, in Formulae 6-1 to 6-27, * indicates a binding site to an adjacent atom.

In the above formulae, b11 may be an integer from 1 to 4. In some embodiments, in the above formulae, b11 may be 1 or 2.

In some embodiments, in the above formulae, b11 may be 1, but embodiments are not limited thereto.

In the above formulae, $R_1$ to $R_6$, $R_{12}$, and $R_{13}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$.

In some embodiments, in the above formulae, $R_1$ to $R_6$, $R_{12}$, and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a biphenyl group, a terphenyl group, and a naphthyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and $-Si(Q_{31})(Q_{32})(Q_{33})$; and $-Si(Q_1)(Q_2)(Q_3)$, wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, in the above formulae, $R_1$ to $R_6$, $R_{12}$, and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, groups represented by Formulae 7-1 to 7-75, and $-Si(Q_1)(Q_2)(Q_3)$, wherein $Q_1$ to $Q_3$ may each independently be selected from a $C_1$-$C_{10}$ alkyl group, a $C_1$-$C_{10}$ alkoxy group, a phenyl group, a biphenyl group, a terphenyl group, and a naphthyl group:

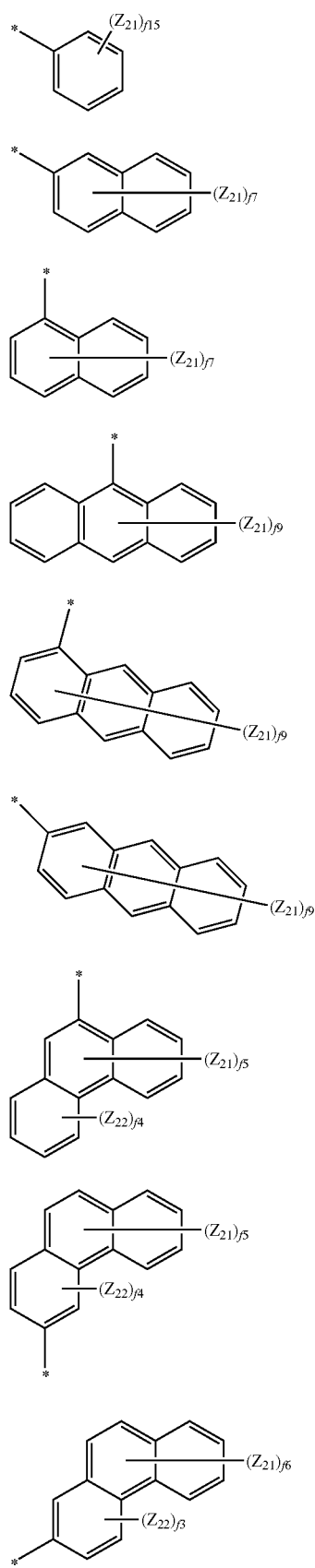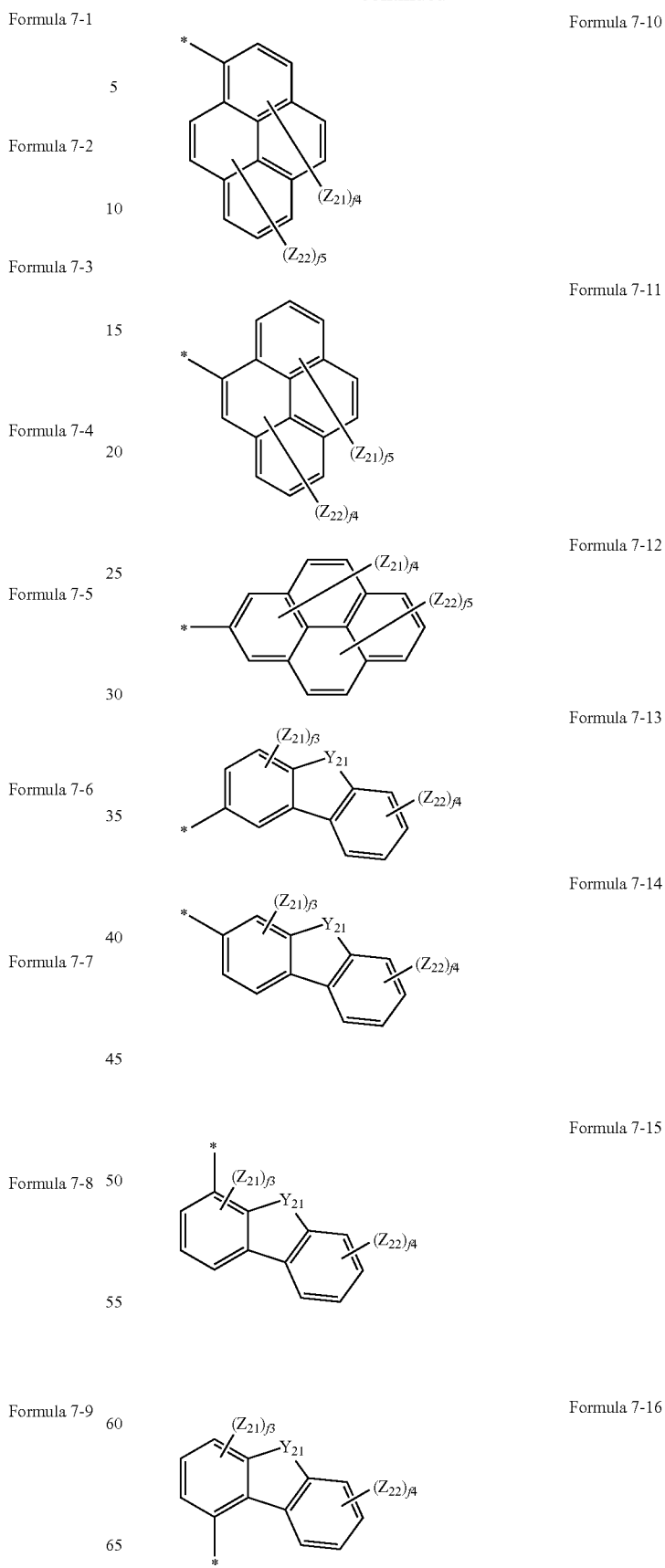

-continued
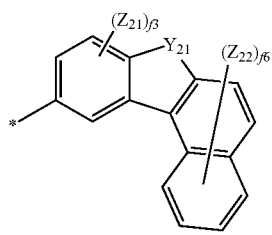
Formula 7-17
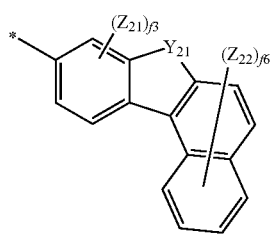
Formula 7-18
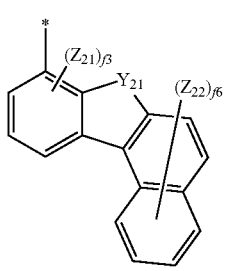
Formula 7-19
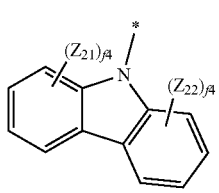
Formula 7-20
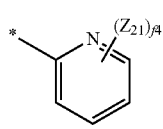
Formula 7-21
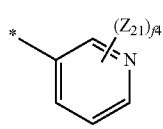
Formula 7-22
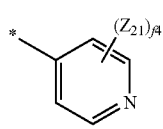
Formula 7-23
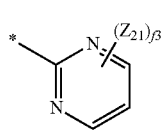
Formula 7-24
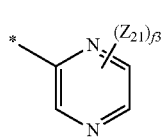
Formula 7-25
-continued
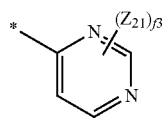
Formula 7-26
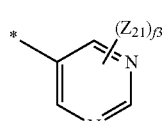
Formula 7-27
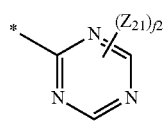
Formula 7-28
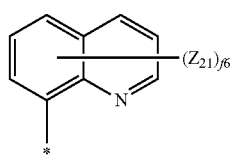
Formula 7-29
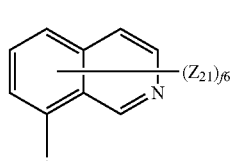
Formula 7-30
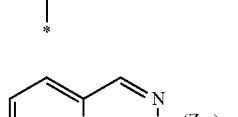
Formula 7-31
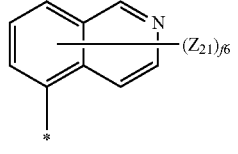
Formula 7-31
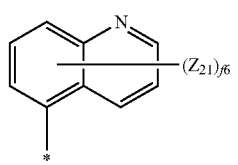
Formula 7-32
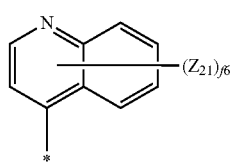
Formula 7-33
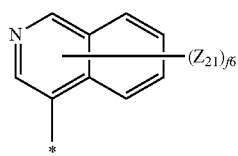
Formula 7-34
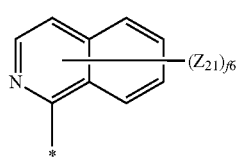
Formula 7-35

| | |
|---|---|
| 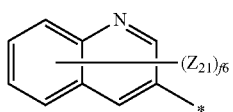 Formula 7-36 | 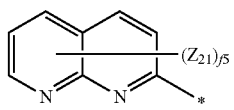 Formula 7-49 |
| 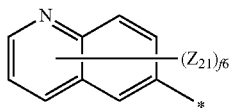 Formula 7-37 | 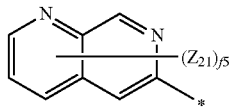 Formula 7-50 |
| 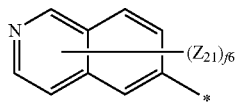 Formula 7-38 | 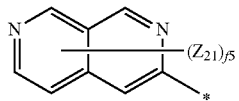 Formula 7-51 |
| 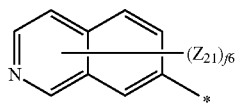 Formula 7-39 | 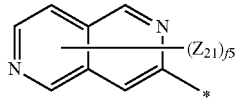 Formula 7-52 |
| 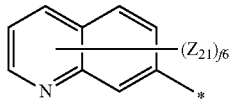 Formula 7-40 | 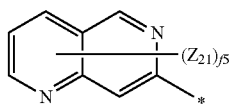 Formula 7-53 |
| 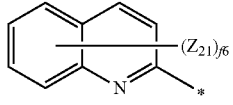 Formula 7-41 | 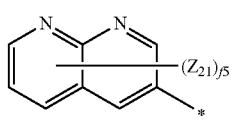 Formula 7-54 |
| 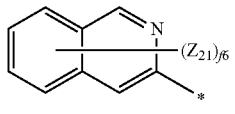 Formula 7-42 |  Formula 7-55 |
| 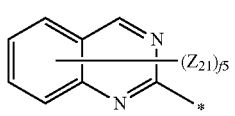 Formula 7-43 | 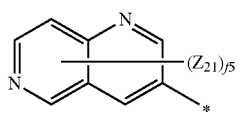 Formula 7-56 |
| 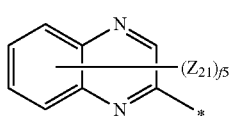 Formula 7-44 |  Formula 7-57 |
| 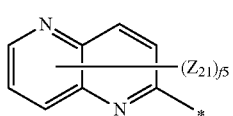 Formula 7-45 | 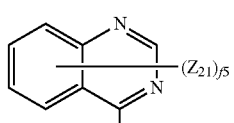 Formula 7-58 |
| 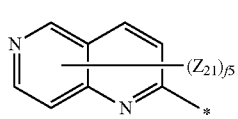 Formula 7-47 |  Formula 7-59 |
| 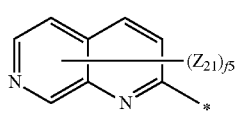 Formula 7-48 | |

-continued

Formula 7-60 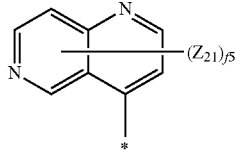

Formula 7-61 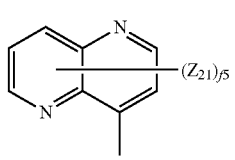

Formula 7-62 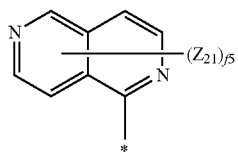

Formula 7-61 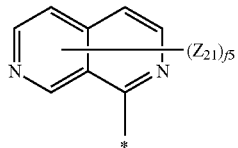

Formula 7-62 

Formula 7-63 

Formula 7-64 

Formula 7-65 

Formula 7-66 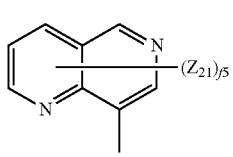

Formula 7-67 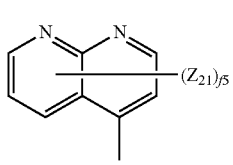

Formula 7-68 (not clearly identifiable separately)

Formula 7-69 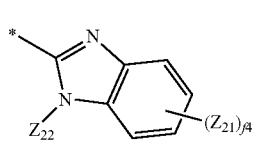

Formula 7-70 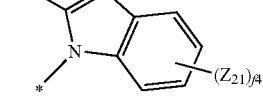

Formula 7-71 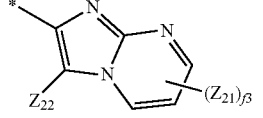

Formula 7-72 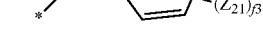

Formula 7-73 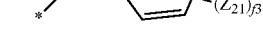

Formula 7-74 

Formula 7-75 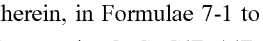

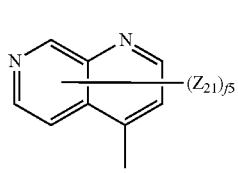
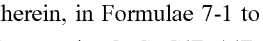

wherein, in Formulae 7-1 to 7-75, $Y_{21}$ may be O, S, $C(Z_{23})(Z_{24})$, $N(Z_{25})$, or $Si(Z_{26})(Z_{27})$, $Z_{21}$ to $Z_{27}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, f2 may be an integer selected from 1 and 2,
f3 may be an integer from 1 to 3,
f4 may be an integer from 1 to 4,
f5 may be an integer from 1 to 5,
f6 may be an integer from 1 to 6,
f7 may be an integer from 1 to 7,
f8 may be an integer from 1 to 8,
f9 may be an integer from 1 to 9, and
* indicates a binding site to an adjacent atom.

In one embodiment, in the above formulae, $R_1$ to $R_6$, $R_{12}$, and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, groups represented by Formulae 8-1 to 8-159, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto:

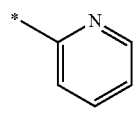

Formula 8-1

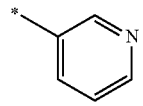

Formula 8-2


Formula 8-3

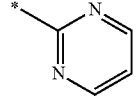

Formula 8-4


Formula 8-5

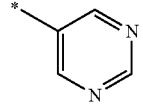

Formula 8-6

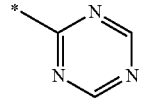

Formula 8-7

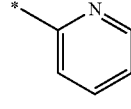

Formula 8-8

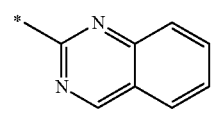

Formula 8-9

Formula 8-10

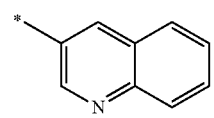

Formula 8-11

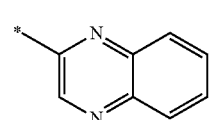

Formula 8-12

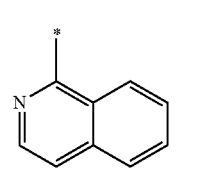

Formula 8-13

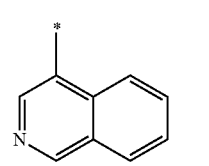

Formula 8-14

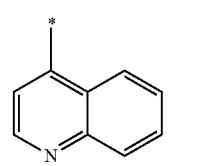

Formula 8-15

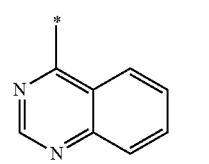

Formula 8-16

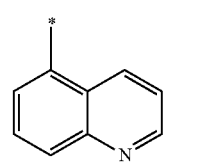

Formula 8-17

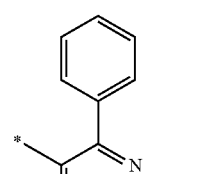

Formula 8-18

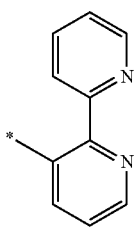
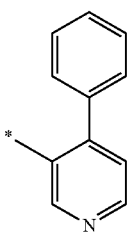
Formula 8-19
Formula 8-20
Formula 8-21
Formula 8-22
Formula 8-23
Formula 8-24
Formula 8-25
Formula 8-26
Formula 8-27
Formula 8-28
Formula 8-29
Formula 8-30
Formula 8-31

Formula 8-32
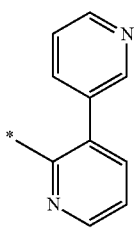
Formula 8-33
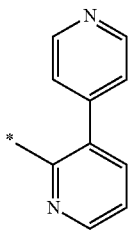
Formula 8-34
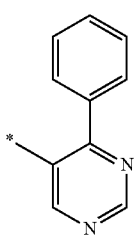
Formula 8-35
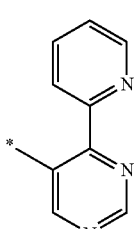
Formula 8-36
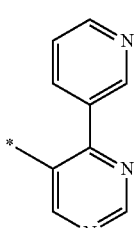
Formula 8-37
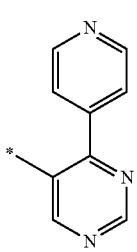
Formula 8-38
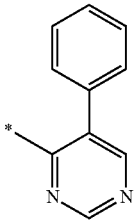
Formula 8-39
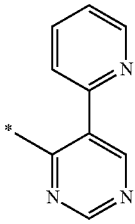
Formula 8-40
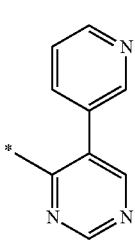
Formula 8-41
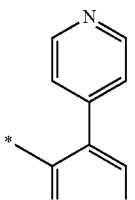
Formula 8-42
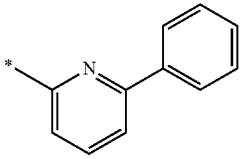
Formula 8-43
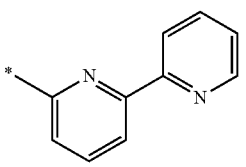
Formula 8-44
Formula 8-45
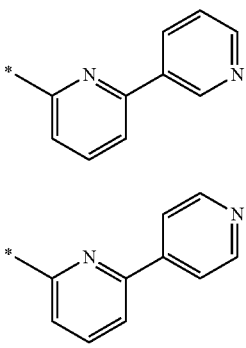

-continued
Formula 8-46
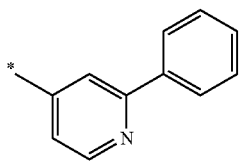
Formula 8-47
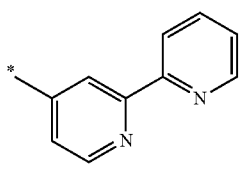
Formula 8-48
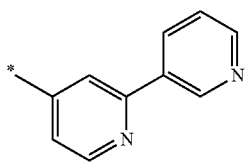
Formula 8-49
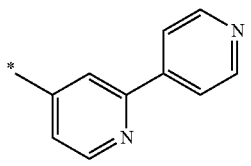
Formula 8-50
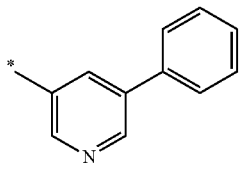
Formula 8-51
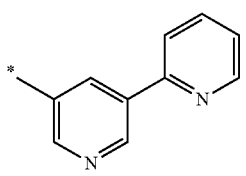
Formula 8-52
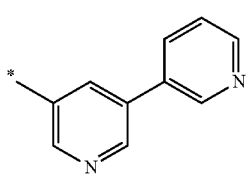
Formula 8-53
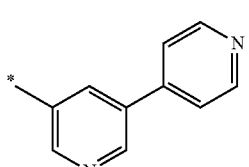
Formula 8-54
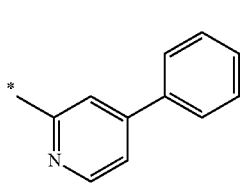
-continued
Formula 8-55
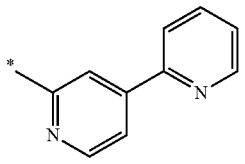
Formula 8-56
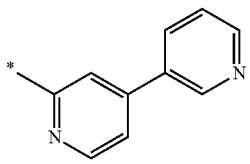
Formula 8-57
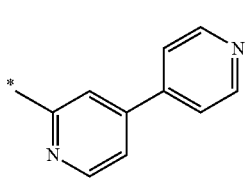
Formula 8-58
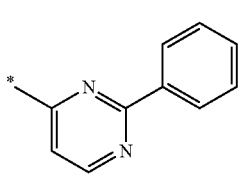
Formula 8-59
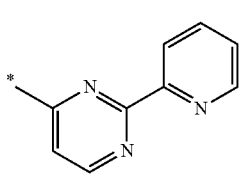
Formula 8-60
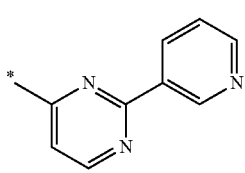
Formula 8-61
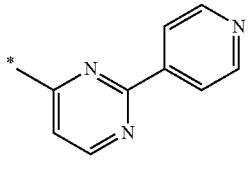
Formula 8-62
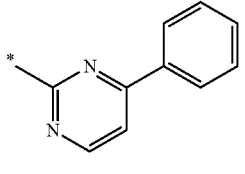
Formula 8-63

Formula 8-64
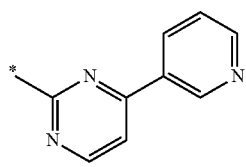
Formula 8-65
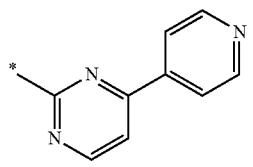
Formula 8-66
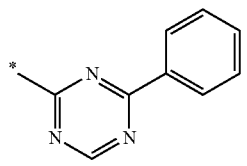
Formula 8-67
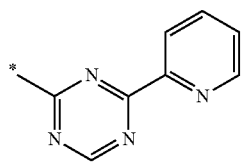
Formula 8-68
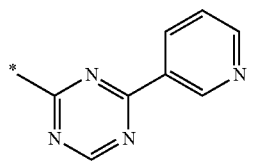
Formula 8-69
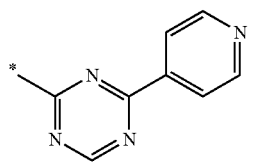
Formula 8-70
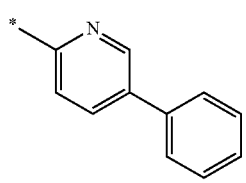
Formula 8-71
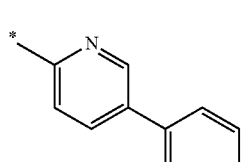
Formula 8-72
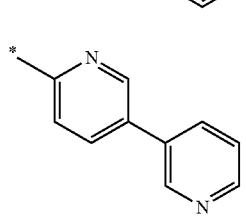
Formula 8-73
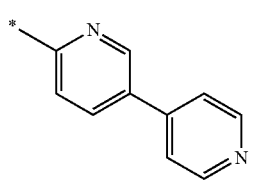
Formula 8-74
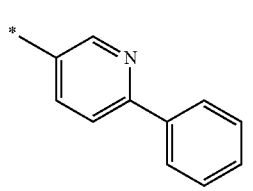
Formula 8-75
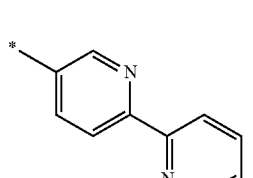
Formula 8-76
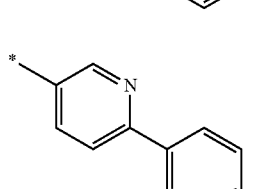
Formula 8-77
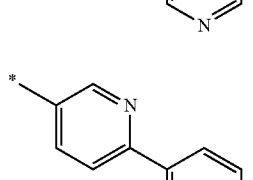
Formula 8-78

Formula 8-79
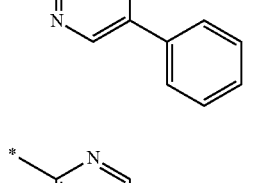
Formula 8-80
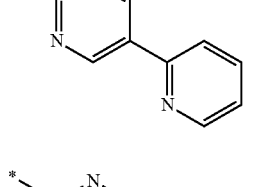
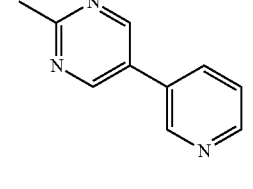

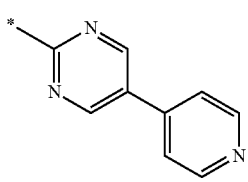
Formula 8-81
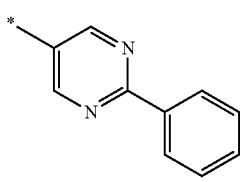
Formula 8-82
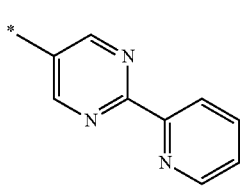
Formula 8-83
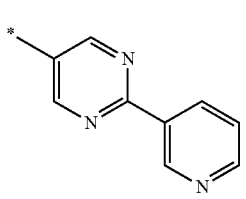
Formula 8-84
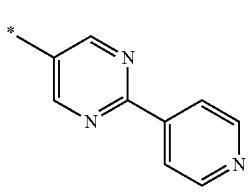
Formula 8-85
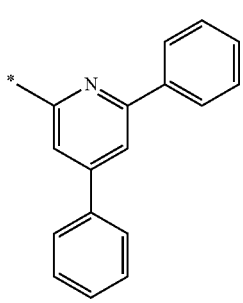
Formula 8-86
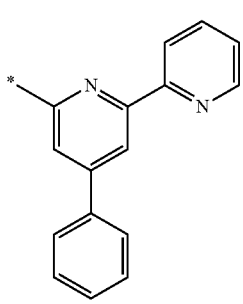
Formula 8-87
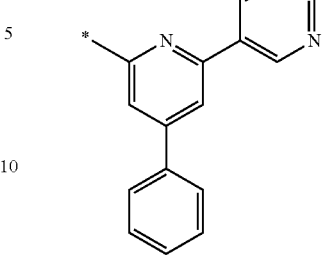
Formula 8-88
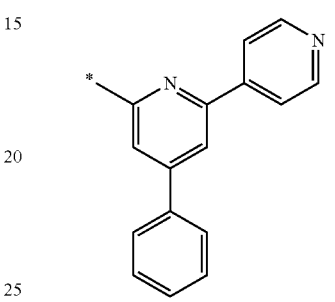
Formula 8-89
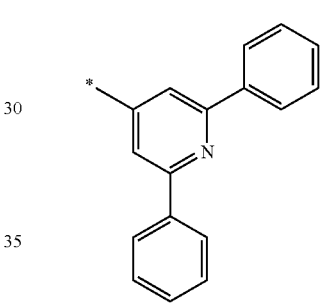
Formula 8-90
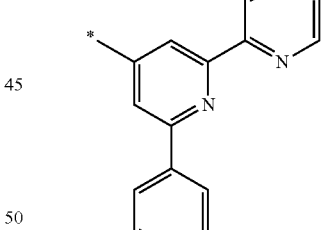
Formula 8-91
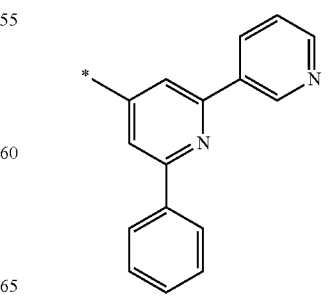
Formula 8-92

Formula 8-93
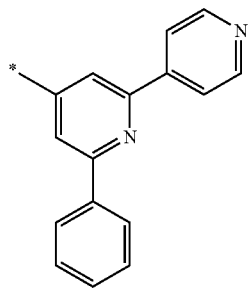
Formula 8-94
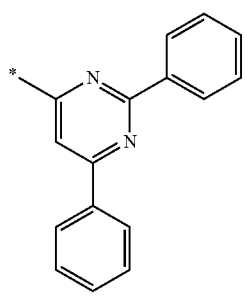
Formula 8-95
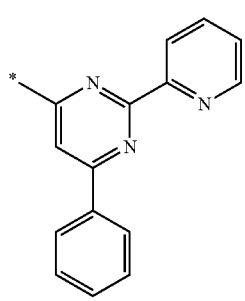
Formula 8-96
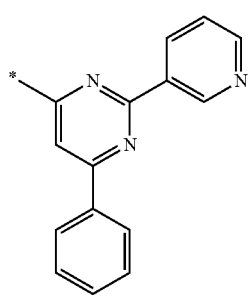
Formula 8-97
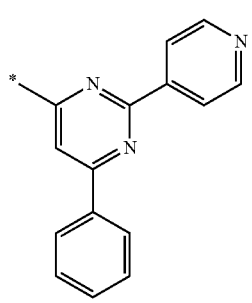
Formula 8-98

Formula 8-99

Formula 8-100
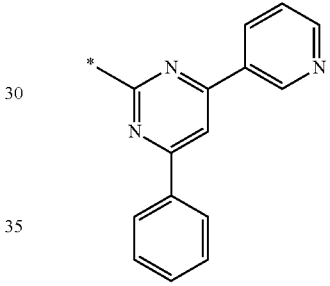
Formula 8-101
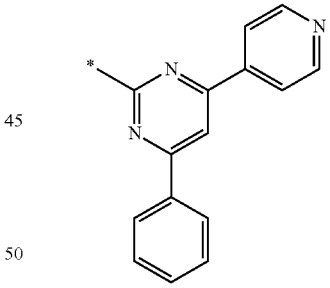
Formula 8-102
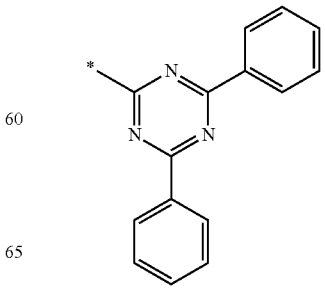

Formula 8-103
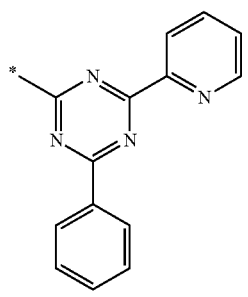
Formula 8-104
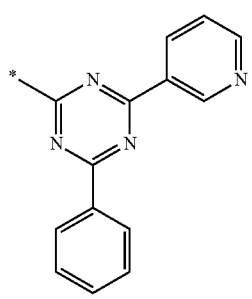
Formula 8-105
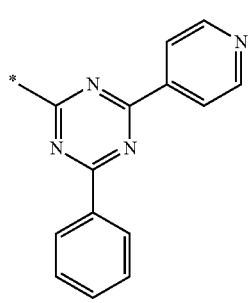
Formula 8-106
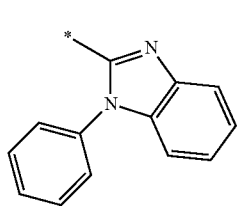
Formula 8-107
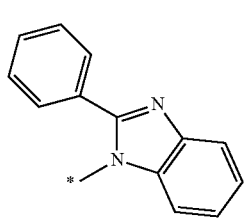
Formula 8-108
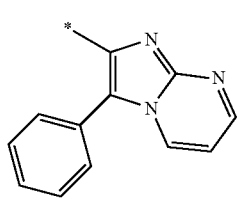
Formula 8-109
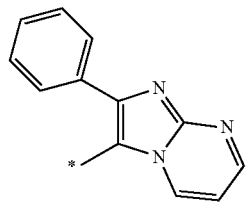
Formula 8-110
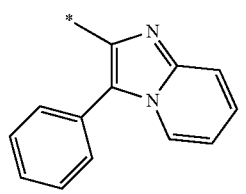
Formula 8-111
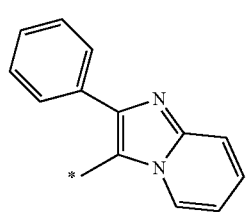
Formula 8-112
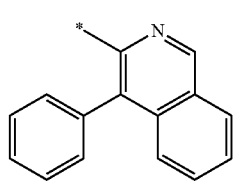
Formula 8-113
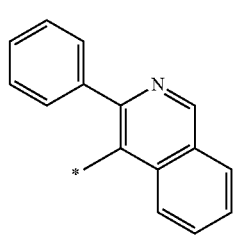
Formula 8-114
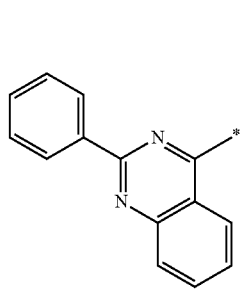
Formula 8-115

-continued
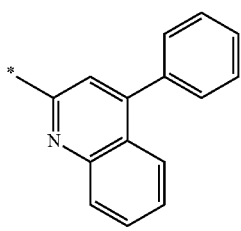
Formula 8-116
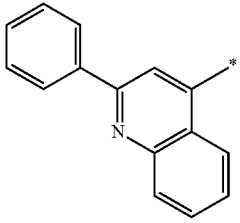
Formula 8-117
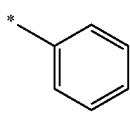
Formula 8-118
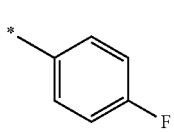
Formula 8-119
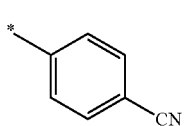
Formula 8-120
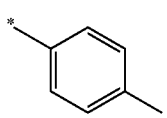
Formula 8-121
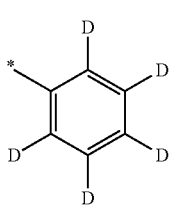
Formula 8-122
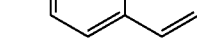
Formula 8-123
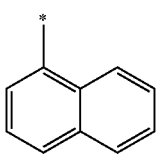
Formula 8-124
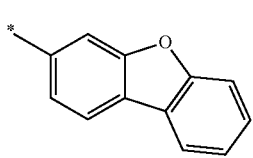
Formula 8-125
-continued
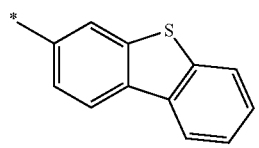
Formula 8-126
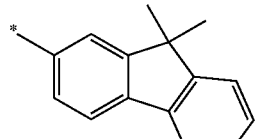
Formula 8-127
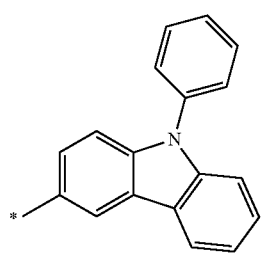
Formula 8-128
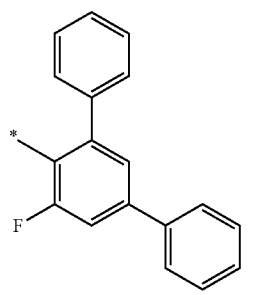
Formula 8-129
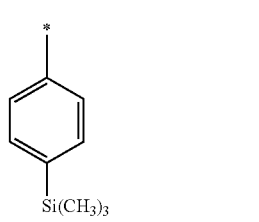
Formula 8-130
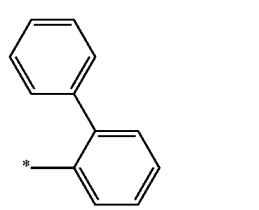
Formula 8-131
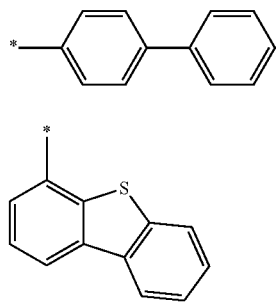
Formula 8-132
Formula 8-133

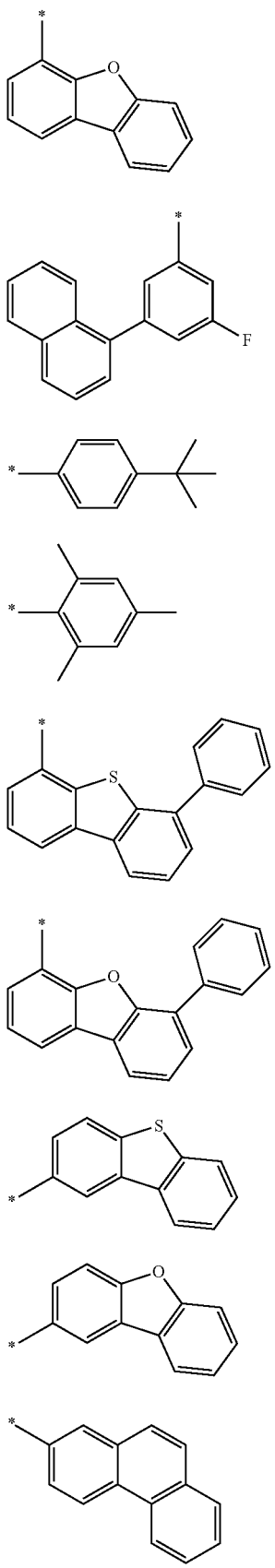
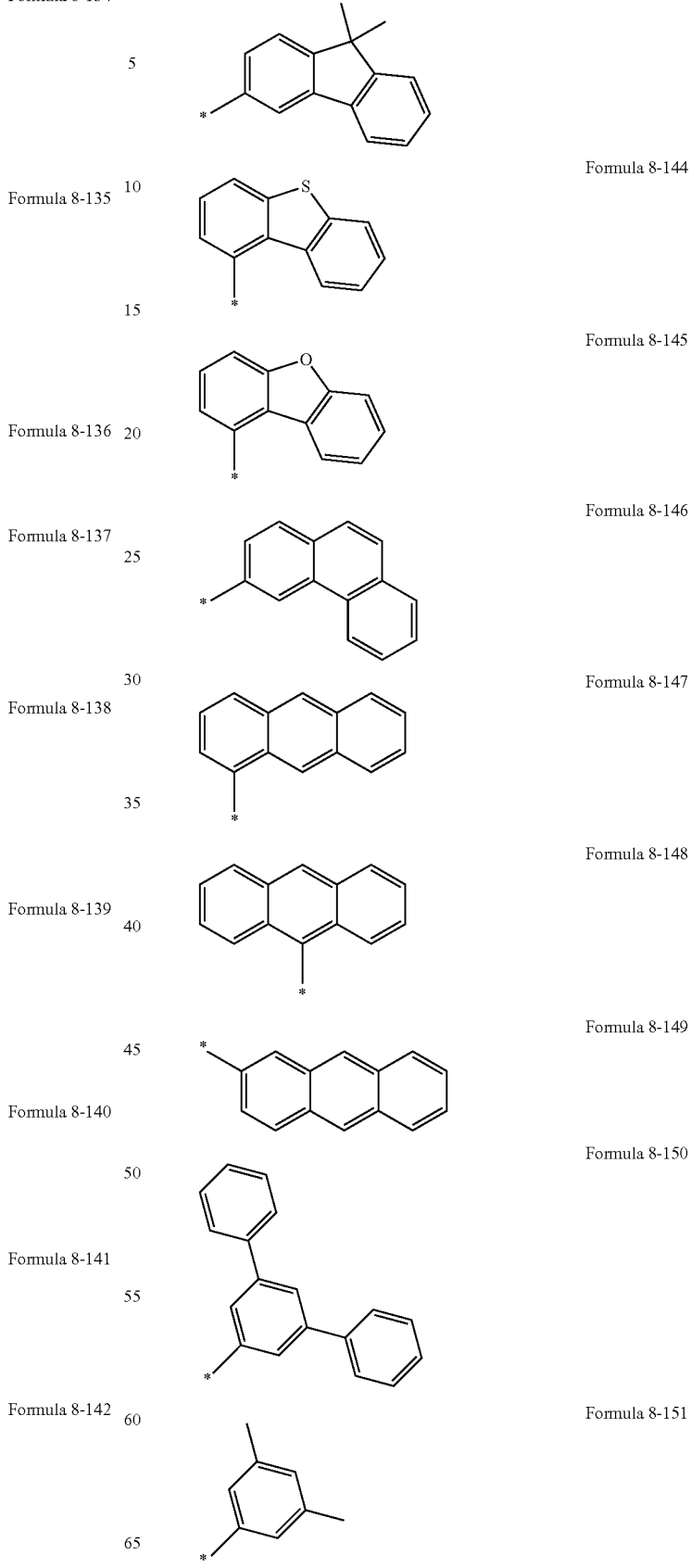
Formula 8-134
Formula 8-135
Formula 8-136
Formula 8-137
Formula 8-138
Formula 8-139
Formula 8-140
Formula 8-141
Formula 8-142
Formula 8-143
Formula 8-144
Formula 8-145
Formula 8-146
Formula 8-147
Formula 8-148
Formula 8-149
Formula 8-150
Formula 8-151

-continued

Formula 8-152
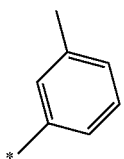

Formula 8-153
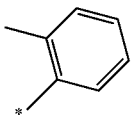

Formula 8-154
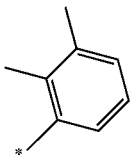

Formula 8-155
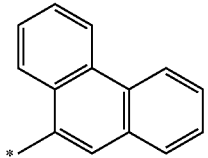

Formula 8-156
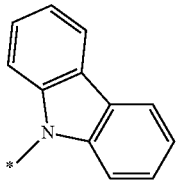

Formula 8-157
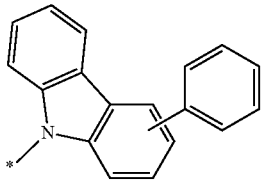

Formula 8-158
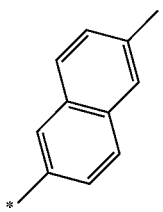

Formula 8-159
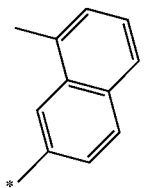

wherein, in Formulae 8-1 to 8-159, * indicates a binding site to an adjacent atom.

In one or more embodiments, in the above formulae, $R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a naphthyl group, and —Si($Q_1$)($Q_2$)($Q_3$), $R_1$, $R_2$, and $R_{12}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (e.g., groups represented by Formulae 7-1 to 7-75 or groups represented by Formulae 8-1 to 8-159).

In one or more embodiments, in the above formulae,
$R_3$ to $R_6$ and $R_{13}$ may be hydrogen,
$R_1$, $R_2$, and $R_{12}$ may each independently be selected from groups represented by Formulae 7-1 to 7-75 (e.g., groups represented by Formulae 8-1 to 8-159), but embodiments are not limited thereto.

In the above formulae, b1, b2, b5, b6, and b12 may each independently be an integer from 0 to 4; b3 and b4 may each independently be an integer from 0 to 6; and b13 may be 0, 1, or 2.

In some embodiments, in the above formulae, b1, b2, and b12 may each independently be 0, 1, or 2. In some embodiments, in the above formulae, b1, b2, and b12 may each independently be 1 or 2.

In some embodiments, in the above formulae, b1, b2, and b12 may be 1, but embodiments are not limited thereto.

In some embodiments, in the above formulae, b3 to b6 and b13 may each independently be 0, 1, or 2. In some embodiments, in the above formulae, b3 to b6 and b13 may each independently be 0 or 1, but embodiments are not limited thereto.

In Formula 1, c1 and c2 may each independently be an integer from 0 to 4, and a sum of c1 and c2 may be 1 or greater. That is, at least one selected from a group represented by *-[($L_1$)$_{a1}$-($R_1$)$_{b1}$] and a group represented by *-[($L_2$)$_{a2}$-($R_2$)$_{b2}$] may be essentially present in Formula 1.

In one embodiment, in Formula 1, a sum of c1 and c2 may be 1 or 2.

In one or more embodiments, in Formula 1,
c1 may be 1, and c2 may be 0;
c1 may be 1, and c2 may be 1; or
c1 may be 0, and c2 may be 1, but embodiments are not limited thereto.

In one embodiment, the condensed-cyclic compound may be represented by one of Formulae 1A to 1E:

Formula 1A
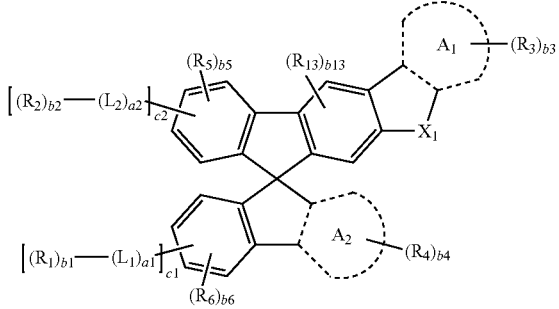

-continued

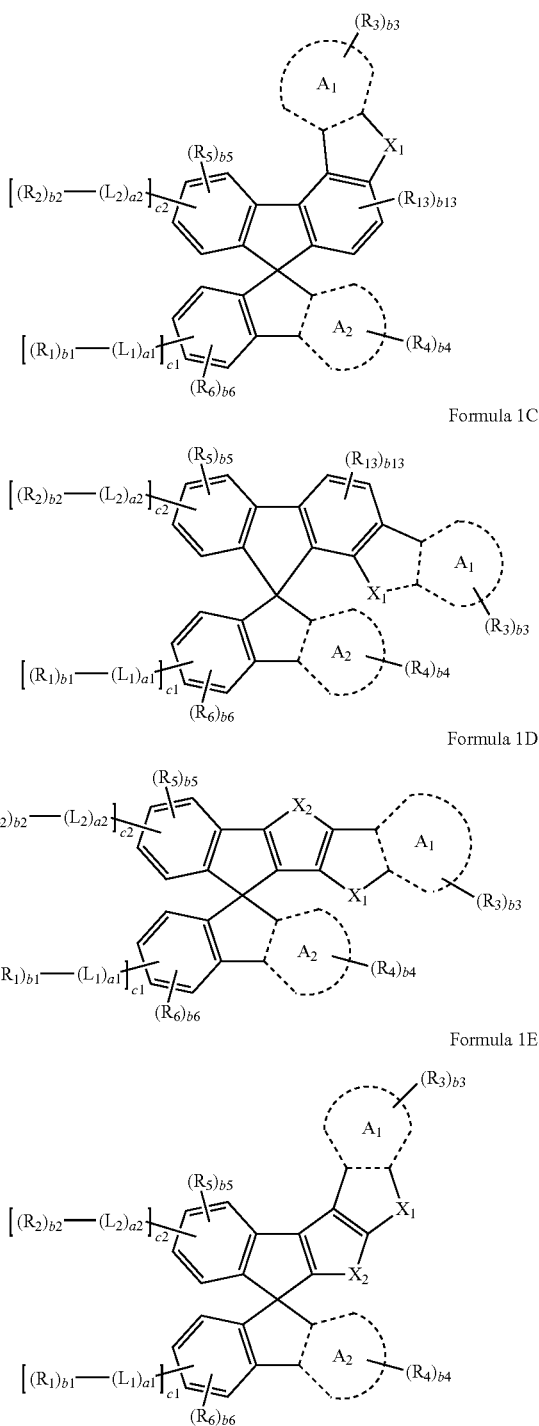

Formula 1B

Formula 1C

Formula 1D

Formula 1E wherein, in Formulae 1A to 1E, ring $A_1$, ring $A_2$, $X_1$, $X_2$, $L_1$, $L_2$, a1, a2, $L_{11}$, $L_{12}$, a11, a12, $R_1$ to $R_6$, $R_{11}$ to $R_{13}$, b1 to b6, b11 to b13, c1, and c2 may be the same as those described herein.

In some embodiments, in Formulae 1A and 1E, ring $A_1$ may be a benzene group or a naphthalene group, ring $A_2$ may be selected from a pyridine group, a quinoline group, and an isoquinoline group, $X_1$ may be N-[$(L_{11})_{a11}$-$(R_{11})_{b11}$], $X_2$ may be O or S, $L_1$ and $L_2$ may each independently be selected from groups represented by Formulae 3-8, 3-9, 3-25, and 3-35 to 3-41 (e.g., groups represented by Formulae 4-11, 4-13, 4-27 and 4-29 to 4-35), a1 and a2 may each independently be 0, 1, or 2, $L_{11}$ may be selected from groups represented by Formulae 3-1 to 3-9 (provided that $Y_1$ in Formulae 3-3 and 3-4 may be $C(Z_3)(Z_4)$), 3-25, and 3-33 to 3-41 (e.g., groups represented by Formulae 4-1, 4-3, 4-5, 4-7 to 4-13, 4-17, and 4-24 to 4-35), a11 may be 0, 1, or 2, $R_{11}$ may be selected from groups represented by Formulae 5-1 to 5-19 (e.g., groups represented by Formulae 6-1 to 6-27), b11 may be 1 or 2, $R_1$ and $R_2$ may each independently be selected from groups represented by Formulae 7-1 to 7-75 (e.g., groups represented by Formulae 8-1 to 8-159), b1 and b2 may each independently be 1 or 2, $R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, a biphenyl group, a terphenyl group, and a naphthyl group, b3 to b6 and b13 may each independently be 0, 1, or 2, and c1 may be 1, and c2 may be 0; c1 may be 1, and c2 may be 1; or c1 may be 0, and c2 may be 1, but embodiments are not limited thereto.

In one or more embodiments, the condensed-cyclic compound may be represented by one of Formulae 1-1 to 1-7:

Formula 1-1

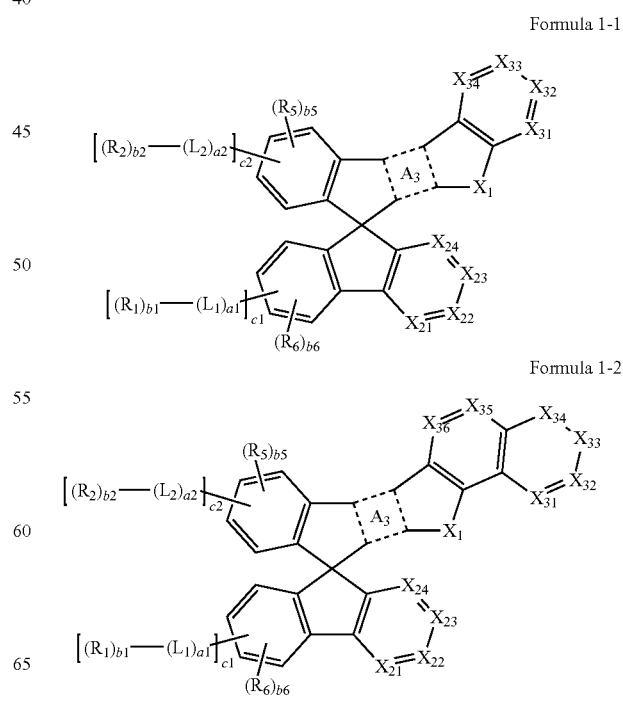

Formula 1-2

-continued

Formula 1-3
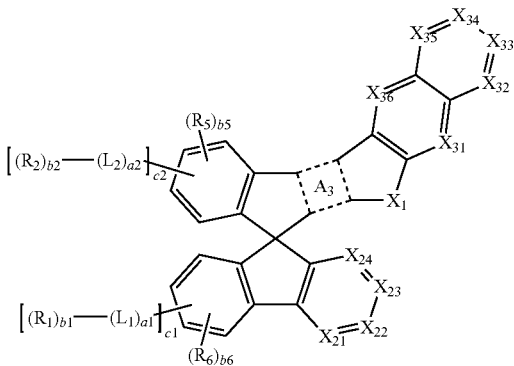

Formula 1-4
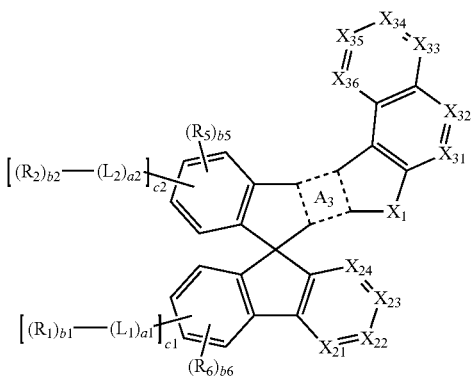

Formula 1-5
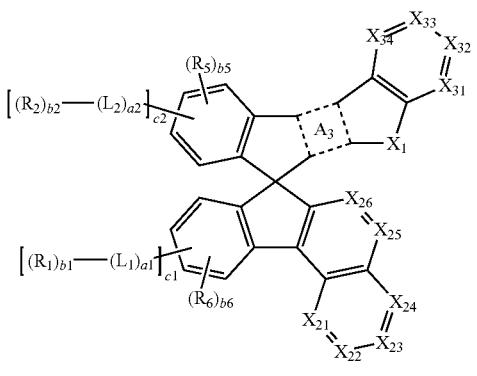

Formula 1-6
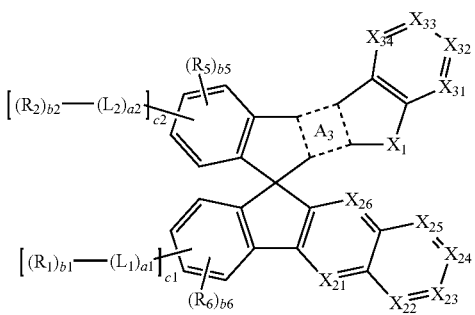

-continued

Formula 1-7
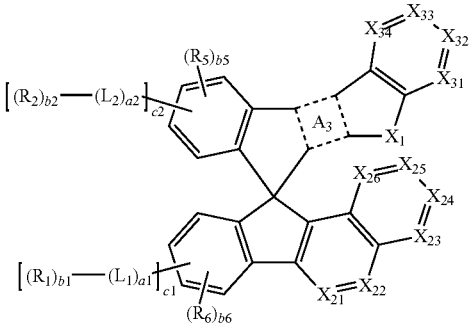

wherein, in Formulae 1-1 to 1-7, ring $A_3$, $X_1$, $X_2$, $L_1$, $L_2$, a1, a2, $L_{11}$, $L_{12}$, a11, a12, $R_1$, $R_2$, $R_5$, $R_6$, $R_{11}$ to $R_{13}$, $b_1$, b2, b5, b6, b11 to b13, c1, and c2 may be the same as those described herein, $X_{21}$ may be N or $G(R_{21})$, $X_{22}$ may be N or $G(R_{22})$, $X_{23}$ may be N or $G(R_{23})$, $X_{24}$ may be N or $G(R_{24})$, $X_{25}$ may be N or $G(R_{25})$, $X_{26}$ may be N or $G(R_{26})$, at least one selected from $X_{21}$ to $X_{26}$ may be N, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{35}$ may be N or $C(R_{35})$, $X_{36}$ may be N or $C(R_{36})$, $R_{21}$ and $R_{26}$ may each independently be the same as describe herein with reference to $R_3$, and $R_{31}$ and $R_{36}$ may each independently be the same as describe herein with reference to $R_4$.

In one embodiment, in Formula 1-1, one or two of $X_{21}$ to $X_{24}$ may be N, and none, one, or two of $X_{31}$ to $X_{34}$ may be N, in Formulae 1-2 to 1-4, one or two of $X_{21}$ to $X_{24}$ may be N, and none, one, or two of $X_{31}$ to $X_{36}$ may be N, in Formulae 1-5 to 1-7, one or two of $X_{21}$ to $X_{26}$ may be N, and none, one, or two of $X_{31}$ to $X_{36}$ may be N.

In one or more embodiments, in Formulae 1-1 to 1-4, one of $X_{21}$ to $X_{24}$ may be N, in Formulae 1-1 and 1-5 to 1-7, none or one of $X_{31}$ to $X_{34}$ may be N, in Formulae 1-5 to 1-7, one of $X_{21}$ to $X_{26}$ may be N, and in Formulae 1-2 to 1-4, none or one of $X_{31}$ to $X_{36}$ may be N.

In some embodiments, in Formulae 1-1 to 1-7, ring $A_3$ may be a group represented by Formula 2A.

In one embodiment, in Formulae 1-1 to 1-7, $X_1$ may be N-$[(L_{11})_{a11}$-$(R_{11})_{b11}]$, $X_2$ may be O or S, $L_1$ and $L_2$ may each independently be selected from groups represented by Formulae 3-8, 3-9, 3-25, and 3-35 to 3-41 (e.g., groups represented by Formulae 4-11, 4-13, 4-27 and 4-29 to 4-35), a1 and a2 may each independently be 0, 1, or 2, $L_{11}$ may be selected from groups represented by Formulae 3-1 to 3-9 (provided that $Y_1$ in Formulae 3-3 and 3-4 may be $C(Z_3)(Z_4)$), 3-25, and 3-33 to 3-41 (e.g., groups represented by Formulae 4-1, 4-3, 4-5, 4-7 to 4-13, 4-17, and 4-24 to 4-35), a11 may be 0, 1, or 2, $R_{11}$ may be selected from groups represented by Formulae 5-1 to 5-19 (e.g., groups represented by Formulae 6-1 to 6-27), b11 may be 1 or 2, $R_1$ and $R_2$ may each independently be selected from groups represented by Formulae 7-1 to 7-75 (e.g., groups represented by Formulae 8-1 to 8-159), b1 and b2 may each independently be 1 or 2, $R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, a biphenyl group, a terphenyl group, and a naphthyl group, b3 to b6 and b13 may each independently be 0, 1, or 2, and c1 may be 1, and c2 may be 0; c1 may be 1, and c2 may be 1; or c1 may be 0, and c2 may be 1, but embodiments are not limited thereto.

In one or more embodiments, the condensed-cyclic compound may be represented by one of Formulae 1(1) to 1(19), but embodiments are not limited thereto:

Formula 1(1)

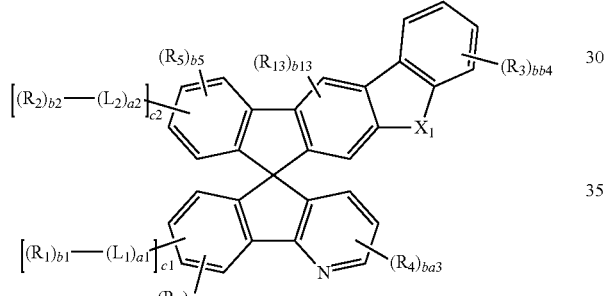

Formula 1(2)

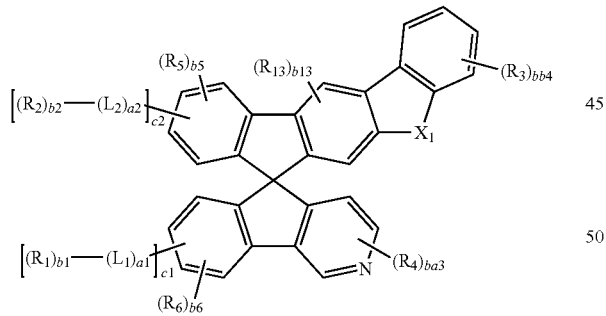

Formula 1(3)

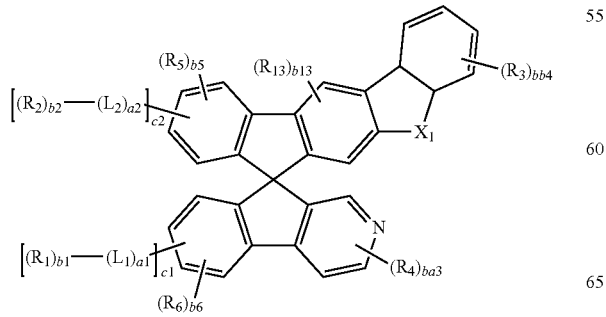

Formula 1(4)

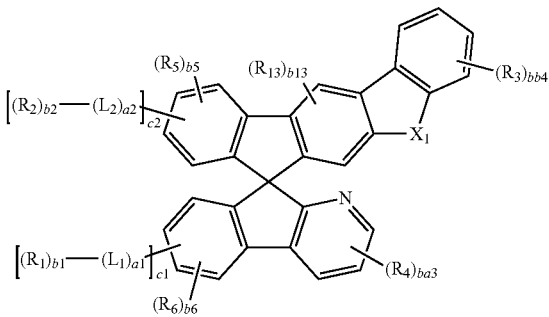

Formula 1(5)

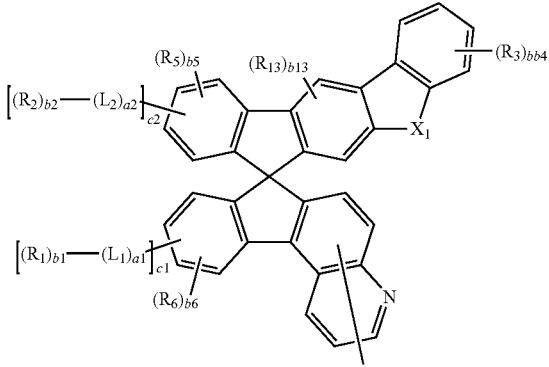

Formula 1(6)

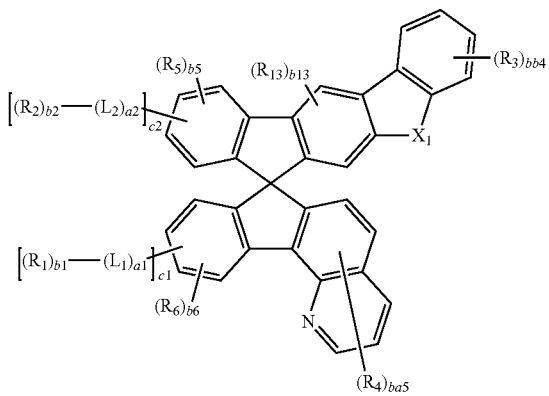

Formula 1(7)

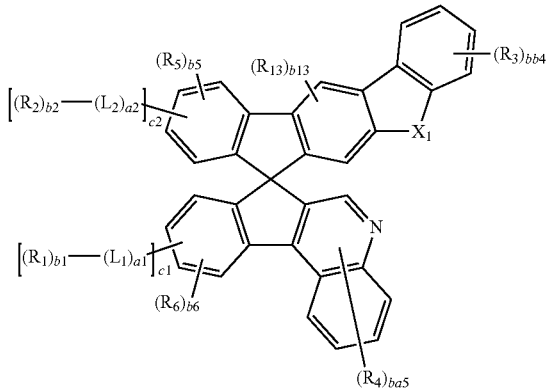

Formula 1(8)
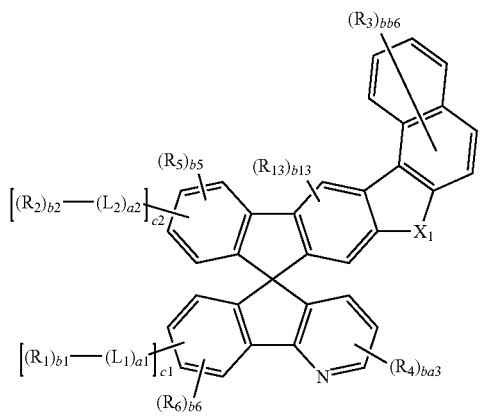
Formula 1(9)
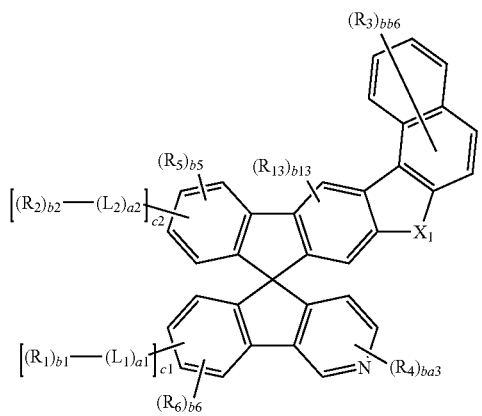
Formula 1(10)
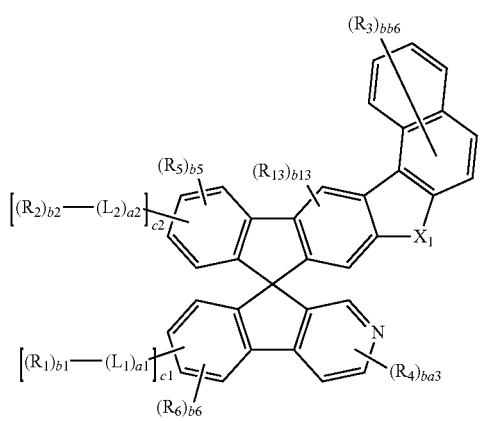
Formula 1(11)
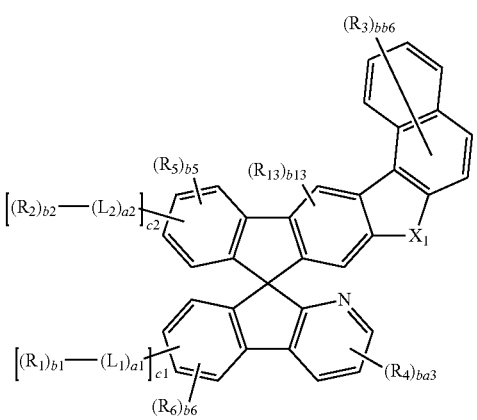
Formula 1(12)
Formula 1(13)
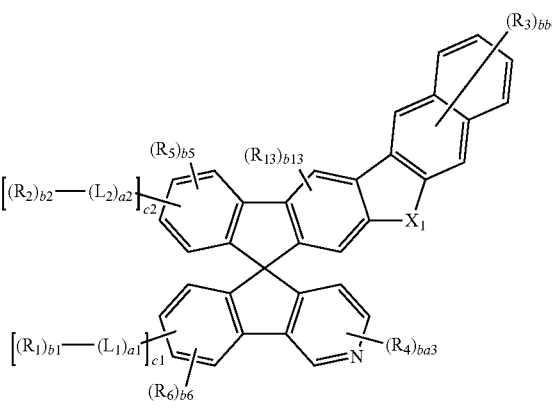

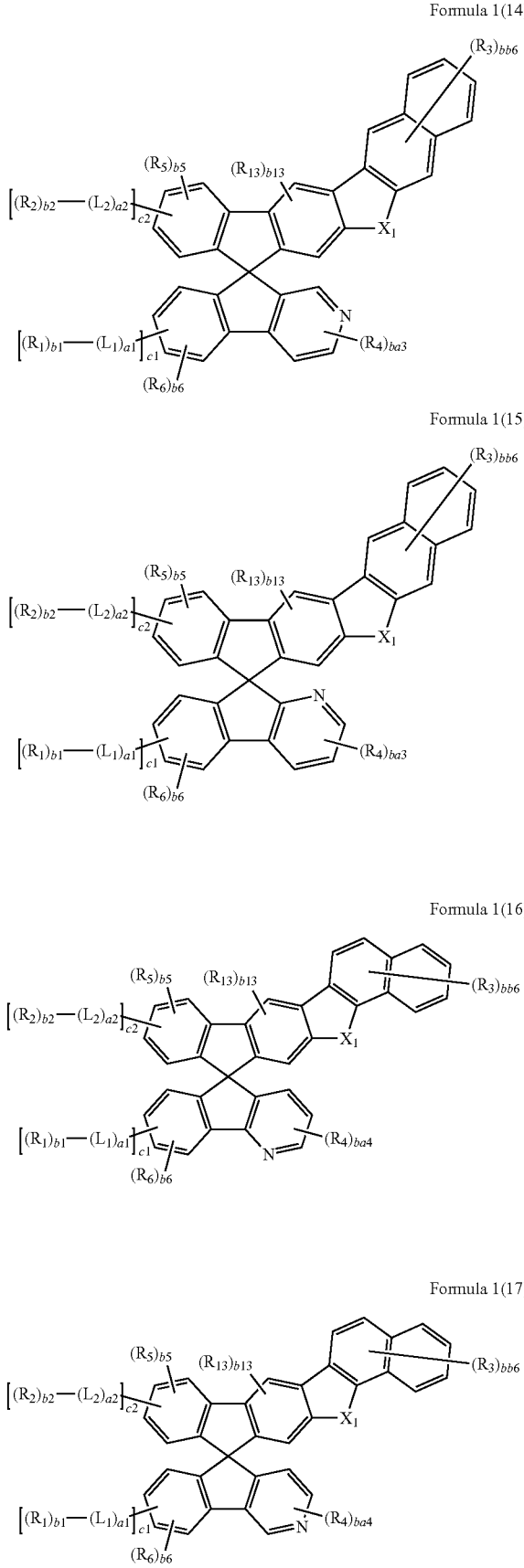

Formula 1(14)

Formula 1(15)

Formula 1(16)

Formula 1(17)

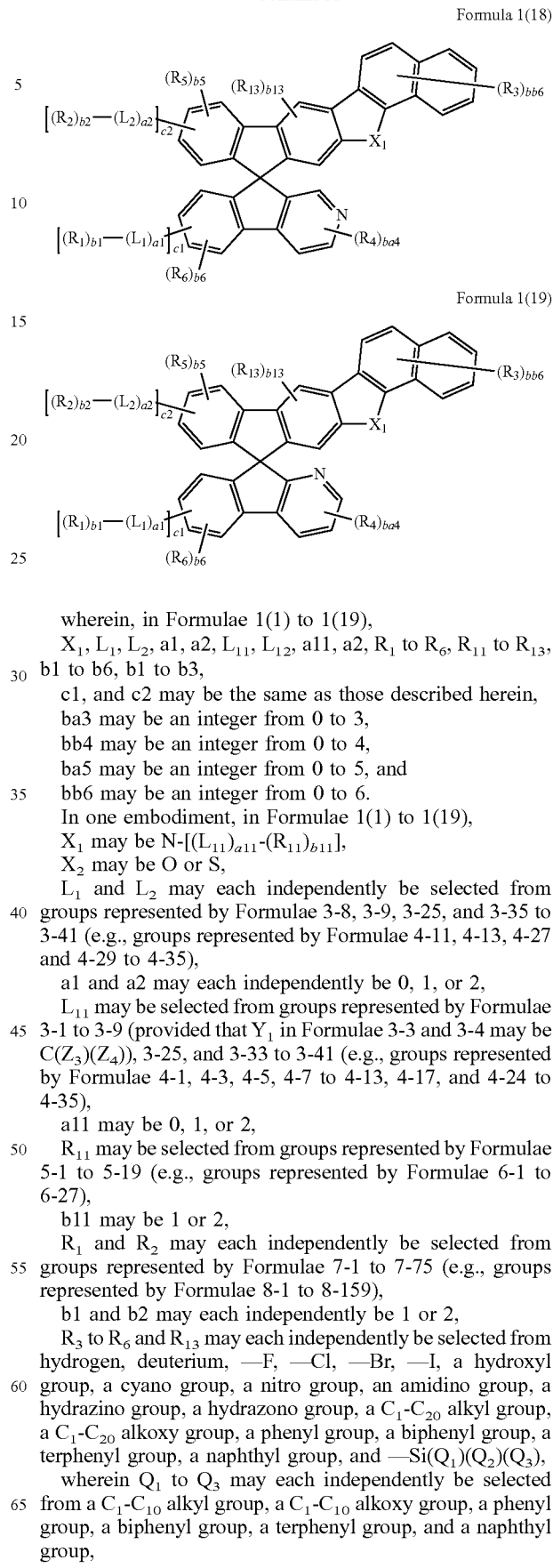

Formula 1(18)

Formula 1(19)

wherein, in Formulae 1(1) to 1(19), $X_1, L_1, L_2, a1, a2, L_{11}, L_{12}, a11, a2, R_1$ to $R_6, R_{11}$ to $R_{13}$, b1 to b6, b1 to b3, c1, and c2 may be the same as those described herein, ba3 may be an integer from 0 to 3, bb4 may be an integer from 0 to 4, ba5 may be an integer from 0 to 5, and bb6 may be an integer from 0 to 6.

In one embodiment, in Formulae 1(1) to 1(19), $X_1$ may be N-[$(L_{11})_{a11}$-$(R_{11})_{b11}$], $X_2$ may be O or S, $L_1$ and $L_2$ may each independently be selected from groups represented by Formulae 3-8, 3-9, 3-25, and 3-35 to 3-41 (e.g., groups represented by Formulae 4-11, 4-13, 4-27 and 4-29 to 4-35), a1 and a2 may each independently be 0, 1, or 2, $L_{11}$ may be selected from groups represented by Formulae 3-1 to 3-9 (provided that $Y_1$ in Formulae 3-3 and 3-4 may be $C(Z_3)(Z_4)$), 3-25, and 3-33 to 3-41 (e.g., groups represented by Formulae 4-1, 4-3, 4-5, 4-7 to 4-13, 4-17, and 4-24 to 4-35), a11 may be 0, 1, or 2, $R_{11}$ may be selected from groups represented by Formulae 5-1 to 5-19 (e.g., groups represented by Formulae 6-1 to 6-27), b11 may be 1 or 2, $R_1$ and $R_2$ may each independently be selected from groups represented by Formulae 7-1 to 7-75 (e.g., groups represented by Formulae 8-1 to 8-159), b1 and b2 may each independently be 1 or 2, $R_3$ to $R_6$ and $R_{13}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, and —Si($Q_1$)($Q_2$)($Q_3$), wherein $Q_1$ to $Q_3$ may each independently be selected from a $C_1$-$C_{10}$ alkyl group, a $C_1$-$C_{10}$ alkoxy group, a phenyl group, a biphenyl group, a terphenyl group, and a naphthyl group, ba3, bb4, ba5, bb6, b5, and b6 may each independently be 0, 1, or 2, and c1 may be 1, and c2 may be 0; c1 may be 1, and c2 may be 1; or c1 may be 0, and c2 may be 1, but embodiments are not limited thereto.

In one or more embodiments, the condensed-cyclic compound may be represented by one of Formulae 1A-1 to 1A-3, but embodiments are not limited thereto:

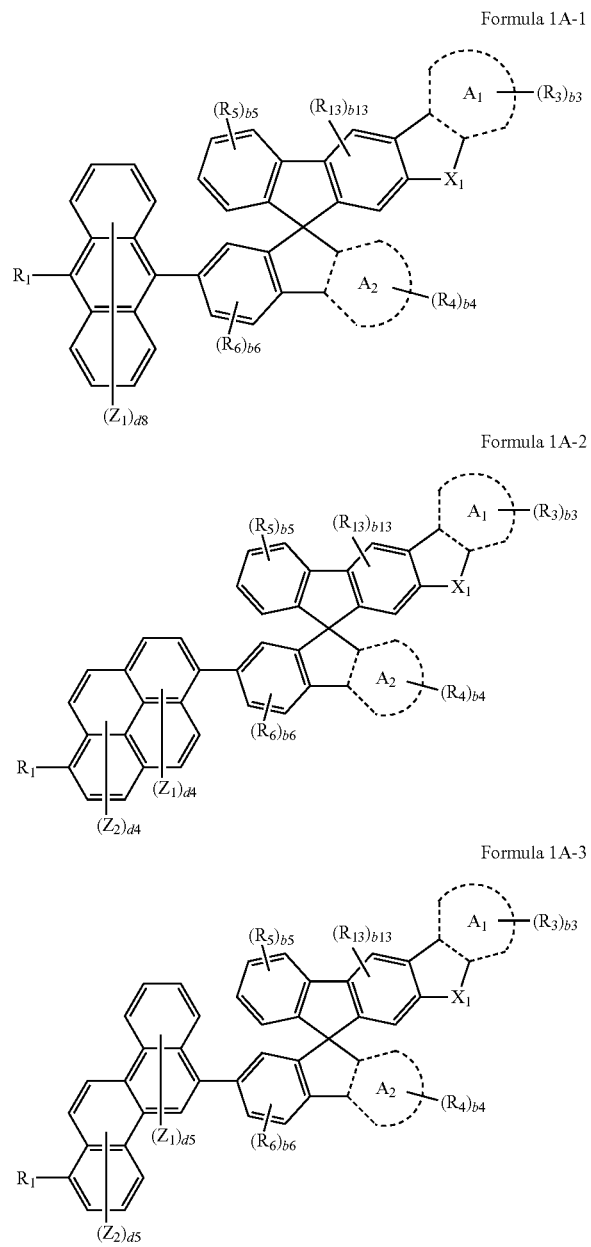

Formula 1A-1

Formula 1A-2

Formula 1A-3 wherein, in Formulae 1A-1 to 1A-3, ring $A_1$, ring $A_2$, $X_1$, $L_{11}$, $L_{12}$, a11, a12, $R_1$, $R_3$ to $R_6$, $R_{11}$ to $R_{13}$, b3 to b6, b11 to b13, c1, and c2 may be the same as those described herein.

In some embodiments, in Formulae 1A-1 to 1A-3, ring $A_1$ may be selected from a benzene group and a naphthalene group, ring $A_2$ may be selected from a pyridine group, a quinoline group, and an isoquinoline group, $X_1$ may be N-$[(L_{11})_{a11}$-$(R_{11})_{b11}]$, $L_{11}$ may be selected from groups represented by Formulae 3-1 to 3-9 (provided that $Y_1$ in Formulae 3-3 and 3-4 may be $C(Z_3)(Z_4)$), 3-25, and 3-33 to 3-41 (e.g., groups represented by Formulae 4-1, 4-3, 4-5, 4-7 to 4-13, 4-17, and 4-24 to 4-35), a11 may be 0, 1, or 2, $R_{11}$ may be selected from groups represented by Formulae 5-1 to 5-19 (e.g., groups represented by Formulae 6-1 to 6-27), b11 may be 1 or 2, $R_1$ may be selected from groups represented by Formulae 7-1 to 7-75 (e.g., groups represented by Formulae 8-1 to 8-159), b1 may be 1 or 2, $R_3$ to $R_6$, $R_{13}$, $Z_1$, and $Z_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group, and b3 to b6, b13, d4, d5, and d8 may each independently be selected from 0, 1, and 2, but embodiments are not limited thereto:

In some embodiments, the condensed-cyclic compound represented by Formula 1 may be represented by one of Compounds 1 to 35, but embodiments are not limited thereto:

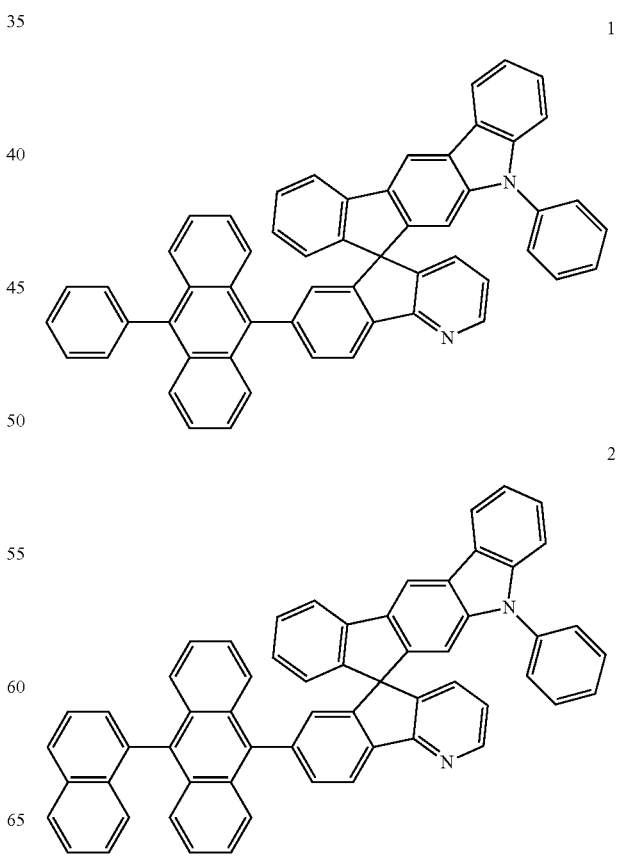

1

2

3
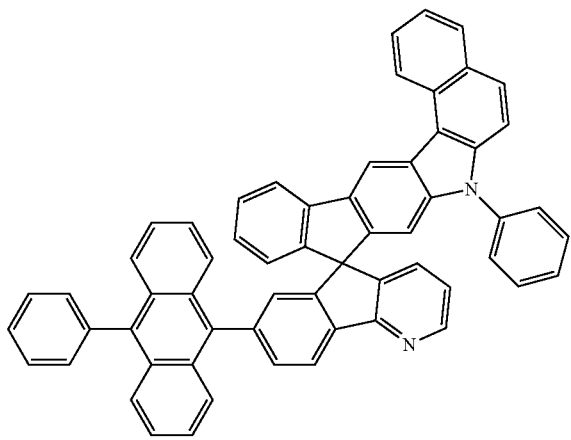
4
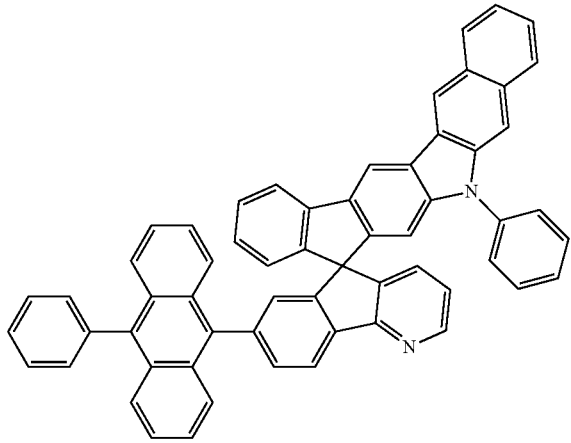
5
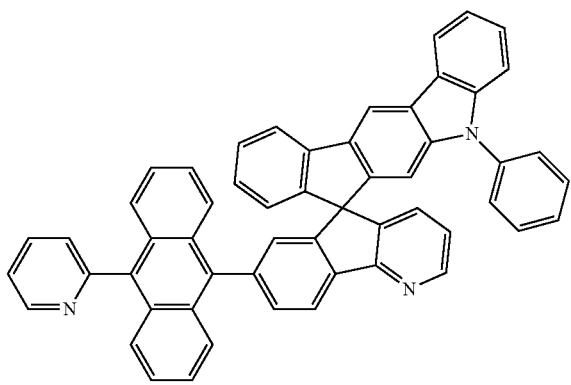
6
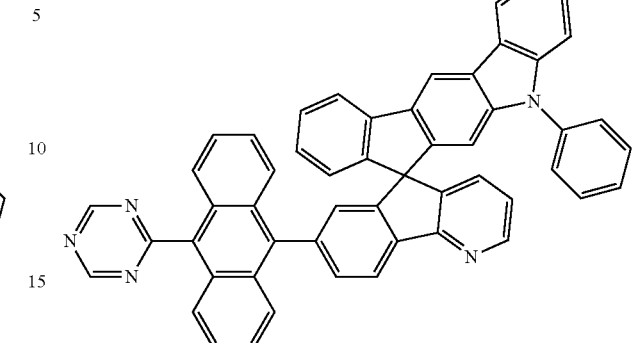
7
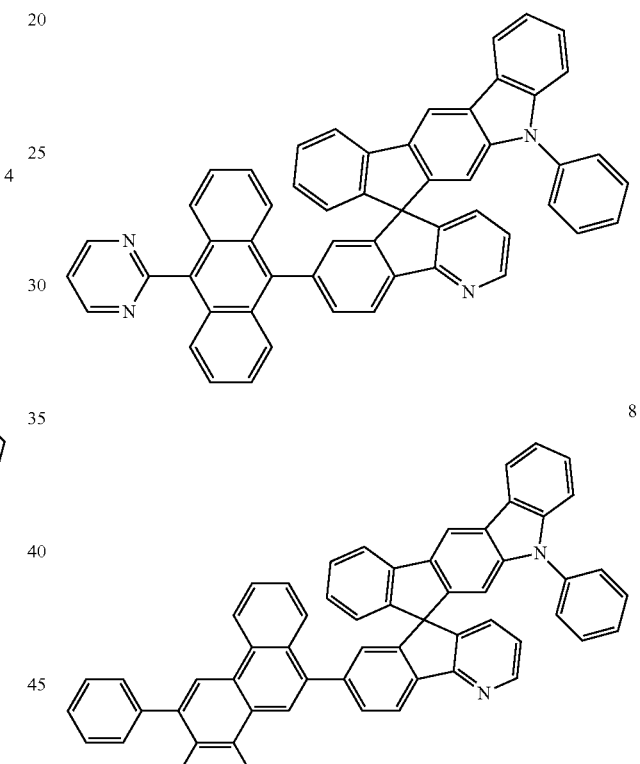
8
9
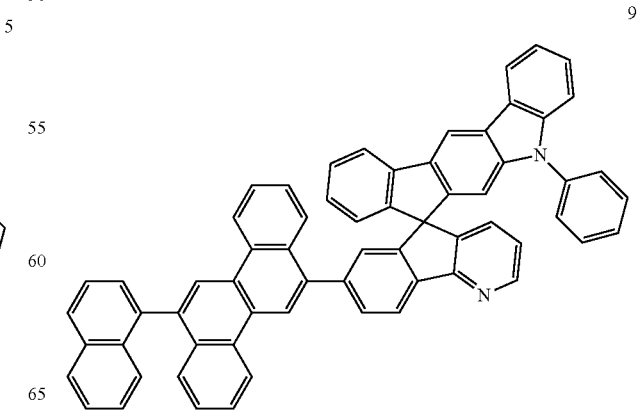

10
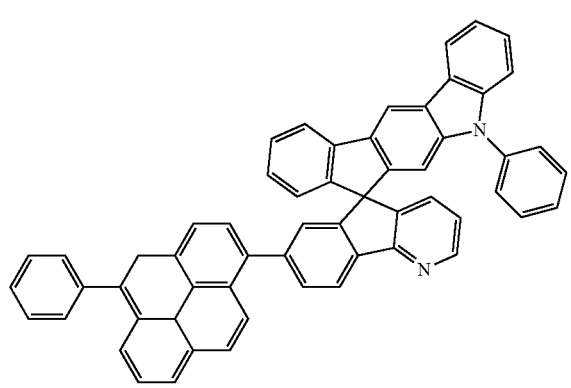
11
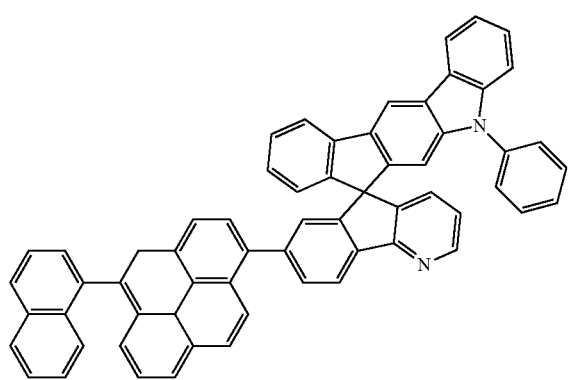
12
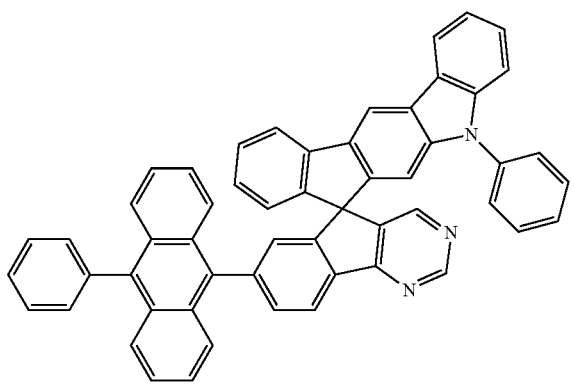
13
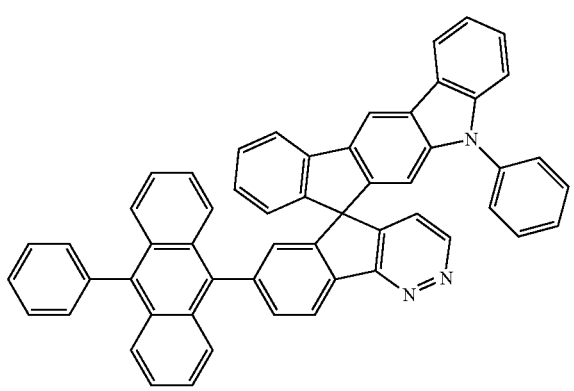
14
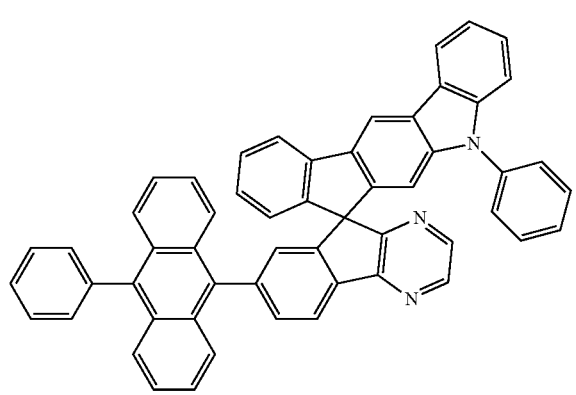
15
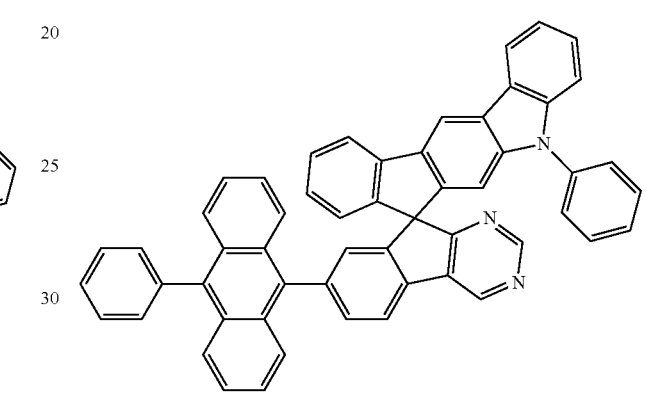
16
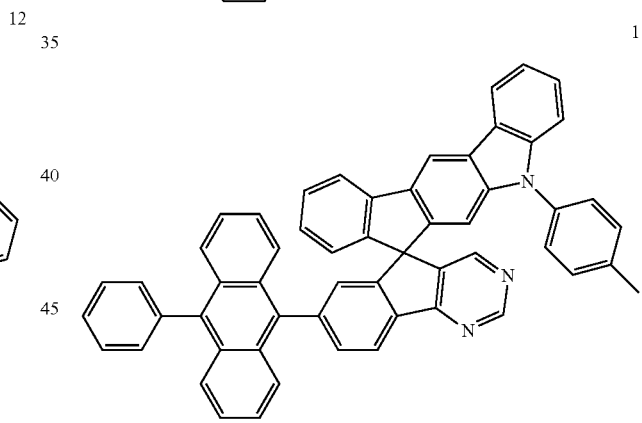
17
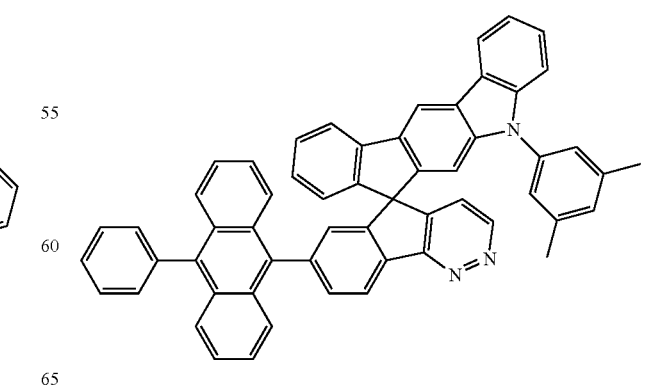

18
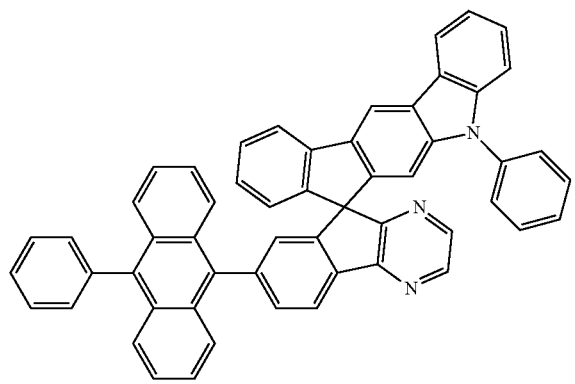
19
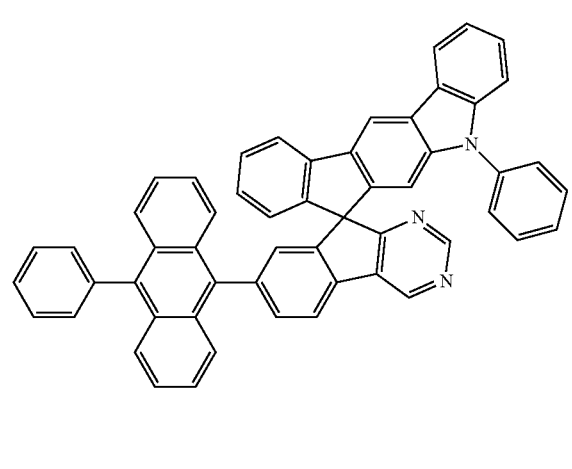
20
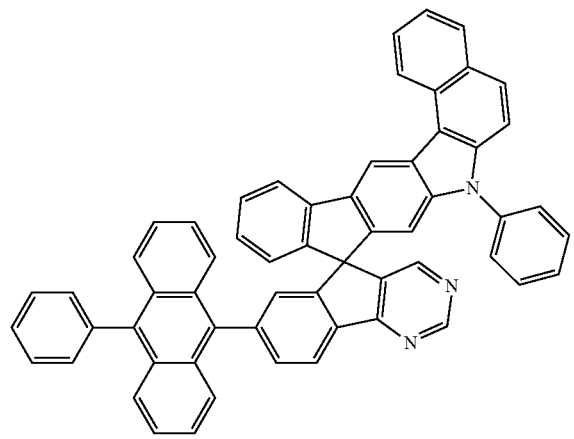
21
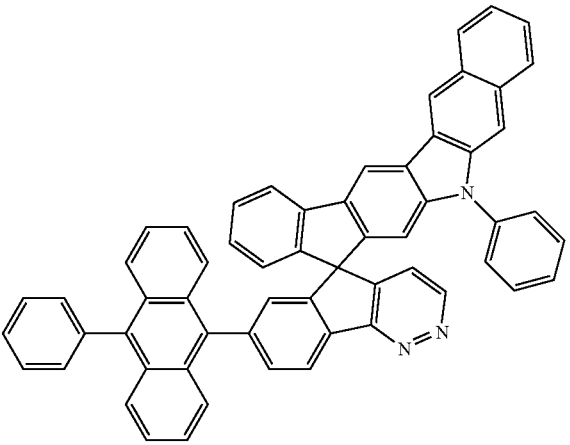
22
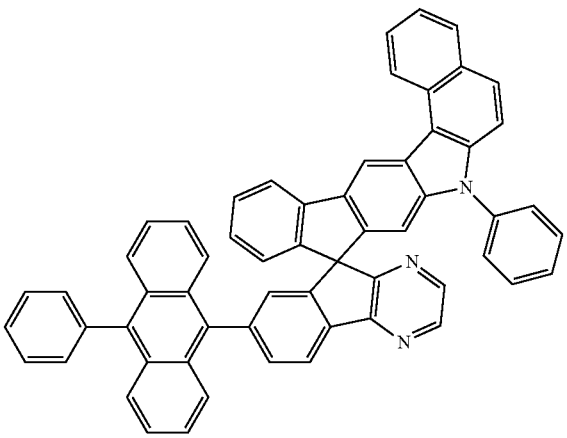
23
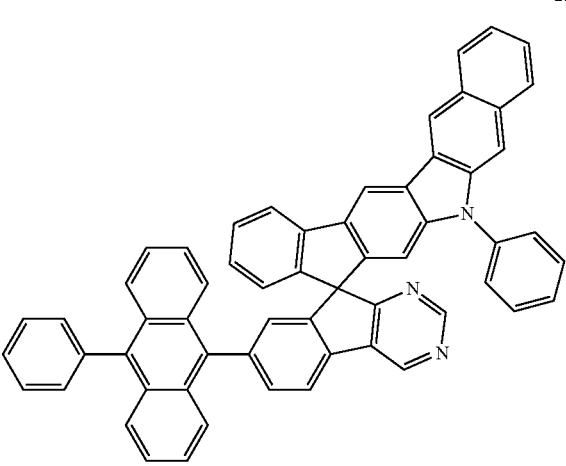

24
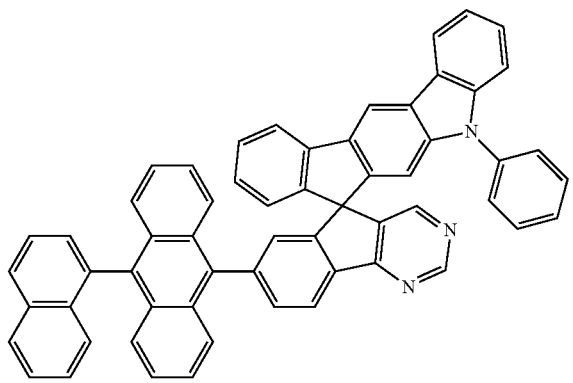
25
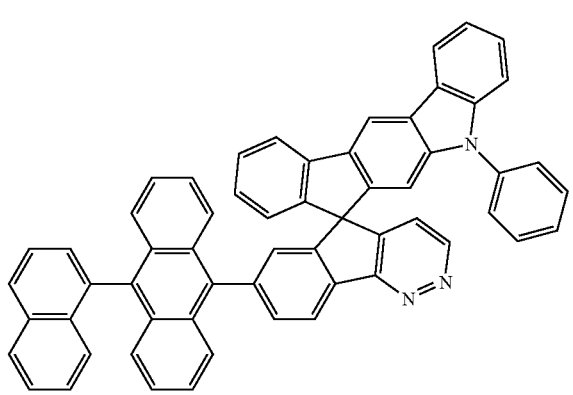
26
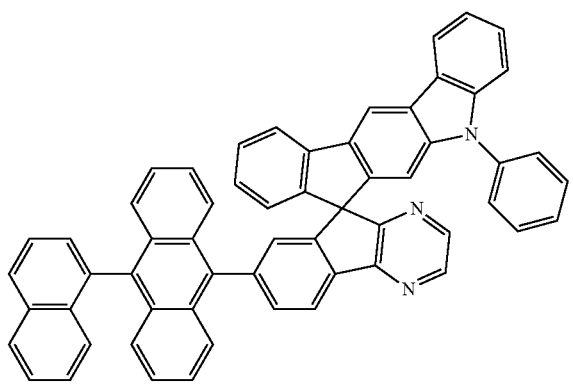
27
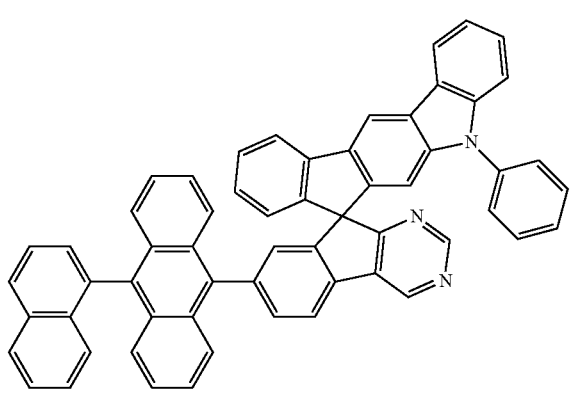
28
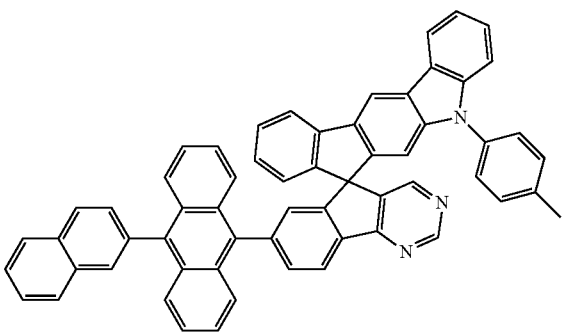
29
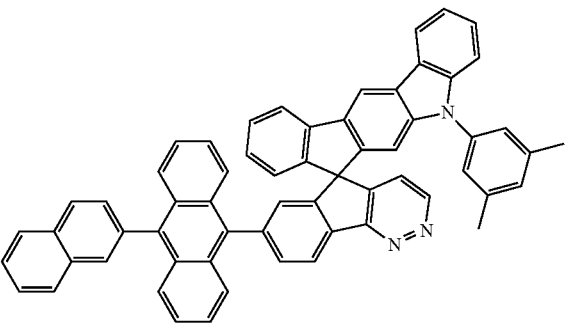
30
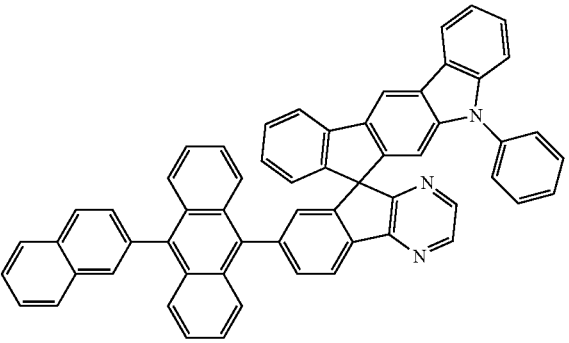
31
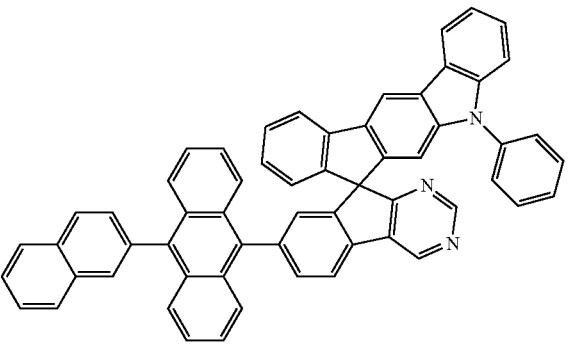

32

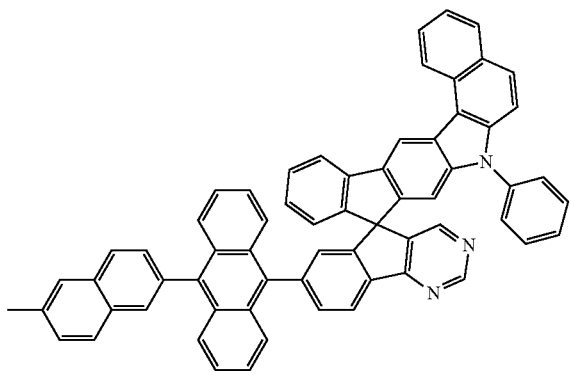

33

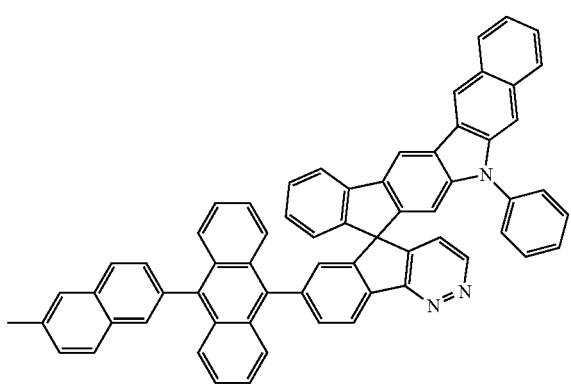

34

35

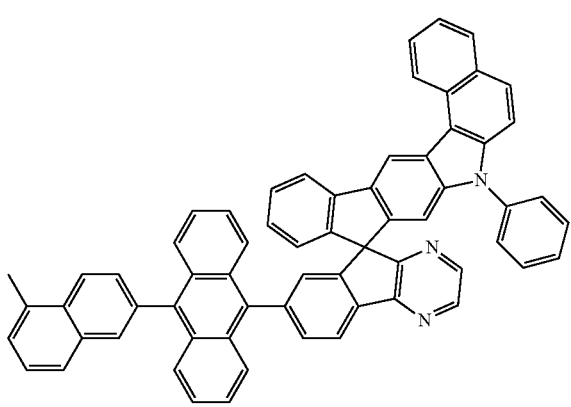

35

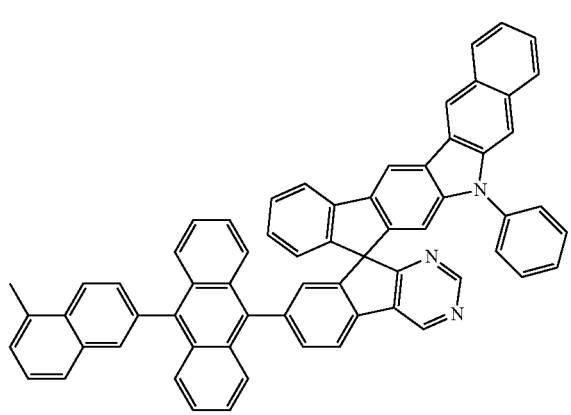

The condensed-cyclic compound represented by Formula 1 has a condensed ring core based on spirobifluorene. Thus, the molecular structure of the condensed-cyclic compound may have strong resistance against electrons, and accordingly, in an organic light-emitting device, deterioration of the molecular structure by electrons may be reduced, which may result in an increase in lifespan of the organic light-emitting device. In addition, the condensed-cyclic compound may have a high triplet (T1) energy level, and accordingly, in an emission layer, triplet excitons may be more prone to collide with one another. Due to triplet-triplet annihilation (TTA) effect, the organic light-emitting device may have improved efficiency.

In the condensed-cyclic compound represented by Formula 1, ring $A_2$ may be selected from a pyridine group, a pyrimidine group, a pyrazine group, a quinoline group, an isoquinoline group, a quinoxaline group, a quinazoline group, and a cinnoline group. That is, the condensed-cyclic compound may have at least one nitrogen atom in the condensed ring core based on spirobifluorene. Therefore, the condensed-cyclic compound represented by Formula 1 may have improved electron injecting characteristics into the emission layer, and thus formation of excitons may be more prone to occur in the emission layer. Consequently, efficiency of the organic light-emitting device may be improved.

In the condensed-cyclic compound represented by Formula 1, $L_1$ and $L_2$ may each independently be selected from substituted or unsubstituted condensed polycyclic groups not including heteroatoms as ring-forming atoms, in which 3 or more carbocyclic groups are condensed with each other. Both a1 and a2 are not 0, wherein a1 and a2 each denote the number of $L_1$ (s) and $L_2$ (s), respectively. That is, in Formula 1, $L_1$ may be essentially present in a group represented by *-$[(L_1)_{a1}$-$(R_1)_{b1}]$, and $L_2$ may be essentially present in a group represented by *-$[(L_2)_{a2}$-$(R_2)_{b2}]$. In Formula 1, a sum of c1 and c2 is 1 or greater. That is, at least one selected from a group represented by *-$[(L_1)_{a1}$-$(R_1)_{b1}]$ and a group represented by *-$[(L_2)_{a2}$-$(R_2)_{b2}]$ may be essentially present in Formula 1. Therefore, when the condensed-cyclic compound represented by Formula 1 is used, a suitable energy level between a host and a dopant may be obtained, and exciton energy generated from the host may be efficiently transferred, and thus the organic light-emitting device may have improved efficiency.

The condensed cyclic compound represented by Formula 1 may be synthesized by using a known organic synthetic method. A method of synthesizing the condensed cyclic compound may be recognizable by one of ordinary skill in the art in view of the following embodiments.

The at least one condensed cyclic compound of Formula 1 may be used between a pair of electrodes of an organic light-emitting device. For example, the condensed cyclic compound may be included in an emission layer. In one or more embodiments, the condensed cyclic compound of Formula 1 may be used as a material for a forming capping layer positioned outside a pair of electrodes of an organic light-emitting device.

According to an aspect, an organic light-emitting device includes: a first electrode, a second electrode, and an organic layer between the first electrode and the second electrode, wherein the organic layer may include an emission layer and at least one condensed cyclic compound represented by Formula 1 described above.

The expression "(an organic layer) includes at least one condensed-cyclic compound" as used herein refer to an embodiment in which "(an organic layer) includes identical compounds represented by Formula 1 and to an embodiment in which (an organic layer) includes two or more different condensed-cyclic compounds represented by Formula 1."

In some embodiments, the organic layer may include only Compound 1 as the condensed-cyclic compound. In this case, Compound 1 may be included in an emission layer of the organic light-emitting device. In one or more embodiments, the organic layer may include both Compounds 1 and 2 as the condensed-cyclic compound. In this regard, Compounds 1 and 2 may be situated in the same layer (for example, Compounds 1 and 2 may all be situated in an emission layer), or in different layers (for example, Compound 1 may be situated in a hole transport layer, and Compound 2 may be situated in an emission layer).

The organic layer may include i) a hole transport region disposed between the first electrode (anode) and the emission layer, the hole transport region including at least one of a hole injection layer, a hole transport layer, an emission auxiliary layer, and an electron blocking layer, and ii) an electron transport region disposed between the emission layer and the second electrode (cathode), the electron transport region including at least one of a hole blocking layer, an electron transport layer, and an electron injection layer. At least one of the hole transport region and the emission layer may include the at least one condensed cyclic compound represented by Formula 1. For example, the emission layer of the organic light-emitting device may include the at least one condensed cyclic compound represented by Formula 1. The at least one condensed cyclic compound represented by Formula 1 included in the emission layer may act as a host, and the emission layer may further include a dopant. The dopant may be a phosphorous dopant or a fluorescent dopant. In an embodiment, the dopant may be a fluorescent dopant.

The organic light-emitting device may further include at least one of a first capping layer disposed on a pathway through which light extracted or emitted from an emission layer proceeds toward the outside through the first electrode; and a second capping layer disposed on a pathway through which light extracted or emitted from an emission layer proceeds toward the outside through the second electrode, wherein the at least one of the first capping layer and the second capping layer may include the at least one condensed-cyclic compound.

In some embodiments, an organic light-emitting device may have i) a stack structure including a first electrode, an organic layer, a second electrode, and a second capping layer, which are sequentially stacked in this stated order, ii) a stack structure including a first capping layer, a first electrode, an organic layer, and a second electrode, which are sequentially stacked in this stated order, or iii) a stack structure including a first capping layer, a first electrode, an organic layer, a second electrode, and a second capping layer, which are sequentially stacked in this stated order, wherein at least one of the first capping layer and the second capping layer may include the at least one condensed-cyclic compound.

The term "organic layer" as used herein refers to a single layer and/or a plurality of layers disposed between the first electrode and the second electrode of the organic light-emitting device. Materials included in the "organic layer" are not limited to organic materials.

Description of FIG. 1

Figure 1:
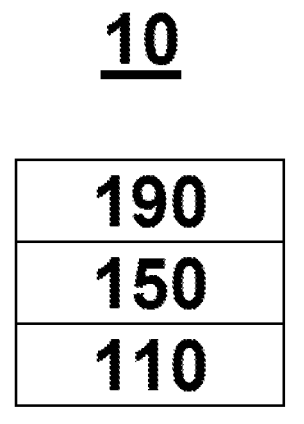

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of an organic light-emitting device and a method of manufacturing an organic light-emitting device, according to an embodiment, will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but embodiments are not limited thereto. In one or more embodiments, when the first electrode 110 is a semi-transmissive electrode or a reflective electrode, the material for the first electrode 110 may be selected from magnesium (Mg), aluminum (Al), aluminum-lithium (Al—Li), calcium (Ca), magnesium-indium (Mg—In), magnesium-silver (Mg—Ag), and any combinations thereof, but embodiments are not limited thereto.

The first electrode 110 may have a single-layered structure, or a multi-layered structure including two or more layers. For example, the first electrode 110 may have a three-layered ITO/Ag/ITO structure, but embodiments of the structure of the first electrode 110 are not limited thereto.

Organic Layer 150

The organic layer 150 may be disposed on the first electrode 110. The organic layer 150 may include an emission region.

The organic layer 150 may include a hole transport region between the first electrode 110 and the emission region and an electron transport region between the emission region and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein layers of each structure are sequentially stacked on the first electrode 110 in each stated order, but embodiments of the structure of the hole transport region are not limited thereto.

The hole transport region may include at least one selected from m-MTDATA, TDATA, 2-TNATA, NPB (NPD), p-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202, but embodiments are not limited thereto:

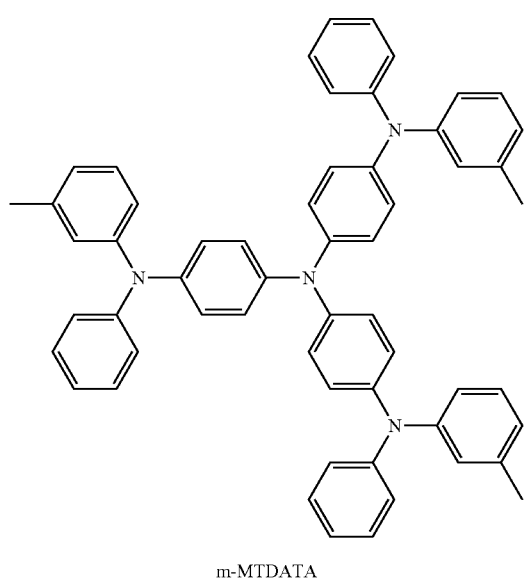

m-MTDATA

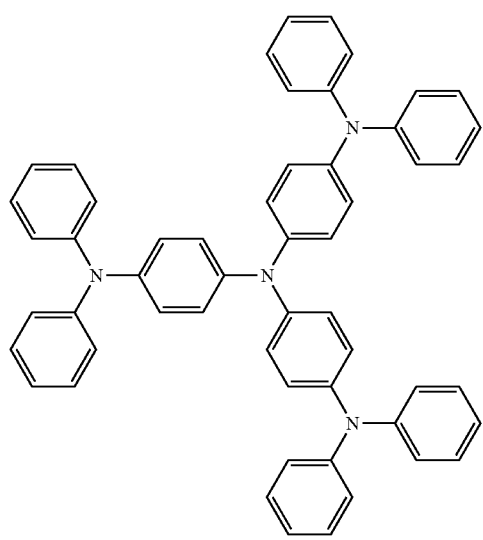

TDATA

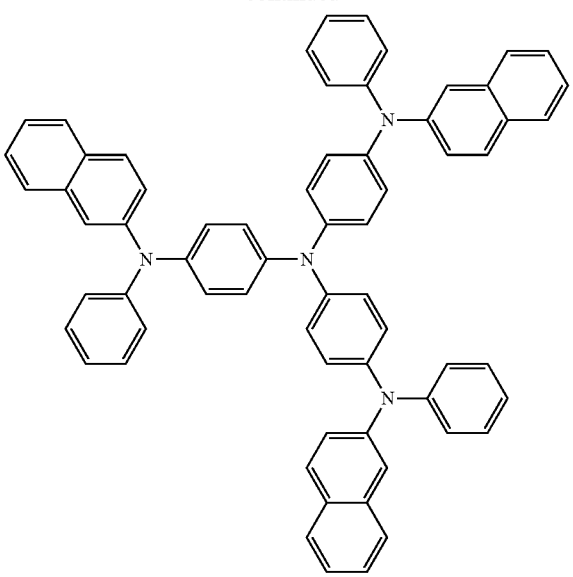

2-TNATA

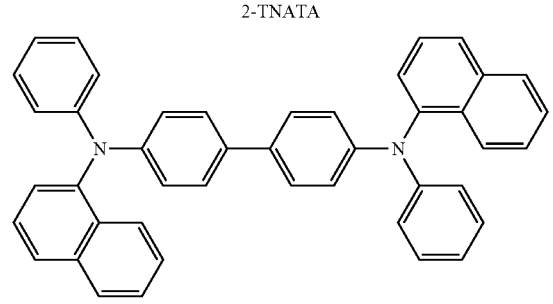

NPB

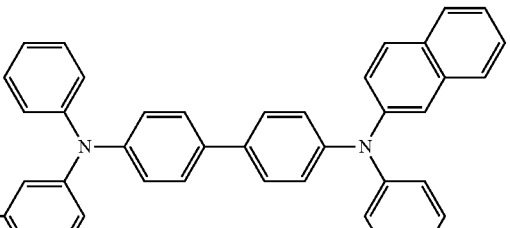

β-NPB

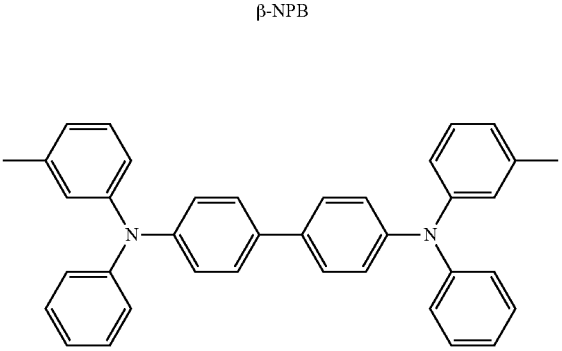

TPD

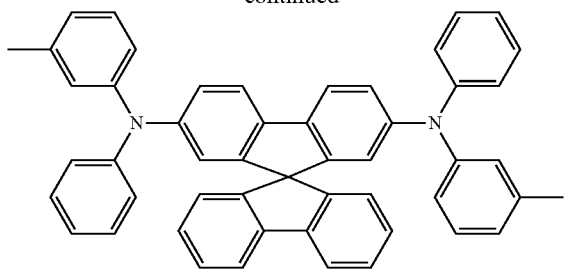

Spiro-TPD

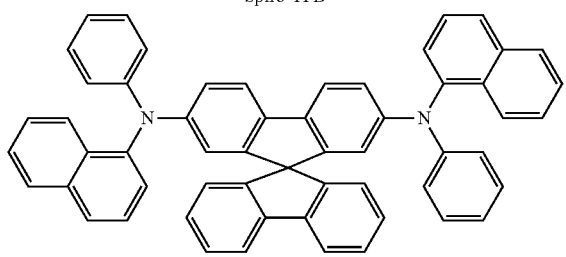

Spiro-NPB

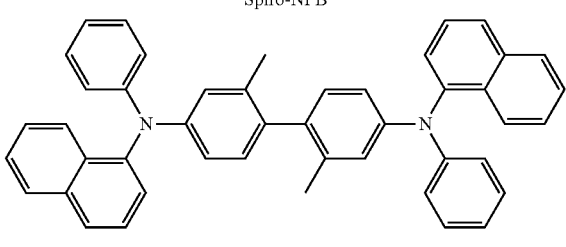

methylated NPB

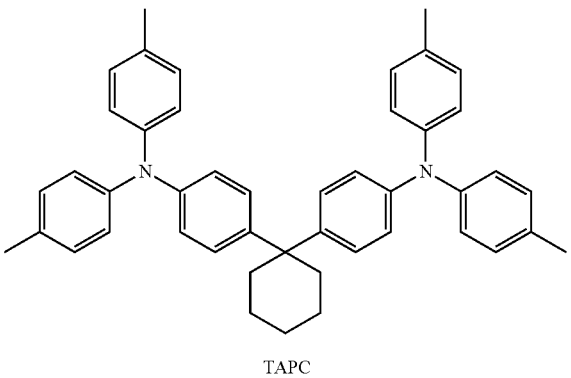

TAPC

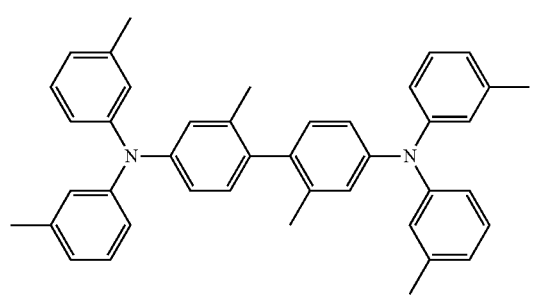

HMTPD

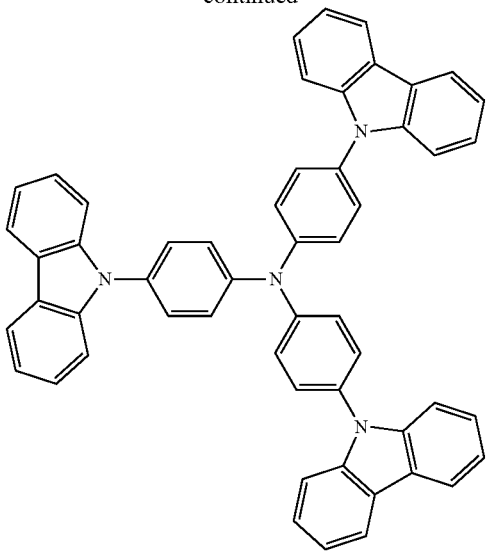

TCTA

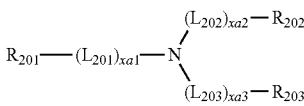

Formula 201

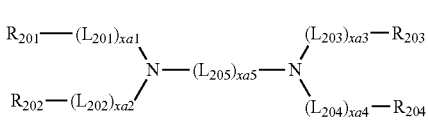

Formula 202 wherein, in Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be bound via a single bond, a dimethyl-methylene group, or a diphenyl-methylene group, and $R_{203}$ and $R_{204}$ may optionally be bound via a single bond, a dimethyl-methylene group, or a diphenyl-methylene group.

In one embodiment, in Formulae 201 and 202, $L_{201}$ to $L_{205}$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may be the same as those described herein.

In one or more embodiments, in Formula 201, at least one of $R_{201}$ to $R_{203}$ may be selected from a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In one or more embodiments, in Formula 202, i) $R_{201}$ and $R_{202}$ may be bound via a single bond, and/or ii) $R_{203}$ and $R_{204}$ may be bound via a single bond.

In one or more embodiments, in Formula 202, at least one of $R_{201}$ to $R_{204}$ may be selected from a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201A:

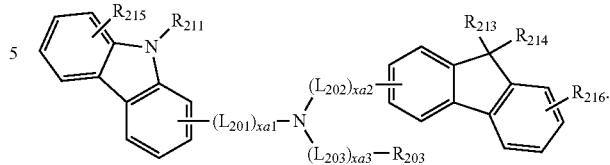

Formula 201A

In some embodiments, the compound represented by Formula 201 may be represented by Formula 201A(1), but embodiments are not limited thereto:

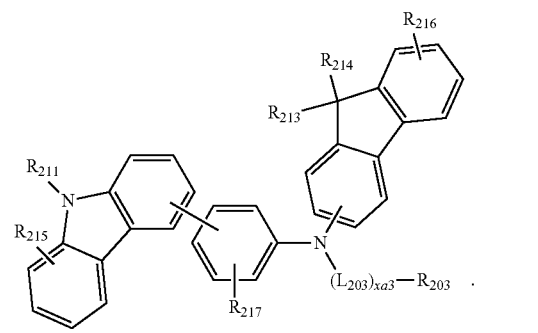

Formula 201A(1)

In some embodiments, the compound represented by Formula 201 may be represented by Formula 201A-1, but embodiments are not limited thereto:

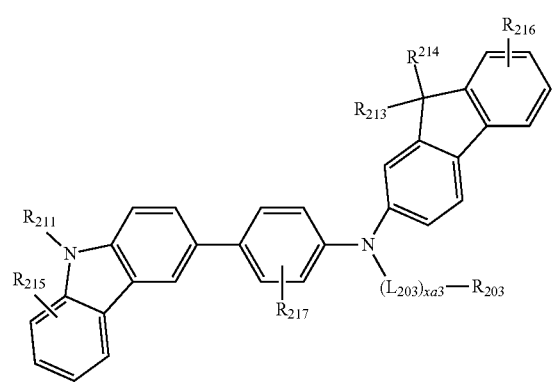

Formula 201A-1

In some embodiments, the compound represented by Formula 202 may be represented by Formula 202A:

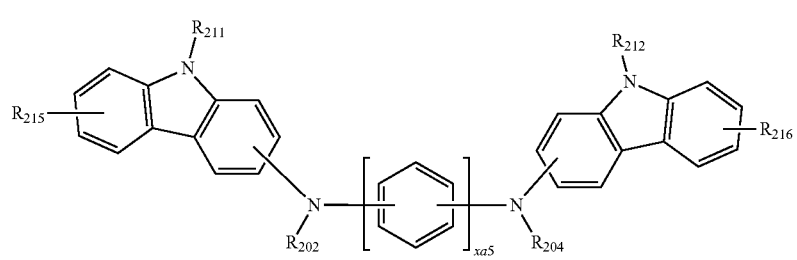

Formula 202A

In some embodiments, the compound represented by Formula 202 may be represented by Formula 202A-1:

Formula 202A-1

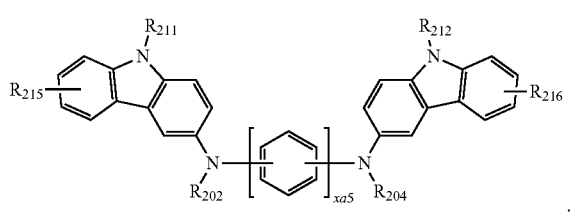

In Formulae 201A, 201A(1), 201A-1, 202A, and 202A-1,
$L_{201}$ to $L_{203}$, xa1 to xa3, and $R_{202}$ to $R_{204}$ may be the same as those described herein, $R_{211}$ and $R_{212}$ may each be the same as described above with reference to $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments are not limited thereto:

HT1

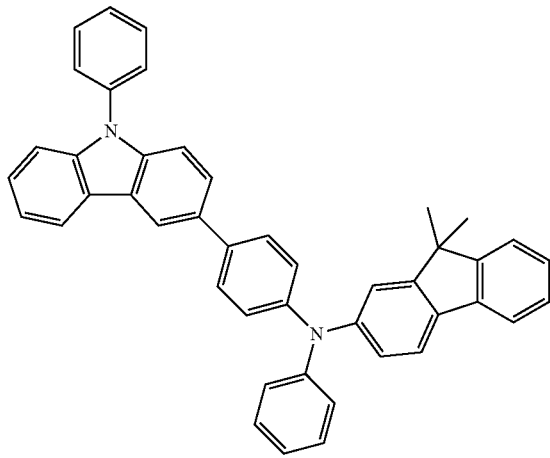

HT2

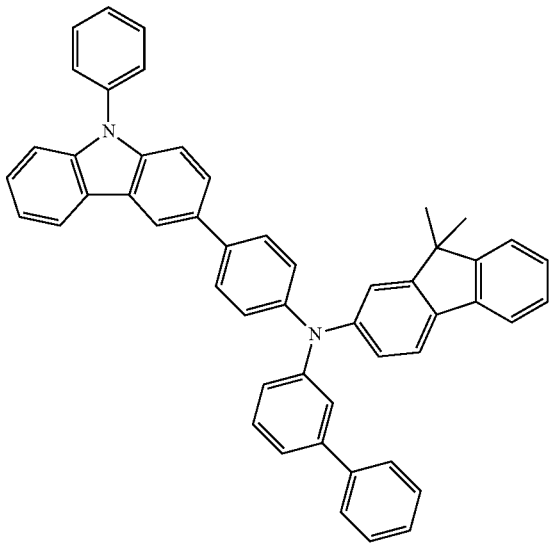

-continued
HT3
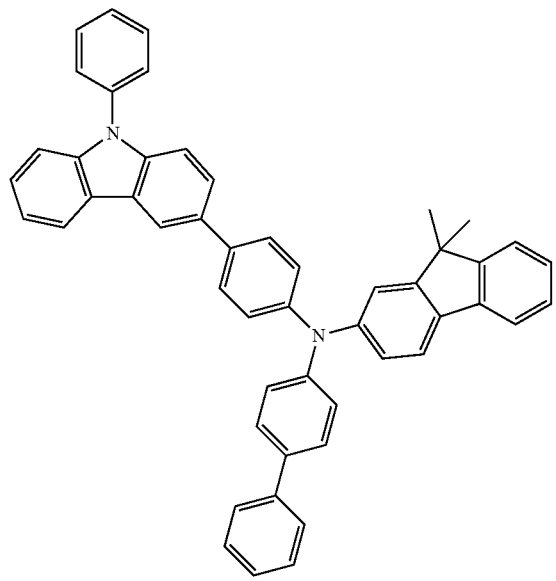
HT4
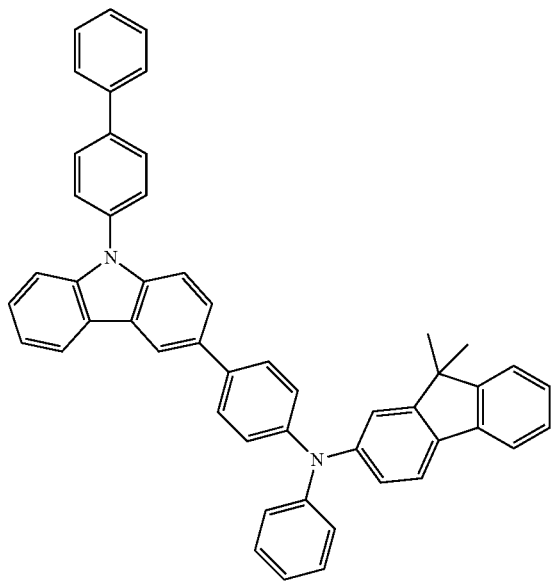
HT5
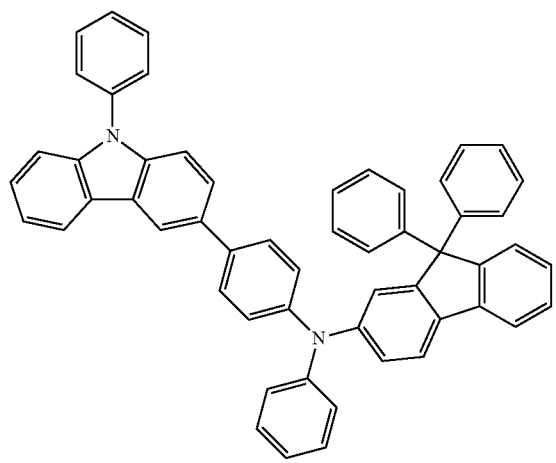
HT6
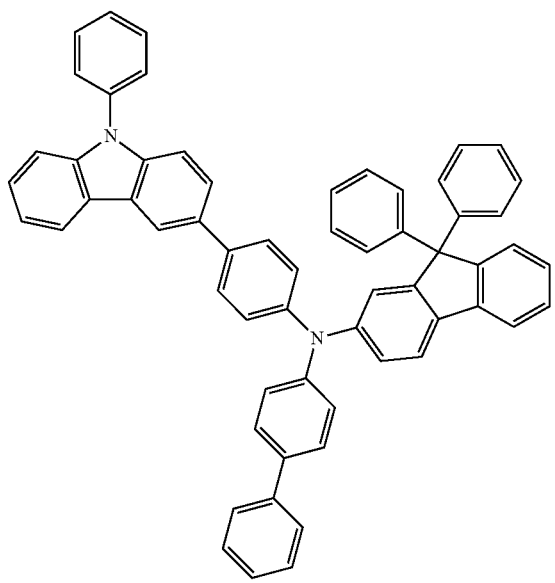

-continued
HT7
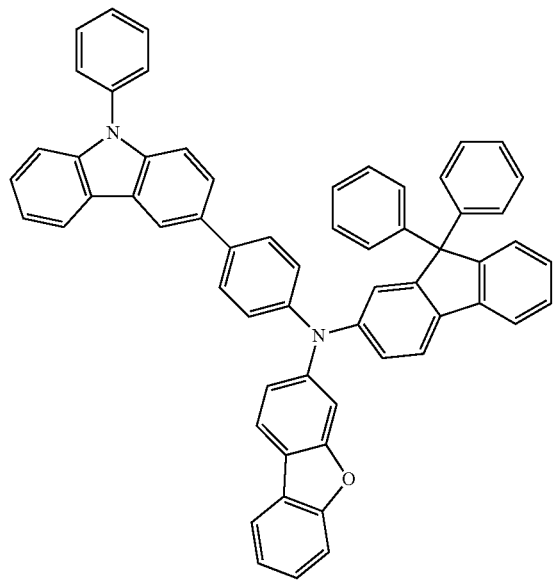
HT8
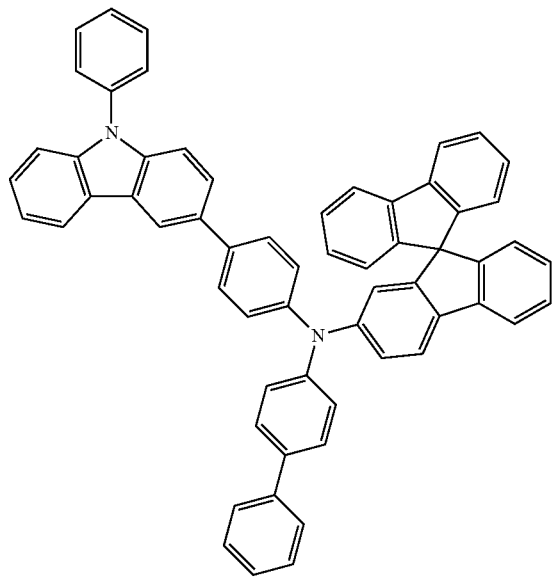
HT-9
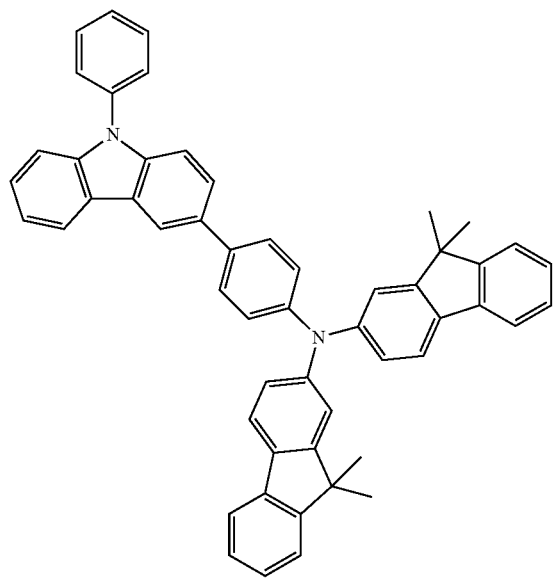
HT-10
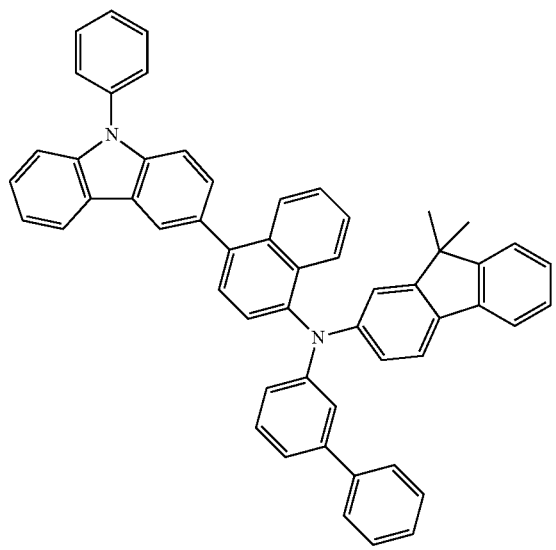

-continued
HT11
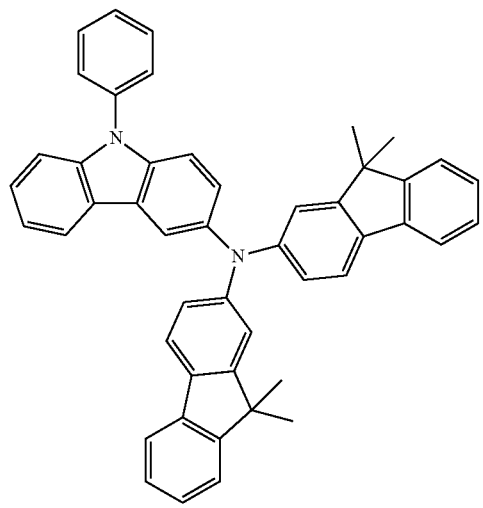
HT12
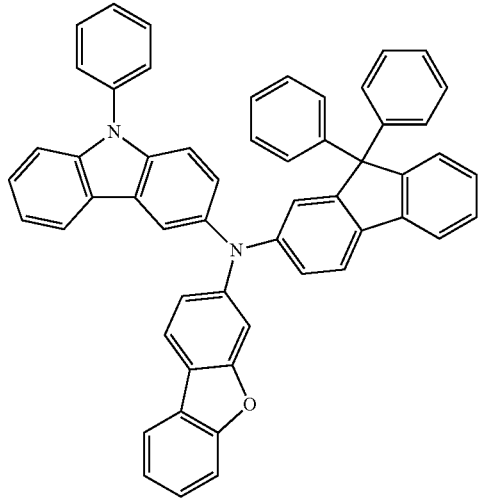
HT13
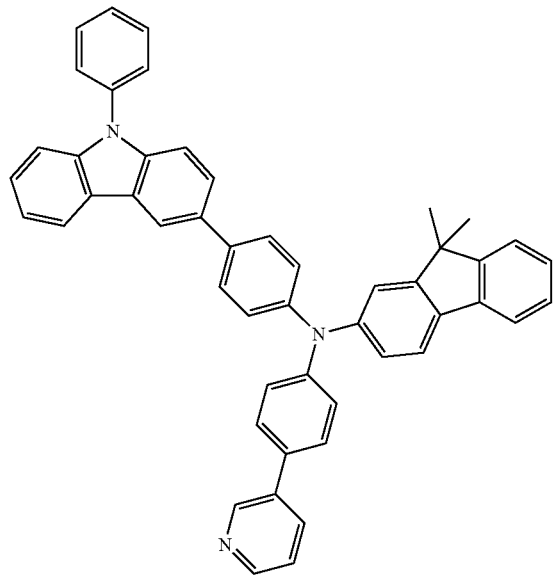
HT14
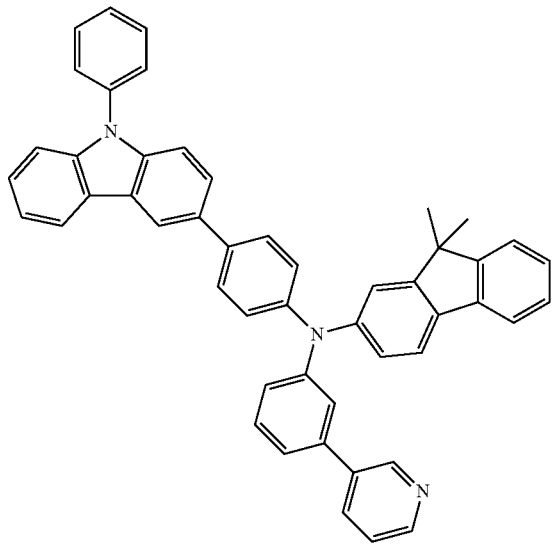
HT15
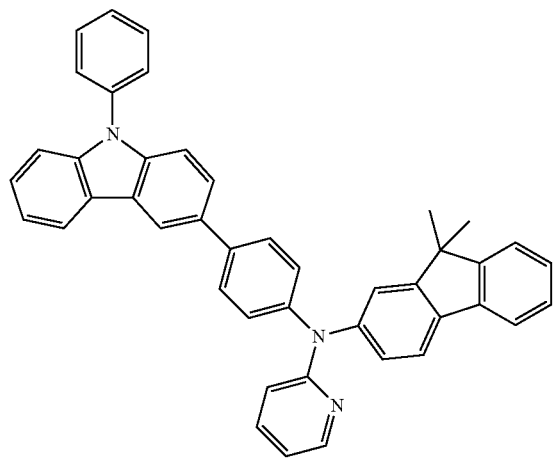
HT16
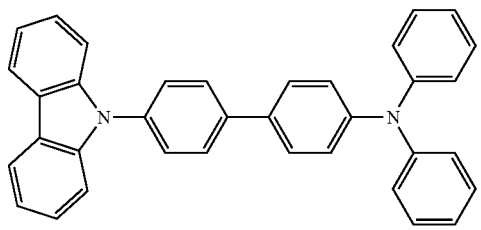

-continued
HT17
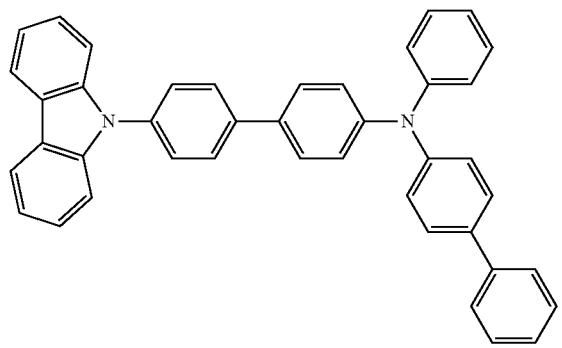
HT18
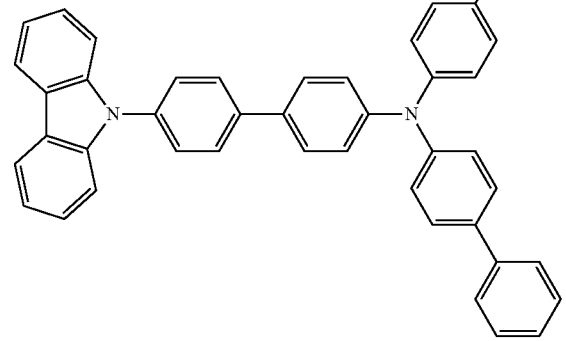
HT19
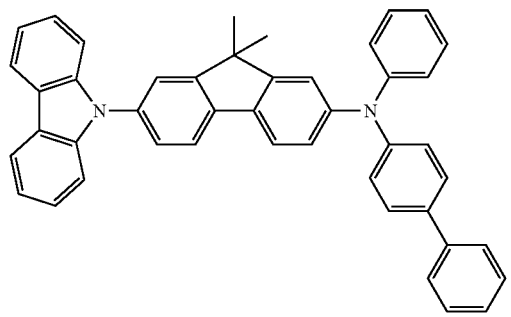
HT20
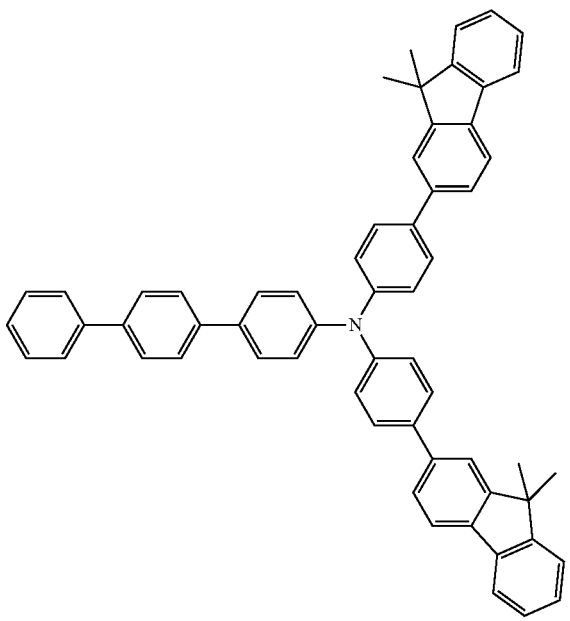
HT21
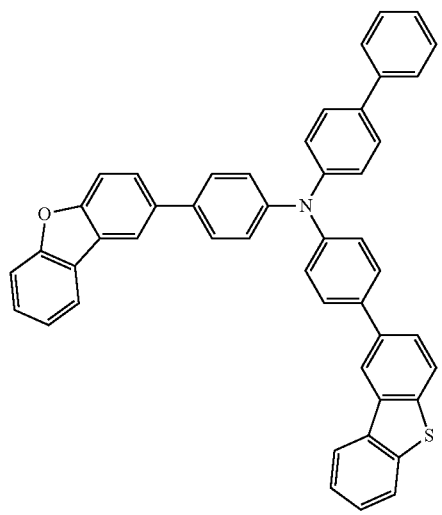
HT22
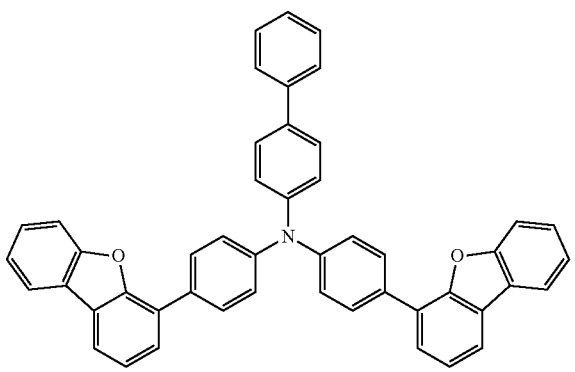

-continued
HT23
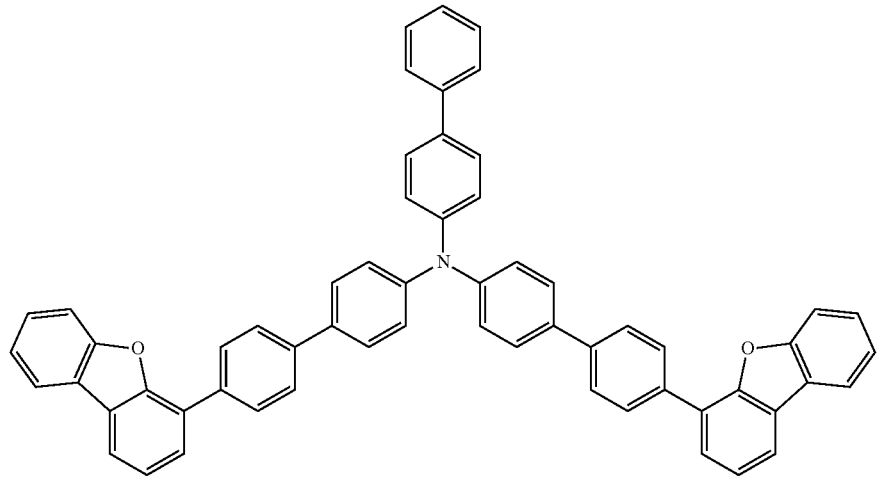
HT24
HT25
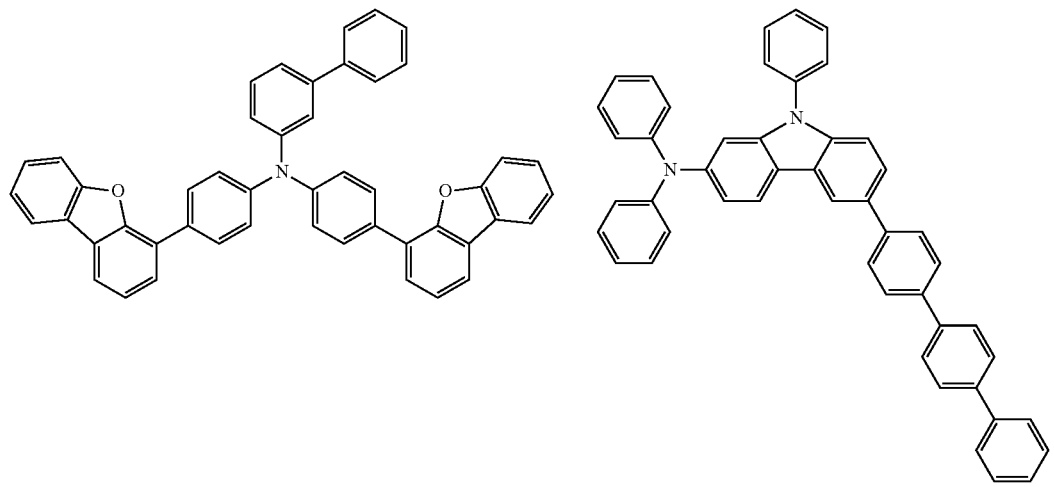
HT26
HT27
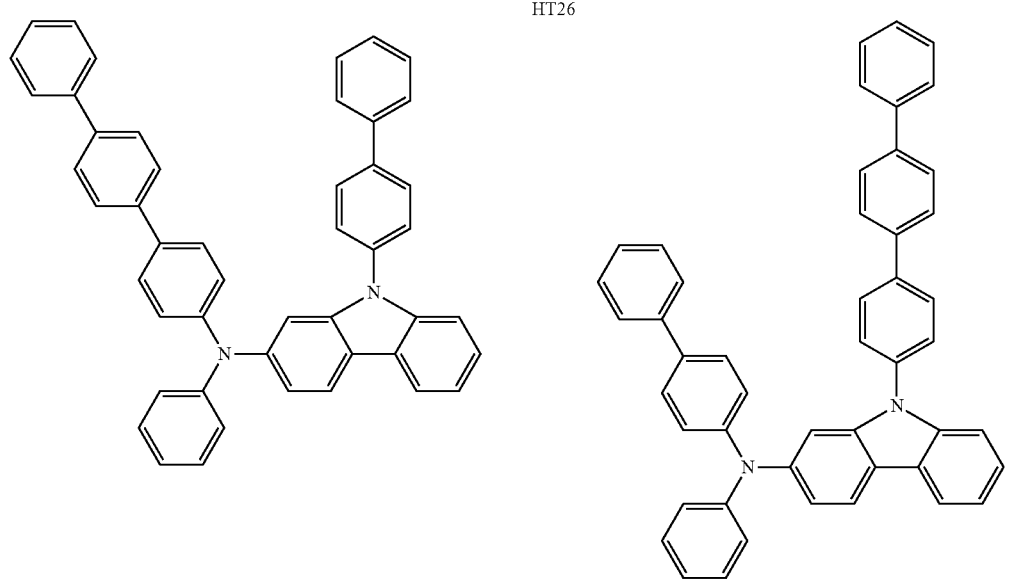

-continued
HT28
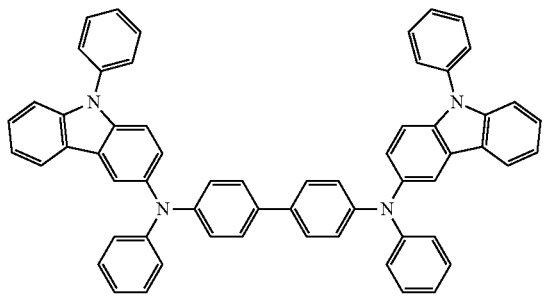
HT29
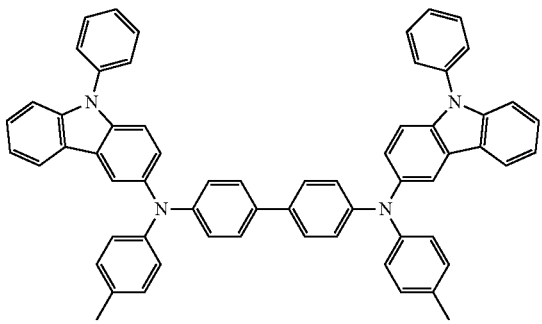
HT30
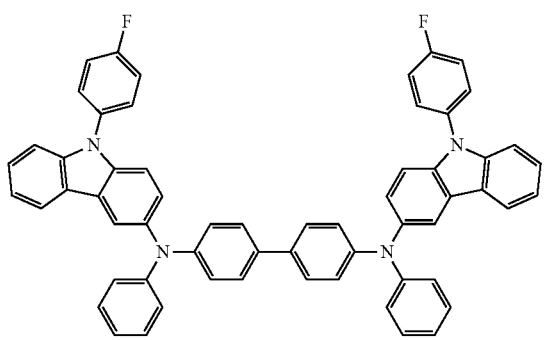
HT31
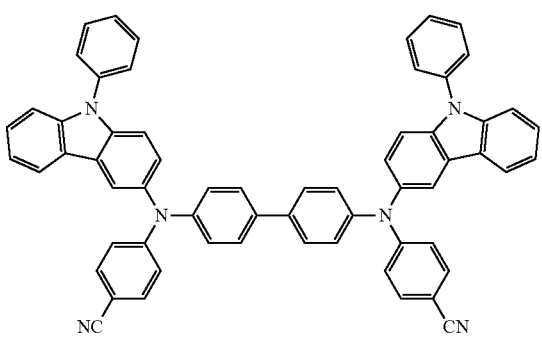
HT32
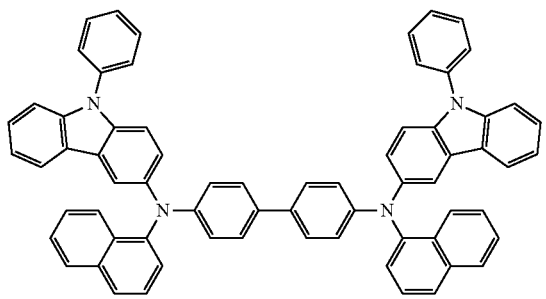
HT33
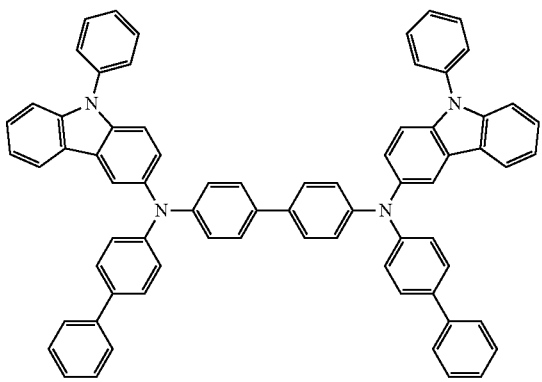
HT34
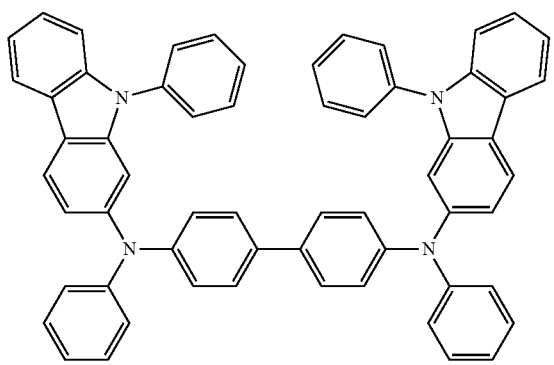
HT35
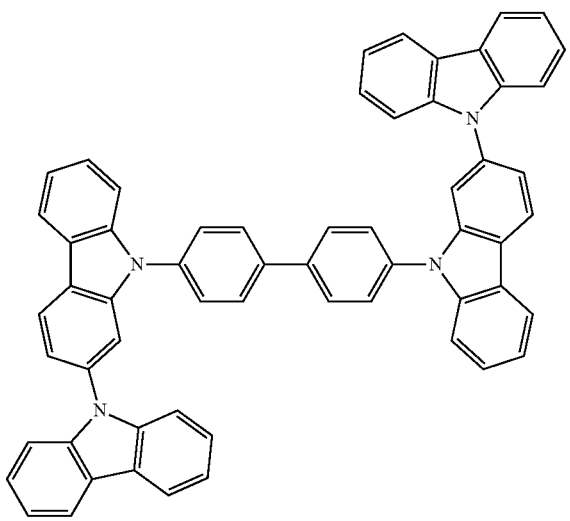

-continued

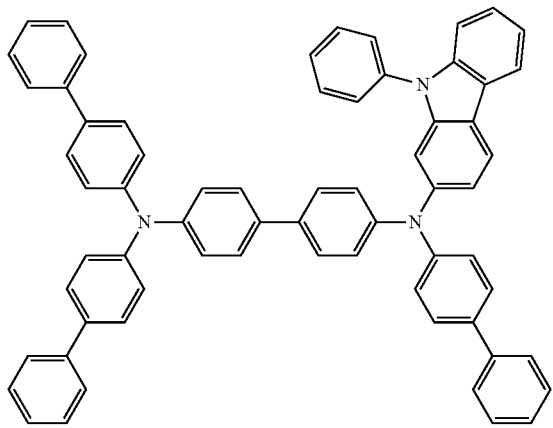

HT36

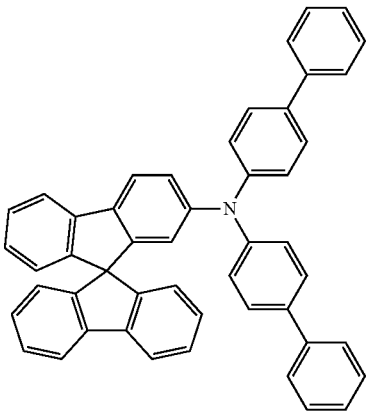

HT37

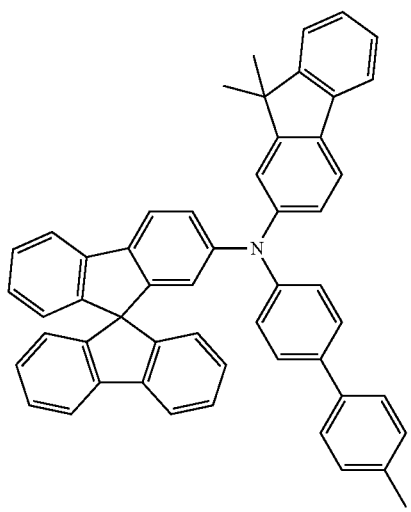

HT38

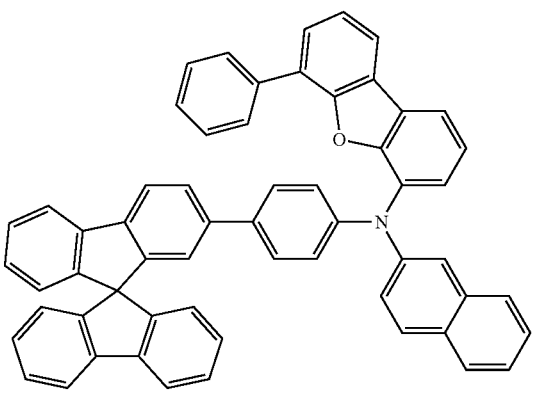

HT39

The thickness of the hole transport region may be in a range of about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The emission auxiliary layer may increase the light-emission efficiency by compensating for an optical resonance distance depending on the wavelength of light emitted by an emission layer, and the electron blocking layer may block or reduce the flow of electrons from an electron transport region. The emission auxiliary layer and the electron blocking layer may include the materials as described above.

p-Dopant

The hole transport region may further include, in addition to these materials, a charge generating material to improve conductive properties. The charge generating material may be homogeneously or non-homogeneously dispersed in the hole transport region.

The charge generating material may be, for example, a p-dopant.

In one embodiment, the p-dopant may have a lowest unoccupied molecular orbital (LUMO) level of about −3.5 eV or less.

The p-dopant may include at least one selected from a quinone derivative, a metal oxide, and a cyano group-containing compound, but embodiments are not limited thereto.

In some embodiments, the p-dopant may include at least one selected from a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221, but embodiments of the present disclosure are not limited thereto:

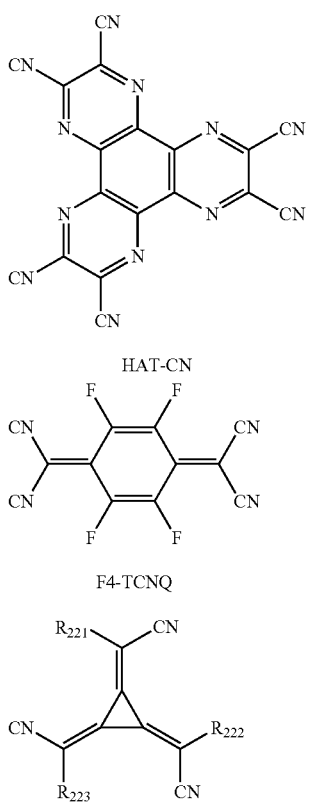

HAT-CN

F4-TCNQ

Formula 221 wherein, in Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, wherein the two or m ore layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

In one embodiment, the emission layer of the organic light-emitting device 10 may be a first color light emission layer, the organic light-emitting device 10 may further include i) at least one second color light emission layer or ii) at least one second color light emission layer and at least one third color light emission layer, between the first electrode 110 and the second electrode 190, a maximum emission wavelength of the first color light emission layer, a maximum emission wavelength of the second color light emission layer, and a maximum emission wavelength of the third color light emission layer are identical to or different from each other, and the organic light-emitting device 10 may emit mixed light including the first color light and the second color light, or mixed light including the first color light, the second color light, and the third color light, but embodiments are not limited thereto.

For example, the maximum emission wavelength of the first color light emission layer is different from a maximum emission wavelength of the second color light emission layer, and the mixed light including first color light and second color light may be white light, but embodiments are not limited thereto.

In one or more embodiments, the maximum emission wavelength of the first color light emission layer, the maximum emission wavelength of the second color light emission layer, and the maximum emission wavelength of the third color light emission layer may be different from one another, and the mixed light including the first color light, the second color light, and the third color light may be white light. However, embodiments are not limited thereto.

The emission layer may include a host and a dopant. The dopant may include a phosphorous dopant or a fluorescent dopant.

The amount of the dopant in the emission layer may be in a range of about 0.01 parts to about 15 parts by weight based on 100 parts by weight of the host, but embodiments are not limited thereto.

The thickness of the emission layer may be in a range of about 100 Å to about 1,000 Å, and in some embodiments, about 200 Å to about 600 Å. When the thickness of the emission layer is within any of these ranges, excellent light-emission characteristics may be obtained without a substantial increase in driving voltage.

Host in Emission Layer

The host may include the condensed cyclic compound represented by Formula 1.

In one or more embodiments, the host may include a compound represented by Formula 301:

wherein, in Formula 301, $Ar_{301}$ may be selected from a substituted or unsubstituted $C_5$-$C_{60}$ carbocyclic group and a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In one embodiment, in Formula 301, $Ar_{301}$ may be selected from a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is 2 or greater, at least two $Ar_{301}$ (s) may be bound via a single bond.

In one or more embodiments, the compound represented by Formula 301 may be represented by Formula 301-1 or 301-2:

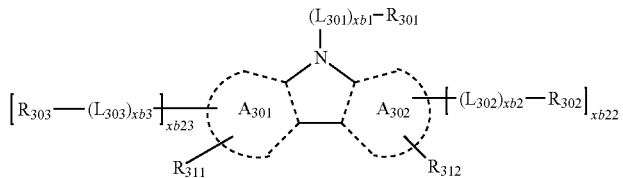

Formula 301-1

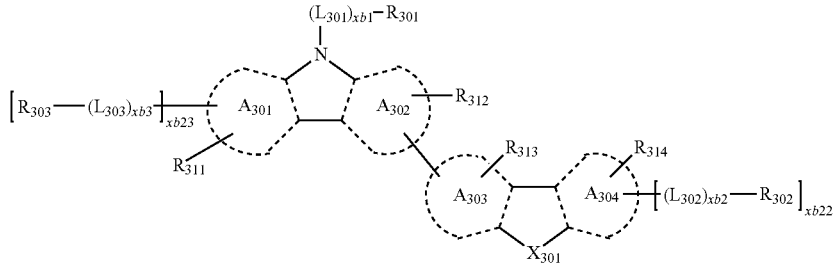

Formula 301-2 wherein, in Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may be the same as those described herein, $L_{302}$ to $L_{304}$ may each independently be substantially the same as described herein with reference to $L_{301}$, xb2 to xb4 may each independently be substantially the same as described herein with reference to xb1, and $R_{302}$ to $R_{304}$ may each independently be substantially the same as described herein with reference to $R_{301}$.

In some embodiments, in Formulae 301, 301-1, and 301-2, $L_{301}$ to $L_{304}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as those described above.

In some embodiments, in Formulae 301, 301-1, and 301-2, $R_{301}$ to $R_{304}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as those described above.

In some embodiments, the host may include an alkaline earth metal complex.

For example, the host may include a beryllium (Be) complex, for example, Compound H55, a magnesium (Mg) complex, or a zinc (Zn) complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments are not limited thereto:

H1

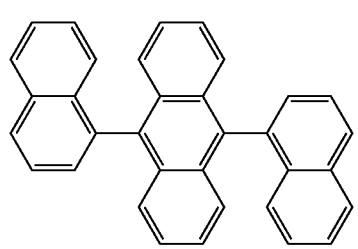

H2

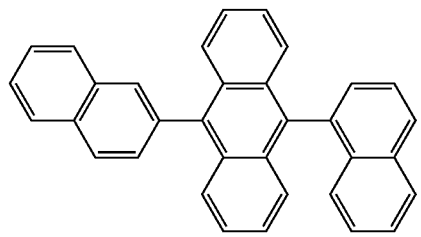

H3

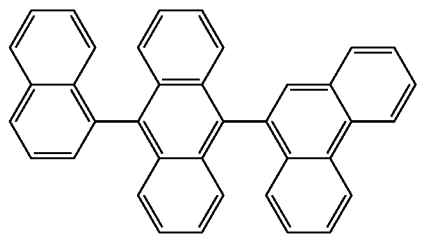

H4

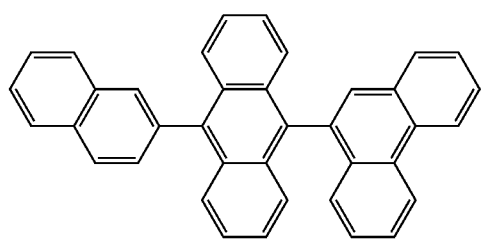

H5

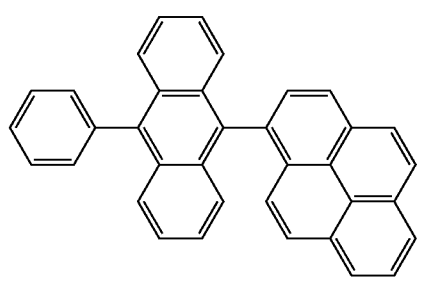

H6

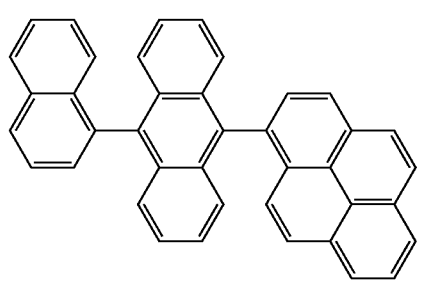

H7

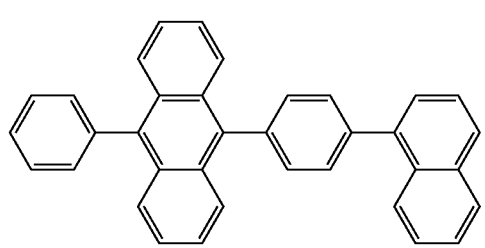

-continued
H8
H9
H10
H11
H12
H13
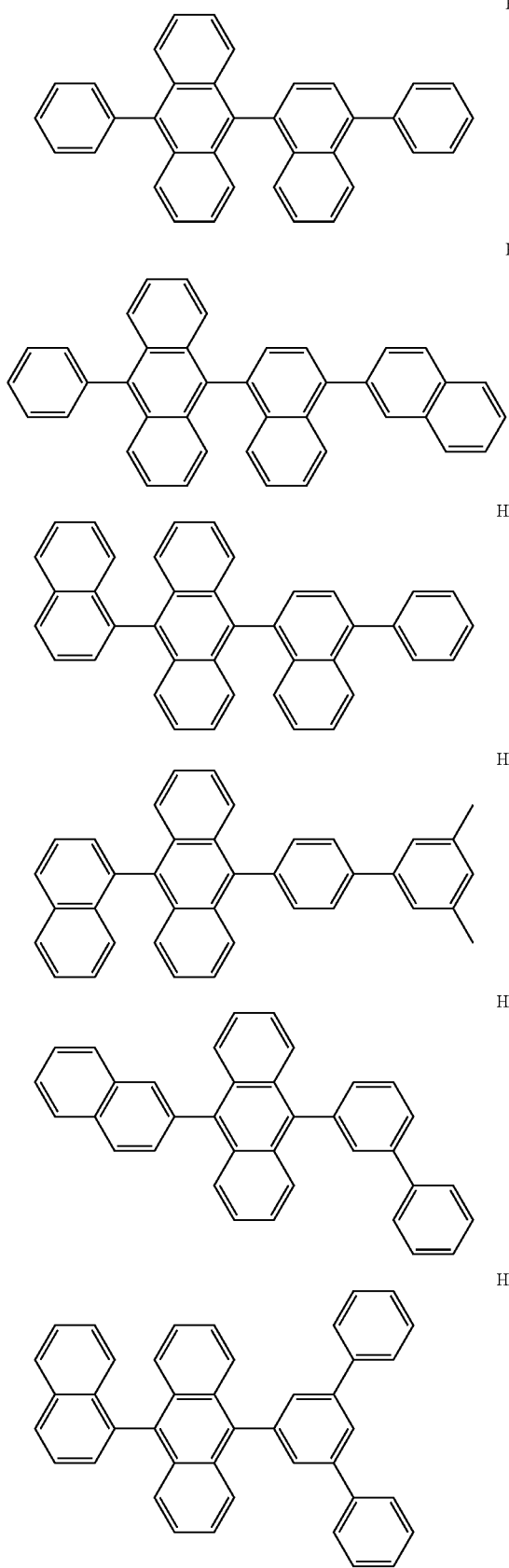
-continued
H14
H15
H16
H17
H18
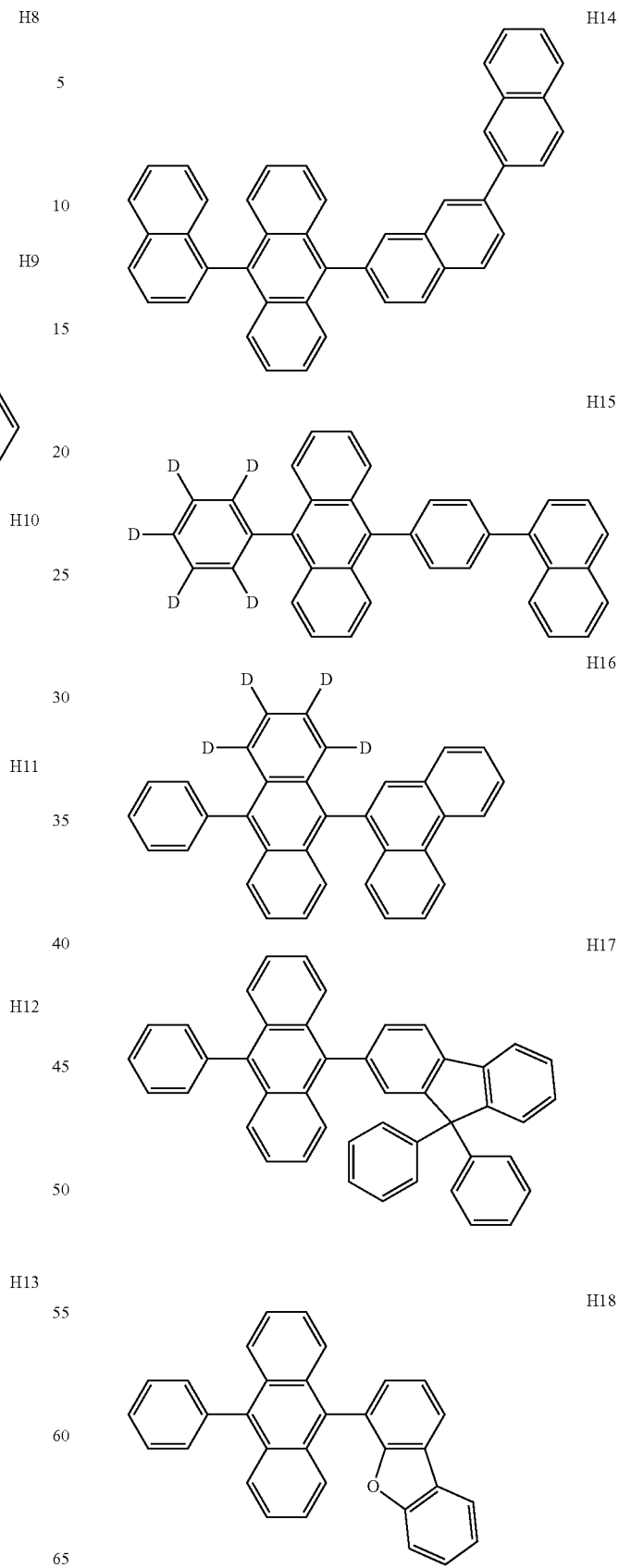

H19
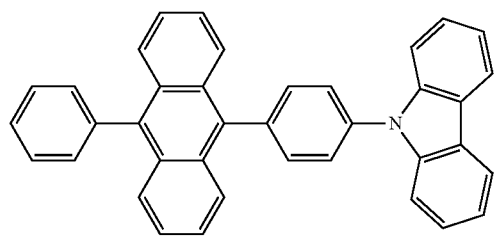
HT20
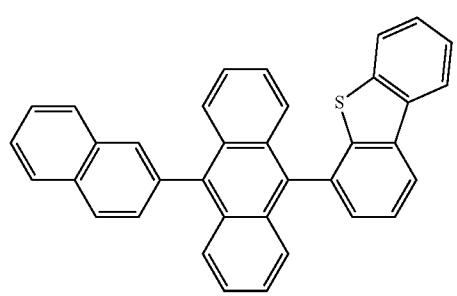
HT21
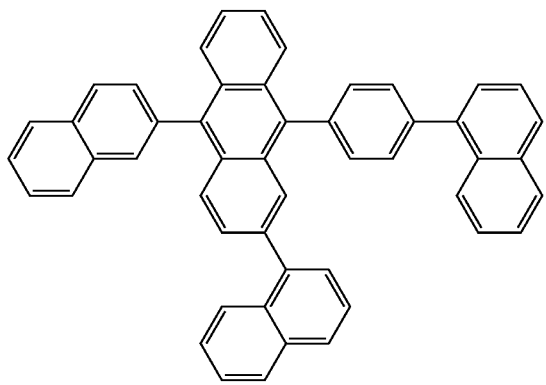
HT22
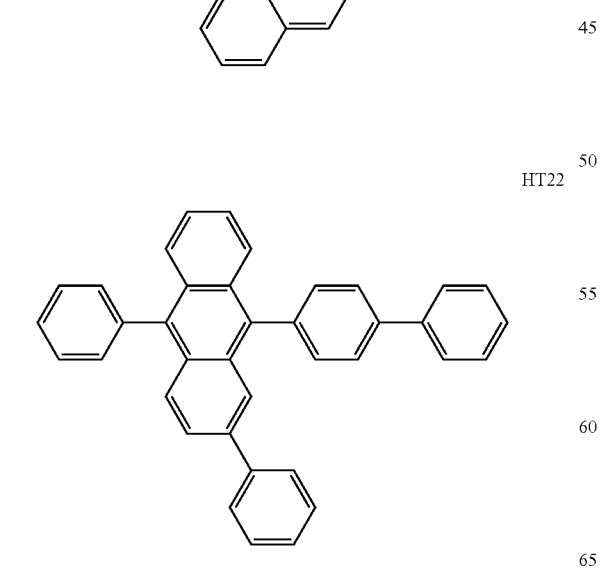
HT23
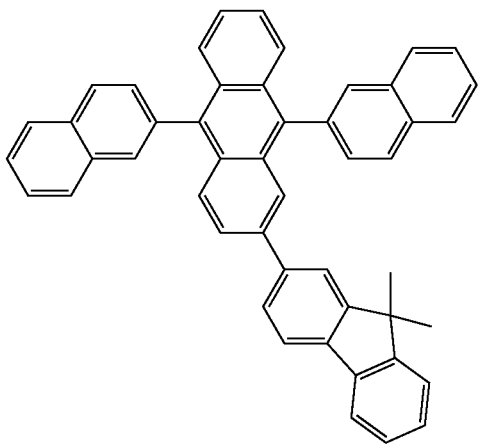
H24
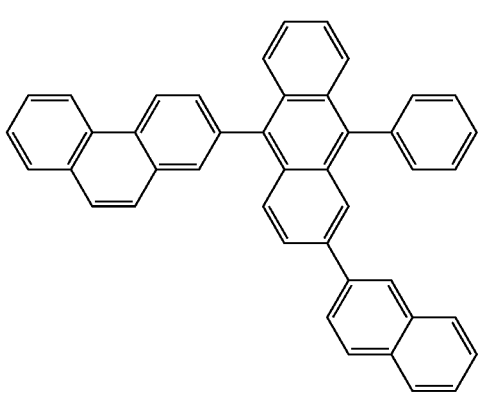
H25
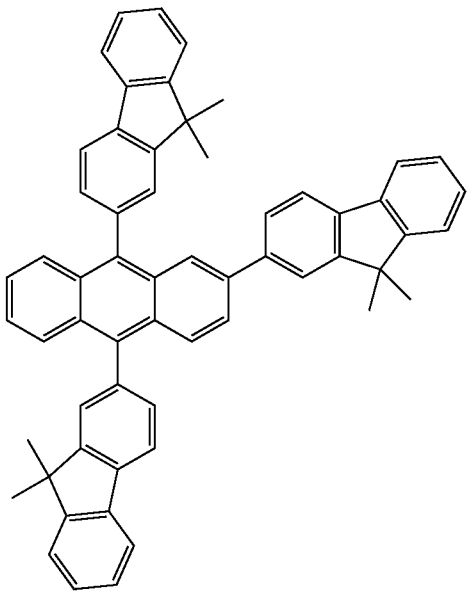

119
-continued
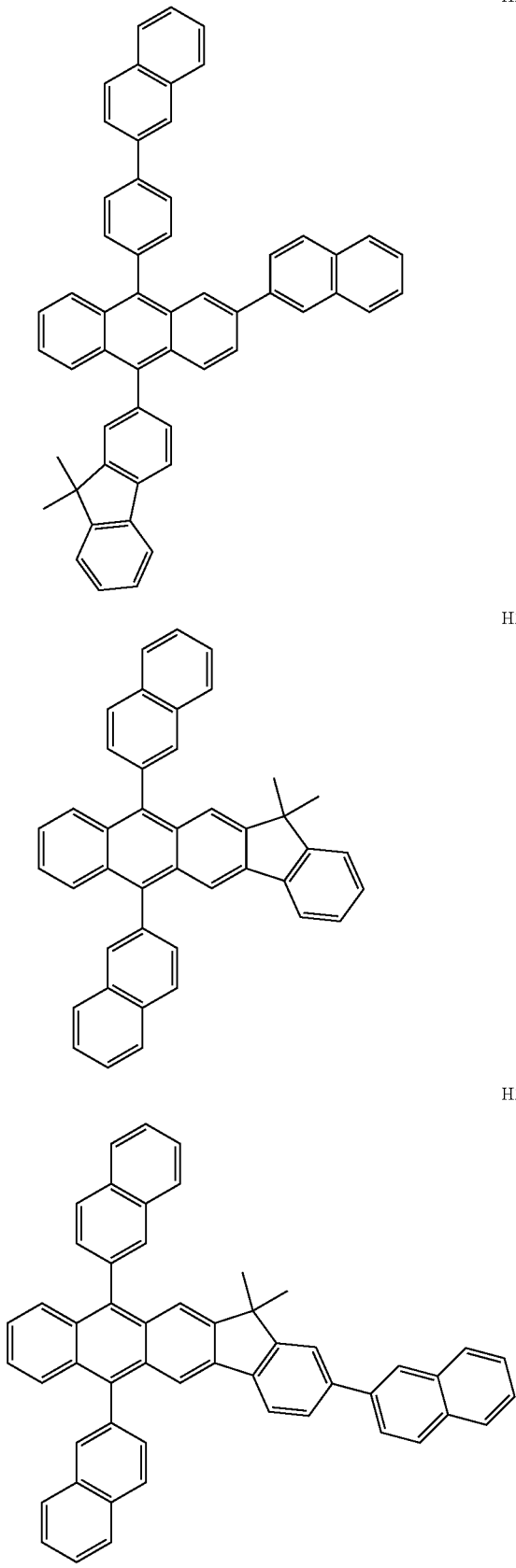
H26
120
-continued
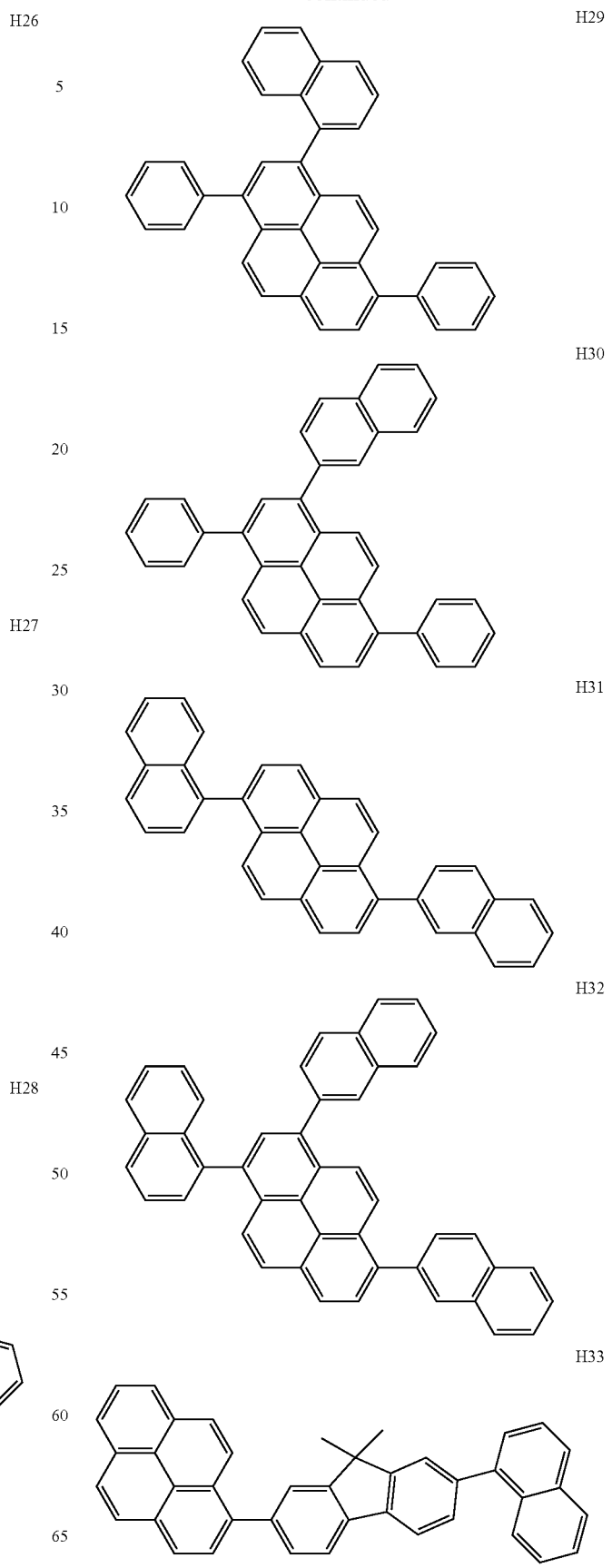
H29
H30
H31
H32
H33
H27
H28

H34
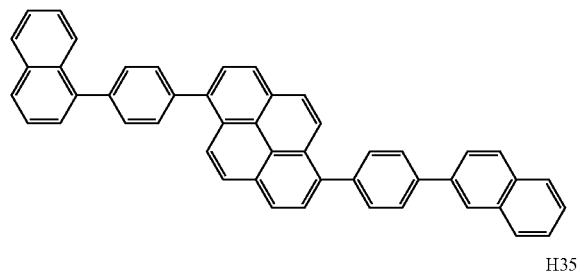
H35
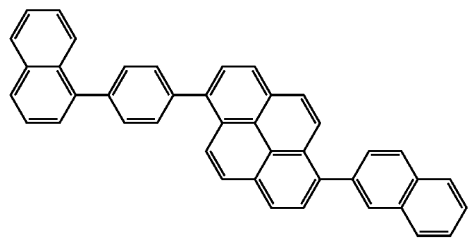
H36
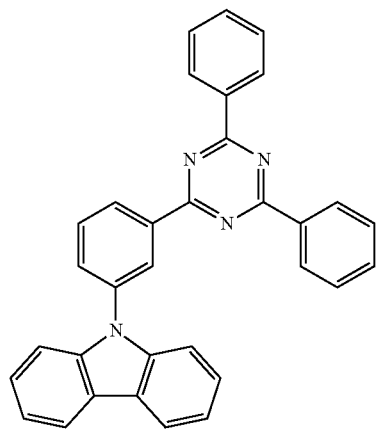
H37
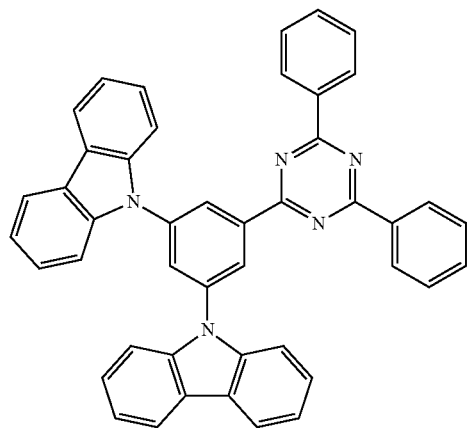
H38
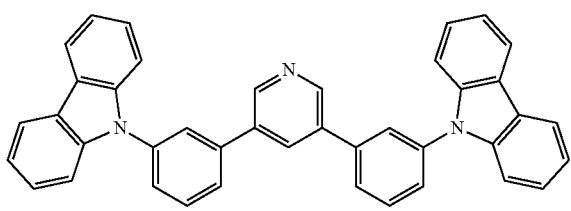
H39
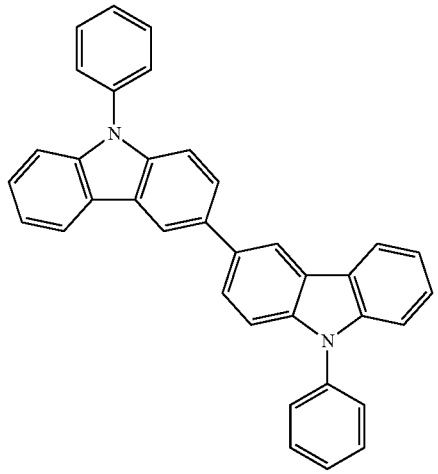
H40
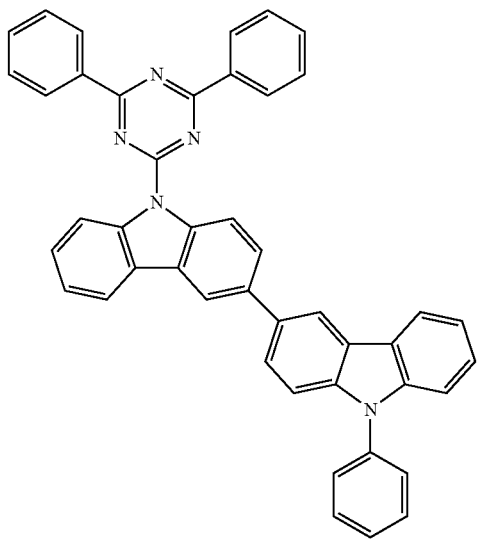
H41
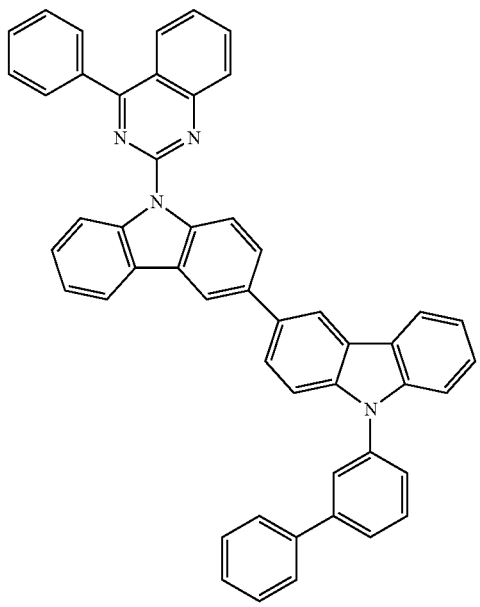

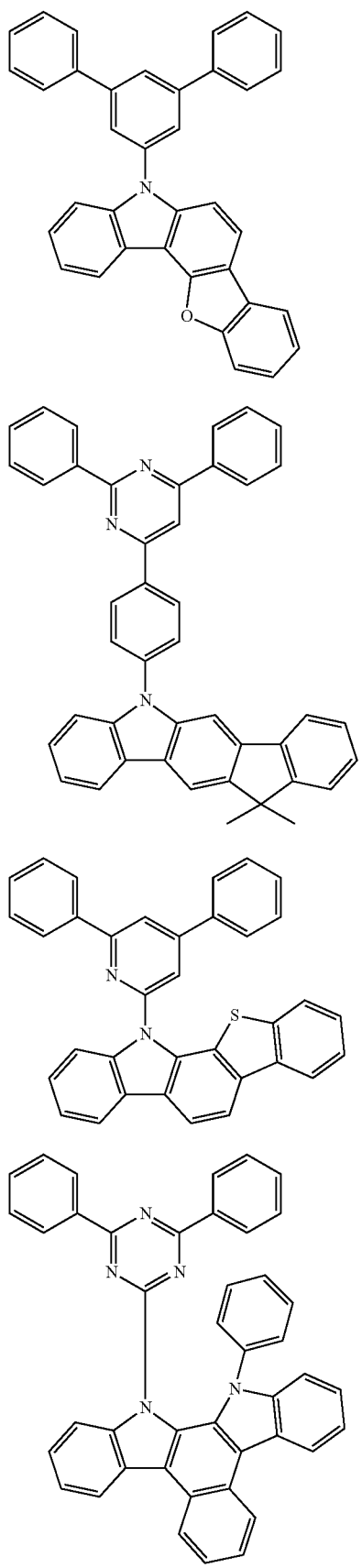
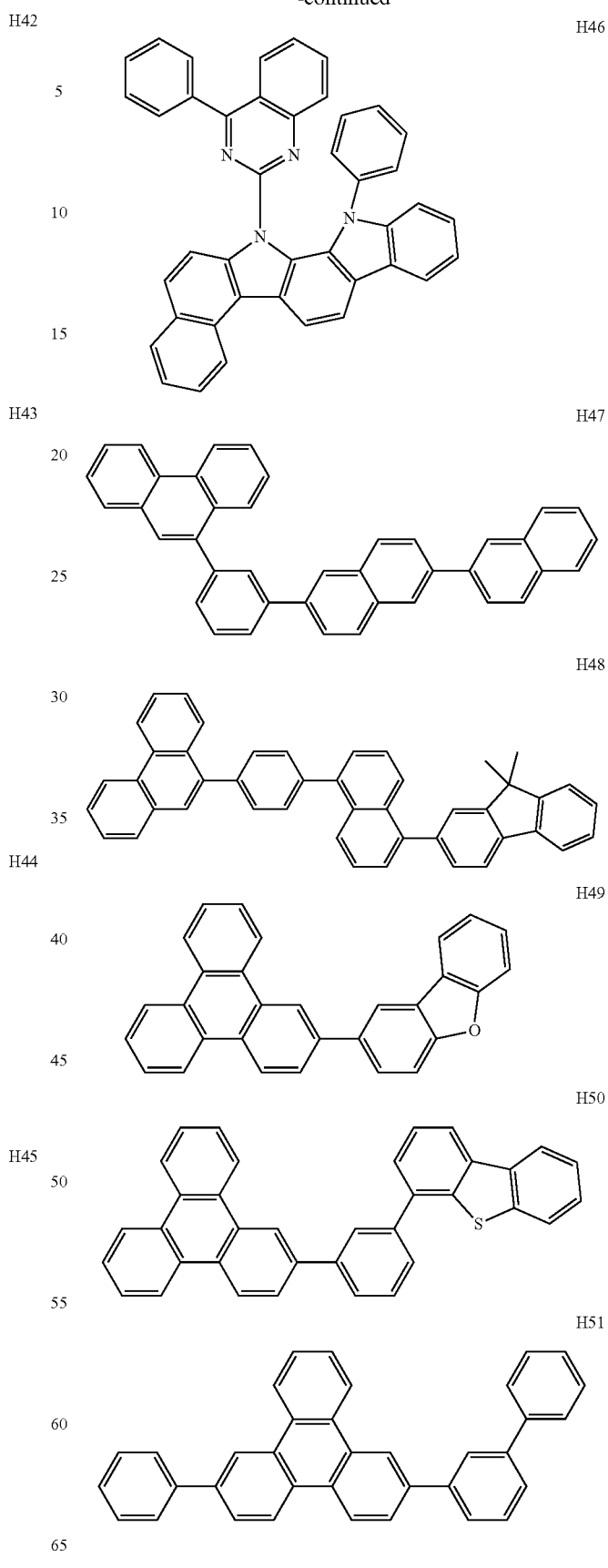

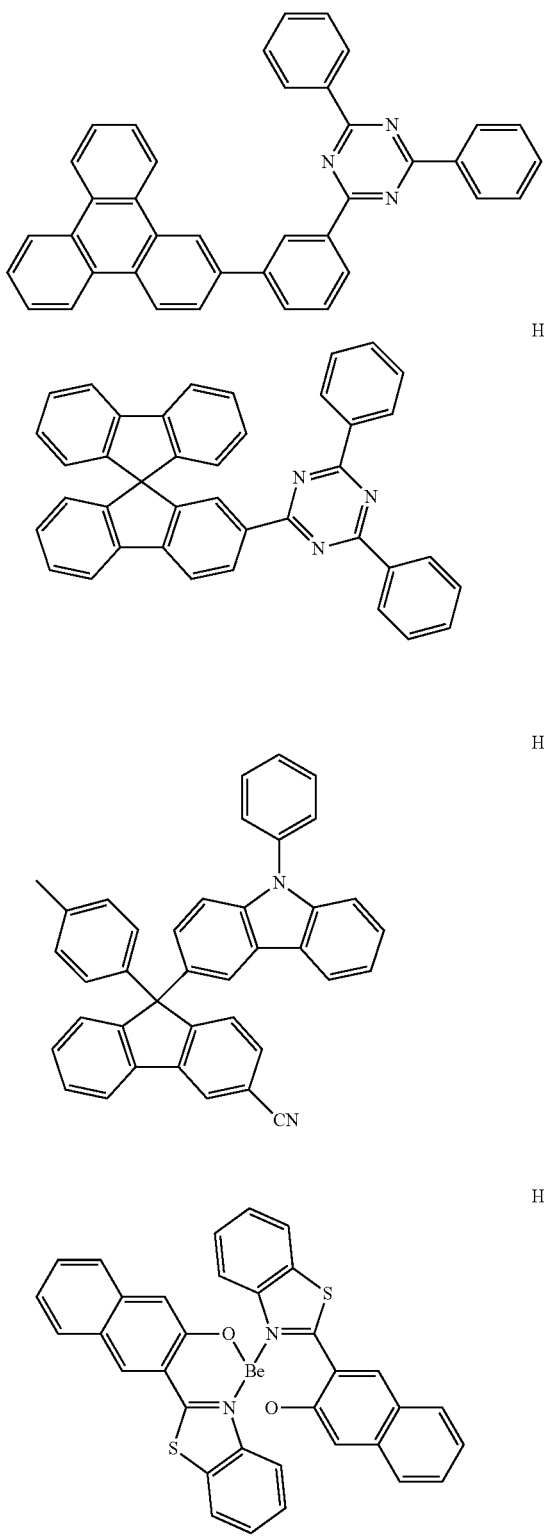

Fluorescent Dopant in Emission Layer

The fluorescent dopant may include an arylamine compound or a styrylamine compound.

The fluorescent dopant may include a compound represented by Formula 501:

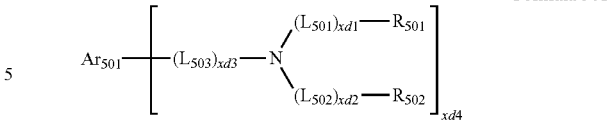

Formula 501 wherein, in Formula 501, $Ar_{501}$ may be selected from a substituted or unsubstituted $C_5$-$C_{60}$ carbocyclic group and a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, in Formula 501, $Ar_{501}$ may be selected from a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formula 501, $L_{501}$ and $L_{503}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one embodiment, in Formula 501, $R_{505}$ and $R_{502}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

In some embodiments, the fluorescent dopant may be selected from Compounds FD1 to FD22:

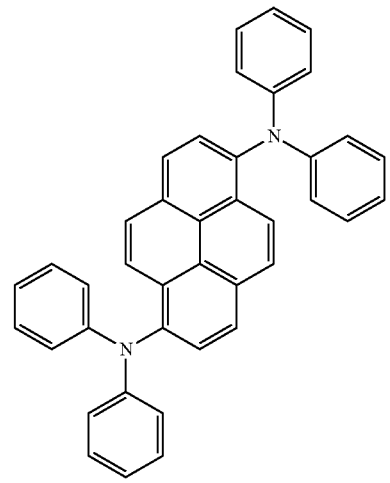

FD1

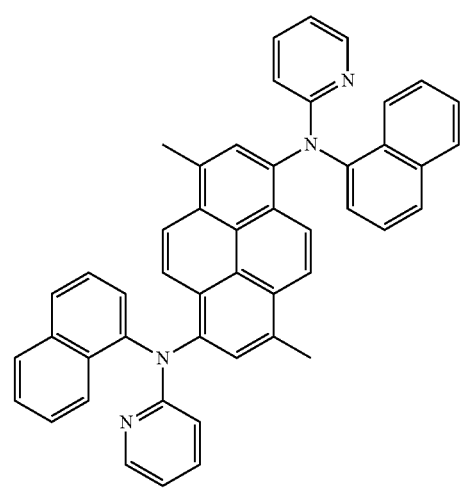

FD2

129
-continued
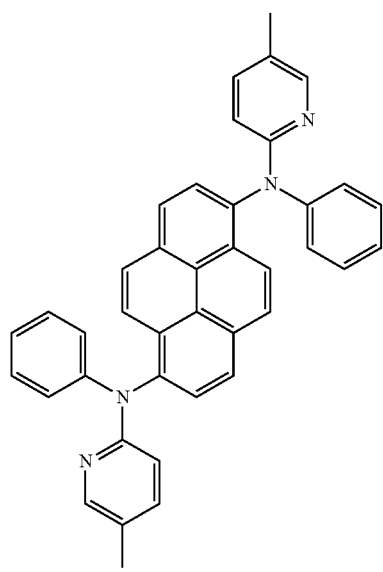
130
-continued
FD3
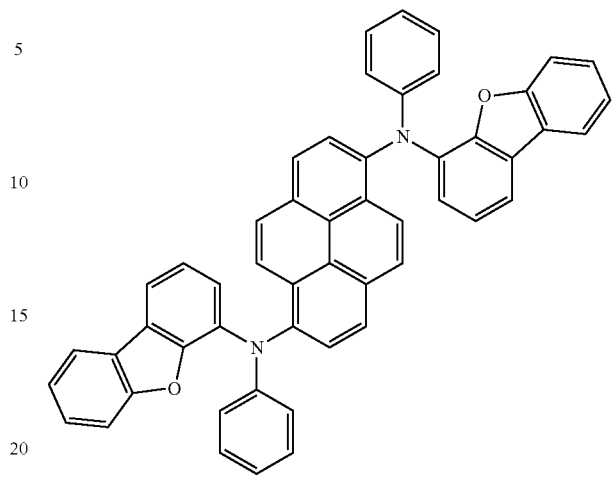
FD5
FD6
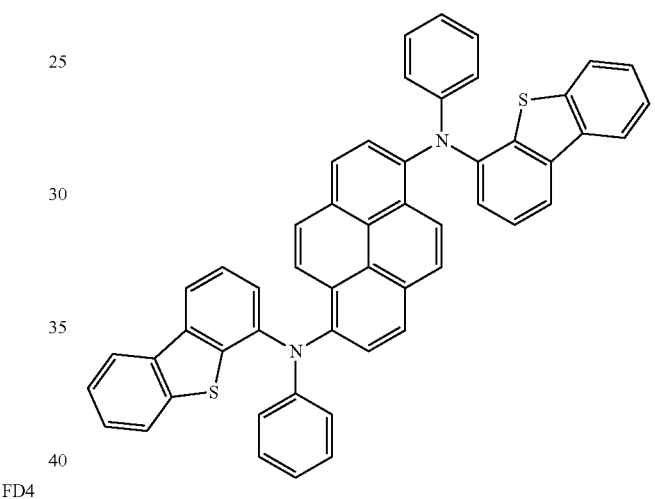
FD4
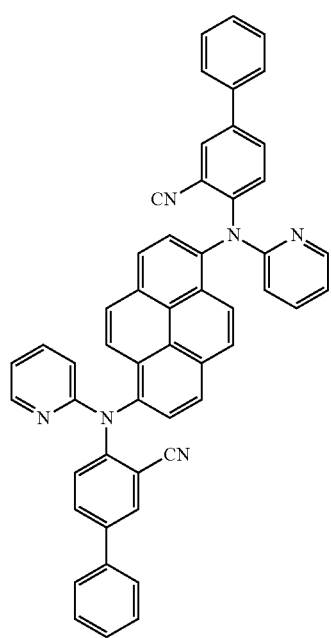
FD7
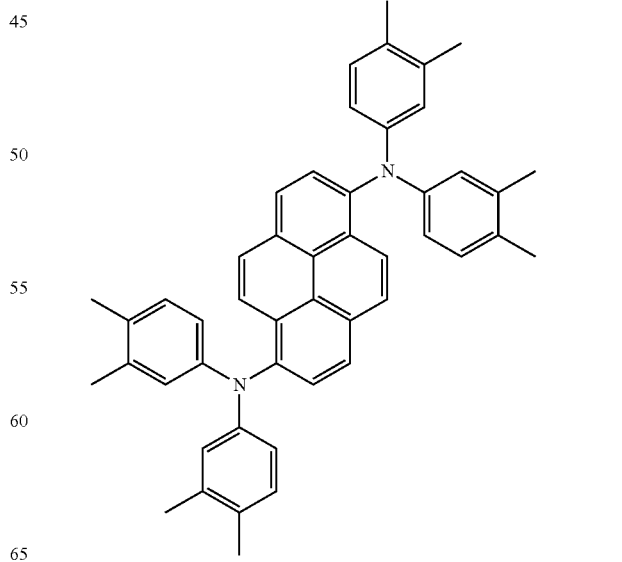

-continued
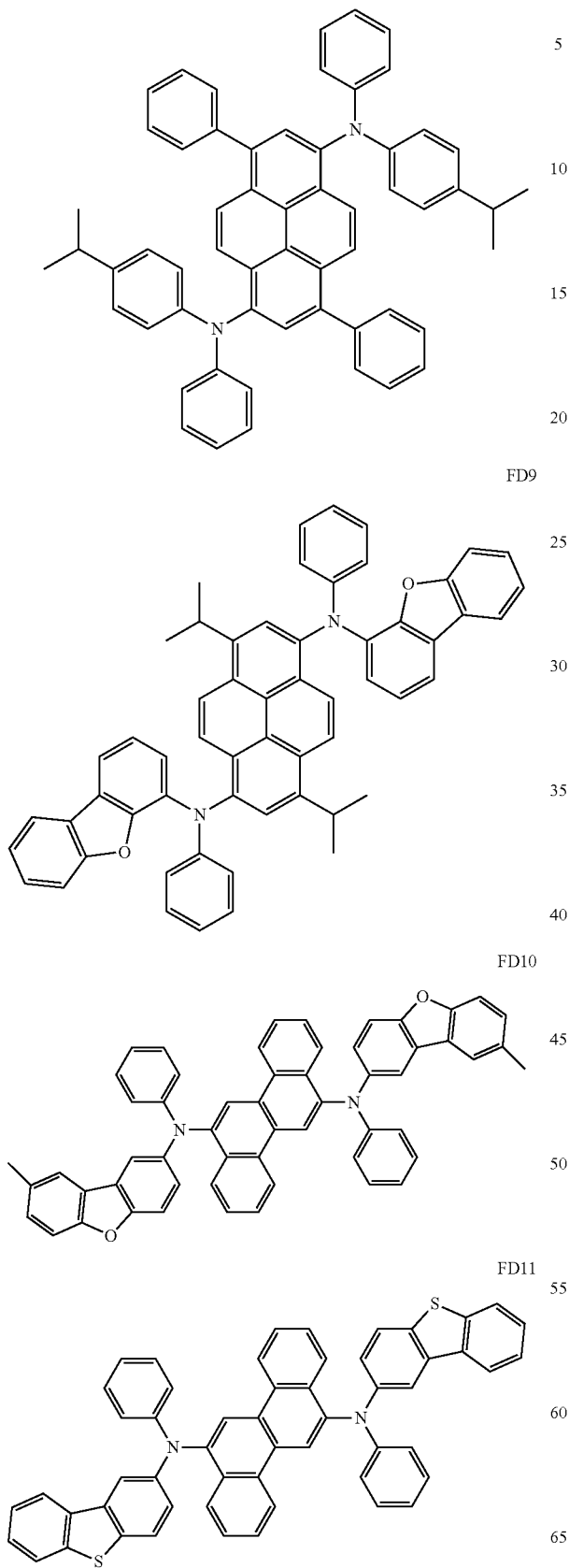
FD8
FD9
FD10
FD11
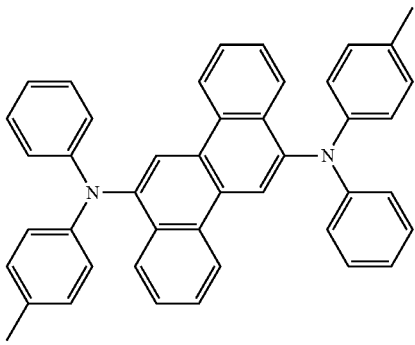
FD12
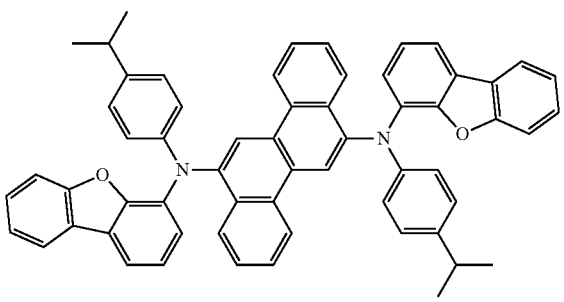
FD13
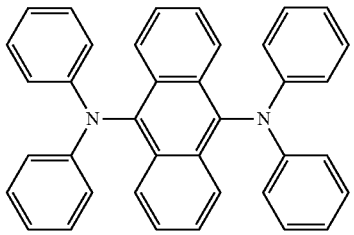
FD14
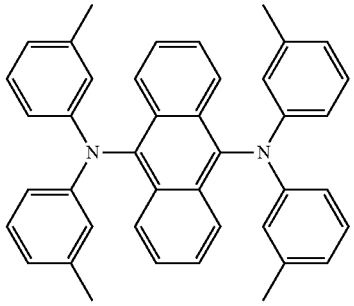
FD15
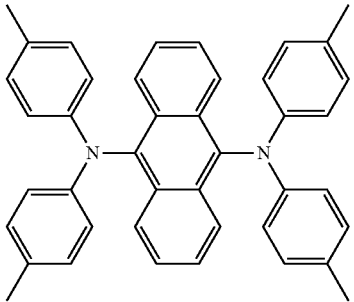
FD16

FD17 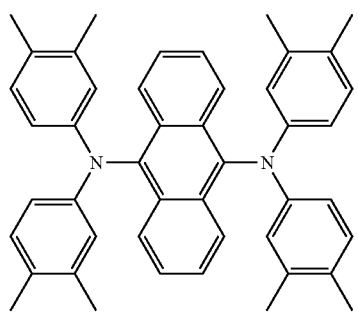
FD18 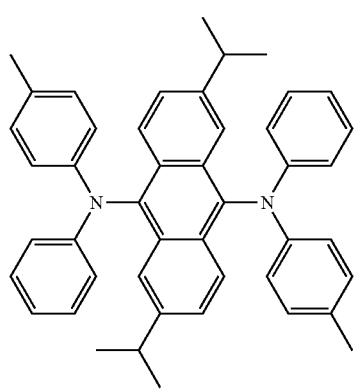
FD19 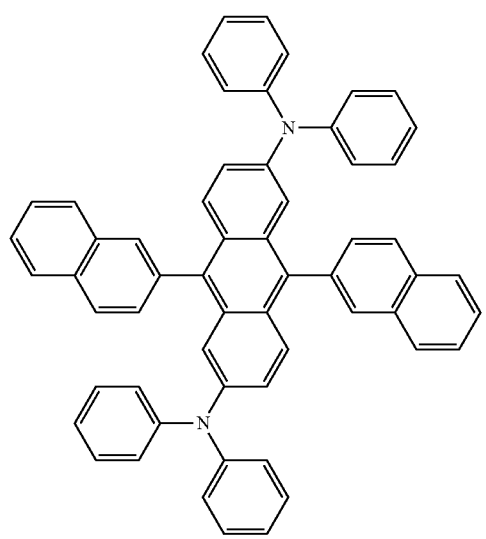
FD20 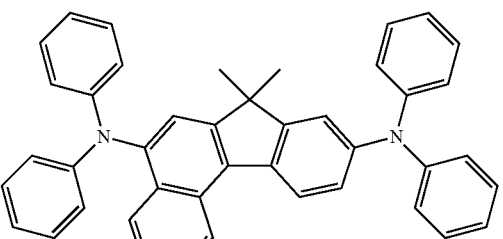
FD21 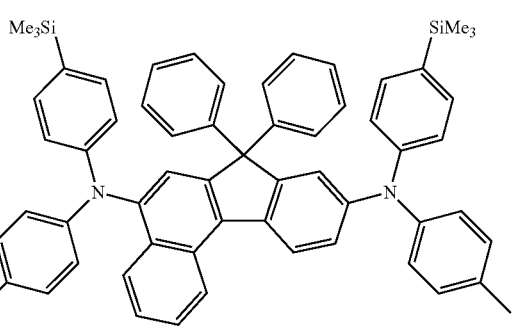
FD22 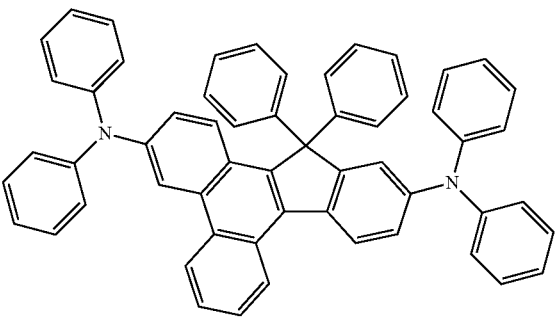
In one or more embodiments, the fluorescent dopant may be selected from the following compounds, but embodiments of the present disclosure are not limited thereto:

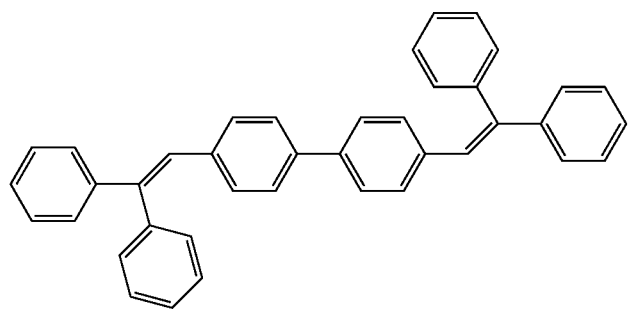
DPVBi
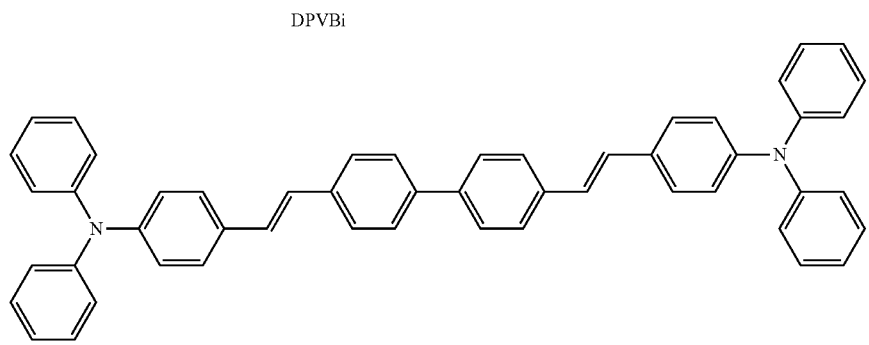
DPAVBi
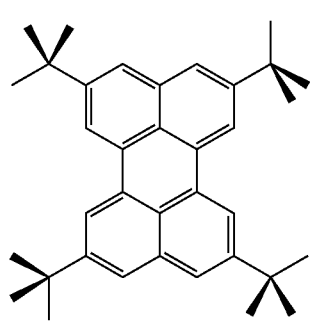
TBPe
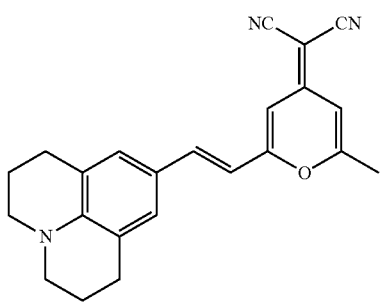
DCM
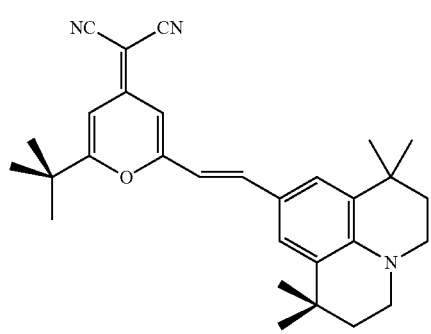
DCJTB
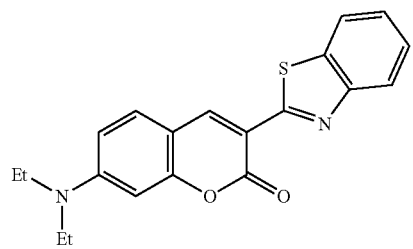
Coumarin 6

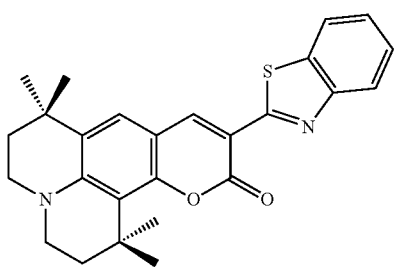

C545T

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

In some embodiments, the electron transport region may have an electron transport layer/electron injection layer structure, a hole blocking layer/electron transport layer/electron injection layer structure, or an electron control layer/electron transport layer/electron injection layer structure, wherein layers of each structure are sequentially stacked on the emission layer, but embodiments are not limited thereto.

The electron transport region (for example, a hole blocking layer, an electron control layer, or an electron transport layer in the electron transport region) may include a metal-free compound containing at least one π electron-depleted nitrogen-containing ring.

The "π electron-depleted nitrogen-containing ring" refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups, each having at least one *—N=*' moiety, are condensed, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, a thiadiazole, an imidazopyridine, an imidazopyrimidine, and an azacarbazole, but embodiments of the present disclosure are not limited thereto.

In some embodiments, the electron transport region may include a compound represented by Formula 601:

wherein, in Formula 601, $Ar_{601}$ may be selected from a substituted or unsubstituted $C_5$-$C_{60}$ carbocyclic group and a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of the xe11 $Ar_{601}$ (s) and the xe21 $R_{601}$ (s) may include the foregoing π electron-depleted nitrogen-containing ring.

In one embodiment, in Formula 601, ring $Ar_{601}$ may be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two Ar$_{601}$ (s) may be bound via a single bond.

In one or more embodiments, Ar$_{601}$ in Formula 601 may be an anthracene group.

In some embodiments, the compound represented by Formula 601 may be represented by Formula 601-1:

Formula 601-1

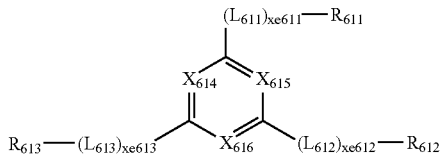

wherein, in Formula 601-1, $X_{614}$ may be N or C($R_{614}$), $X_{615}$ may be N or C($R_{615}$), $X_{616}$ may be N or C($R_{616}$), at least one selected from $X_{614}$ to $X_{616}$ may be N, $L_{611}$ to $L_{613}$ may each independently be substantially the same as described above with reference to $L_{601}$, xe611 to xe613 may each independently be substantially the same as those described herein with reference to xe1, $R_{611}$ to $R_{613}$ may each independently be substantially the same as described above with reference to $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, xe1 and xe611 to xe613 in Formulae 601 and 601-1 may each independently be 0, 1, or 2.

In one or more embodiments, in Formulae 601 and 601-1, $R_{601}$ and $R_{611}$ to $R_{613}$ may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein $Q_{601}$ and $Q_{602}$ may be each independently the same as those described above.

The electron transport region may include at least one compound selected from Compounds ET1 to ET36, but is not limited thereto:

ET1
ET2
ET3
ET4
ET5
ET6

ET7
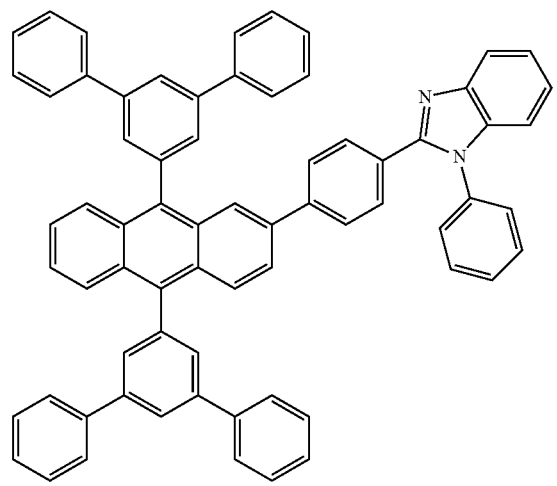
ET8
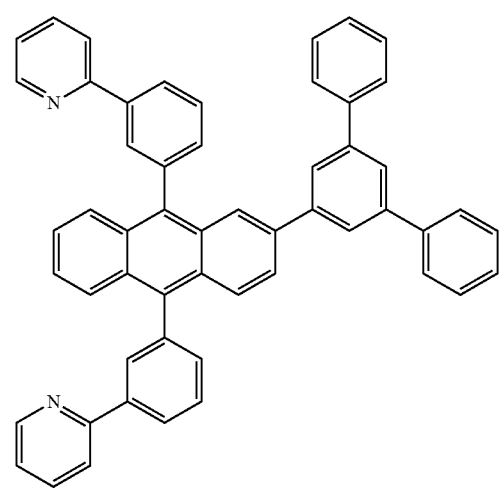
ET9
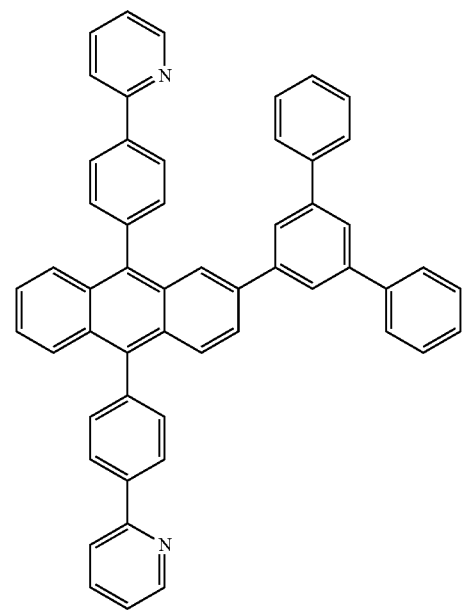
ET10
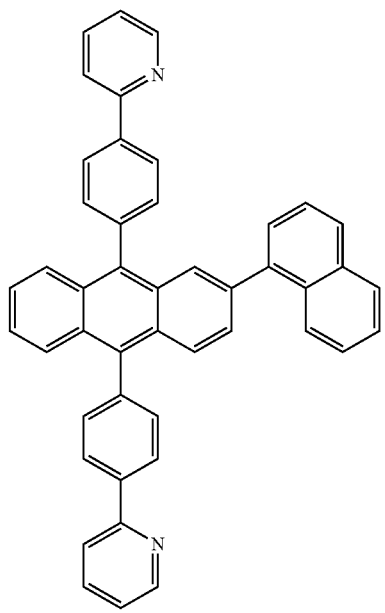
ET11
ET12
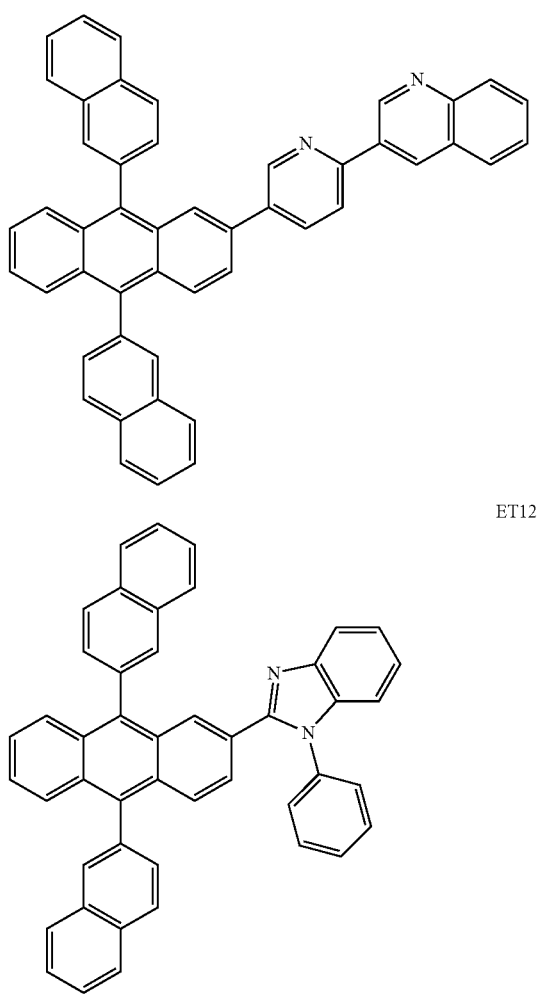

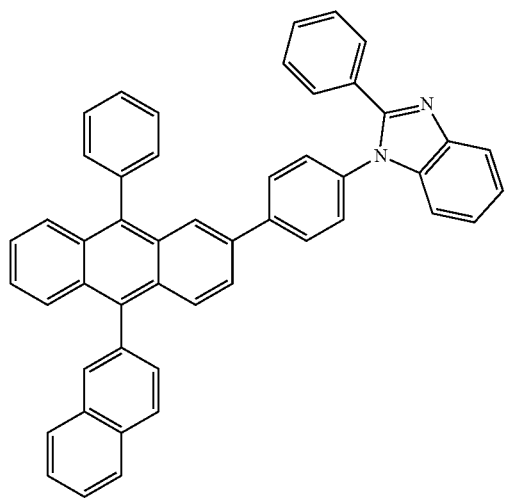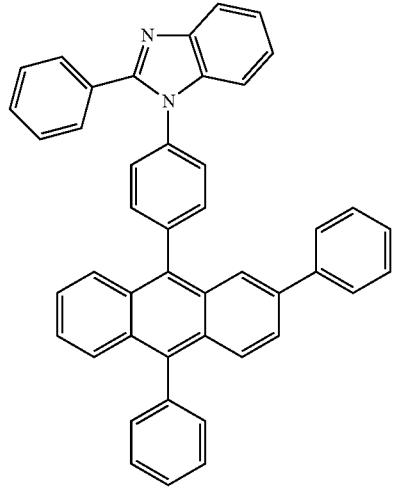

-continued
ET19
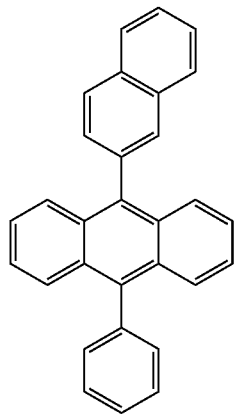
ET20
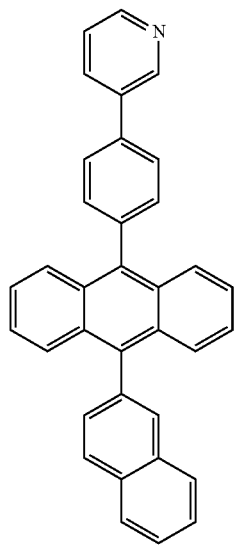
ET21
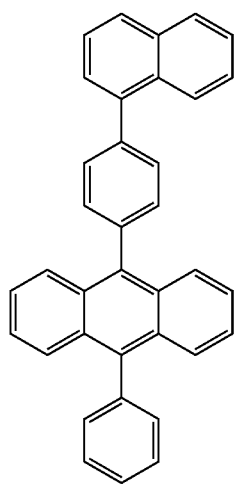
-continued
ET22
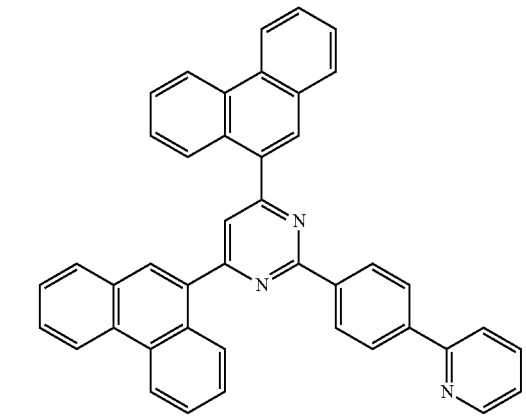
ET23
ET24
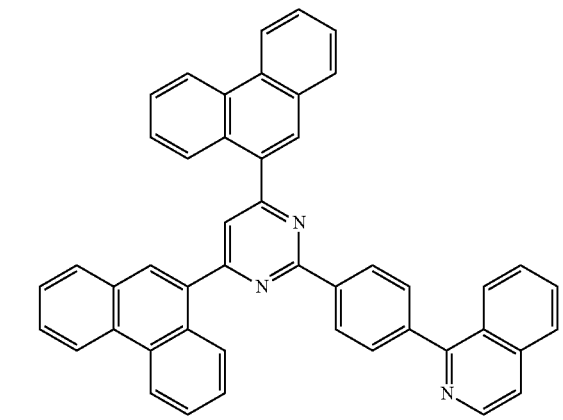

ET25
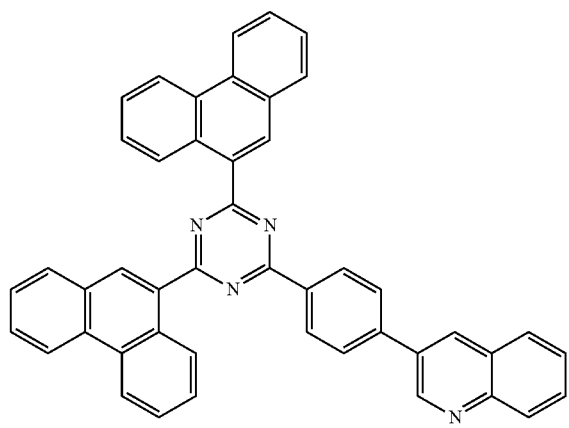
ET28
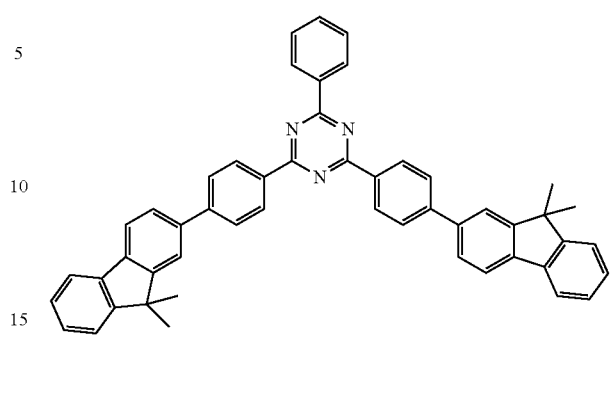
ET26
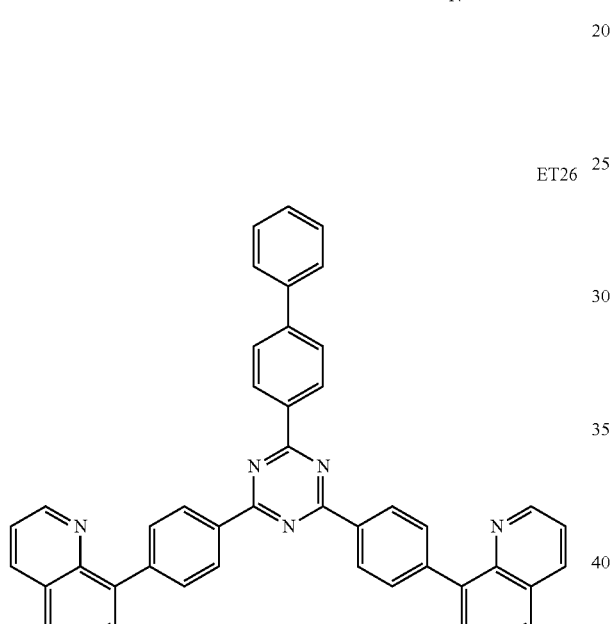
ET29
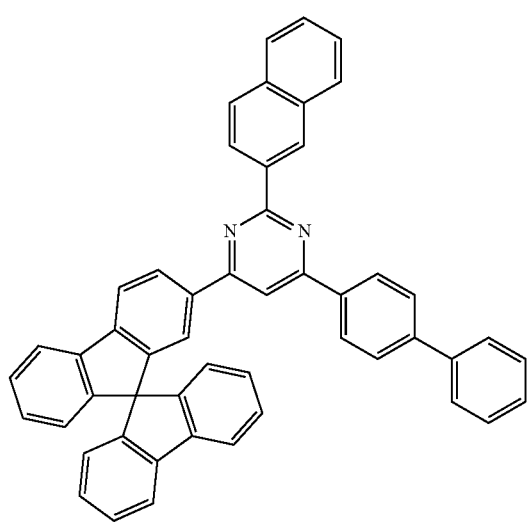
ET27
ET30
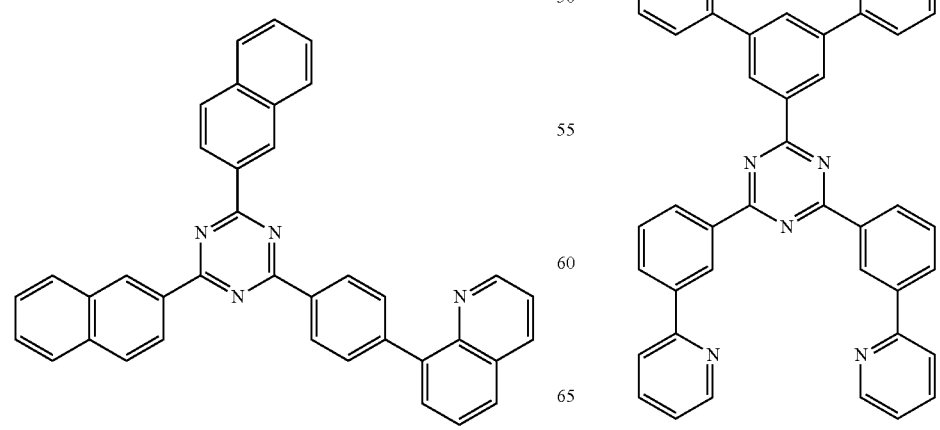

ET31
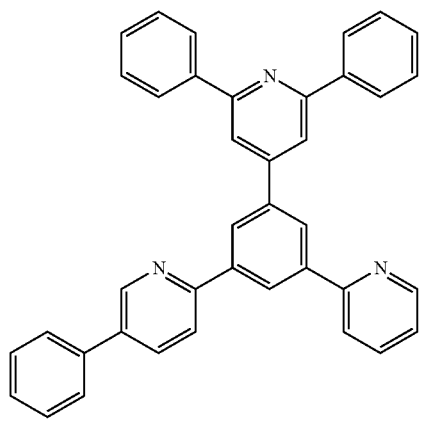
ET34
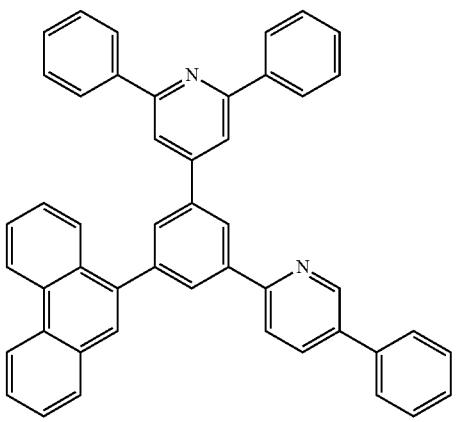
ET32
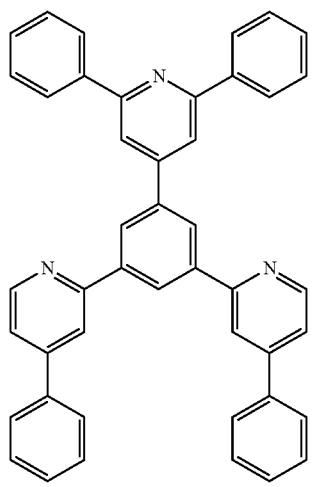
ET35
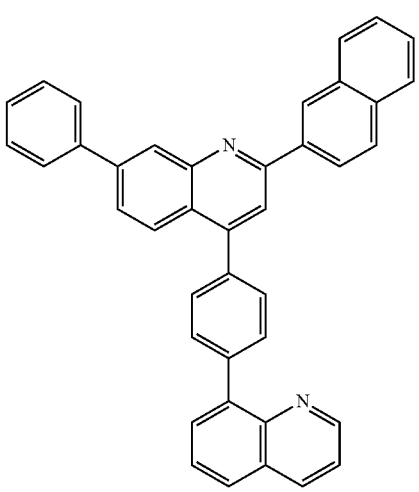
ET33
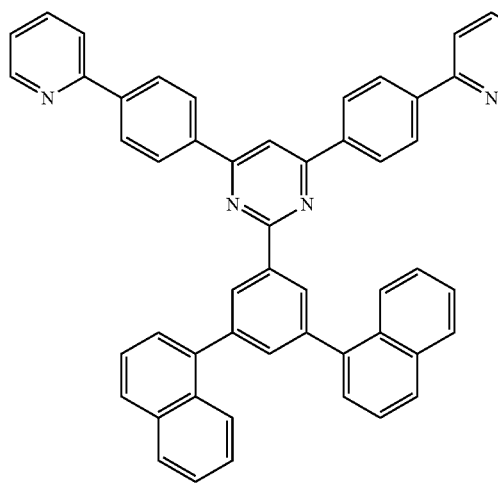
ET36
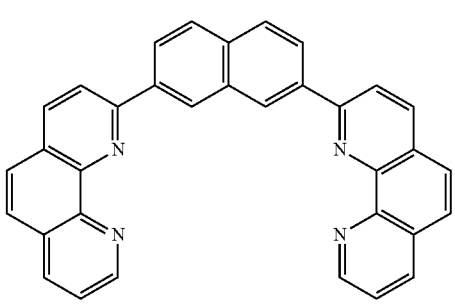
In one or more thickness of the hole blocking layer orts, the electron transport region may include in at one compound selected from 2,9-dimethyl-4,7-diphenyl-1,10-phenanthroline (BCP), 4,7-diphenyl-1,10-phenanthroline (Bphen), Alq3, BAlq, 3-(biphenyl-4-yl)-5-(4-tert-butylphenyl)-4-phenyl-4H-1,2,4-triazole (TAZ), and NTAZ:

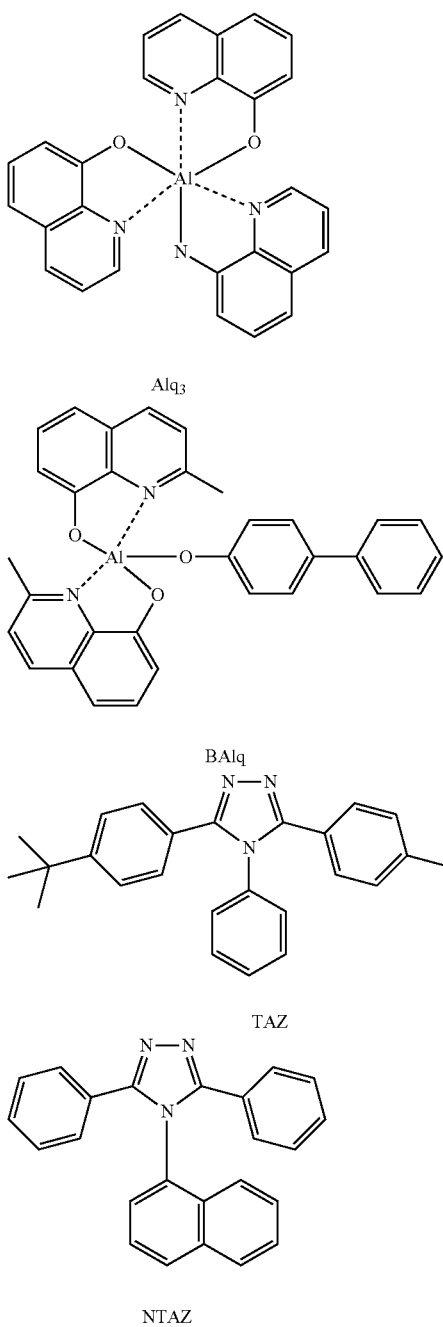

Alq₃

BAlq

TAZ

NTAZ

The thickness of the hole blocking layer or the electron control layer may be in a range of about 20 Å to about 1,000 Å, and in some embodiments, about 30 Å to about 300 Å. When the thicknesses of the hole blocking layer and the electron control layer are each within any of these ranges, the electron transport region may have excellent electron blocking characteristics or electron control characteristics without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, the electron transport layer may have satisfactory electron transport characteristics without a substantial increase in driving voltage.

The electron transport region (e.g., the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from a Li ion, a Na ion, a K ion, a Rb ion, and a Cs ion. The alkaline earth metal complex may include a metal ion selected from a Be ion, a Mg ion, a Ca ion, a Sr ion, and a Ba ion. Ligands respectively coordinated with the metal ion of the alkali metal complex or the alkaline earth-metal complex may each independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments of the present disclosure are not limited thereto.

In some embodiments, the metal-containing material may include a Li complex. The Li complex may include, for example, Compound ET-D1 (lithium quinolate, LiQ) or ET-D2:

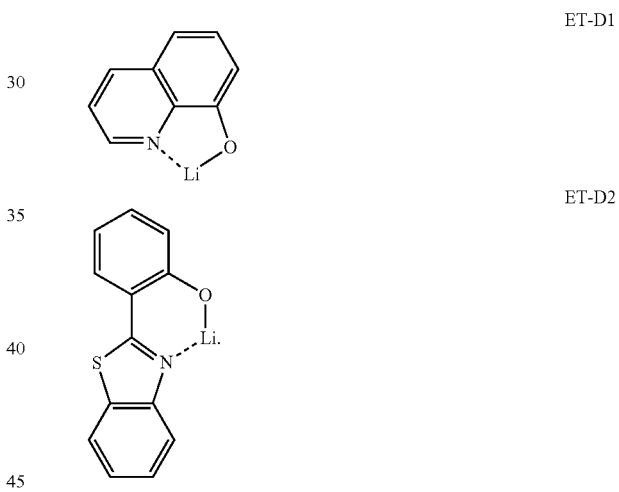

ET-D1

ET-D2

The electron transport region may include an electron injection layer that facilitates the injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include at least one selected from an alkali metal, an alkaline earth metal, a rare earth metal, an alkali metal compound, an alkaline earth-metal compound, a rare earth metal compound, an alkali metal complex, an alkaline earth metal complex, and a rare earth metal complex.

The alkali metal may be selected from Na, K, Rb, and Cs. In one embodiment, the alkali metal may be K, Rb, or Cs. In one or more embodiments, the alkali metal may be Rb or Cs, but embodiments of the present disclosure are not limited thereto.

The alkaline earth-metal may be selected from Ca, Sr, and Ba.

The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth metal compound may be selected from alkaline earth metal compounds, such as BaO, SrO, CaO, $Ba_xSr_{1-x}O$ (wherein 0<x<1), or $Ba_xCa_{1-x}O$ (wherein 0<x<1). In one embodiment, the alkaline earth metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments are not limited thereto.

The alkali metal complex, the alkaline earth metal complex, and the rare earth metal complex may include an alkali metal ion, an alkaline earth metal ion, and a rare earth metal ion, respectively, as described above, and ligands respectively coordinated with the metal ion of the alkali metal complex, the alkaline earth metal complex, and the rare earth metal complex may each independently be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazole, a hydroxyphenyl pyridine, a hydroxyphenyl benzimidazole, a hydroxyphenyl benzothiazole, a bipyridine, a phenanthroline, and a cyclopentadiene, but embodiments of the present disclosure are not limited thereto.

The electron injection layer may only include the foregoing reducing dopant, or may include the reducing dopant and an organic material. When the electron injection layer includes the reducing dopant and an organic material, the reducing dopant may be homogeneously or un-homogeneously dispersed in a matrix consisting of the organic material.

The thickness of the electron injection layer may be in a range of about 1 Å to about 100 Å, and in some embodiments, about 3 Å to about 90 Å. When the thickness of the electron injection layer is within any of these ranges, the electron injection layer may have satisfactory electron injection characteristics without a substantial increase in driving voltage.

Second Electrode 190

The second electrode 190 may be disposed on the organic layer 150. The second electrode 190 may be a cathode, which is an electron injection electrode, and in this regard, the material for forming the second electrode 190 may be selected from a metal, an alloy, an electrically conductive compound, and a mixture thereof, which may have a relatively low work function.

The second electrode 190 may include at least one selected from lithium (Li), magnesium (Mg), aluminum (Al), aluminum-lithium (Al—Li), calcium (Ca), magnesium-indium (Mg—In), magnesium-silver (Mg—Ag), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
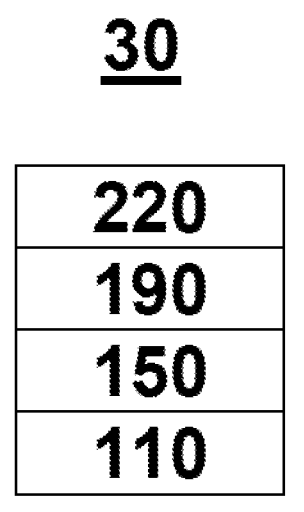
Figure 4:
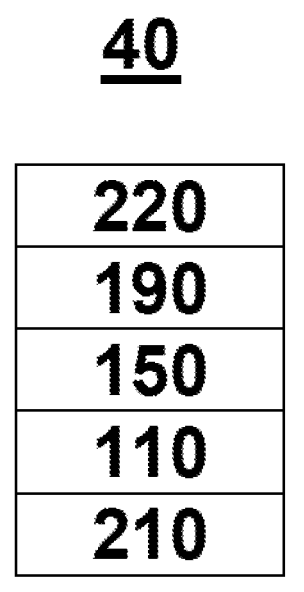

Description of FIGS. 2 to 4

Figure 2:
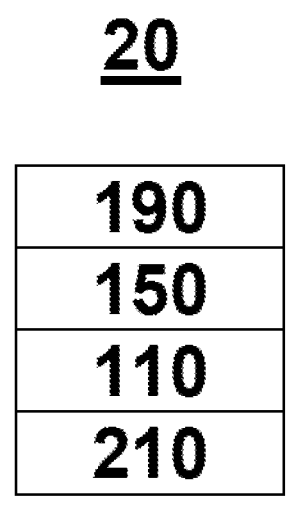

An organic light-emitting device 20 illustrated in FIG. 2 includes a first capping layer 210, a first electrode 110, an organic layer 150, and a second electrode 190 which are sequentially stacked in this stated order. An organic light-emitting device 30 illustrated in FIG. 3 includes a first electrode 110, an organic layer 150, a second electrode 190, and a second capping layer 220 which are sequentially stacked in this stated order. An organic light-emitting device 40 illustrated in FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may each independently be the same as those described above with reference to FIG. 1.

In the organic layer 150 of each of the organic light-emitting devices 20 and 40, light emitted from the emission layer may pass through the first electrode 110, which is a semi-transmissive electrode or a transmissive electrode, and through the first capping layer 210 toward the outside. In the organic layer 150 of each of the organic light-emitting devices 30 and 40, light emitted from the emission layer may pass through the second electrode 190, which is a semi-transmissive electrode or a transmissive electrode, and through the second capping layer 220 toward the outside.

The first capping layer 210 and the second capping layer 220 may increase external luminescent efficiency, based on the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may include at least one material selected from carbocyclic compounds, heterocyclic compounds, amine-based compounds, porphyrin derivatives, phthalocyanine derivatives, naphthalocyanine derivatives, alkali metal-based complexes, and alkaline earth metal-based complexes. The carbocyclic compound, the heterocyclic compound, and the amine-based compound may optionally be substituted with a substituent including at least one element selected from oxygen (O), nitrogen (N), sulfur (S), selenium (Se), silicon (Si), fluorine (F), chlorine (Cl), bromine (Br), and iodine (I).

In one embodiment, at least one selected from the first capping layer 210 and the second capping layer 220 may include an amine-based compound.

In one or more embodiments, at least one selected from the first capping layer 210 and the second capping layer 220 may include a compound selected from Compounds CP1 to CP5, but embodiments of the present disclosure are not limited thereto:

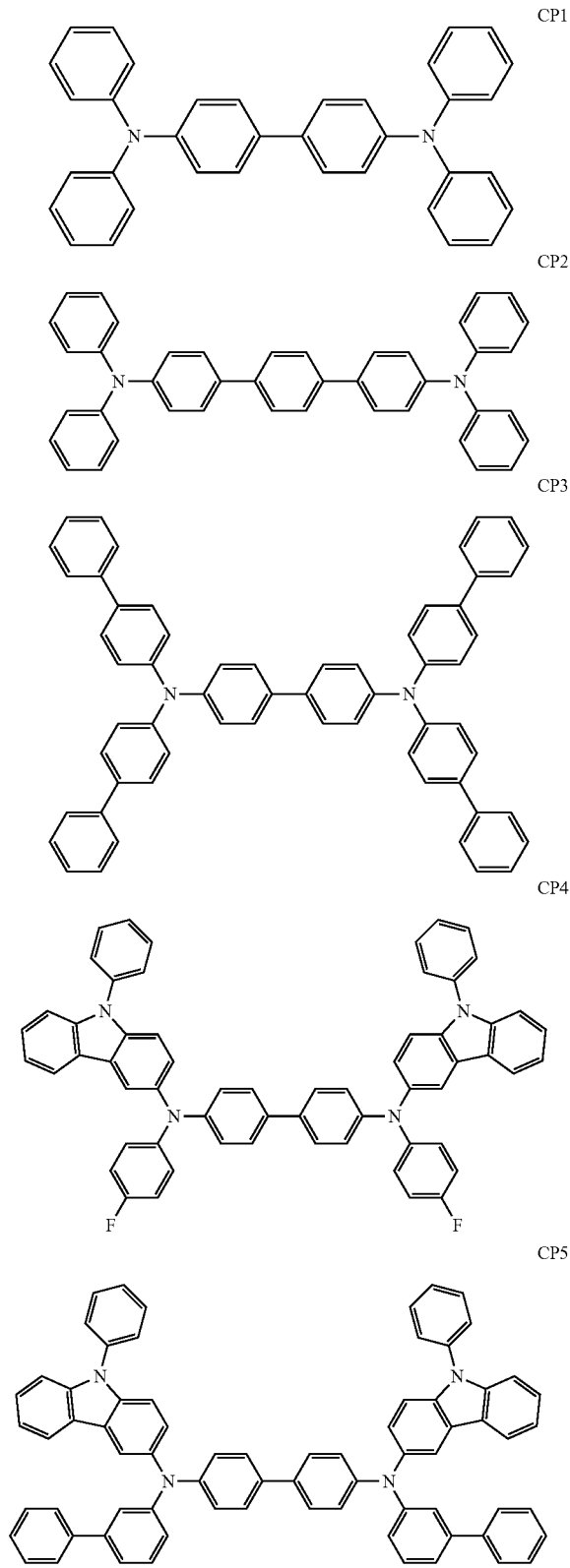

The layers constituting the hole transport region, the emission layer, and the layers constituting the electron transport region may be formed in a specific region using one or more suitable methods selected from vacuum deposition, spin coating, casting, Langmuir-Blodgett (LB) deposition, ink-jet printing, laser-printing, and laser-induced thermal imaging (LITI).

When the layers constituting the hole transport region, the emission layer, and the layers constituting the electron transport region are each formed by vacuum deposition, for example, vacuum deposition may be performed at a temperature of about 100 to about 500° C., at a vacuum degree of about $10^{-8}$ to about $10^{-3}$ torr, and at a rate of about 0.01 Angstroms per second (Å/sec) to about 100 Å/sec depending on the compound to be included in each layer and the structure of each layer to be formed.

When the layers constituting the hole transport region, the emission layer, the and the layers constituting the electron transport region are each independently formed by spin coating, the spin coating may be performed, for example, at a rate of about 2,000 revolutions per minute (rpm) to about 5,000 rpm and at a heat treatment temperature of about 80° C. to 200° C., depending on the compound to be included in each layer and the structure of each layer to be formed.

General Definition of Substituents

The term "$C_1$-$C_{60}$ alkyl group" as used herein refers to a linear or branched saturated aliphatic hydrocarbon monovalent group having 1 to 60 carbon atoms.

Examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group). Examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The Hereinbefore, an organic light-emitting device according to one or more embodiment has been described in connection with FIGS. 1 to 4. However, embodiments are not limited thereto.

term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring and is not aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Examples of the $C_1$-$C_{10}$ heterocycloalkenyl group include a 4,5-dihydro-1,2,3,4-oxatriazolyl group, a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group that has an aromatic system having 6 to 60 carbon atoms. The term "$C_6$-$C_{60}$ arylene group" as used herein refers to a divalent group that has an aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having an aromatic system that has at least one heteroatom selected from N, O, Si, P, and S as a ring-forming atom, in addition to 1 to 1 carbon atoms. The term "$C_1$-$C_{60}$ heteroarylene group" as used herein refers to a divalent group having an aromatic system that has at least one heteroatom selected from N, O, Si, P, and S as a ring-forming atom, in addition to 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused.

The term "$C_6$-$C_{60}$ aryloxy group" as used herein refers to —$OA_{102}$ (wherein $A_{102}$ is the $C_6$-$C_{60}$ aryl group). The term "$C_6$-$C_{60}$ arylthio group" as used herein refers to —$SA_{103}$ (wherein $A_{103}$ is the $C_6$-$C_{60}$ aryl group).

The term "monovalent non-aromatic condensed polycyclic group" as used herein refers to a monovalent group having two or more rings condensed and only carbon atoms (e.g., 8 to 60 carbon atoms) as ring-forming atoms, wherein the entire molecular structure is non-aromatic. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed and at least one heteroatom selected from N, O, Si, P, and S, in addition to carbon atoms (e.g., 1 to 60 carbon atoms), as ring-forming atoms, wherein the entire molecular structure is non-aromatic. Examples of the monovalent non-aromatic condensed heteropolycyclic group may include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The $C_5$-$C_{60}$ carbocyclic group may be a ring such as a benzene group, a monovalent group such as a phenyl group, or a divalent group such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having substantially the same structure as a $C_5$-$C_{60}$ carbocyclic group, with the alteration that at least one heteroatom selected from N, O, Si, P, and S may be used as a ring-forming atom, in addition to carbon atoms (e.g., 1 to 60 carbon atoms).

In the present specification, at least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph" as used herein represents a phenyl group. The term "Me" as used herein represents a methyl group The term "Et" as used herein represents an ethyl group. The term "ter-Bu" or "But" as used herein represents a tert-butyl group. The term "OMe" as used herein represents a methoxy group.

The term "biphenyl group" as used therein refers to a phenyl group substituted with a phenyl group. In other words, the "biphenyl group" is a substituted phenyl group having a $C_6$-$C_{60}$ aryl group as a substituent.

The term "terphenyl group" as used herein refers to "a phenyl group substituted with a biphenyl group. In other words, the "terphenyl group" is a substituted phenyl group having a $C_6$-$C_{60}$ aryl group substituted with a $C_6$-$C_{60}$ aryl group as a substituent.

* and *' as used herein, unless defined otherwise, each indicate a binding site to an adjacent atom in the corresponding formula.

Hereinafter, a compound and an organic light-emitting device, according to one or more embodiments, will be described in detail with reference to Synthesis Examples and Examples. The wording "B was used instead of A" used in describing Synthesis Examples means that an identical molar equivalent of B was used in place of A.

EXAMPLES

Synthesis Example

Synthesis Example 1: Synthesis of Compound 1

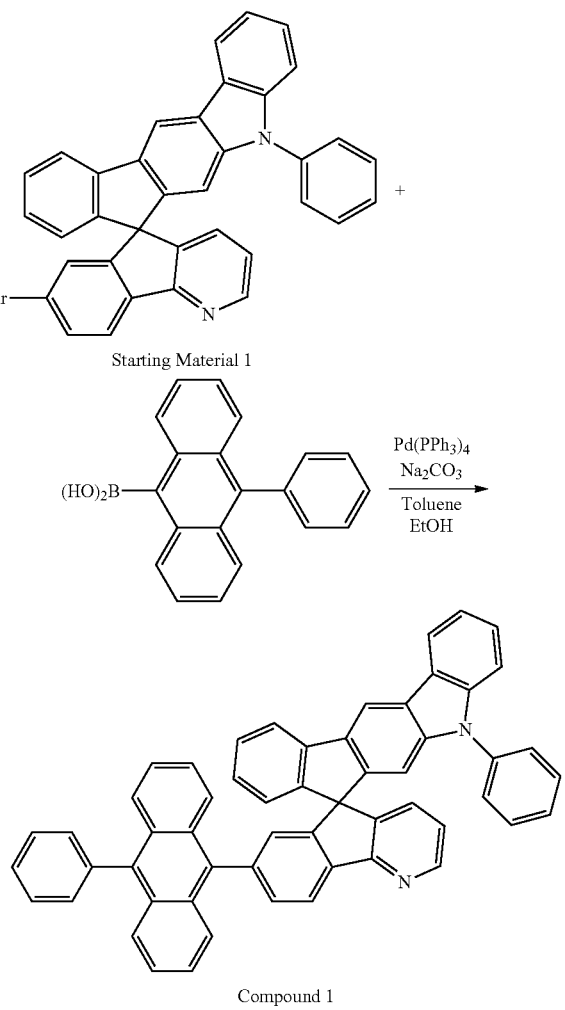

0.73 g (1 eq, 1.30 mmol) of Starting Material 1 and 0.43 g (1.1 eq, 1.43 mmol) of (10-phenylanthracen-9-yl)boronic acid, and 0.06 g (0.04 eq, 0.052 mmol) of tetrakis(triphenylphosphine)palladium(0) were added to a reaction vessel, and then were dried under vacuum. Next, the reaction vessel was filled with nitrogen gas. 13 ml of toluene was added to the reaction vessel to dissolve the compounds. Then, 6.5 ml of ethanol and 6.5 ml (10 eq, 13.0 mmol) of a 2.0 molar (M) sodium carbonate aqueous solution were added thereto. Then, the mixture was refluxed and stirred at a temperature of 80° C. for 3 hours. Once the reaction was complete, the resultant solution was washed with distilled water, and an organic layer was extracted therefrom using ethyl acetate. The organic layer was dried over magnesium sulfate, filtered by using a Celite filter, and then separated and purified through column chromatography to obtain 0.745 g of Compound 9 (7-(10-phenylanthracen-9-yl)-5'-(1,3,5-triazin-2-yl)-5'H-spiro[indeno[1,2-b]pyridine-5,7'-indeno[2,1-b]carbazole]) (yield: 75%). The obtained compound was identified by mass spectroscopy/fast atom bombardment (MS/FAB).

APCI-MS (m/z): 731[M$^+$]

Synthesis Example 2: Synthesis of Compound 2

Compound 2 was synthesized in substantially the same manner as in Synthesis Example 1: Synthesis of Compound 1, except that (10-naphtylanthracen-9-yl)boronic acid was used instead of (10-phenylanthracen-9-yl)boronic acid. The obtained compound was identified by MS/FAB.

APCI-MS (m/z): 786[M$^+$]

Synthesis Example 3: Synthesis of Compound 17

Compound 17 was synthesized in substantially the same manner as in Synthesis Example 1: Synthesis of Compound 1, except that Starting Material 2 was used instead of Starting Material 1. The obtained compound was identified by $^1$H NMR and MS/FAB.

APCI-MS (m/z): 774[M$^+$]

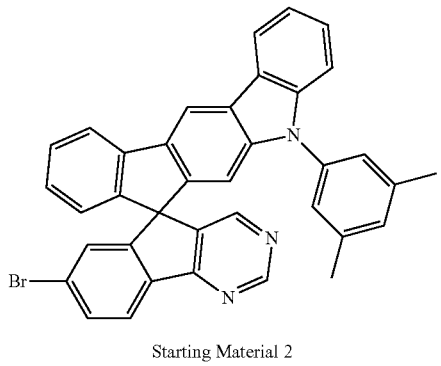 [SMILES: Cc1cc(C)cc(-n2c3ccccc3c3cc4c(cc32)C2(c3ccccc3-4)c3cc(Br)ccc3-c3ncncc32)c1]

Starting Material 2

Example 1

A Corning 15 Ohms per square centimeter ($\Omega/cm^2$, 1,200 Å) ITO glass substrate was cut to a size of 50 millimeters (mm)×50 mm×0.7 mm, sonicated in isopropyl alcohol and pure water for 5 minutes each, and cleaned by exposure to ultraviolet rays and ozone, so that the resulting glass substrate could be used as a substrate and an anode. Then, the glass substrate was mounted on a vacuum deposition apparatus.

2-TNATA was vacuum-deposited on the ITO anode to form a hole injection layer having a thickness of 600 Å, and 4,4'-bis[N-(1-naphthyl)-N-phenylamino]biphenyl (hereinafter, referred as "NPB") was vacuum-deposited on the hole injection layer to form a hole transport layer having a thickness of 300 Å.

Compound 1 (host) and DPAVBi (dopant) were co-deposited on the hole transport layer at a weight ratio of about 95:5 to form an emission layer having a thickness of about 20 nm.

Compound ET1 was deposited on the emission layer to form an electron transport layer having a thickness of 300 Å, LiF was deposited on the electron transport layer to form an electron injection layer having a thickness of 10 Å, and Al was vacuum-deposited on the electron injection layer to form a cathode having a thickness of about 3,000 Å, thereby completing the manufacture of an organic light-emitting device.

Examples 2 and 3 and Comparative Examples 1 to 5

Organic light-emitting devices were manufactured in substantially the same manner as in Example 1, except that the compounds shown in Table 1 were used instead of Compound 1 as a host in forming each emission layer.

Evaluation Example 1

The driving voltage, current density, luminance, and efficiency of the organic light-emitting devices manufactured in Examples 1 to 3 and Comparative Examples 1 to 5 were measured by using a Keithley 236 source-measure unit (SMU) and a PR650 luminance meter. The results thereof are shown in Table 1.

TABLE 1

| | Host | Driving voltage (V) | Current density (mA/cm$^2$) | Luminance (cd/m$^2$) | Efficiency (cd/A) |
|---|---|---|---|---|---|
| Example 1 | Compound 1 | 3.65 | 10 | 550 | 5.50 |
| Example 2 | Compound 2 | 3.7 | 10 | 520 | 5.20 |
| Example 3 | Compound 17 | 3.2 | 10 | 475 | 4.75 |
| Comparative Example 1 | Compound A | 4.6 | 10 | 311 | 3.11 |
| Comparative Example 2 | Compound B | 4.3 | 10 | 367 | 3.67 |
| Comparative Example 3 | Compound C | 4.2 | 10 | 416 | 4.16 |
| Comparative Example 4 | Compound D | 4.4 | 10 | 378 | 3.78 |
| Comparative Example 5 | Compound E | 4.5 | 10 | 252 | 2.52 |

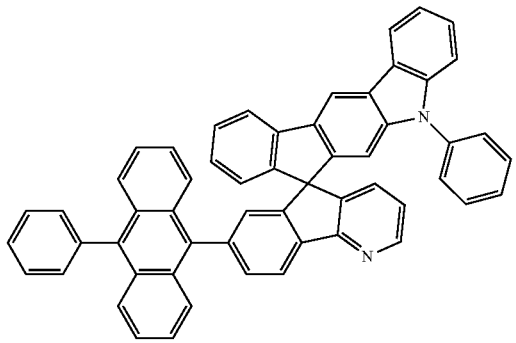

1

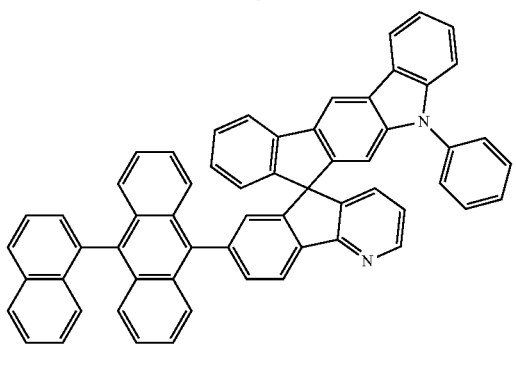

2

TABLE 1-continued

| Host | Driving voltage (V) | Current density (mA/cm$^2$) | Luminance (cd/m$^2$) | Efficiency (cd/A) |
|---|---|---|---|---|

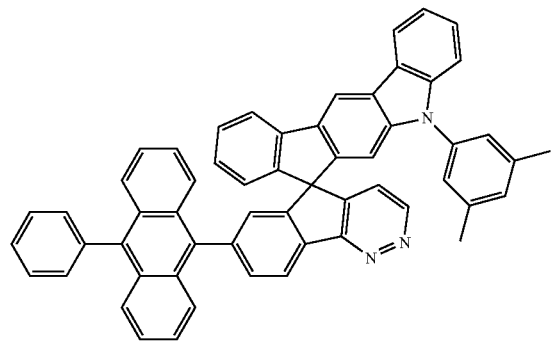

17

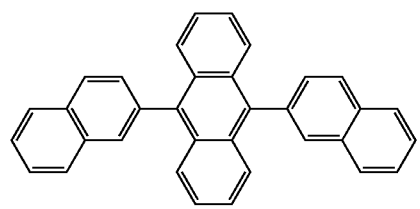

Formula A

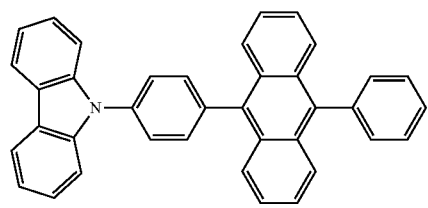

Formula B

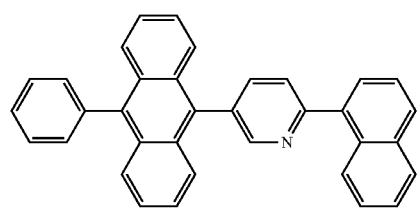

Formula C

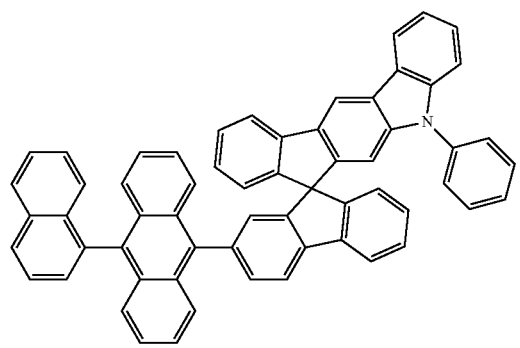

Formula D

TABLE 1-continued

| Host | Driving voltage (V) | Current density (mA/cm$^2$) | Luminance (cd/m$^2$) | Efficiency (cd/A) |
|---|---|---|---|---|

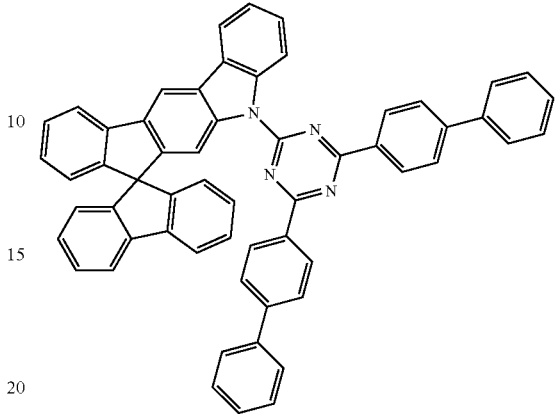

Formula E

According to the results of Table 1, each of the organic light-emitting devices of Examples 1 to 3 were found to have a low-driving voltage, high luminance, and high efficiency, as compared with the organic light-emitting devices of Comparative Examples 1 to 5.

As apparent from the foregoing description, an organic light-emitting device including the condensed-cyclic compound may have a low driving voltage, excellent efficiency, and excellent luminance.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A condensed-cyclic compound represented by Formula 1:

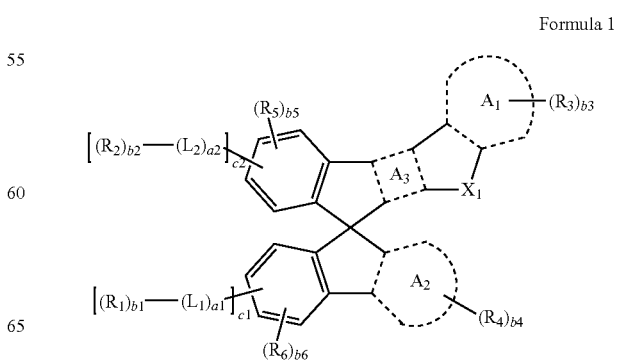

Formula 1

-continued

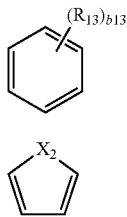

Formula 2A

Formula 2B wherein, in Formulae 1, 2A, and 2B,
ring $A_1$ is selected from a benzene group, a naphthalene group, a pyridine group, a pyrimidine group, a pyrazine group, a quinoline group, an isoquinoline group, a quinoxaline group, a quinazoline group, and a cinnoline group,
ring $A_2$ is selected from a pyridine group, a pyrimidine group, a pyrazine group, a quinoline group, an isoquinoline group, a quinoxaline group, a quinazoline group, and a cinnoline group,
ring $A_3$ is selected from groups represented by Formula 2A and groups represented by Formula 2B,
$X_1$ is selected from N-[$(L_{11})_{a11}$-$(R_{11})_{b11}$], O, and S,
$X_2$ is selected from N-[$(L_{12})_{a12}$-$(R_{12})_{b12}$], O, and S,
$L_1$ and $L_2$ are each independently selected from substituted or unsubstituted condensed polycyclic groups, in which 3 or more carbocyclic groups are condensed with each other,
a1 and a2 are each independently an integer from 1 to 5; when a1 is 2 or greater, at least two $L_1$ (s) are identical to or different from each other; when a2 is 2 or greater, at least two $L_2$ (s) are identical to or different from each other,
$L_{11}$ is selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group,
a11 is an integer from 0 to 5,
$L_{12}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a12 is an integer from 0 to 5,
$R_{11}$ is selected from a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group,
b11 is an integer from 1 to 4,
$R_1$ to $R_4$, $R_6$, $R_{12}$, and $R_{13}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
$R_5$ is each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group,
b1, b2, b5, b6, and b12 are each independently an integer from 0 to 4,
b3 and b4 are each independently an integer from 0 to 6,
b13 is selected from 0, 1, and 2,
c1 is an integer from 1 to 4 and c2 is 0,
at least one substituent of the substituted condensed polycyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:
deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group.

2. The condensed-cyclic compound of claim 1, wherein ring $A_1$ is selected from a benzene group and a naphthalene group, and ring $A_2$ is selected from a pyridine group, a quinoline group, and an isoquinoline group.

3. The condensed-cyclic compound of claim 1, wherein $X_1$ is N-[($L_{11}$)$_{a11}$-($R_{11}$)$_{b11}$].

4. The condensed-cyclic compound of claim 1, wherein $L_1$ to $L_2$ are each independently selected from an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

5. The condensed-cyclic compound of claim 1, wherein $L_1$ and $L_2$ are each independently selected from groups represented by Formulae 3-8, 3-9, 3-25, and 3-35 to 3-41, $L_{11}$ is selected from groups represented by Formulae 3-1 to 3-9, 3-25, and 3-33 to 3-41, wherein $Y_1$ in Formulae 3-3 and 3-4 is C($Z_3$)($Z_4$), and $L_{12}$ is selected from groups represented by Formulae 3-1 to 3-41:

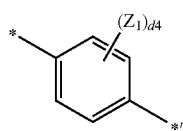
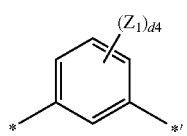
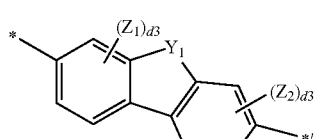
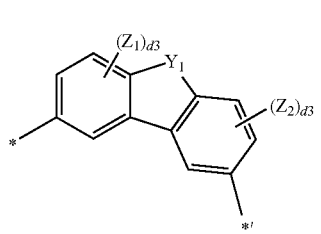
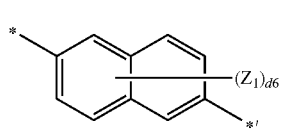
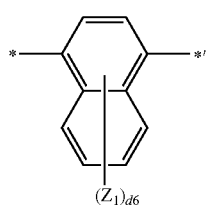
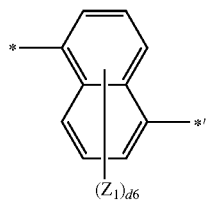
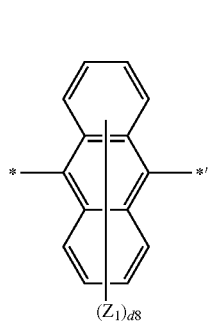
Formula 3-1
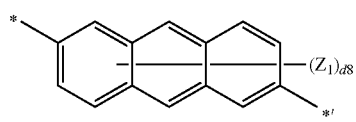
Formula 3-9
Formula 3-2
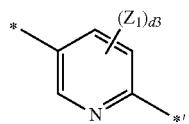
Formula 3-10
Formula 3-3
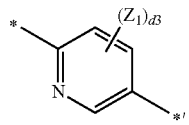
Formula 3-11
Formula 3-4
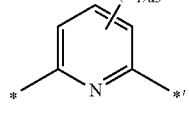
Formula 3-12
Formula 3-5
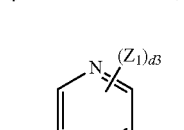
Formula 3-13
Formula 3-6
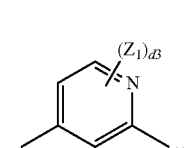
Formula 3-14
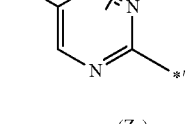
Formula 3-15
Formula 3-7
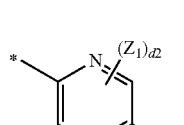
Formula 3-16
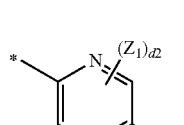
Formula 3-17
Formula 3-8
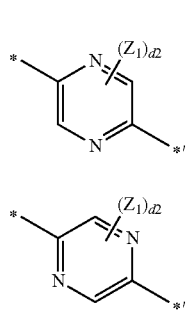
Formula 3-18
Formula 3-19

Formula 3-20

Formula 3-21

Formula 3-22

Formula 3-23

Formula 3-24

Formula 3-25

Formula 3-26

Formula 3-27

Formula 3-28

Formula 3-29

Formula 3-30

Formula 3-31

Formula 3-32

Formula 3-33

Formula 3-34

Formula 3-35

Formula 3-36

-continued

Formula 3-37

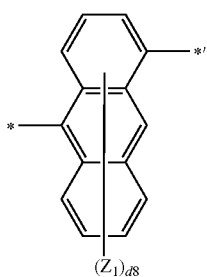

Formula 3-38

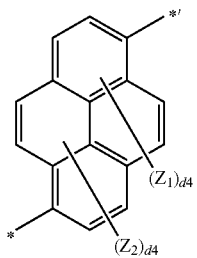

Formula 3-39

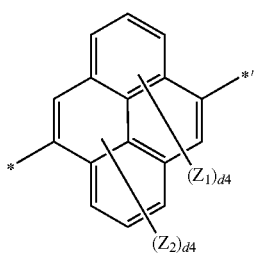

Formula 3-40

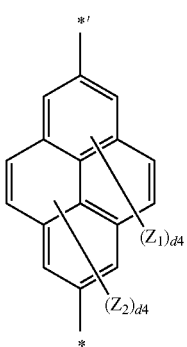

Formula 3-41

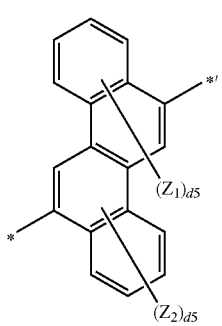

wherein, in Formulae 3-1 to 3-41, $Y_1$ is selected from O, S, $C(Z_3)(Z_4)$, $N(Z_5)$, and $Si(Z_6)(Z_7)$, $Z_1$ to $Z_7$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, a phenanthrolinyl group, and —$Si(Q_{31})(Q_{32})(Q_{33})$, wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, d2 is an integer selected from 1 and 2,
d3 is an integer from 1 to 3,
d4 is an integer from 1 to 4,
d5 is an integer from 1 to 5,
d6 is an integer from 1 to 6,
d8 is an integer from 1 to 8, and
* and *' each indicate a binding site to an adjacent atom.

6. The condensed-cyclic compound of claim 1, wherein
$L_1$ and $L_2$ are each independently selected from groups represented by Formulae 4-11, 4-13, 4-27, and 4-29 to 4-35,
$L_{11}$ is selected from groups represented by Formulae 4-1, 4-3, 4-5, 4-7 to 4-13, 4-17, and 4-24 to 4-35, and
$L_{12}$ is selected from groups represented by Formulae 4-1 to 4-35:

Formula 4-1

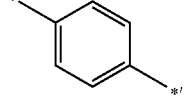

Formula 4-2

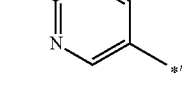

Formula 4-3

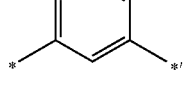

Formula 4-4

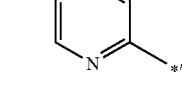

Formula 4-5

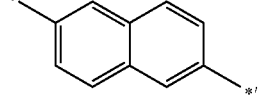

Formula 4-6

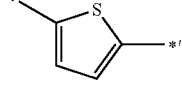

-continued
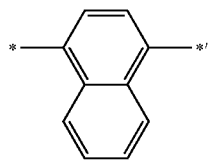
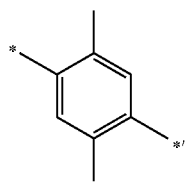
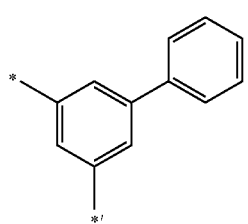
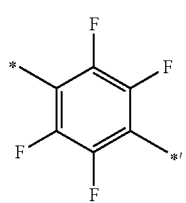
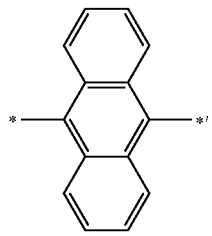
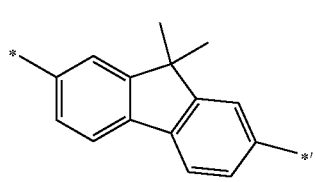
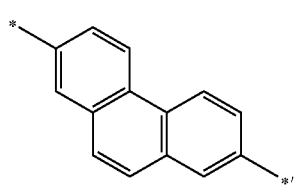
-continued
Formula 4-7
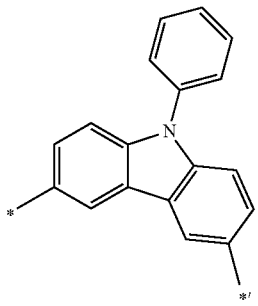
Formula 4-8
Formula 4-9
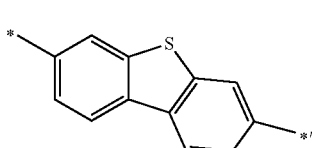
Formula 4-10
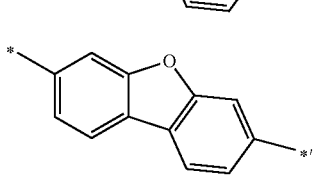
Formula 4-11
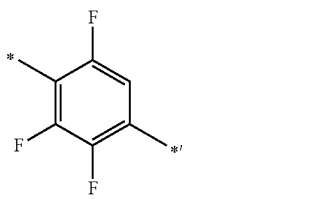
Formula 4-12
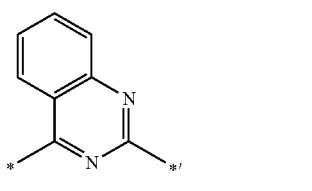
Formula 4-13
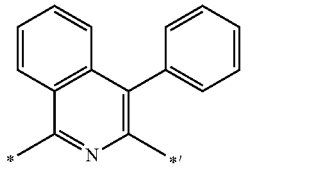
Formula 4-14
Formula 4-15
Formula 4-16
Formula 4-17
Formula 4-18
Formula 4-19
Formula 4-20
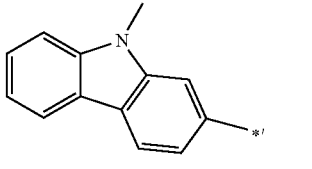
Formula 4-21
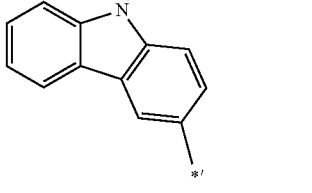

-continued
Formula 4-22
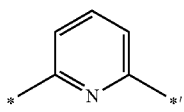
Formula 4-23
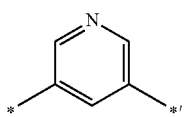
Formula 4-24
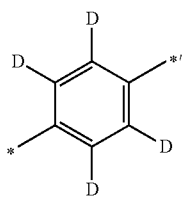
Formula 4-25
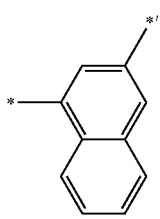
Formula 4-26
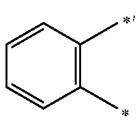
Formula 4-27
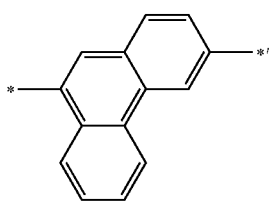
Formula 4-28
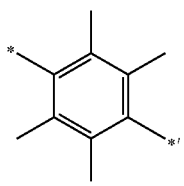
Formula 4-29
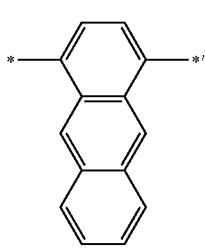
-continued
Formula 4-30
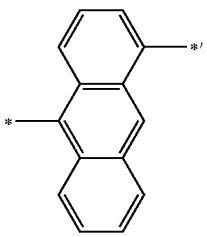
Formula 4-31
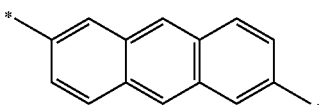
Formula 4-32
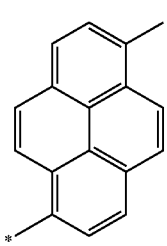
Formula 4-33
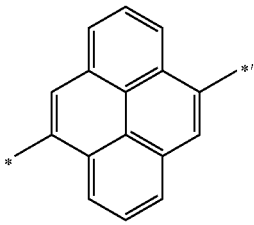
Formula 4-34
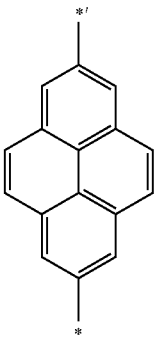
Formula 4-35
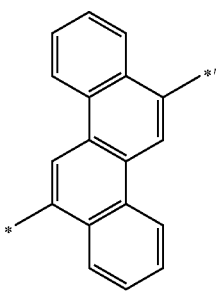
wherein, in Formulae 4-1 to 4-35, * and *' each indicate a binding site to an adjacent atom.
7. The condensed-cyclic compound of claim 1, wherein $R_{11}$ is selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, and —Si($Q_{33}$)($Q_{34}$)($Q_{35}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The condensed-cyclic compound of claim 1, wherein $R_{11}$ is selected from groups represented by Formulae 5-1 to 5-19:

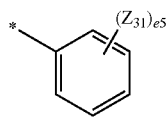

Formula 5-1

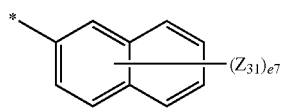

Formula 5-2

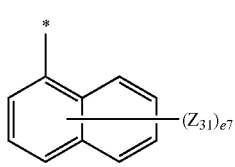

Formula 5-3

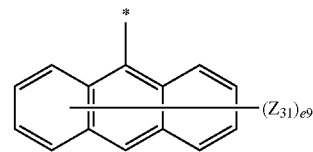

Formula 5-4

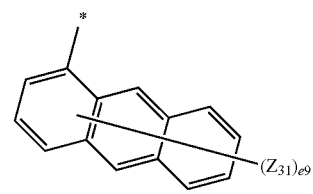

Formula 5-5

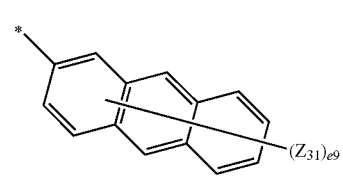

Formula 5-6

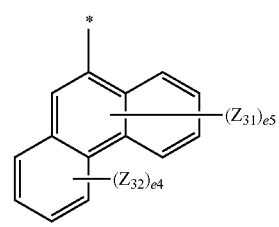

Formula 5-7

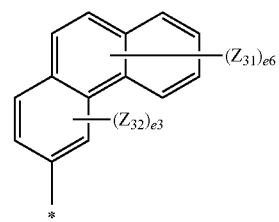

Formula 5-8

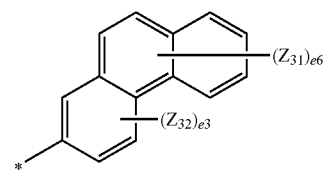

Formula 5-9

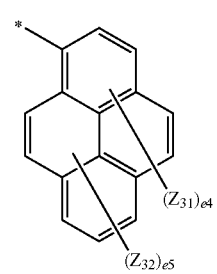

Formula 5-10

-continued

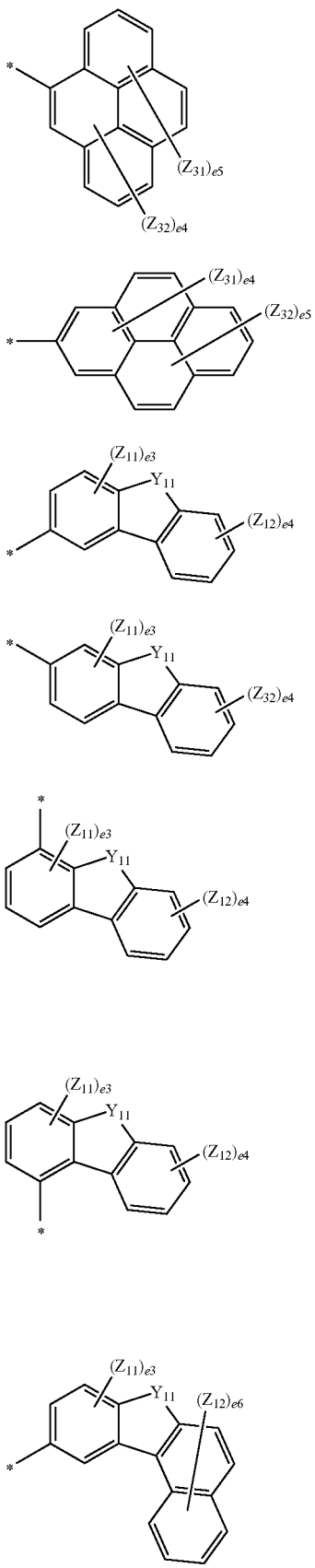

Formula 5-11

Formula 5-12

Formula 5-13

Formula 5-14

Formula 5-15

Formula 5-16

Formula 5-17

-continued

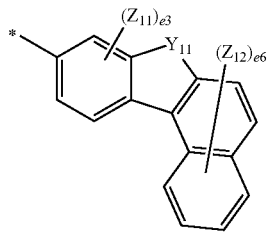
Formula 5-18

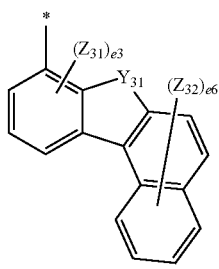
Formula 5-19 wherein, in Formulae 5-1 to 5-19, $Y_{11}$ is $C(Z_{13})(Z_{14})$, $Z_{11}$ to $Z_{14}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a biphenyl group, a terphenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, e3 is an integer selected from 1 to 3,
e4 is an integer selected from 1 to 4,
e5 is an integer selected from 1 to 5,
e6 is an integer selected from 1 to 6,
e7 is an integer selected from 1 to 7,
e9 is an integer selected from 1 to 9, and
* indicates a binding site to an adjacent atom.

9. The condensed-cyclic compound of claim 1, wherein $R_{11}$ is selected from groups represented by Formulae 6-1 to 6-27:

Formula 6-1

Formula 6-2
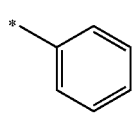

Formula 6-3
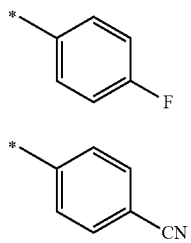

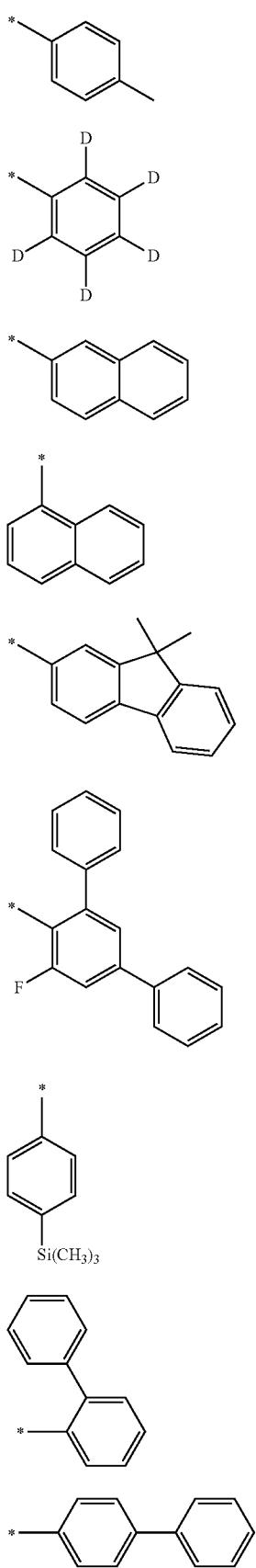
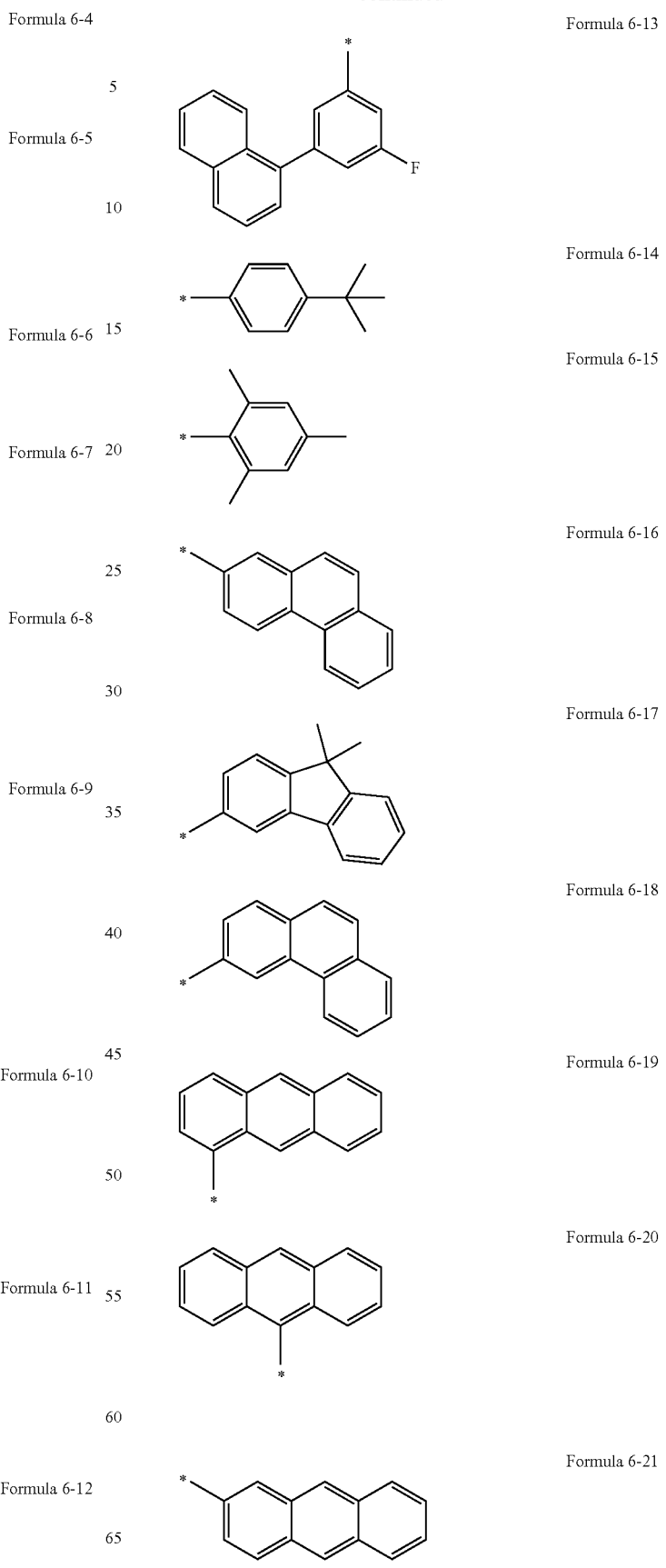

Formula 6-22
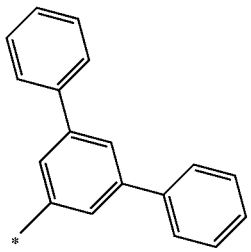

Formula 6-23
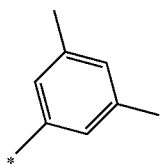

Formula 6-24
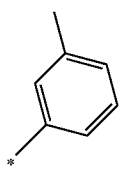

Formula 6-25
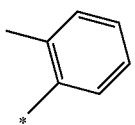

Formula 6-26
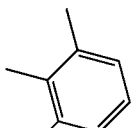

Formula 6-27
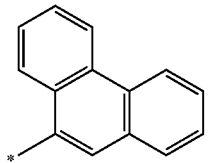

wherein, in Formulae 6-1 to 6-27, * indicates a binding site to an adjacent atom.

10. The condensed-cyclic compound of claim 1, wherein $R_1$ to $R_4$, $R_6$ and $R_{12}$ to $R_{13}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a biphenyl group, a terphenyl group, and a naphthyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

11. The condensed-cyclic compound of claim 1, wherein $R_1$ to $R_4$, $R_6$, $R_{12}$, and $R_{13}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, groups represented by Formulae 7-1 to 7-75, and —Si($Q_1$)($Q_2$)($Q_3$), wherein $Q_1$ to $Q_3$ are each independently selected from a $C_1$-$C_{10}$ alkyl group, a $C_1$-$C_{10}$ alkoxy group, a phenyl group, a biphenyl group, a terphenyl group, and a naphthyl group:

Formula 7-1

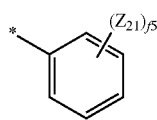

Formula 7-2

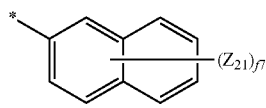

Formula 7-3

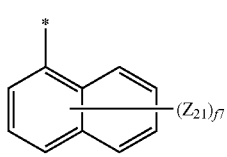

Formula 7-4

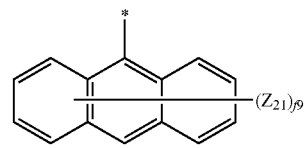

Formula 7-5

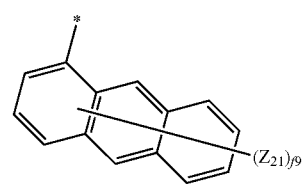

Formula 7-6

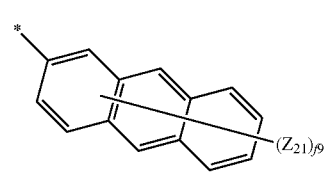

Formula 7-7

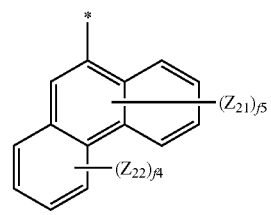

Formula 7-8

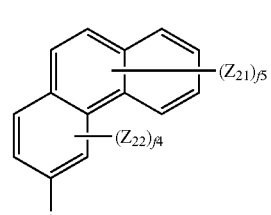

Formula 7-9

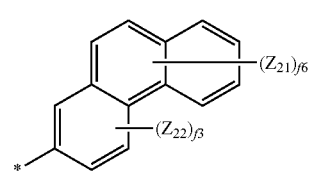

Formula 7-10

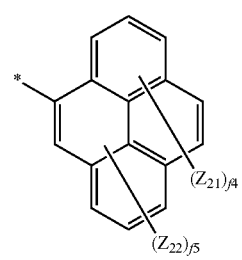

Formula 7-11

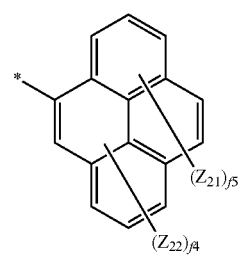

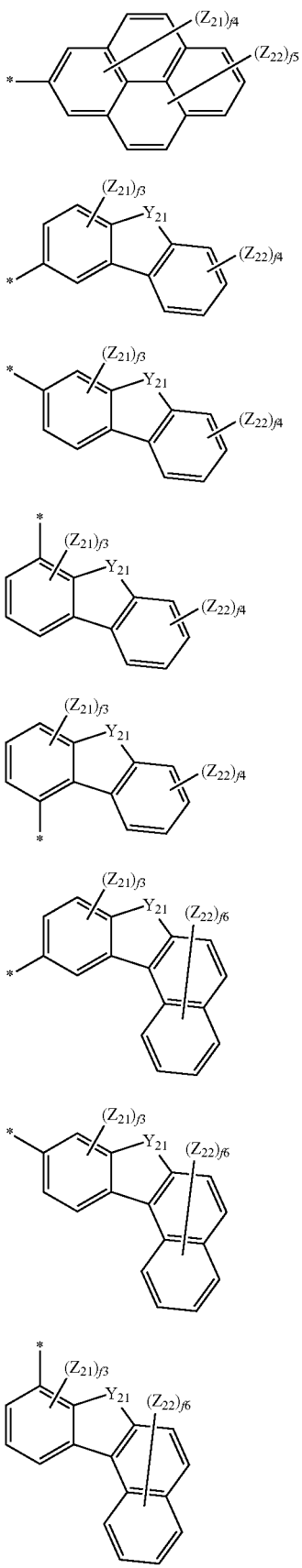
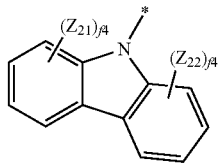
Formula 7-12
Formula 7-13
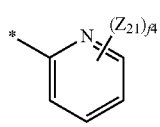
Formula 7-14
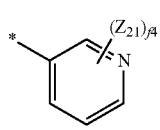
Formula 7-15
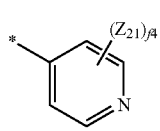
Formula 7-16
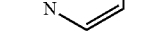
Formula 7-17
Formula 7-18
Formula 7-19
Formula 7-20
Formula 7-21
Formula 7-22
Formula 7-23
Formula 7-24
Formula 7-25
Formula 7-26
Formula 7-27
Formula 7-28
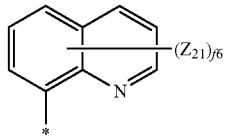
Formula 7-29
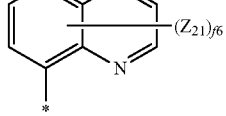
Formula 7-30

Formula 7-31
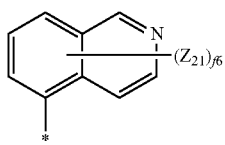
Formula 7-32
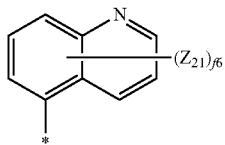
Formula 7-33
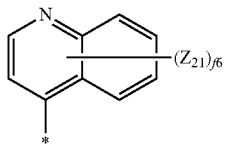
Formula 7-34
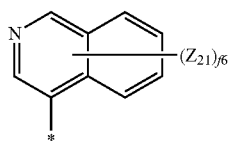
Formula 7-35
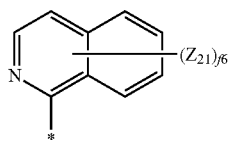
Formula 7-36
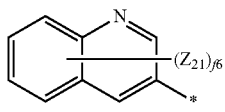
Formula 7-37
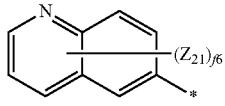
Formula 7-38
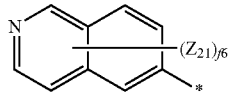
Formula 7-39
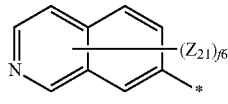
Formula 7-40
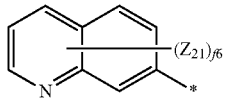
Formula 7-41
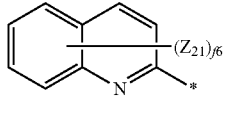
Formula 7-42
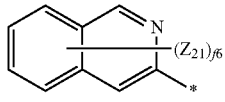
Formula 7-43
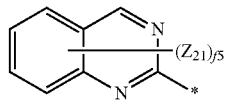
Formula 7-44
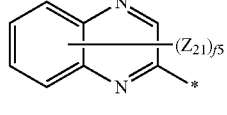
Formula 7-45
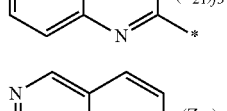
Formula 7-47
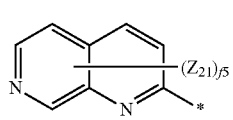
Formula 7-48
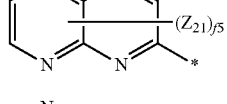
Formula 7-49
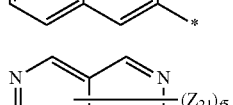
Formula 7-50
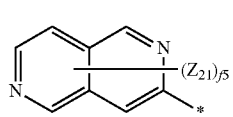
Formula 7-51
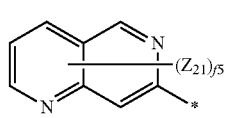
Formula 7-52
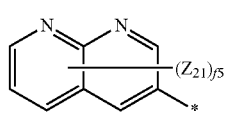
Formula 7-53
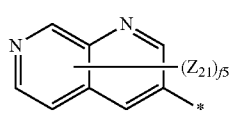
Formula 7-54
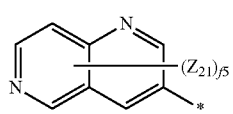
Formula 7-55
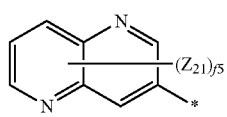
Formula 7-56
Formula 7-57

Formula 7-58
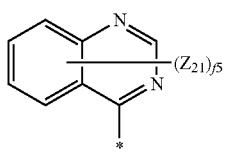

Formula 7-59
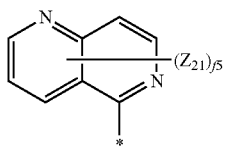

Formula 7-60
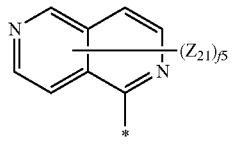

Formula 7-61
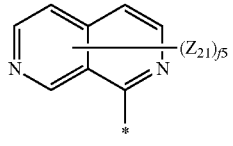

Formula 7-62
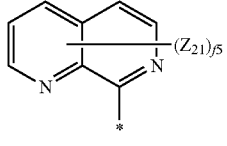

Formula 7-62
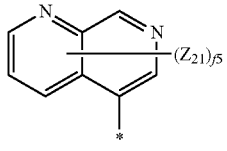

Formula 7-63
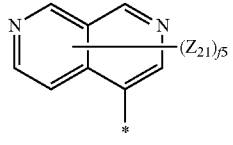

Formula 7-64
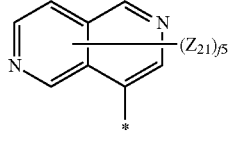

Formula 7-65
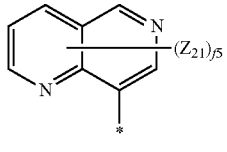

Formula 7-66
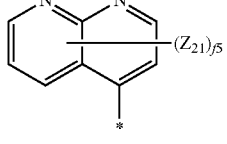

Formula 7-67
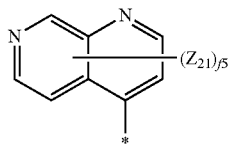

Formula 7-68
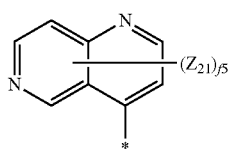

Formula 7-69
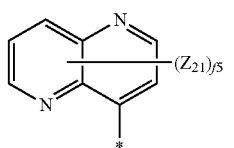

Formula 7-70
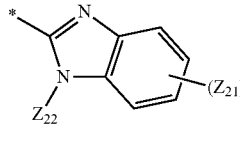

Formula 7-71
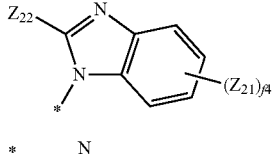

Formula 7-72
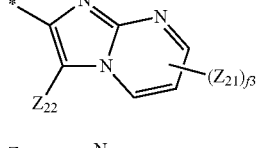

Formula 7-73
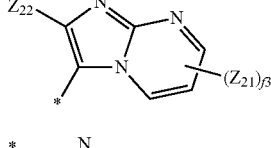

Formula 7-74
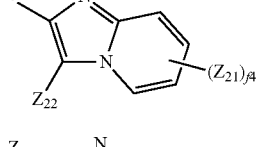

Formula 7-75
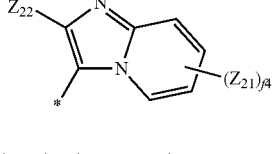

wherein, in Formulae 7-1 to 7-75, $Y_{21}$ is selected from O, S, $C(Z_{23})(Z_{24})$, $N(Z_{25})$, and $Si(Z_{26})(Z_{27})$, $Z_{21}$ to $Z_{27}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, f2 is an integer selected from 1 and 2,
f3 is an integer from 1 to 3,
f4 is an integer from 1 to 4,
f5 is an integer from 1 to 5,
f6 is an integer from 1 to 6,
f7 is an integer from 1 to 7,
f8 is an integer from 1 to 8,
f9 is an integer from 1 to 9, and
* indicates a binding site to an adjacent atom.

12. The condensed-cyclic compound of claim 1, wherein
$R_3$, $R_4$, $R_6$ and $R_{13}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a biphenyl group, a terphenyl group, a naphthyl group, and —Si($Q_1$)($Q_2$)($Q_3$), and $R_1$, $R_2$, and $R_{12}$ are each independently selected from groups represented by Formulae 8-1 to 8-159, wherein $Q_1$ to $Q_3$ are each independently selected from a $C_1$-$C_{10}$ alkyl group, a $C_1$-$C_{10}$ alkoxy group, a phenyl group, a biphenyl group, a terphenyl group, and a naphthyl group:

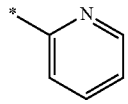
Formula 8-1

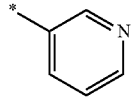
Formula 8-2

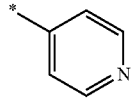
Formula 8-3

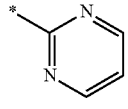
Formula 8-4

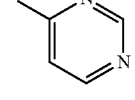
Formula 8-5

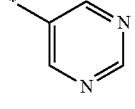
Formula 8-6

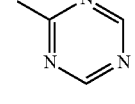
Formula 8-7

-continued

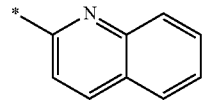
Formula 8-8

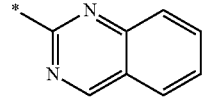
Formula 8-9

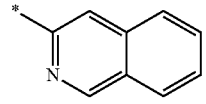
Formula 8-10

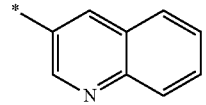
Formula 8-11

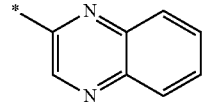
Formula 8-12

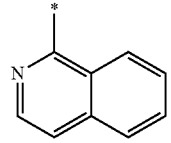
Formula 8-13

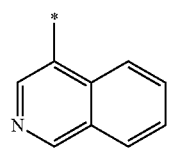
Formula 8-14

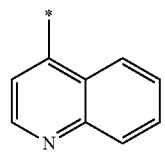
Formula 8-15

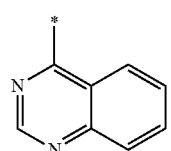
Formula 8-16

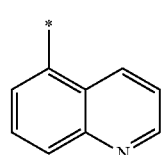
Formula 8-17

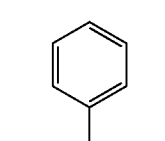
Formula 8-18

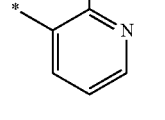

Formula 8-19
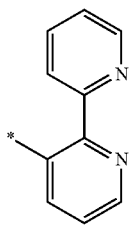
Formula 8-20
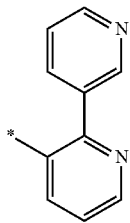
Formula 8-21
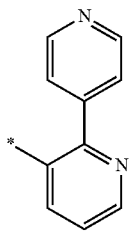
Formula 8-22
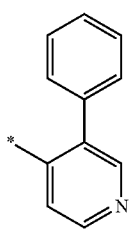
Formula 8-23
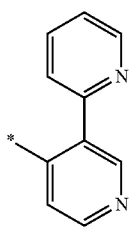
Formula 8-24
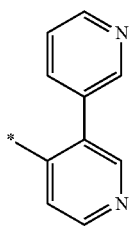
Formula 8-25
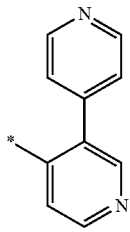
Formula 8-26
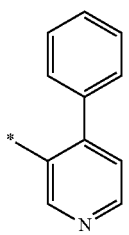
Formula 8-27
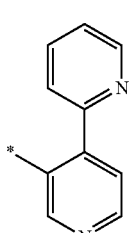
Formula 8-28
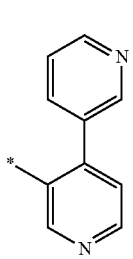
Formula 8-29
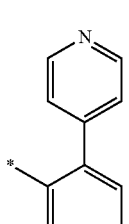
Formula 8-30
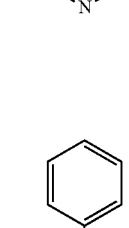
Formula 8-31
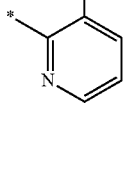

Formula 8-32
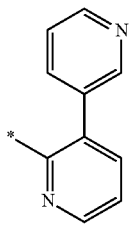
Formula 8-33
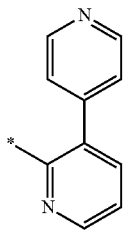
Formula 8-34
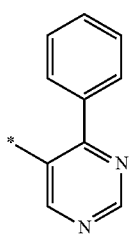
Formula 8-35
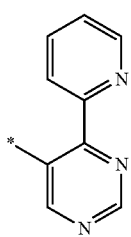
Formula 8-36
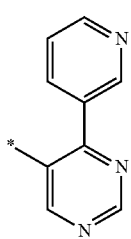
Formula 8-37
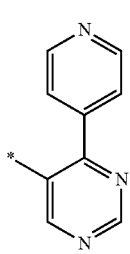
Formula 8-38
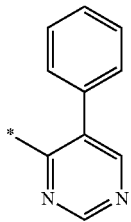
Formula 8-39
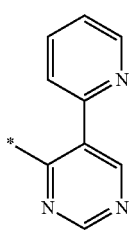
Formula 8-40
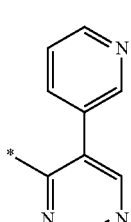
Formula 8-41
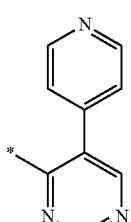
Formula 8-42
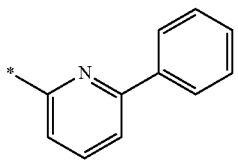
Formula 8-43
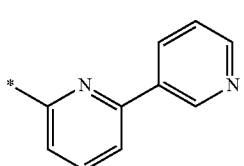
Formula 8-44
Formula 8-45

Formula 8-46
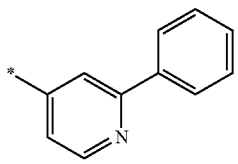
Formula 8-47
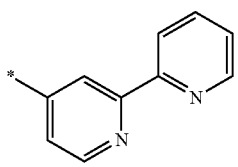
Formula 8-48
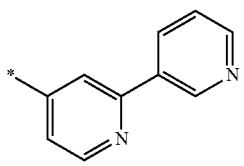
Formula 8-49
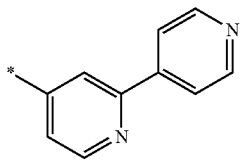
Formula 8-50
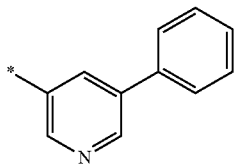
Formula 8-51
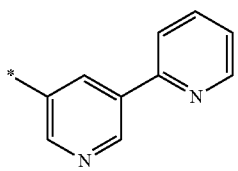
Formula 8-52
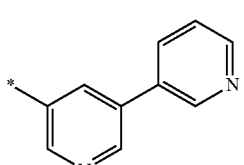
Formula 8-53
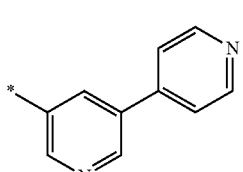
Formula 8-54
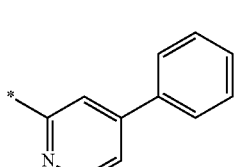
Formula 8-55
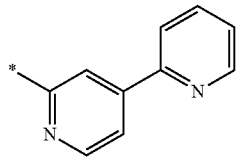
Formula 8-56
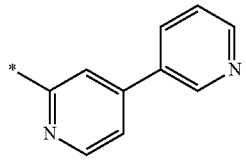
Formula 8-57
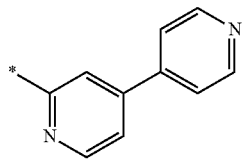
Formula 8-58
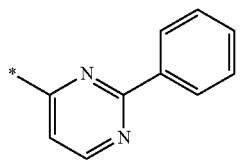
Formula 8-59
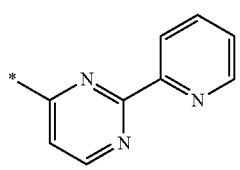
Formula 8-60
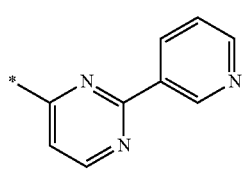
Formula 8-61
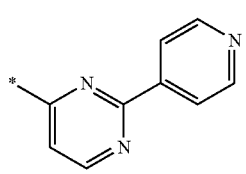
Formula 8-62
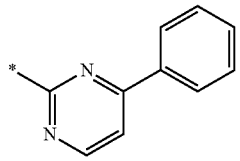
Formula 8-63
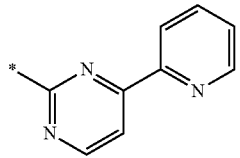

| | |
|---|---|
| 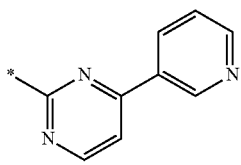 Formula 8-64 | 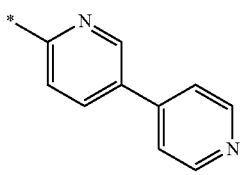 Formula 8-73 |
| 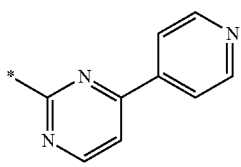 Formula 8-65 |  Formula 8-74 |
| 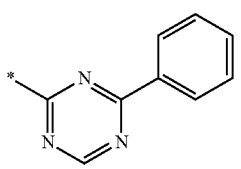 Formula 8-66 | 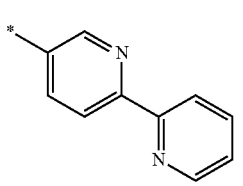 Formula 8-75 |
| 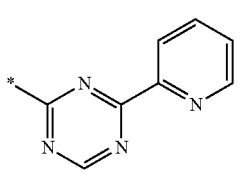 Formula 8-67 | 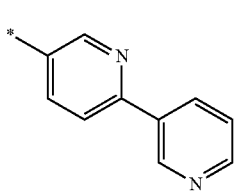 Formula 8-76 |
| 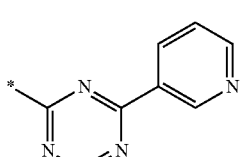 Formula 8-68 |  Formula 8-77 |
| 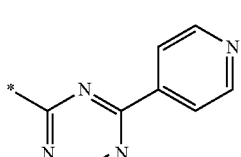 Formula 8-69 | 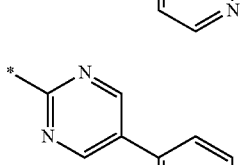 Formula 8-78 |
| 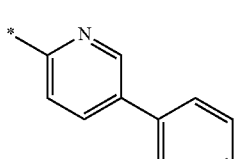 Formula 8-70 | 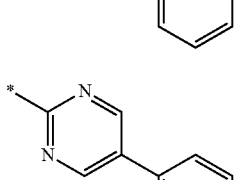 Formula 8-79 |
| 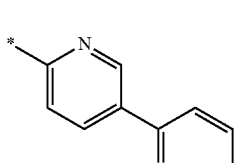 Formula 8-71 | 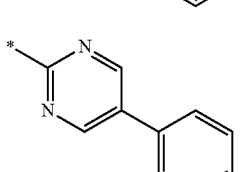 Formula 8-80 |
| 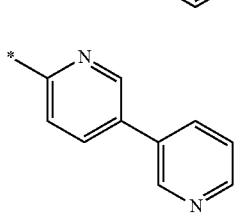 Formula 8-72 | 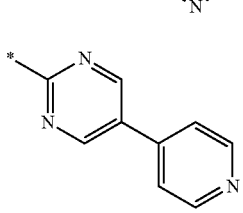 Formula 8-81 |

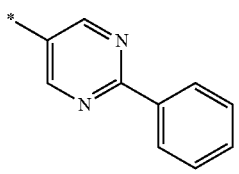
Formula 8-82
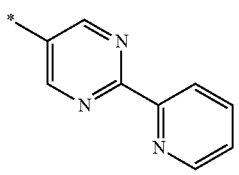
Formula 8-83
Formula 8-84
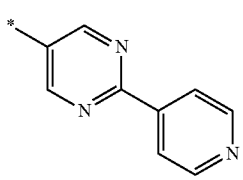
Formula 8-85
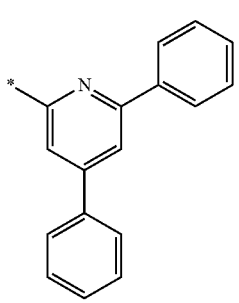
Formula 8-86
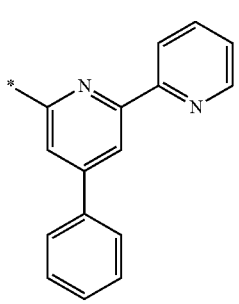
Formula 8-87
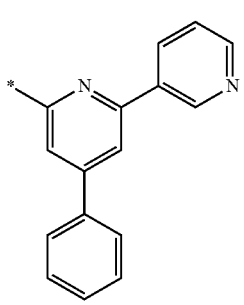
Formula 8-88
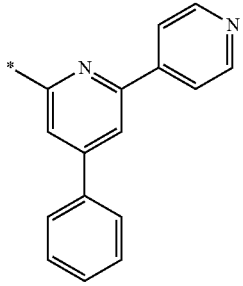
Formula 8-89
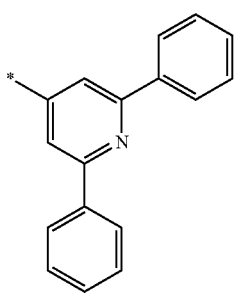
Formula 8-90
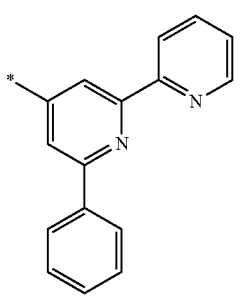
Formula 8-91
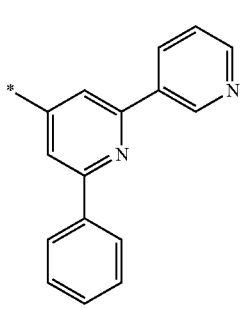
Formula 8-92
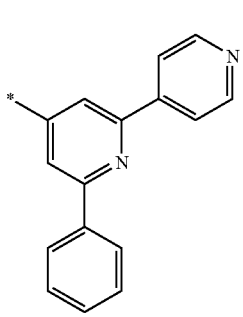
Formula 8-93

Formula 8-94
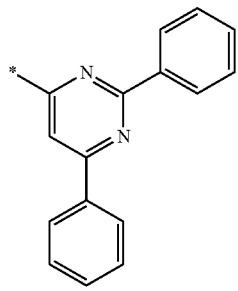
Formula 8-95
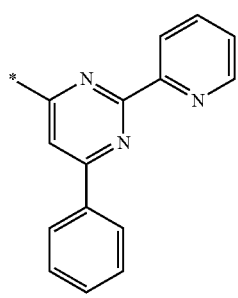
Formula 8-96
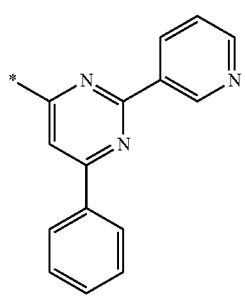
Formula 8-97
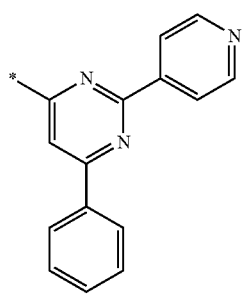
Formula 8-98
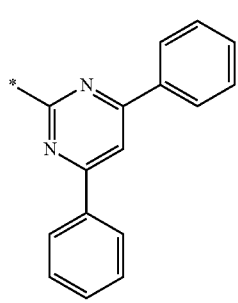
Formula 8-99
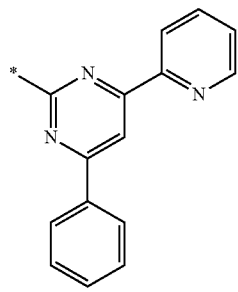
Formula 8-100
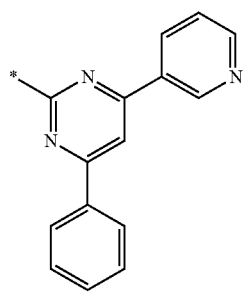
Formula 8-101
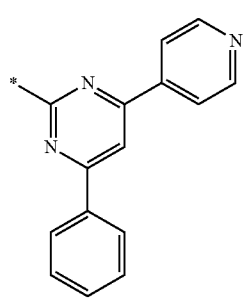
Formula 8-102
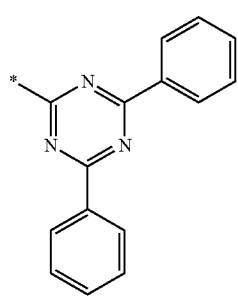
Formula 8-103
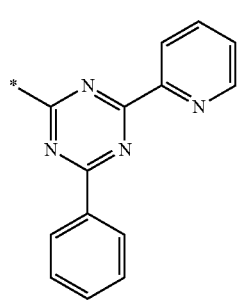

Formula 8-104
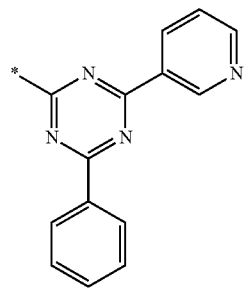
Formula 8-105
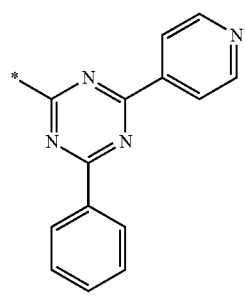
Formula 8-106
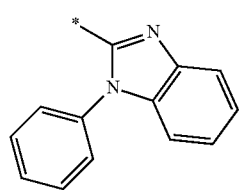
Formula 8-107
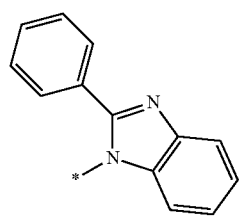
Formula 8-108
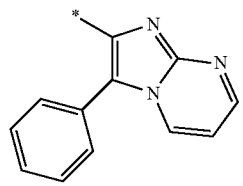
Formula 8-109
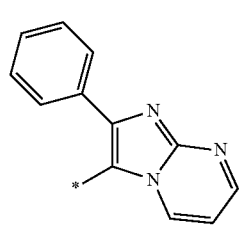
Formula 8-110
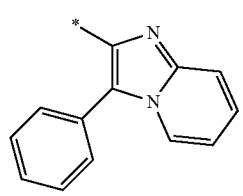
Formula 8-111
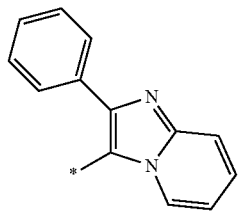
Formula 8-112
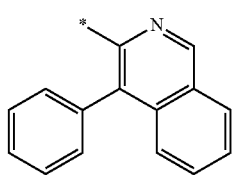
Formula 8-113
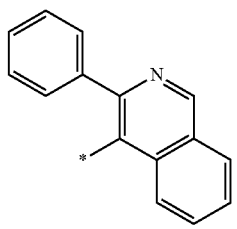
Formula 8-114
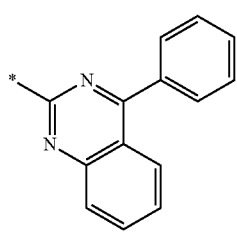
Formula 8-115
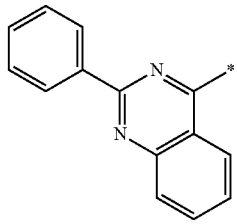
Formula 8-116
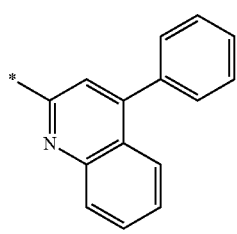
Formula 8-117
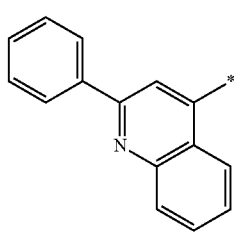

-continued
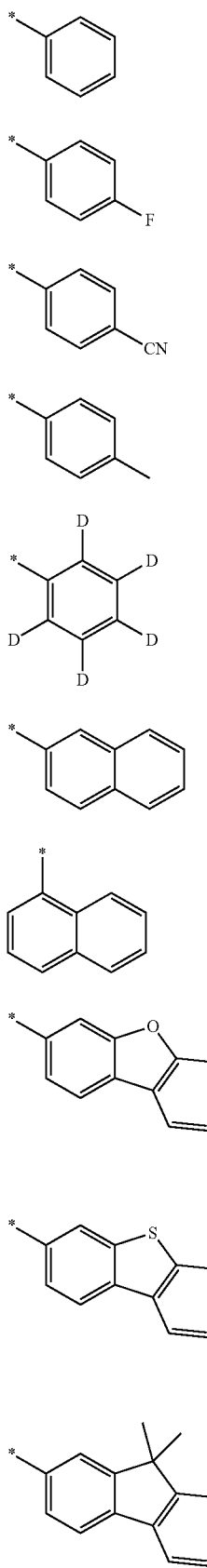
Formula 8-118
Formula 8-119
Formula 8-120
Formula 8-121
Formula 8-122
Formula 8-123
Formula 8-124
Formula 8-125
Formula 8-126
Formula 8-127
-continued
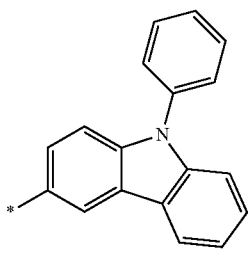
Formula 8-128
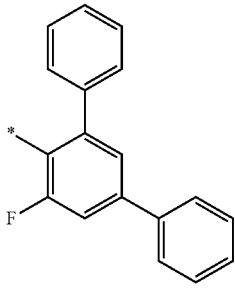
Formula 8-129
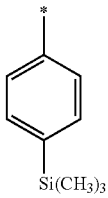
Formula 8-130
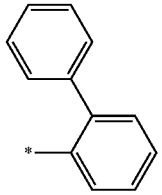
Formula 8-131
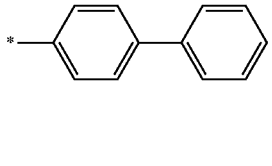
Formula 8-132
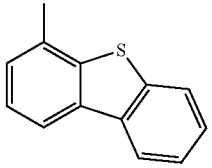
Formula 8-133
Formula 8-134
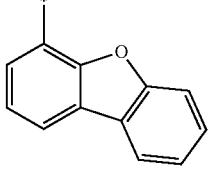

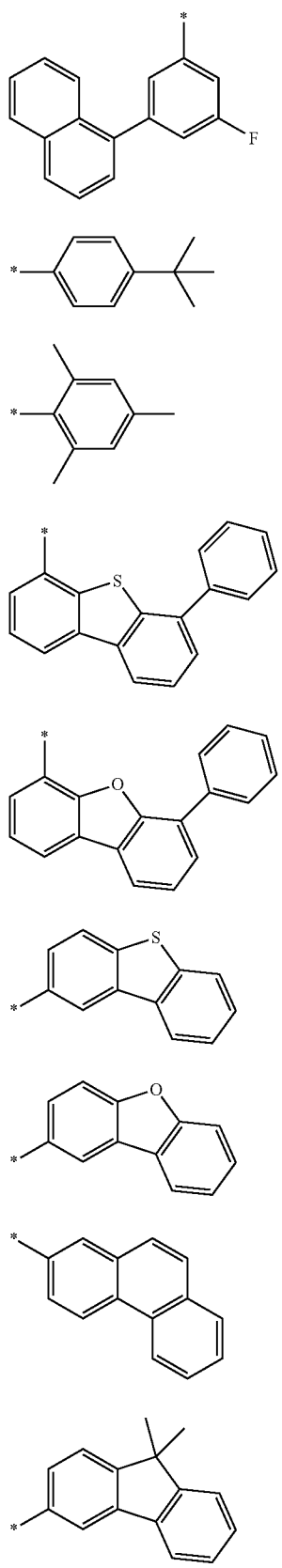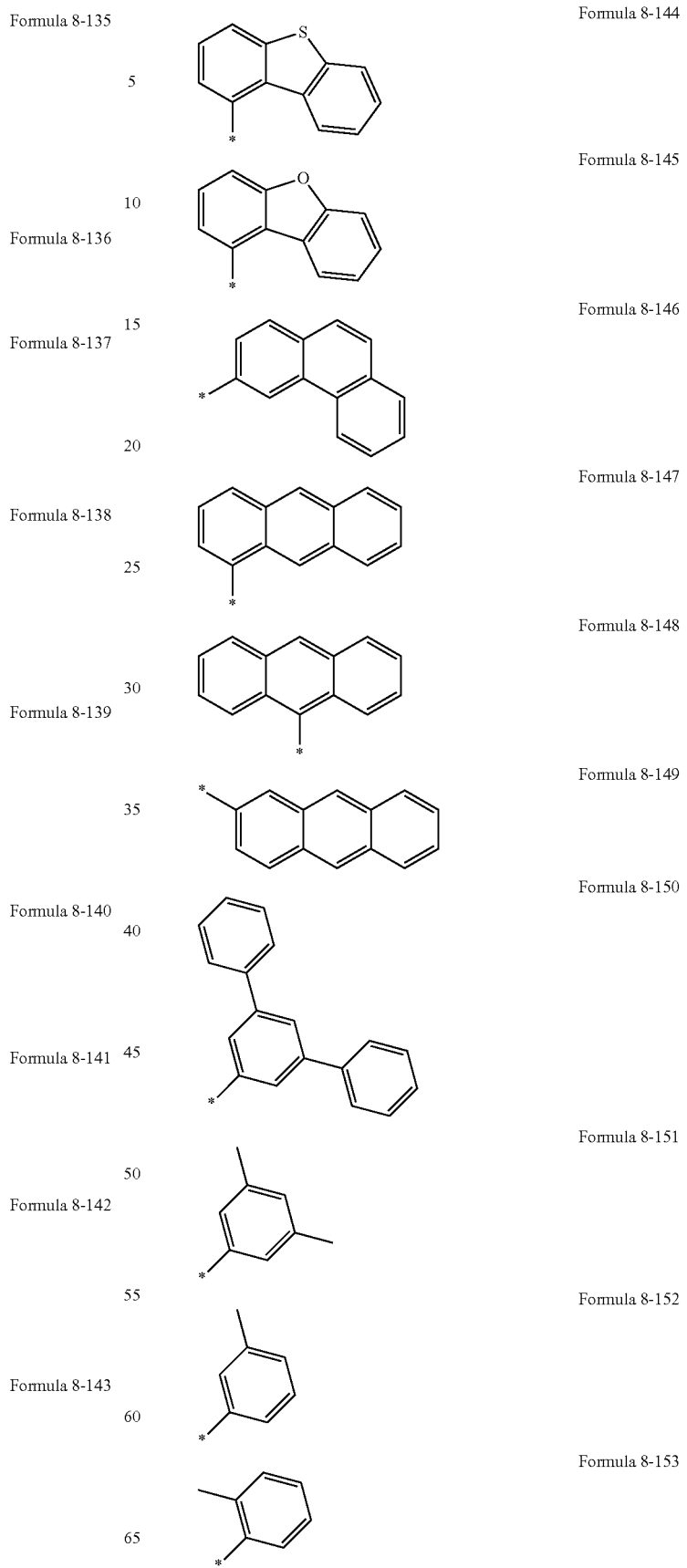

-continued
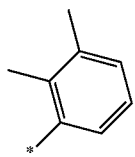
Formula 8-154
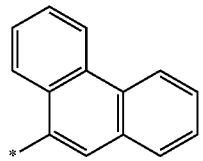
Formula 8-155
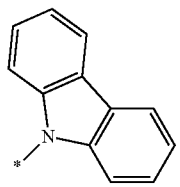
Formula 8-156
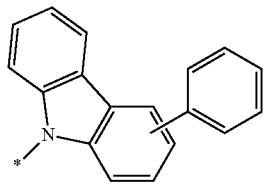
Formula 8-157
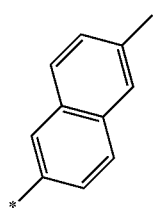
Formula 8-158
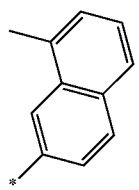
Formula 8-159
wherein, in Formulae 8-1 to 8-159, * indicates a binding site to an adjacent atom.
13. The condensed-cyclic compound of claim 1, wherein the condensed-cyclic compound is represented by one of Formulae 1A to 1E:
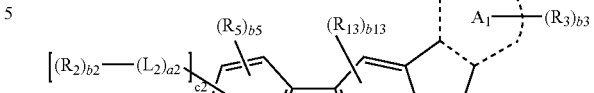
Formula 1A
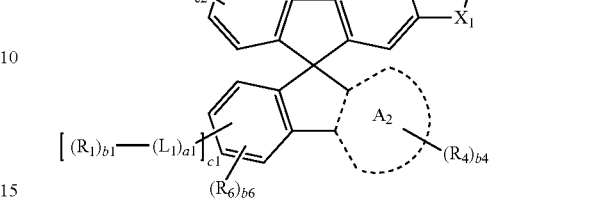
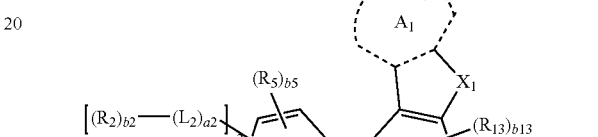
Formula 1B
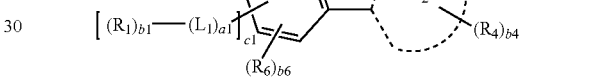
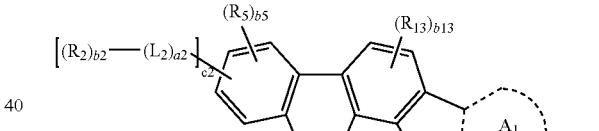
Formula 1C
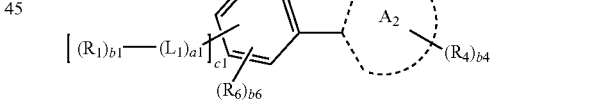
Formula 1D
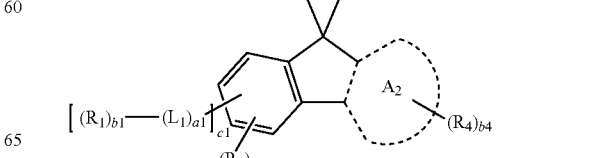

Formula 1E
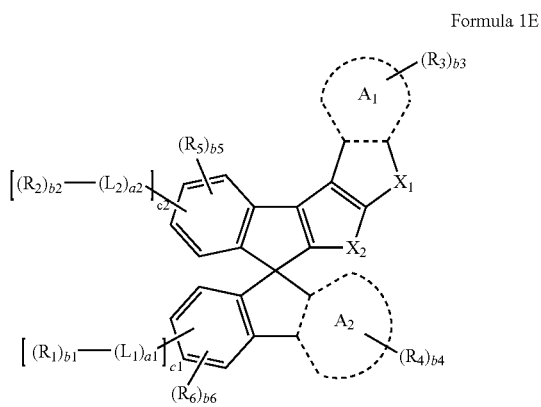
wherein, in Formulae 1A to 1E, ring $A_1$, ring $A_2$, $X_1$, $X_2$, $L_1$, $L_2$, $a_1$, $a_2$, $L_{11}$, $L_{12}$, $a_{11}$, $a_{12}$, $R_1$ to $R_6$, $R_{11}$ to $R_{13}$, $b_1$ to $b_6$, $b_{11}$ to $b_{13}$, c1, and c2 are the same as those defined in claim 1.
14. The condensed-cyclic compound of claim 1, wherein the condensed-cyclic compound is represented by one of Formulae 1-1 to 1-7:
Formula 1-1
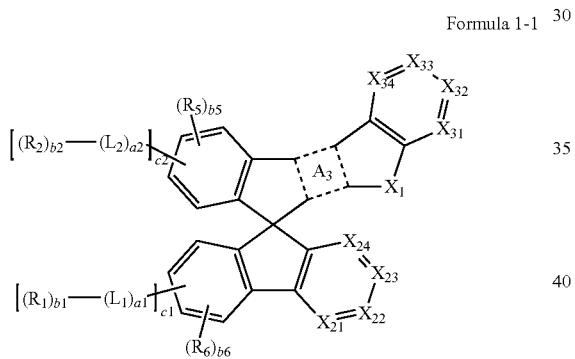
Formula 1-2
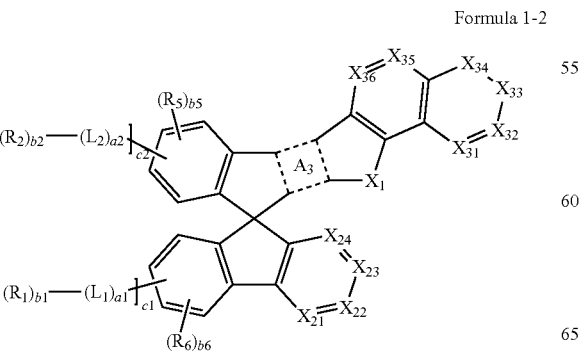
Formula 1-3
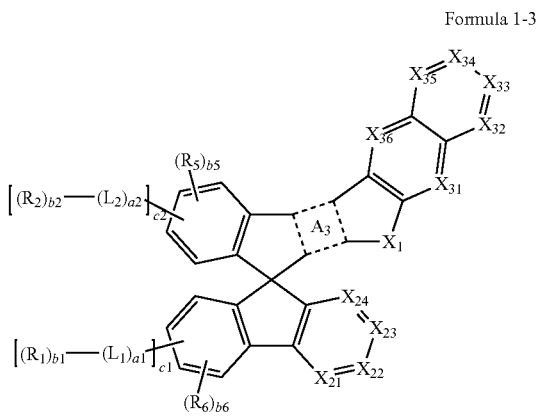
Formula 1-4
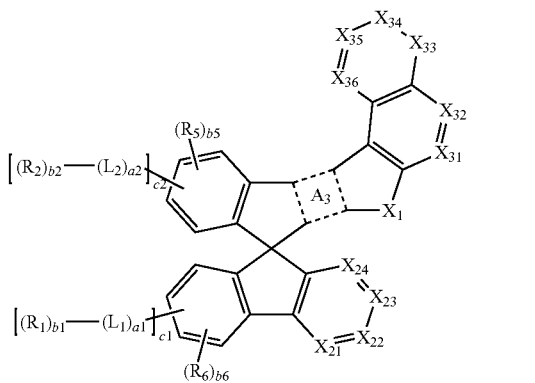
Formula 1-5
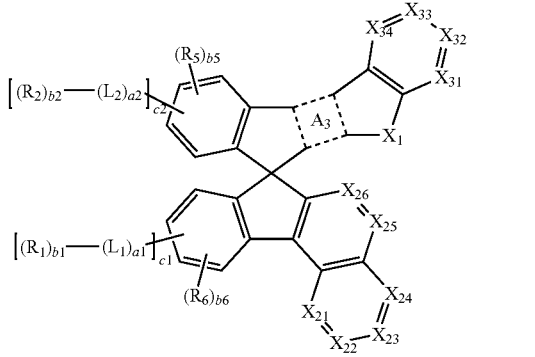
Formula 1-6
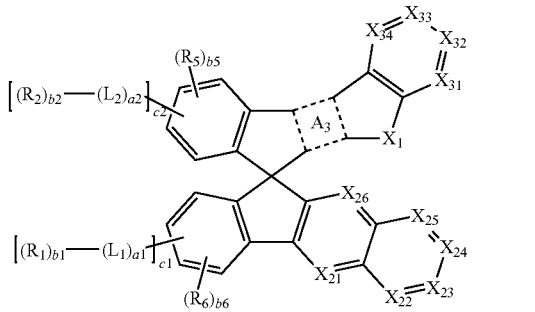

-continued

Formula 1-7

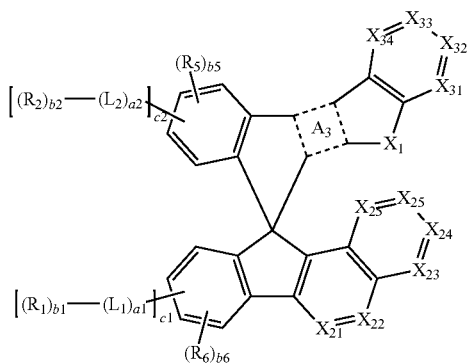

wherein, in Formulae 1-1 to 1-7, ring $A_3$, $X_1$, $X_2$, $L_1$, $L_2$, $a_1$, $a_2$, $L_{11}$, $L_{12}$, $a_{11}$, $a_{12}$, $R_1$, $R_2$, $R_5$, $R_6$, $R_{11}$ to $R_{13}$, $b_1$, $b_2$, $b_5$, $b_6$, $b_{11}$ to $b_{13}$, c1, and c2 are the same as those defined in claim 1, $X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, $X_{26}$ is N or $C(R_{26})$, at least one selected from $X_{21}$ to $X_{26}$ is N, $X_{31}$ is N or $C(R_{31})$, $X_{32}$ is N or $C(R_{32})$, $X_{33}$ is N or $C(R_{33})$, $X_{34}$ is N or $C(R_{34})$, $X_{35}$ is N or $C(R_{35})$, $X_{36}$ is N or $C(R_{36})$, $R_{21}$ and $R_{26}$ are each independently the same as defined in claim 1 with reference to $R_3$, and $R_{31}$ and $R_{36}$ are each independently the same as defined in claim 1 with reference to $R_4$.

15. The condensed-cyclic compound of claim 1, wherein the condensed-cyclic compound is represented by one of Formulae 1(1) to 1(19):

Formula 1(1)

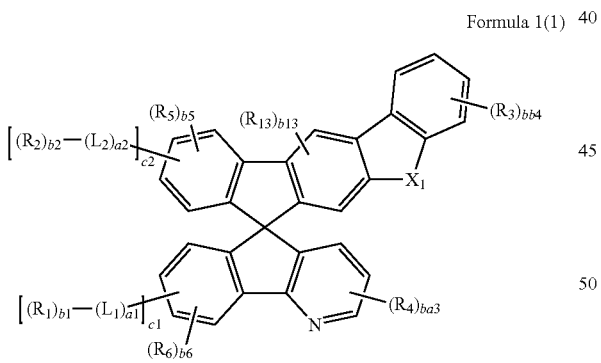

Formula 1(2)

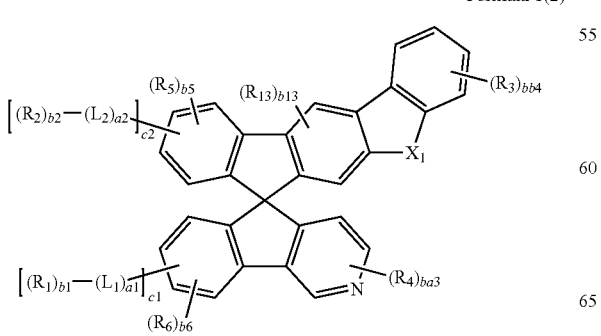

Formula 1(3)

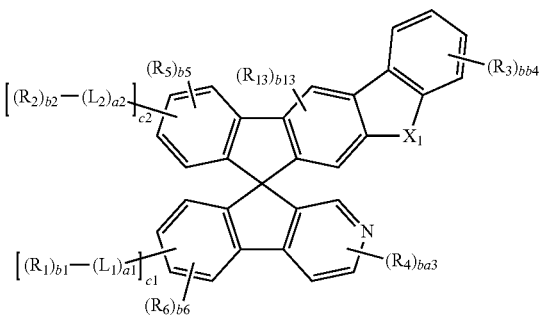

Formula 1(4)

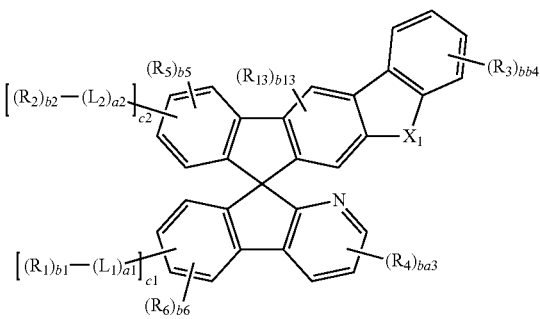

Formula 1(5)

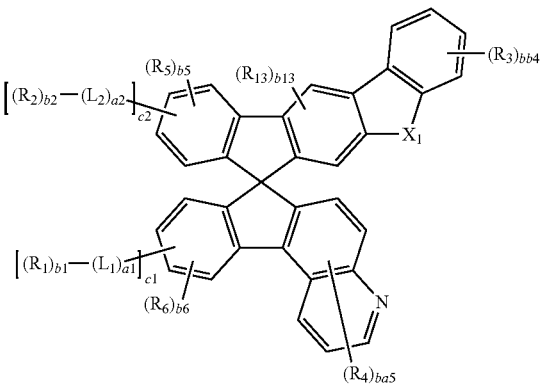

Formula 1(6)

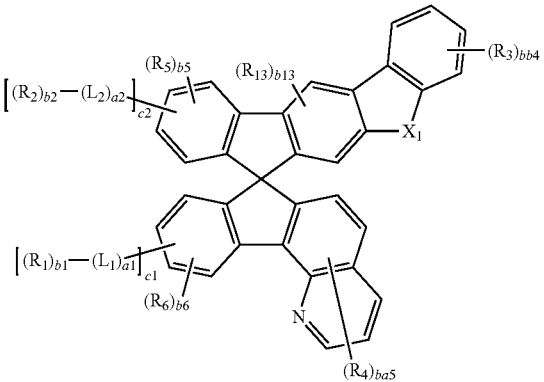

Formula 1(7)
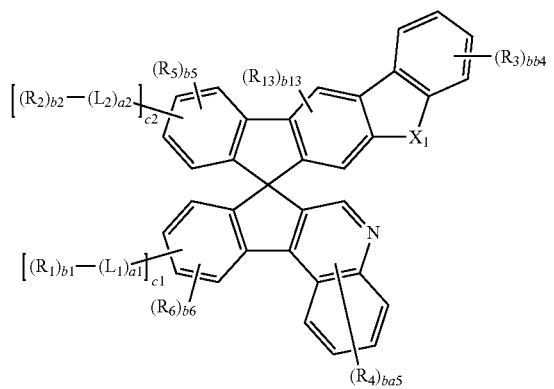
Formula 1(10)
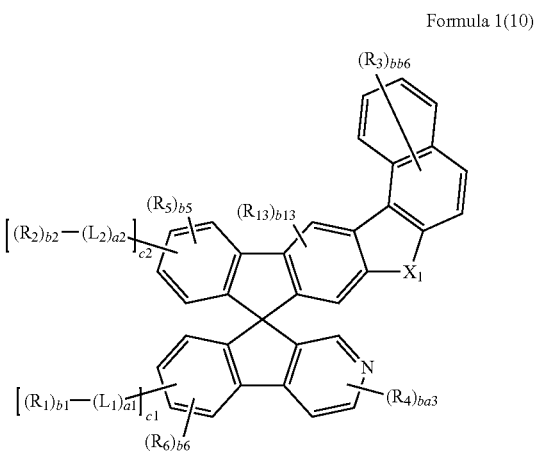
Formula 1(8)
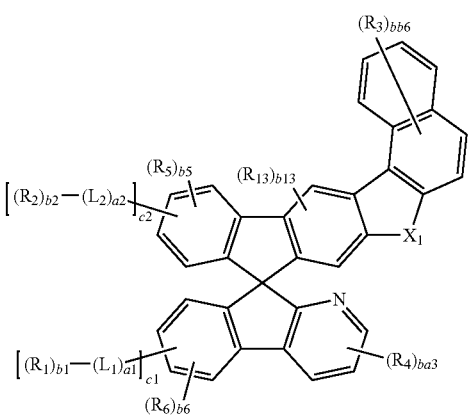
Formula 1(11)
Formula 1(9)
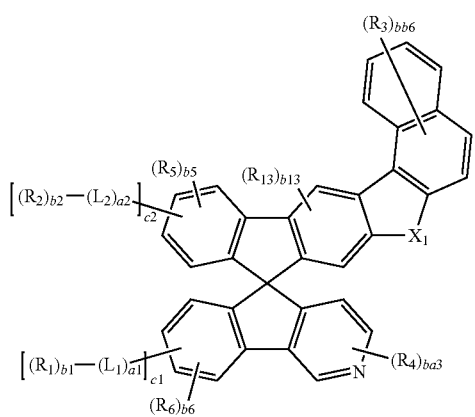
Formula 1(12)
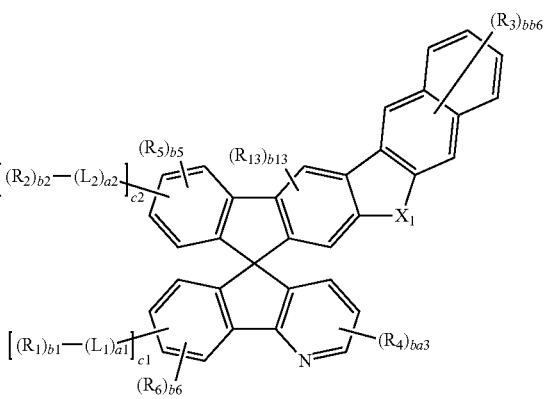

227
-continued

Formula 1(13)
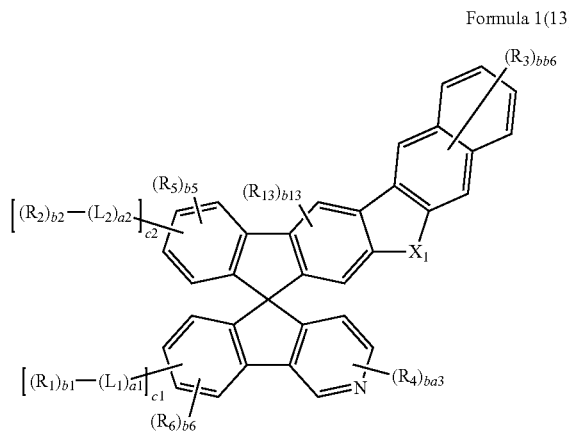

Formula 1(14)
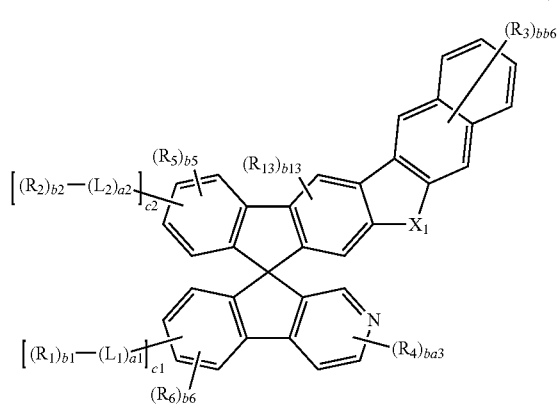

Formula 1(15)
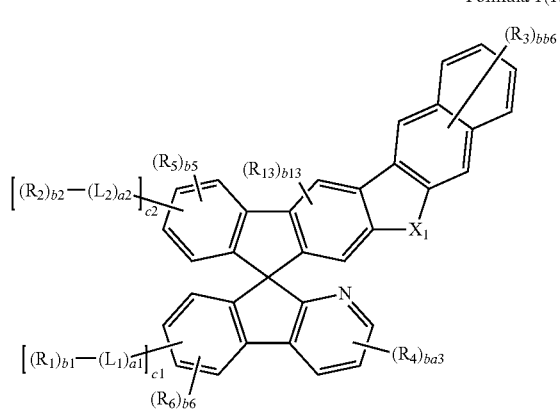

Formula 1(16)
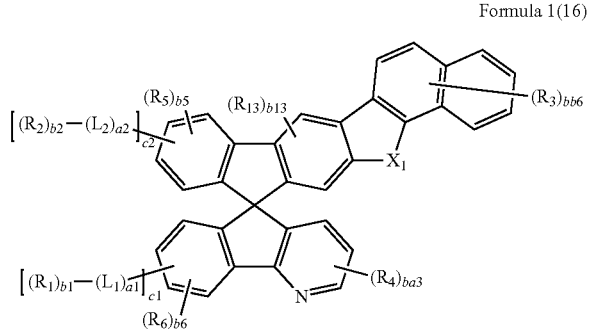

228
-continued

Formula 1(17)
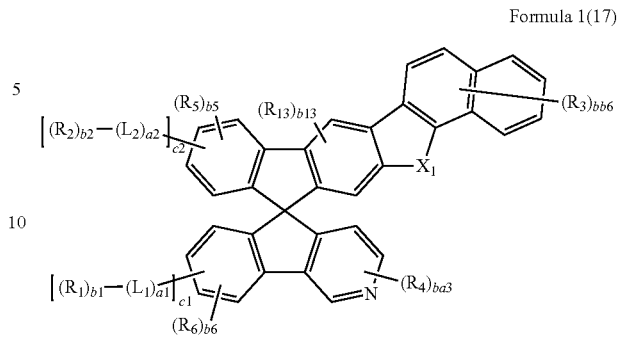

Formula 1(18)
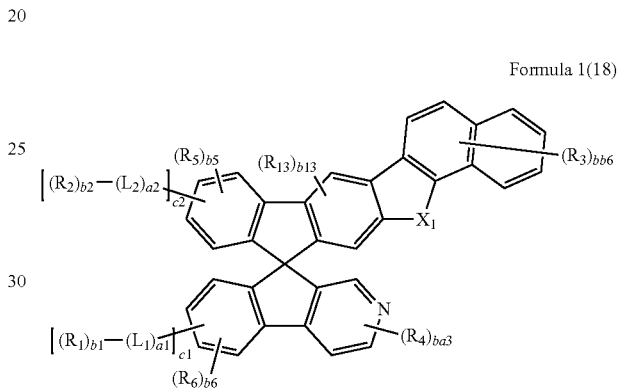

Formula 1(19)
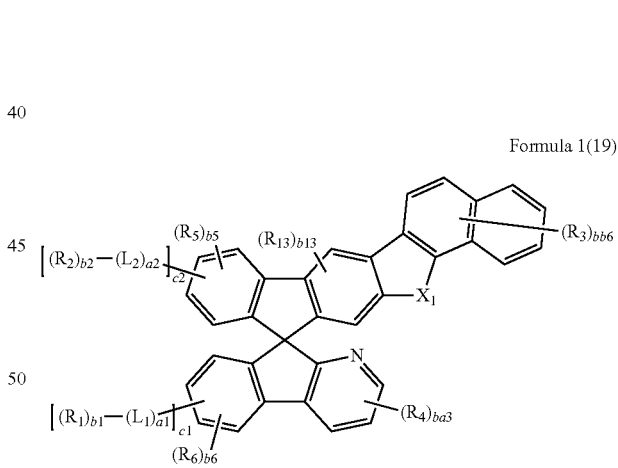

wherein, in Formulae 1(1) to 1(19), $X_1$, $L_1$, $L_2$, $a_1$, $a_2$, $L_{11}$, $L_{12}$, $a_{11}$, $a_{12}$, $R_1$ to $R_6$, $R_{11}$ to $R_{13}$, $b_1$ to $b_6$, $b_{11}$ to $b_{13}$, c1, and c2 are the same as those defined in claim 1, ba3 is an integer from 0 to 3, bb4 is an integer from 0 to 4, ba5 is an integer from 0 to 5, and bb6 is an integer from 0 to 6.

16. A condensed-cyclic compound represented by one of Formulae 1A-1 to 1A-3:

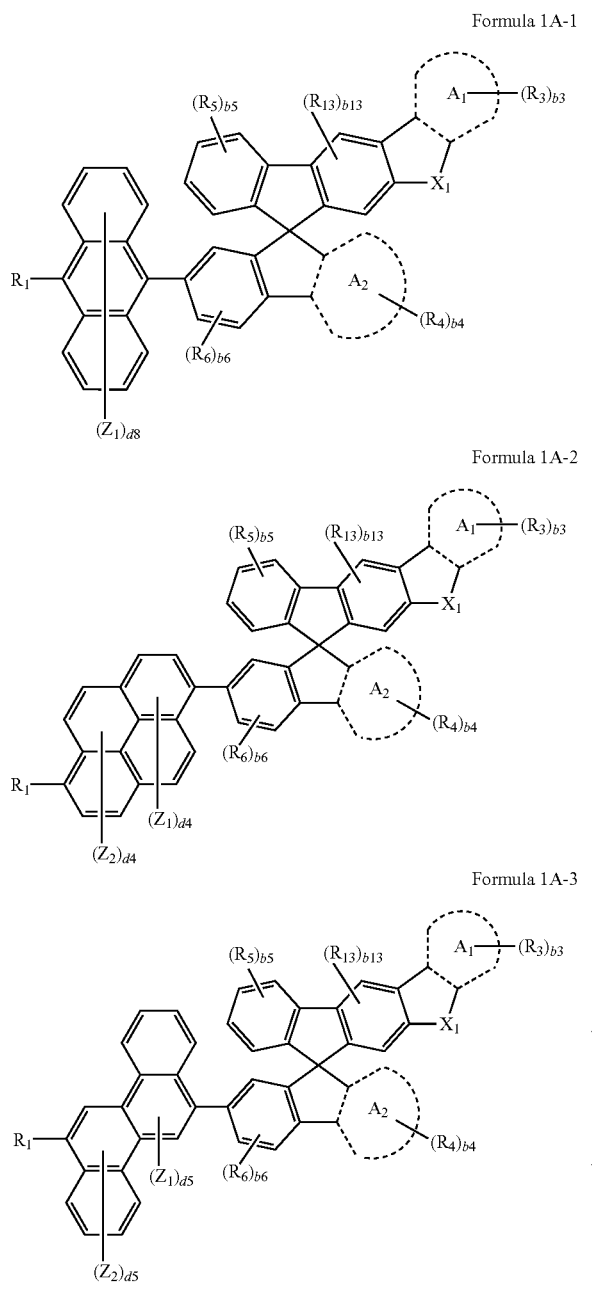

Formula 1A-1

Formula 1A-2

Formula 1A-3 wherein in Formulae 1A-1 to 1A-3,
ring $A_1$ is selected from a benzene group and a naphthalene group, ring $A_2$ is selected from a pyridine group, a quinoline group, and an isoquinoline group,
$X_1$ is $N(R_{11})_{b11}$,
$R_{11}$ is selected from groups represented by Formulae 6-1 to 6-27,
b11 is 1,
$R_1$ is selected from groups represented by Formulae 8-1 to 8-159,
b1 is 1,
$R_3$ to $R_6$, $R_{13}$, $Z_1$, and $Z_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group, and b3 to b6, b13, d4, d5, and d8 are each independently selected from 0, 1, and 2:

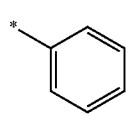

Formula 6-1

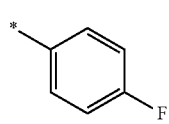

Formula 6-2

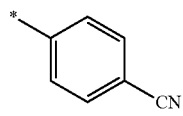

Formula 6-3

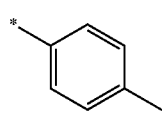

Formula 6-4

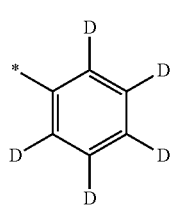

Formula 6-5

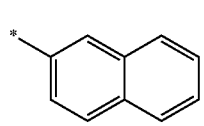

Formula 6-6

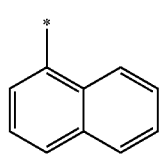

Formula 6-7

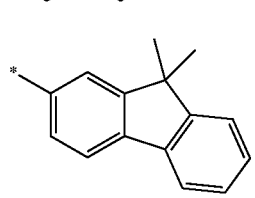

Formula 6-8

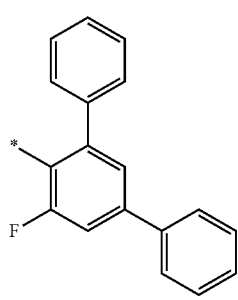

Formula 6-9

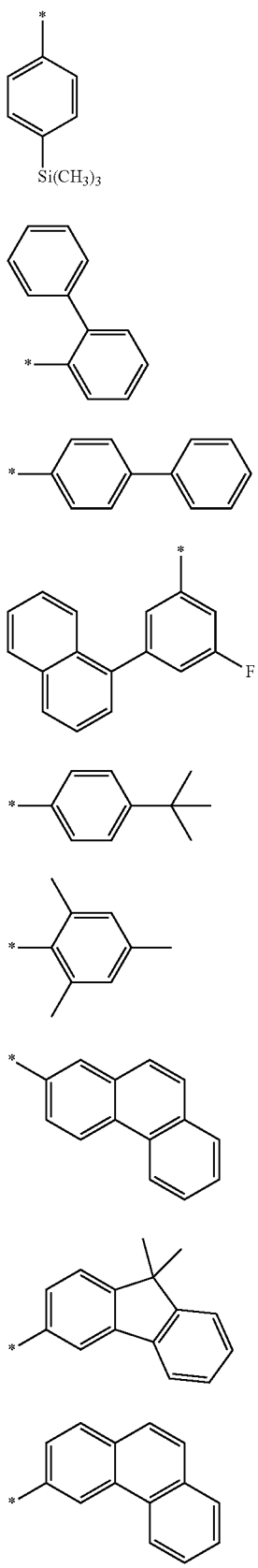
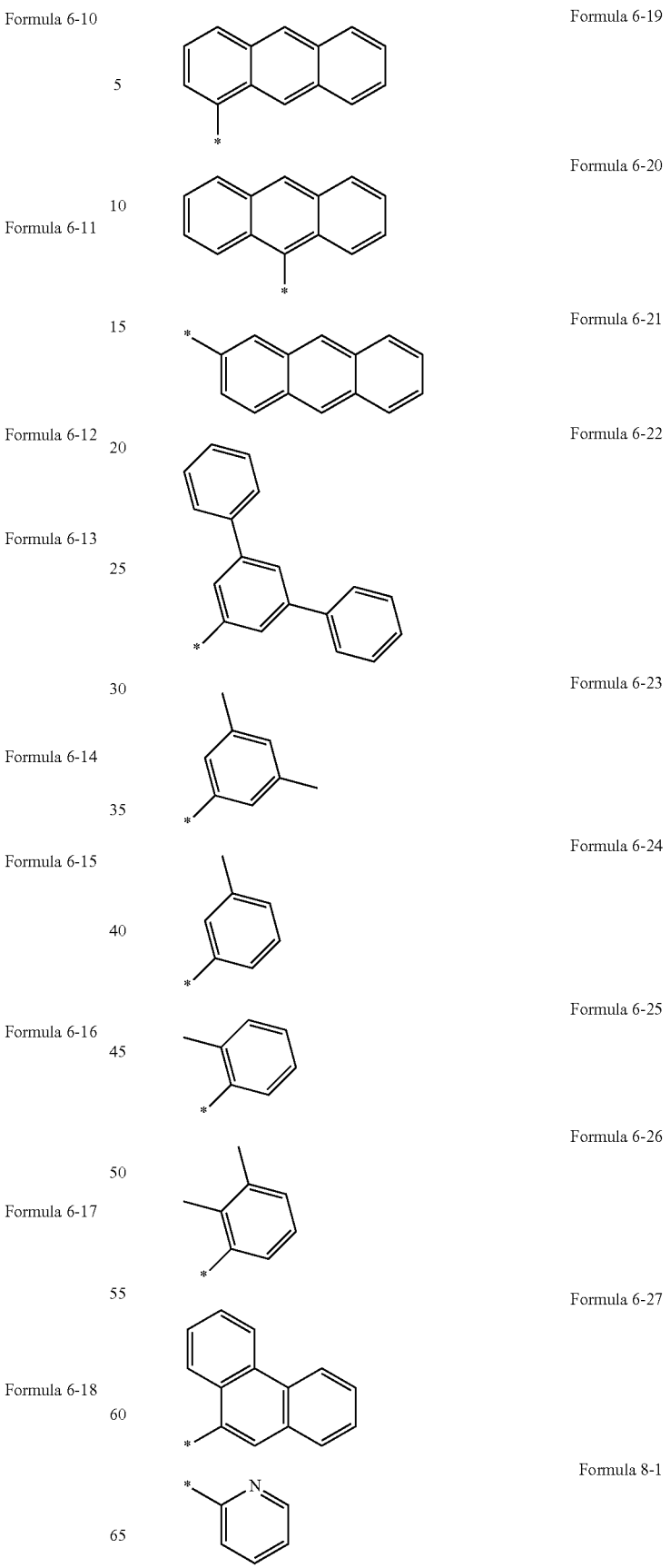

-continued
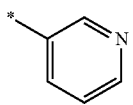
Formula 8-2
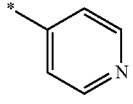
Formula 8-3
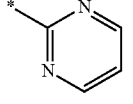
Formula 8-4
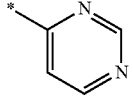
Formula 8-5
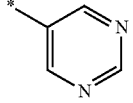
Formula 8-6
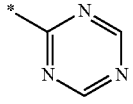
Formula 8-7
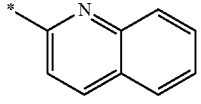
Formula 8-8
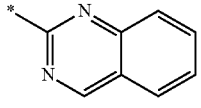
Formula 8-9
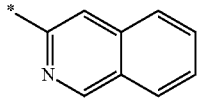
Formula 8-10
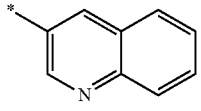
Formula 8-11
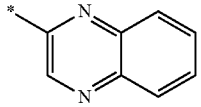
Formula 8-12
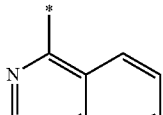
Formula 8-13
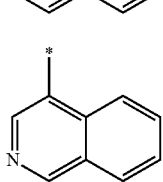
Formula 8-14
-continued
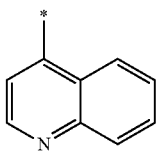
Formula 8-15
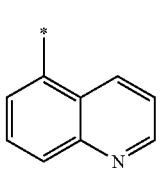
Formula 8-16
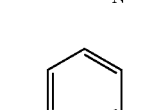
Formula 8-17
Formula 8-18
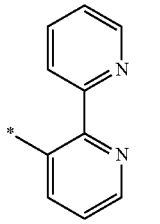
Formula 8-19
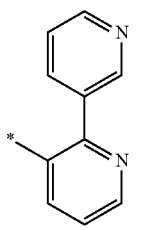
Formula 8-20
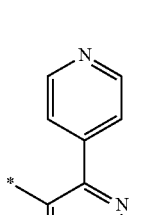
Formula 8-21

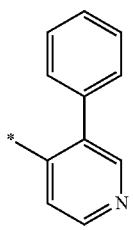
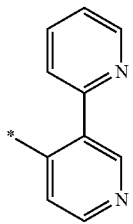
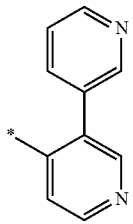
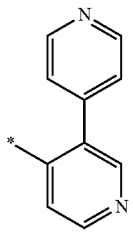
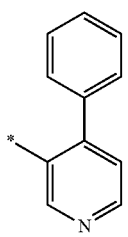
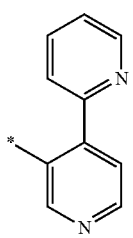
Formula 8-22
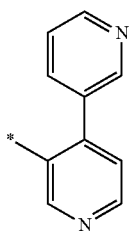
Formula 8-23
Formula 8-24
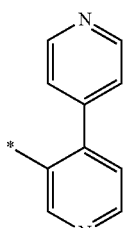
Formula 8-25
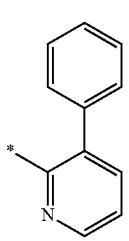
Formula 8-26
Formula 8-27
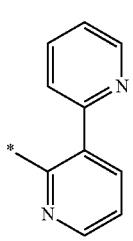
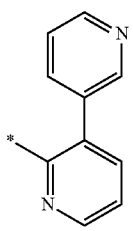
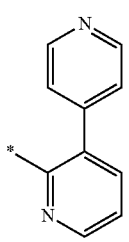
Formula 8-28
Formula 8-29
Formula 8-30
Formula 8-31
Formula 8-32
Formula 8-33

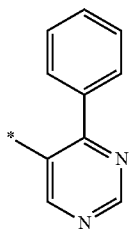
Formula 8-34
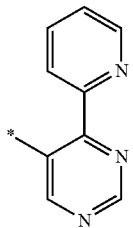
Formula 8-35
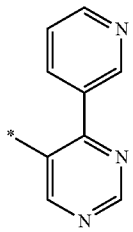
Formula 8-36
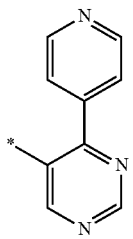
Formula 8-37
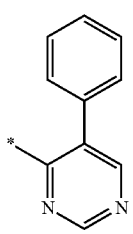
Formula 8-38
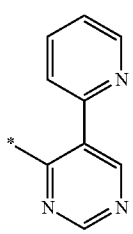
Formula 8-39
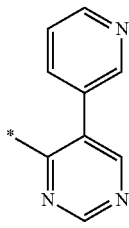
Formula 8-40
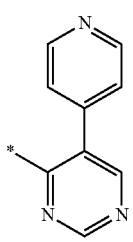
Formula 8-41
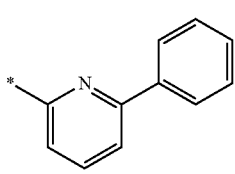
Formula 8-42
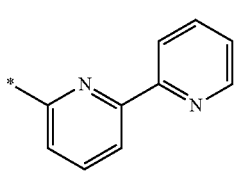
Formula 8-43
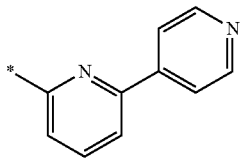
Formula 8-44
Formula 8-45
Formula 8-46
Formula 8-47

Formula 8-48
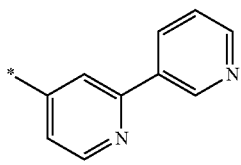
Formula 8-49
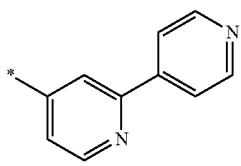
Formula 8-50
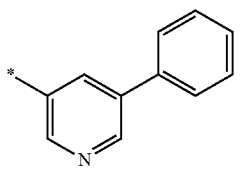
Formula 8-51
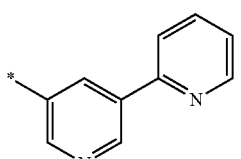
Formula 8-52
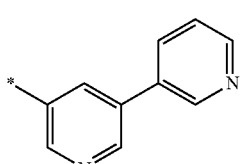
Formula 8-53
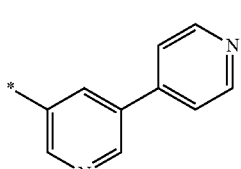
Formula 8-54
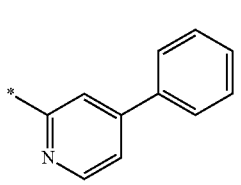
Formula 8-55
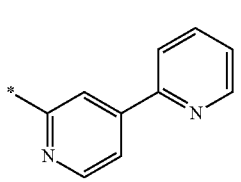
Formula 8-56
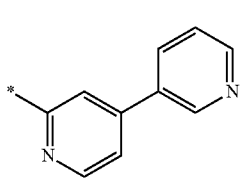
Formula 8-57
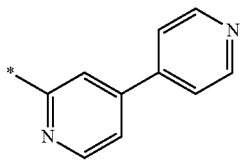
Formula 8-58
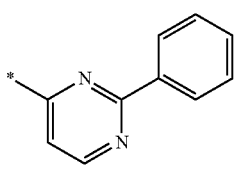
Formula 8-59
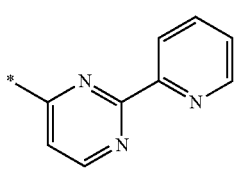
Formula 8-60
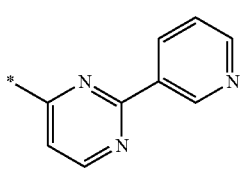
Formula 8-61
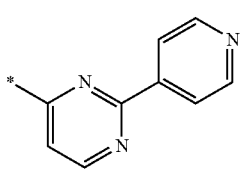
Formula 8-62
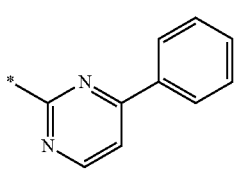
Formula 8-63
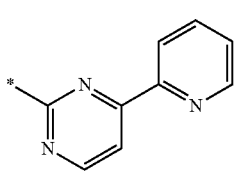
Formula 8-64
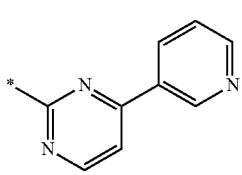
Formula 8-65
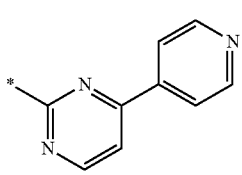

Formula 8-66
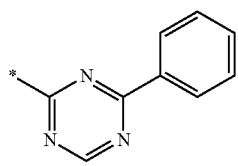
Formula 8-67
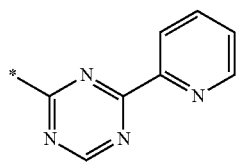
Formula 8-68
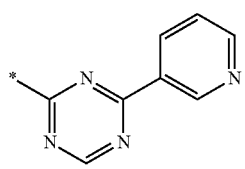
Formula 8-69
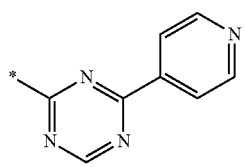
Formula 8-70
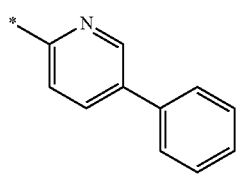
Formula 8-71
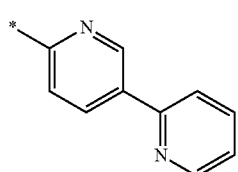
Formula 8-72
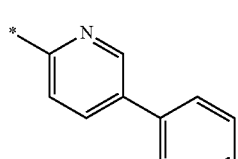
Formula 8-73
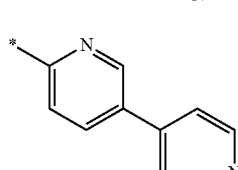
Formula 8-74
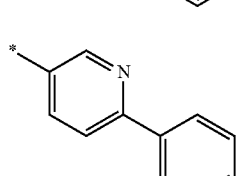
Formula 8-75
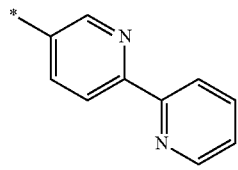
Formula 8-76
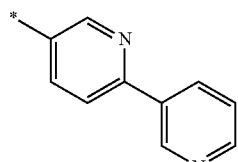
Formula 8-77
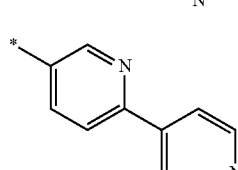
Formula 8-78
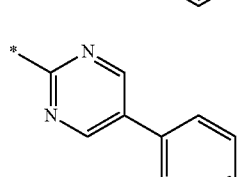
Formula 8-79
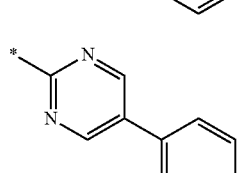
Formula 8-80
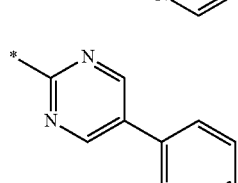
Formula 8-81
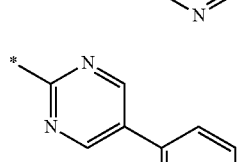
Formula 8-82
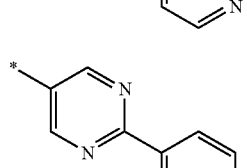
Formula 8-83
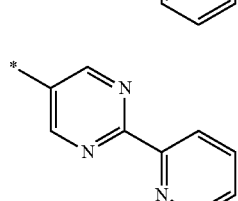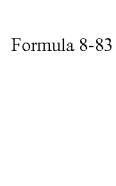

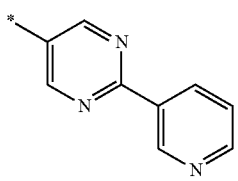
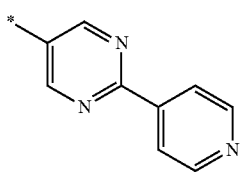
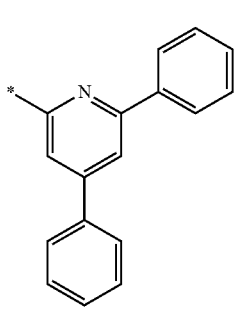
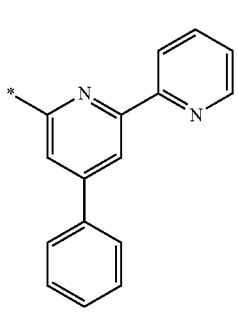
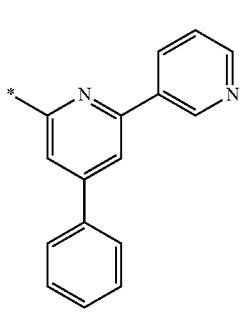
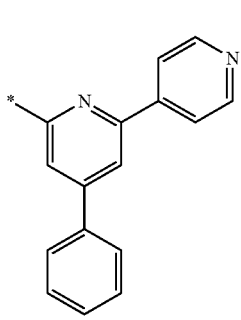
Formula 8-84
Formula 8-85
Formula 8-86
Formula 8-87
Formula 8-88
Formula 8-89
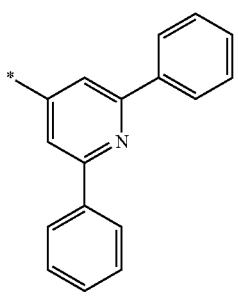
Formula 8-90
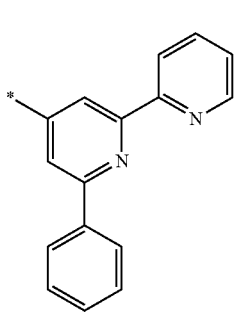
Formula 8-91
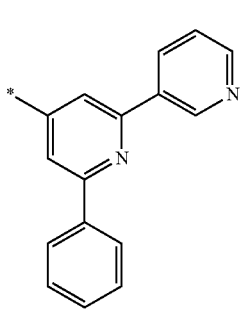
Formula 8-92
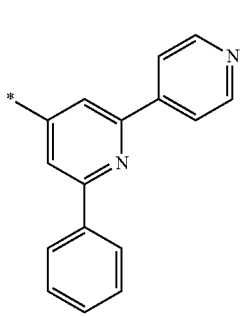
Formula 8-93
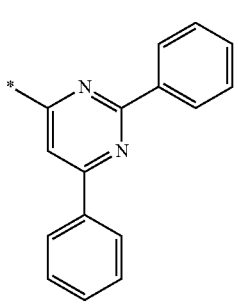
Formula 8-94

Formula 8-95
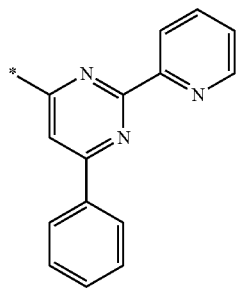
Formula 8-96
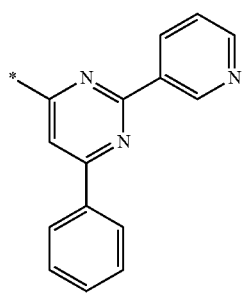
Formula 8-97
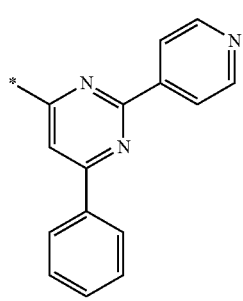
Formula 8-98
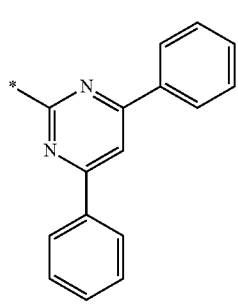
Formula 8-99
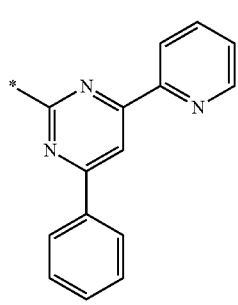
Formula 8-100
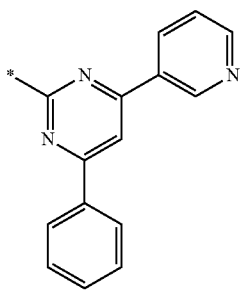
Formula 8-101
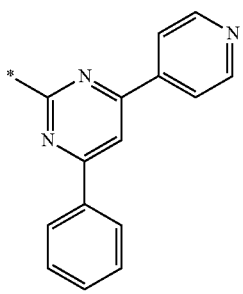
Formula 8-102
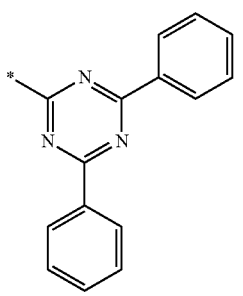
Formula 8-103
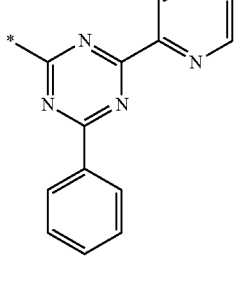
Formula 8-104
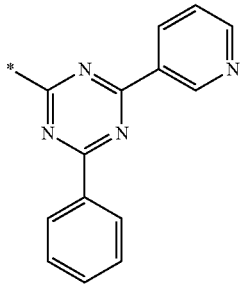

Formula 8-105
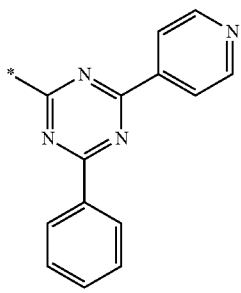
Formula 8-106
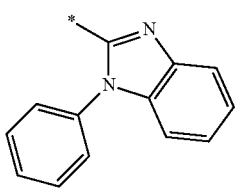
Formula 8-107
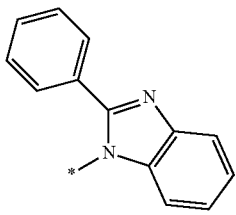
Formula 8-108
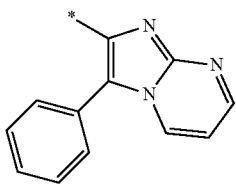
Formula 8-109
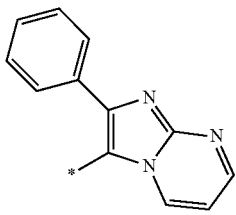
Formula 8-110
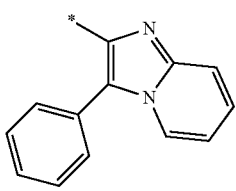
Formula 8-111
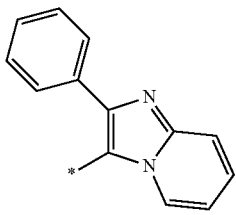
Formula 8-112
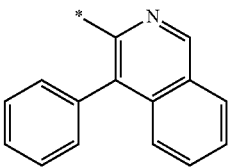
Formula 8-113
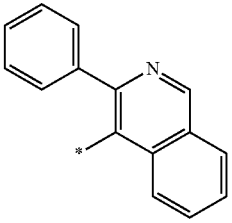
Formula 8-114
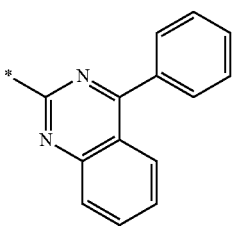
Formula 8-115
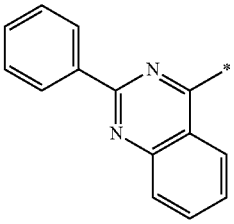
Formula 8-116
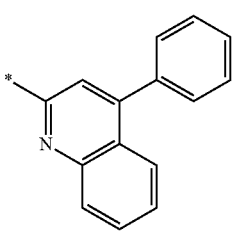
Formula 8-117
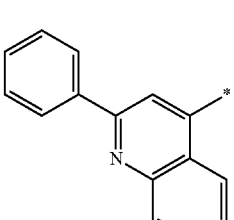
Formula 8-118
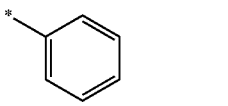
Formula 8-119
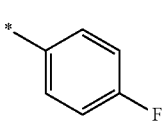

Formula 8-120 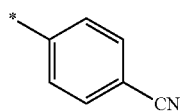
Formula 8-121 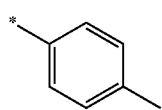
Formula 8-122 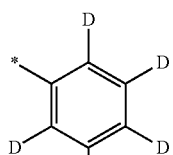
Formula 8-123 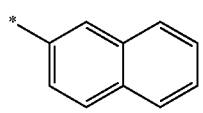
Formula 8-124 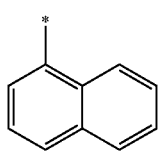
Formula 8-125 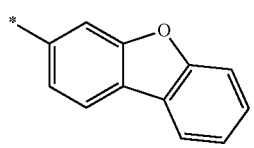
Formula 8-126 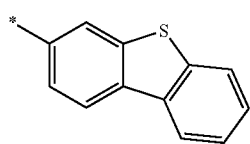
Formula 8-127 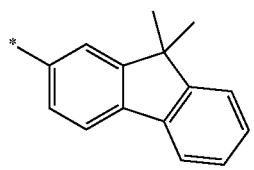
Formula 8-128 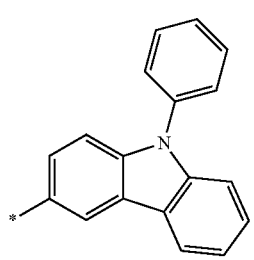
Formula 8-129 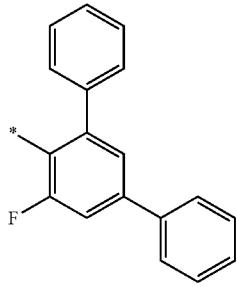
Formula 8-130 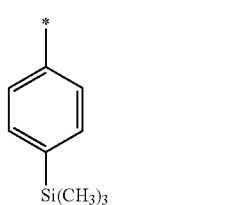
Formula 8-131 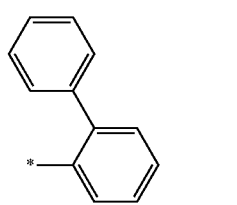
Formula 8-132 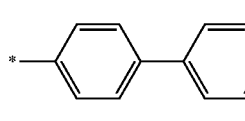
Formula 8-133 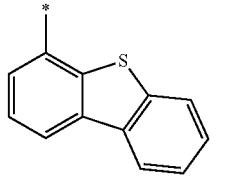
Formula 8-134 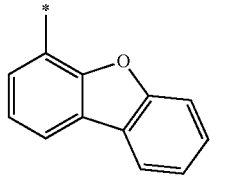
Formula 8-135 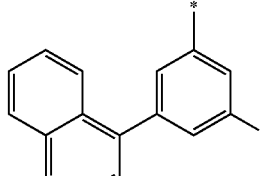
Formula 8-136 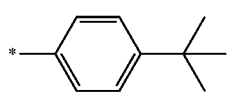

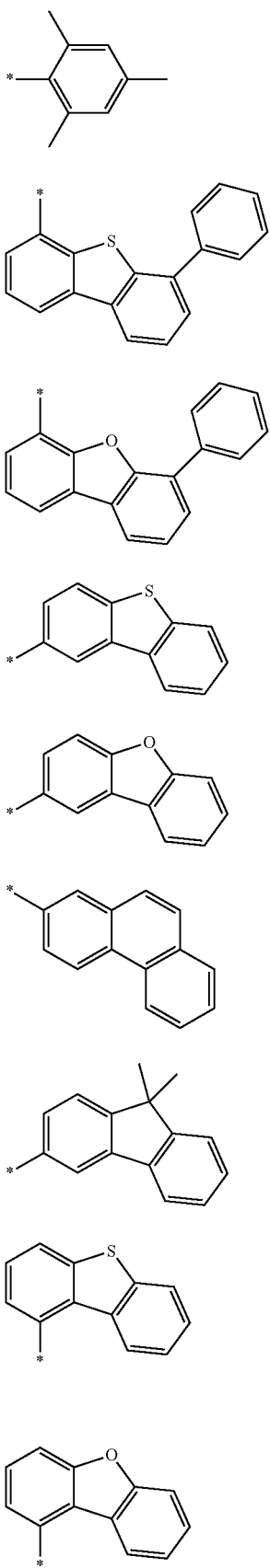
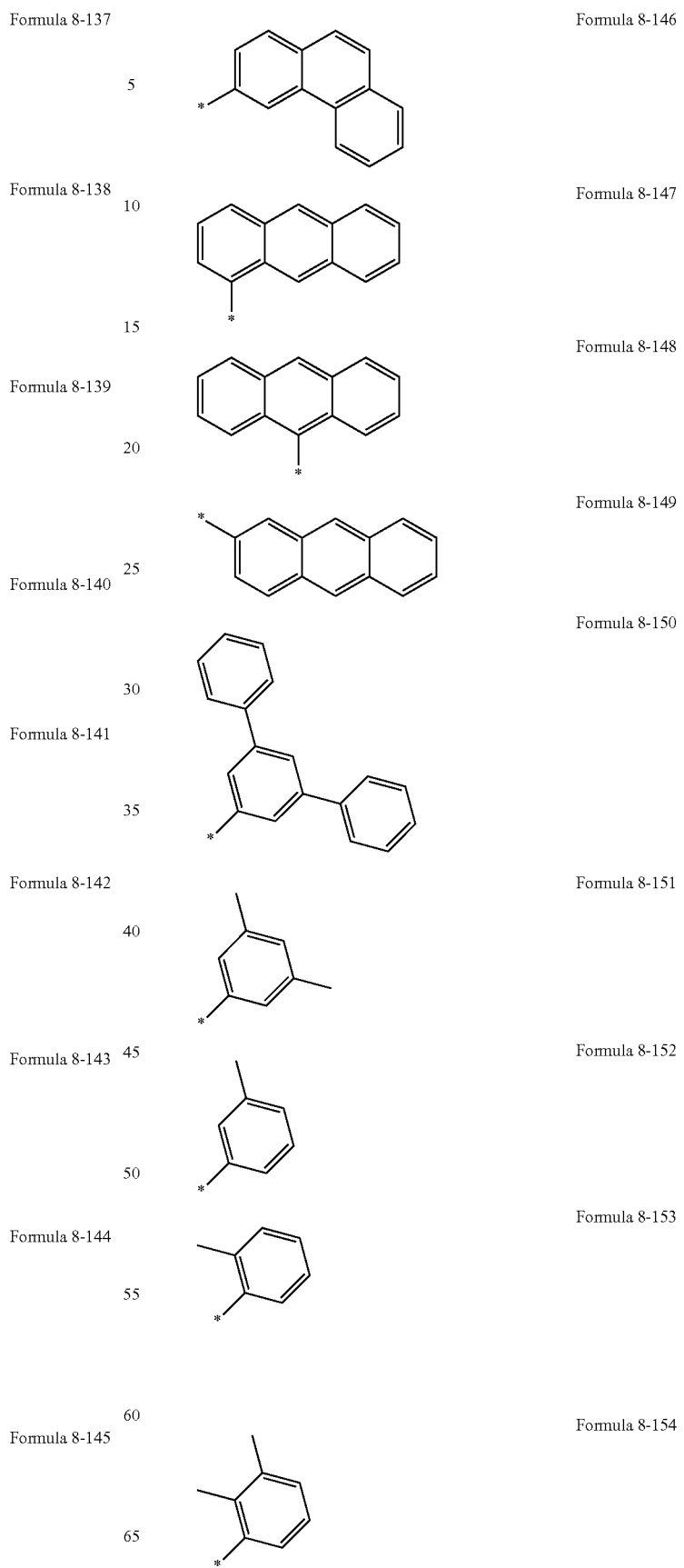
Formula 8-137
Formula 8-138
Formula 8-139
Formula 8-140
Formula 8-141
Formula 8-142
Formula 8-143
Formula 8-144
Formula 8-145
Formula 8-146
Formula 8-147
Formula 8-148
Formula 8-149
Formula 8-150
Formula 8-151
Formula 8-152
Formula 8-153
Formula 8-154

Formula 8-155
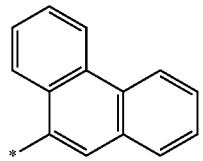
Formula 8-156
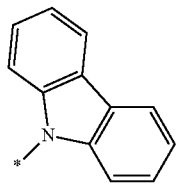
Formula 8-157
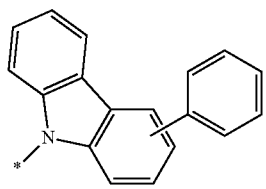
Formula 8-158
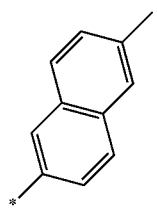
Formula 8-159
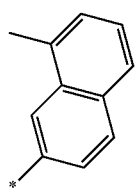
wherein, in Formulae 6-1 to 6-27 and 8-1 to 8-159, * indicates a binding site to an adjacent atom.
17. A condensed-cyclic compound represented by one of Compounds 1 to 35:
1
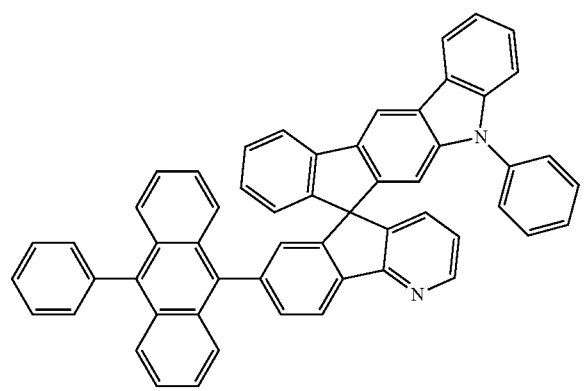
2
3
4
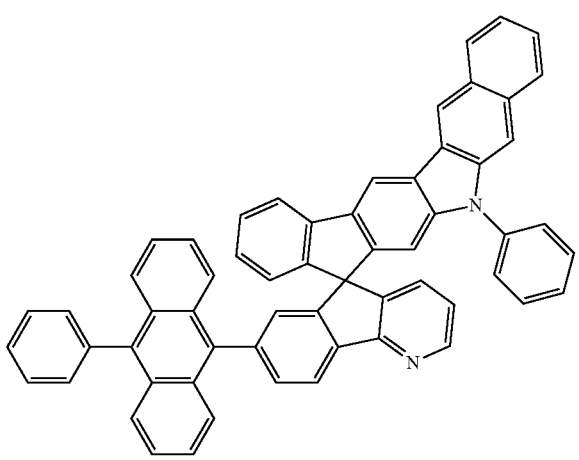

5
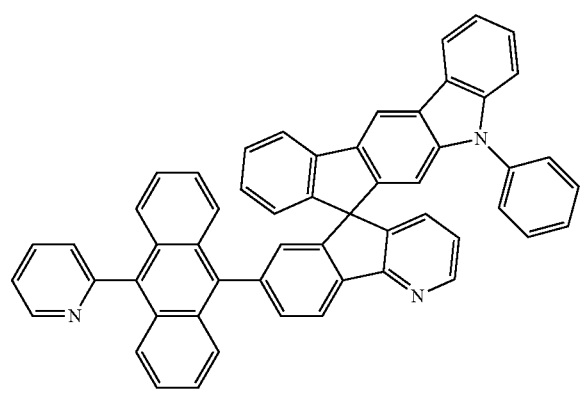
6
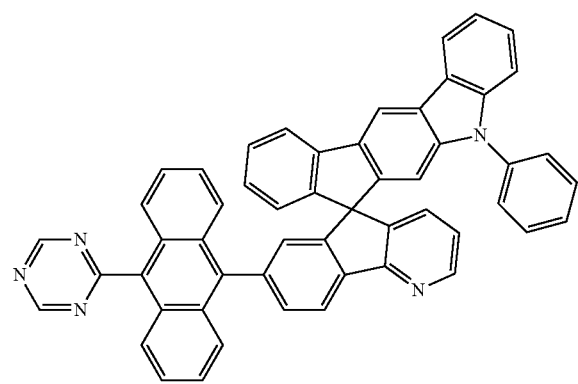
7
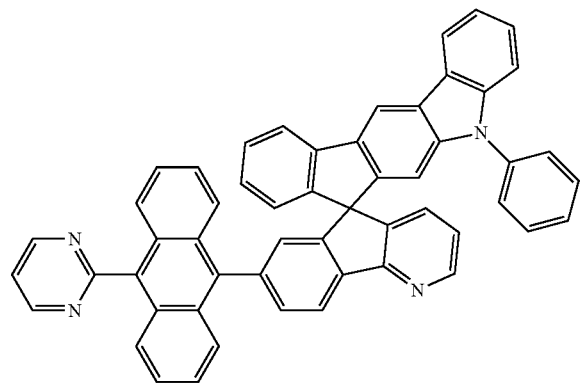
8
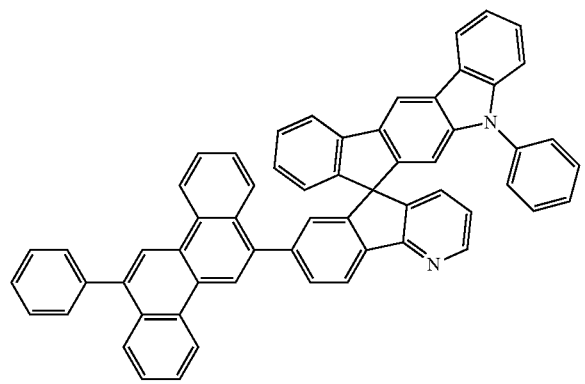
9
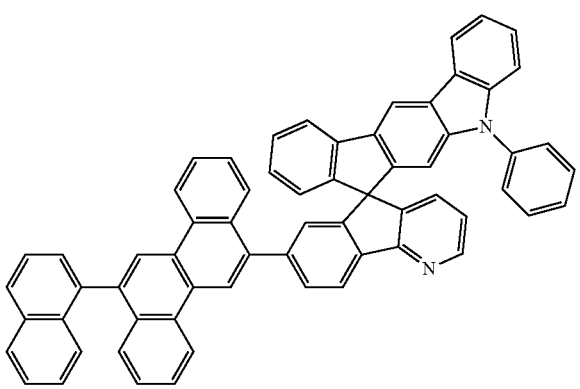
10
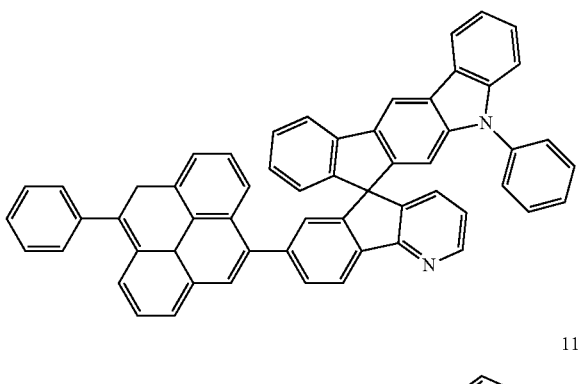
11
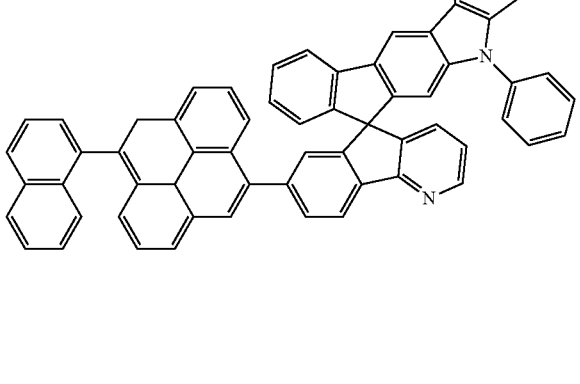
12
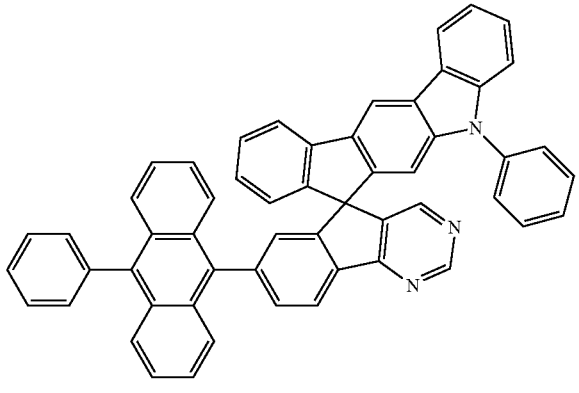

13
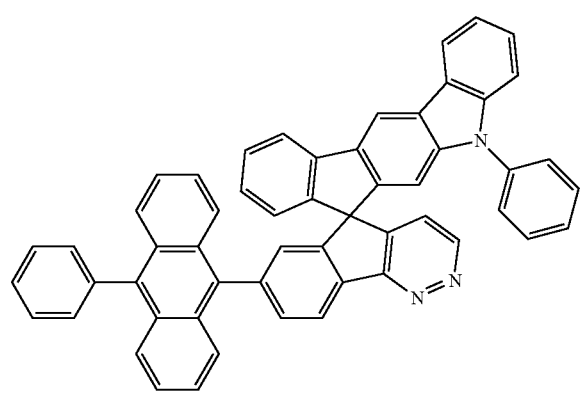
14
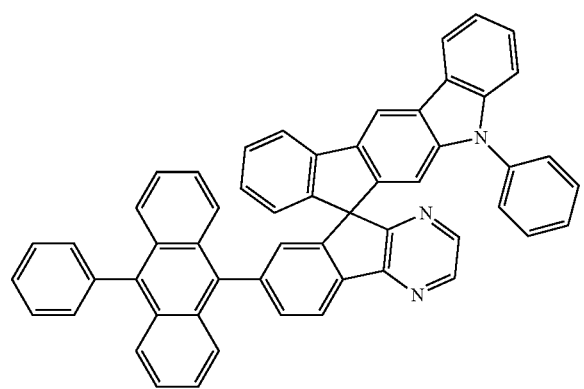
15
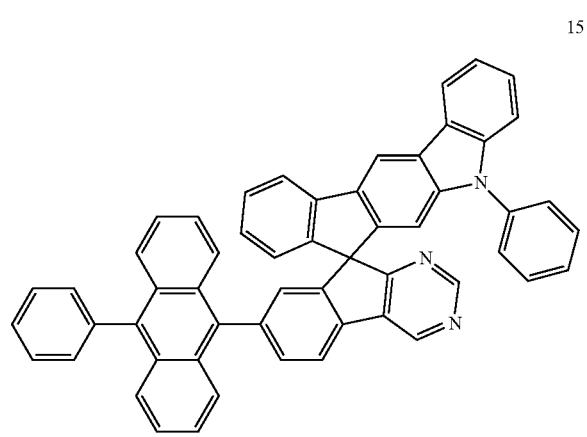
16
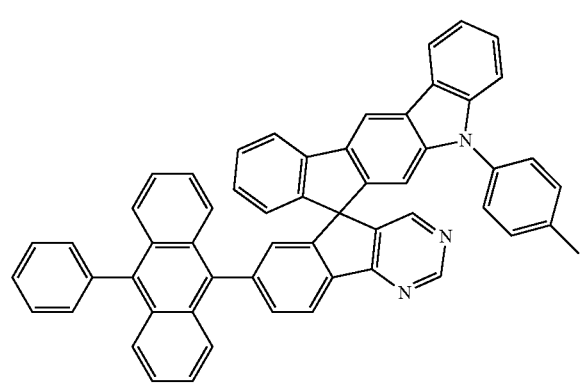
17
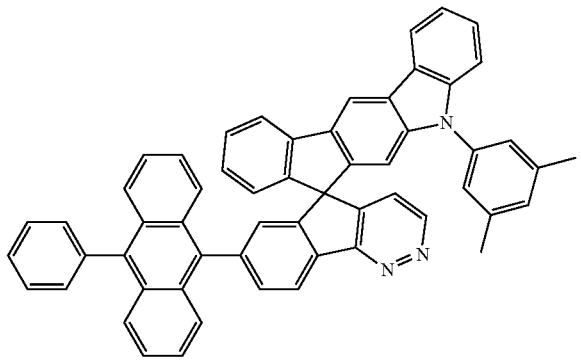
18
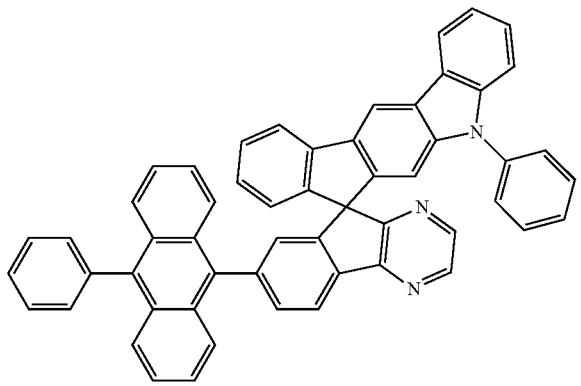
19
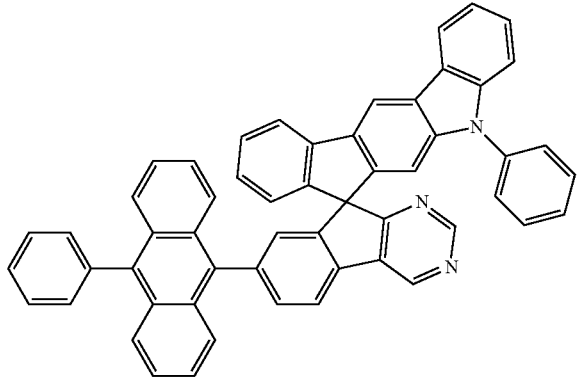
20
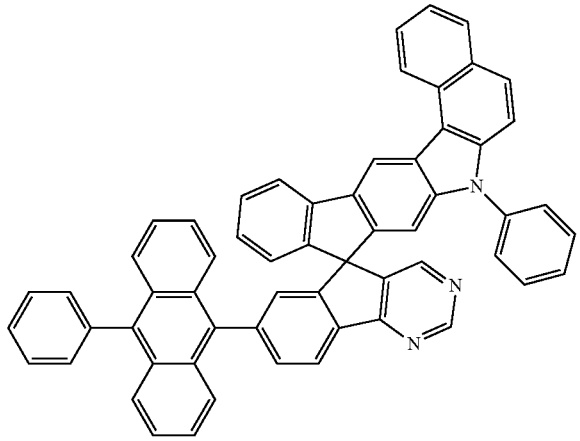

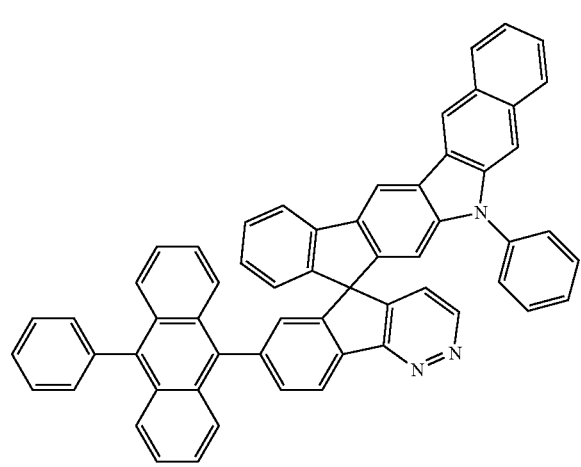
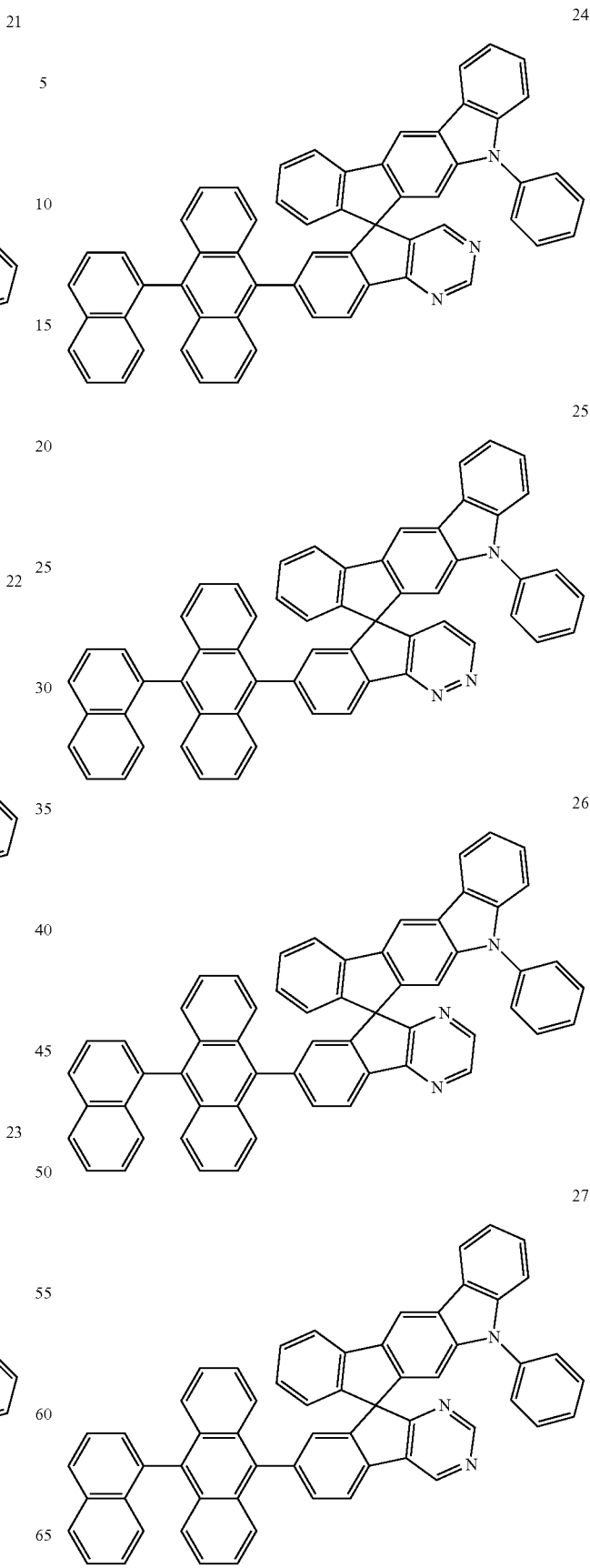

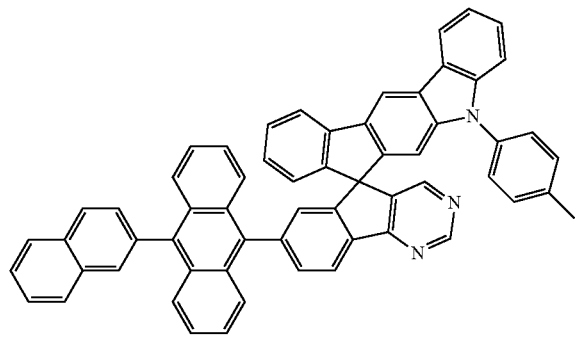
28
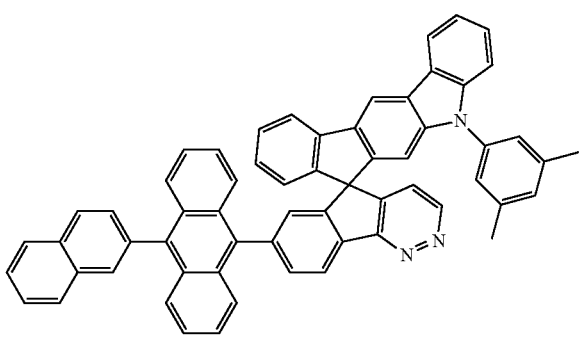
29
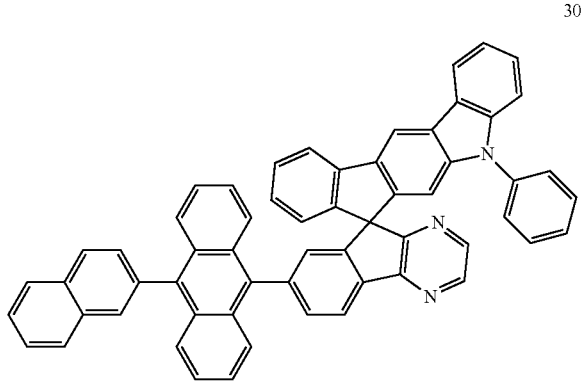
30
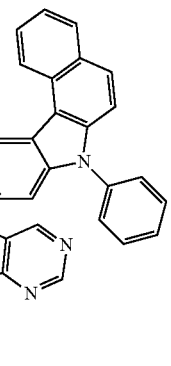
31
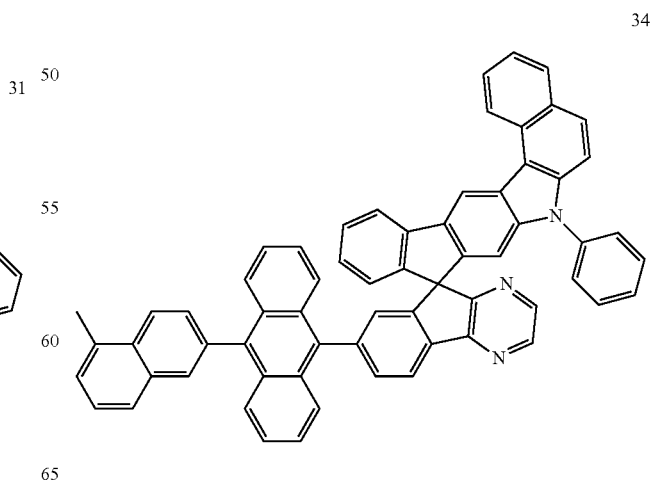
32
33
34

-continued

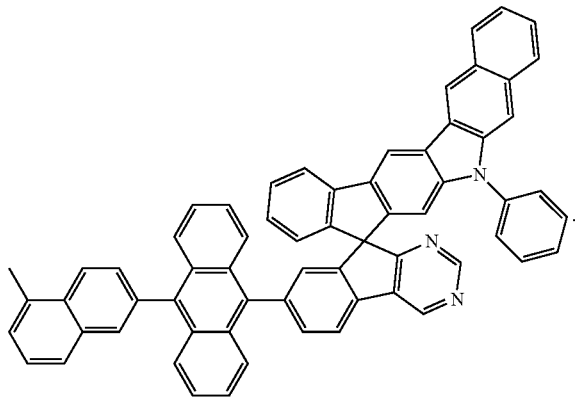

18. An organic light-emitting device comprising: a first electrode; a second electrode facing the first electrode; and an organic layer disposed between the first electrode and the second electrode, wherein the organic layer comprises an emission layer and at least one condensed-cyclic compound of claim 1.

19. The organic light-emitting device of claim 18, wherein
the first electrode is an anode,
the second electrode is a cathode,
the organic layer comprises i) a hole transport region between the first electrode and the emission layer that comprises at least one selected from a hole injection layer, a hole transport layer, an emission auxiliary layer, and an electron blocking layer and ii) an electron transport region between the emission layer and the second electrode that comprises at least one selected from a hole blocking layer, an electron transport layer, and an electron injection layer, and
at least one selected from the hole transport region and the emission layer comprises the at least one condensed-cyclic compound.

20. The organic light-emitting device of claim 18, wherein the emission layer comprises the at least one condensed-cyclic compound.

* * * * *